United States Patent
Parr et al.

(10) Patent No.: US 8,715,960 B2
(45) Date of Patent: May 6, 2014

(54) ABERRANT MITOCHONDRIAL DNA, ASSOCIATED FUSION TRANSCRIPTS AND TRANSLATION PRODUCTS AND HYBRIDIZATION PROBES THEREFOR

(75) Inventors: Ryan Parr, Thunder Bay (CA); Gabriel Dakubo, Thunder Bay (CA); Andrew Harbottle, Newcastle Upon Tyne (GB); Brian Reguly, Vancouver (CA); Jennifer Creed, Broomfield, CO (US); Kerry Robinson, Thunder Bay (CA); Daniel Klein, Thunder Bay (CA)

(73) Assignee: Mitomics Inc., Ontario (CA)

( * ) Notice: Subject to any disclaimer, the term of this patent is extended or adjusted under 35 U.S.C. 154(b) by 0 days.

(21) Appl. No.: 13/260,497

(22) PCT Filed: Mar. 29, 2010
(Under 37 CFR 1.47)

(86) PCT No.: PCT/CA2010/000423
§ 371 (c)(1),
(2), (4) Date: Feb. 21, 2012

(87) PCT Pub. No.: WO2010/115261
PCT Pub. Date: Oct. 14, 2010

(65) Prior Publication Data
US 2013/0059299 A1    Mar. 7, 2013

Related U.S. Application Data

(63) Continuation-in-part of application No. PCT/CA2009/000351, filed on Mar. 27, 2009.

(60) Provisional application No. 61/040,616, filed on Mar. 28, 2008.

(51) Int. Cl.
C12P 21/06     (2006.01)
C12Q 1/68      (2006.01)
G01N 33/00     (2006.01)

(52) U.S. Cl.
USPC .............................. 435/69.1; 436/86; 435/6.1

(58) Field of Classification Search
USPC ........................................ 436/86; 435/6, 69.1
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,807,522 A | 9/1998 | Brown et al. |
| 8,008,008 B2 | 8/2011 | Parr et al. |
| 2011/0172113 A1* | 7/2011 | Parr et al. ............... 506/9 |

FOREIGN PATENT DOCUMENTS

| | | |
|---|---|---|
| WO | 2009039601 A1 | 4/2009 |
| WO | 2009117811 A1 | 10/2009 |
| WO | 2010115261 A1 | 10/2010 |

OTHER PUBLICATIONS

Anderson et al., "Sequence and Organization of the Human Mitochondrial Genome", Nature; Apr. 1981, pp. 457-465, vol. 290.
Andrews et al., "Reanalysis and Revision of the Cambridge Reference Sequence for Human Mitochondrial DNA", Nature Genetics; Oct. 1999, p. 147, vol. 23(2).
Barron et al., "Mitochondrial Abnormalities in Ageing Macular Photoreceptors", Invest Ophthalmol Vis Sci; Nov. 2001, pp. 3016-3022, vol. 42(12).
Brandon et al., "Mitochondrial Mutations in Cancer", Oncogene (2006), pp. 4647-4662, vol. 25.
Croteau et al., "Mitochondrial DNA Repair Pathways" Mutation Research (1999), pp. 137-148; vol. 434(3).
Dai et al., "Correlation of Cochlear Blood Supply With Mitochondrial DNA Common Deletion in Presbyacusis" Acta Otolaryngol, (2004), pp. 130-136, vol. 24(2).
Eguchi et al., "MLL Chimeric Protein Activation Renders Cells Vulnerable to Chromosomal Damage: An Explanation for the Very Short Latency of Infant Leukemia," Genes Chromosomes & Cancer (2006), pp. 754-760, vol. 45(8).
Green et al., "Pharmacological Manipulation of Cell Death: Clinical Applications in Sight?" The Journal of Clinical Investigation; Oct. 2005, pp. 2610-2617, vol. 115(10).
Hayashi et al., "Introduction of Disease-Related Mitochondrial DNA Deletions Into Hela Cells Lacking Mitochondrial DNA Results in Mitochondrial Dysfunction", Proc. Natl. Acad. Sci. USA; Dec. 1991, pp. 10614-10618, vol. 88.
International Search Report for International Application No. PCT/CA2010/000423; International Filing Date: Mar. 29, 2010; 5 pages.
Jakupciak et al., "Analysis of Potential Cancer Biomarkers in Mitochondrial DNA", Current Opinion in Molecular Therapeutics (2006), pp. 500-506, vol. 8(6).
Kazmierczak et al., "Description of a Novel Fusion Transcript Between HMGI-C, A Gene Encoding for a Member of the High Mobility Group Proteins, and the Mitochondrial Aldehyde Dehydrogenase Gene", Cancer Research; Dec. 15, 1995, pp. 6038-6039, vol. 55.
Krishnan et al., "What Causes Mitochondrial DNA Deletions in Human Cells?", Nature Genetics, pp. 275-279, vol. 40(3), 2008.
Lewis et al., "Detection of Damage to the Mitochondrial Genome in the Oncocytic Cells of Warthin's Tumour" Journal of Pathology, (2000), pp. 274-281, vol. 191(3).
Libura et al., Therapy-Related Acute Myeloid Leukemia-Like MLL Rearrangements Are Induced by Etoposide in Primary Human CD34+ Cells and Remain Stable After Clonal Expansion, Blood Journal; Mar. 1, 2005, pp. 2124-2131, vol. 105(5).

(Continued)

Primary Examiner — Maryam Monshipouri
(74) Attorney, Agent, or Firm — Cantor Colburn LLP

(57) ABSTRACT

The present invention provides novel mitochondrial fusion transcripts, the parent mutated mtDNA molecules, and the resulting translation products (proteins) for predicting, diagnosing and/or monitoring cancer. Hybridization probes complementary thereto for use in the methods of the invention are also provided.

10 Claims, 61 Drawing Sheets

(56) References Cited

OTHER PUBLICATIONS

Maki et al., Mitochondrial Genome Deletion Aids in the Identification of False-And-True-Negative Prostate Needle Core Biopsy Specimens, Am J Clin Pathol, (2008), pp. 57-66, vol. 129(1).

Meyer et al., "Diagnostic Tool for the Identification of MLL Rearrangements Including Unknown Partner Genes", Proc Natl Acad Sci USA; Jan. 11, 2005, pp. 449-454, vol. 102(2).

Modica-Napolitano et al., "Mitochondria as Targets for Detection and Treatment of Cancer", Expert Rev Mol Med, pp. 1-19, vol. 4, 2002.

Morgens et al., "A Novel Soybean Mitochondrial Transcript Resulting From a DNA Rearrangement Involving the 5s rRNA Gene", Nucleic Acids Research (1984), pp. 5665-5684, vol. 12(14).

Müller-Höcker et al., "The Common 4977 Base Pair Deletion of Mitochondrial dNA Preferentially Accumulates in the Cardiac Conduction System of Patients With Kearns-Sayre Syndrome" Modern Pathology (1998), pp. 295-301, vol. 11(3).

Nakase et al., "Transcription and Translation of Deleted Mitochondrial Genomes in Kearns-Sayre Syndrome: Implications for Pathogenesis", Am J Hum Genet, (1990), pp. 418-427, vol. 46(3).

Parr et al, "Somatic Mitochondrial DNA Mutations in Prostate Cancer and Normal Appearing Adjacent Glands in Comparison to Age-Matched Prostate Samples Without Malignant Histology", 312-319, vol. 8, 2006.

Porteous et al., "Bioenergetic Consequences of Accumulating the Common 4977-Bp Mitochondrial DNA Deletion", Eur J Biochem (1998), pp. 192-201, vol. 257(1).

Ro et al., "Deleted 4977-Bp Mitochondrial DNA Mutation Is Associated With Sporadic Amyotrophic Lateral Sclerosis: A Hospital-Based Case-Control Study", Muscle Nerve; Dec. 2003, pp. 737-743, vol. 28(6).

Sherratt et al., "Mitochondrial DNA Defects: A Widening Clinical Spectrum of Disorders.", Clinical Science (Great Britain) (1997), pp. 225-235, vol. 92(3).

Written Opinion of the International Searching Authority for International Application No. PCT/CA2010/000423; International Filing Date: Mar. 29, 2010; 6 pages.

Verma et al., "Application of mitochondrial genome information in cancer epidemiology", Clinica Chimica Acta, 2007, 383: pp. 41-50; available online at www.sciencedirect.com.

Database UniProt (online: http://ibis.internal.epo.org/exam/dbfetch.jsp?id=UNIPROT:Q8WCW0); retrieved from EBI accession No. UNIPROT:A6ZHA9; Database accession No. A6ZHA9; Aug. 21, 2007; Cytochrom c oxidase subunit 2; XP-002687300; 1 page.

Database UniProt (online: http://ibis.internal.epo.org/exam/dbfetch.jsp?id=UNIPROT:Q8WCW0); retrieved from EBI accession No. UNIPROT:Q8WCWO; Database accession No. Q8WCWO; Aug. 21, 2007; Cytochrom c oxidase subunit 2; XP-002687301; 3 pages.

European Search Report; EP 10 76 1136; Nov. 16, 2012; Place of Search: Munich; 3 pages.

Gasparre "Disruptive Mitochondrial DNA Mutations in Complex I Subunits are Markers of Oncocytic Phenotype in Thyroid Tumors," Proceedings of the National Aceademy of Sciences, vol. 104, No. 21, May 22, 2007, pp. 9001-9006.

Petros et al "mtDNA mutations increase tumorigenicity in prostate cancer" (PNAS: 2005; vol. 102, No. 3, pp. 719-724) (Petros).

Chabi, Beatrice et al., "Quantification of Mitochondrial DNA Deletion, Depletion, and Overreplication: Application to Diagnosis", Clinical Chemistry 49, No. 8, (2003), pp. 1309-1317.

Dai, Ji Gang et al., "Mitochondrial DNA 4977 BP deletion mutations in lung carcinoma", Indian Journal of Cancer; Jan.-Mar. 2006, vol. 43, Issue 1, pp. 20-25.

He, Langping et al., "Detection and quantification of mitochondrial DNA deletions in individual cells by real-time PCR", XP-002372964; Nucleic Acids Research, 2002, vol. 30, No. 14, e68; pp. 1-6.

Jessie, Benjamin C. et al., "Accumulation of mitochondrial DNA deletions in the malignant prostate of patients of different ages", XP-002524592; Experimental Gerontology 37 (2001) pp. 169-174.

Maitra, Anirban et al., "The Human MitoChip: A High-Throughput Sequencing Microarray for Mitochondrial Mutation Detection", downloaded from www.genome.org on Nov. 21, 2006, pp. 812-819.

Mita, Shuji et al., "Recombination via flanking direct repeats is a major cause of large-scale deletions of human mitochondrial DNA", Nucleic Acids Research, vol. 18, No. 3, Revised and Accepted Dec. 18, 1989; pp. 561-567.

Supplemental European Search Report for Application No. EP09725638, Date of Completion of Search: Oct. 4, 2011; 3 pages.

Uchida, Takafumi et al., "Down-Regulation of Mitochondrial Gene Expression by the Anti-Tumor Arotinoid Mofarotene (Ro 40-8757)", Int. J. Cancer: 58, (1994) pp. 891-897.

Zhu, Weizhu et al., "Large-scale mitochondrial DNA deletion mutations and nuclear genome instability in human breast cancer", Cancer Detection and Prevention 28, (2004), pp. 119-126.

Rupec, et al.; Isolation of a hypoxia-induced cDNA homology to the mammalian growth-related protein p23; Oncology Research; vol. 10, No. 2; p. 69-74; 1998.

* cited by examiner

ROC Curve

Benign to Seminoma

Transcript 3

Benign to Seminoma

Non-Seminoma to Seminoma

Transcript 4

Transcript 11

Benign to Seminoma

Non-Seminoma to Seminoma

Transcript 12

Benign to Seminoma

Non-Seminoma to Seminoma

Transcript 13

Benign to Malignant

Non-Seminoma to Seminoma

Transcript 15

Benign to Malignant

Transcript 16

Benign to Malignant

Benign to Seminoma

Transcript 20
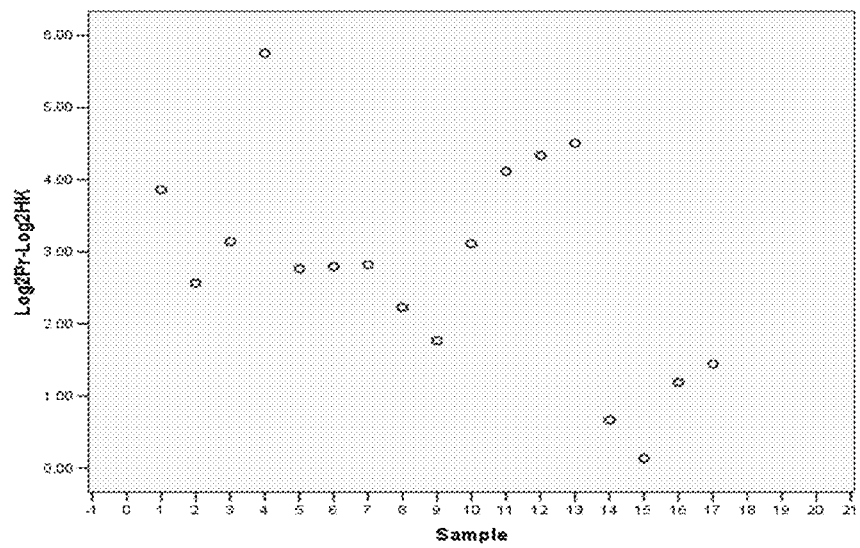
Figure 18a
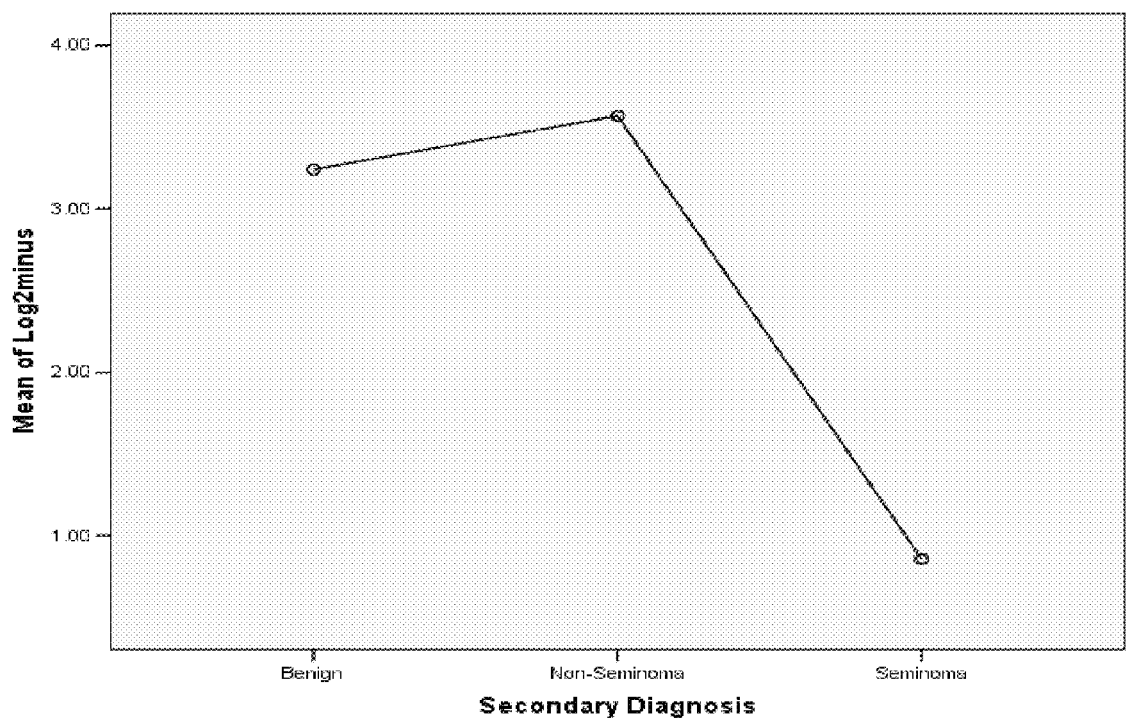

Benign to Seminoma

Non-Seminoma to Seminoma

⊟  sp|P00403|: Cytochrome c oxidase subunit 2; Cytochrome c oxidase polypeptide II;
   log(e) = -69.4

```
  1                                                            60
 61              ILYMTDEVNDPSLTIK                            S 120
121 YMLPPLFLEPGDLRLLDVDNRVVLPIEAPIRMMITSQDVLHSWAVPTIGLKTDAIPGRLN 180
181 QTTFTATR                    IFEMGPVFTL                    227
```

Figure 20b

⊟      PD062:
       log(e) = -41.2

```
  1                      KILGYMQLRKGPNVVGPYGLLQPFADAMK         60
 61                                                          120
121                                                          180
181                                                          240
241           TLLLTSLFLWIR         YDQLMHLLWK                300
301               YLINNRLITTQQWLIK     QMMTMHNTK             360
361                                                          420
421                                                          480
481                                                          514
```

Figure 21a sp|P03886|: NADH-ubiquinone oxidoreductase chain 1; EC 1.6.5.3; NADH dehydrogenase
log(e) = -42.9 subunit 1;

```
1                          KILGYMQLRKGPNVVGPYGLLQPFADAMK              60
61                                                                   120
121                                                                  180
181                                                                  240
241              TLLLTSLFLWIR              YDQLMHLLWK                 300
301                                                                  318
```

Figure 21b

```
1                          KILGYMQLRKGPNVVGPYGLLQPFADAMK              60
61                                                                   120
121                                                                  180
181                                              ITWLTPLIPSTLLSLGGL   240
241 PPLTGFLPKWAIIEEFTK                      LIYSTSITLLPMSNNVK         300
301 WQFEHTKPTPFLPTLIALTTILLPISPFMLMIL                                 333
```

Figure 22

P0176:
log(e) = -33.8

```
  1                           KILGYMQLRKGPNVVGPYGLLQPFADAMK    60
 61                                                           120
121                                                           180
181                                                           240
241                                      AYFTSATMIIAIPTGVKV   300
301 FSWLATLHGSNMK                                             360
361                                                           420
421                                      VLMVEEPSMNLEWLYGCPP  480
481 PYHTFEEPVYMK                                              493
```

Figure 23a log(e) = -14.6

```
  1      WLFSTNHKDIGTLYLLFGAWAGVLGTALSLLIR                    60
 61                                                           120
121                                                           180
181                                                           240
241                                                           300
301 AYFTSATMIIAIPTGVKVFSWLATLHGSNMK                           360
361                                                           420
421                                                           480
481 VLMVEEPSMNLEWLYGCPPPYHTFEEPVYMK                           513
```

Figure 23b

ABERRANT MITOCHONDRIAL DNA, ASSOCIATED FUSION TRANSCRIPTS AND TRANSLATION PRODUCTS AND HYBRIDIZATION PROBES THEREFOR

CROSS REFERENCE TO PRIOR APPLICATIONS

This application is a U.S. national phase application filed pursuant to 35 U.S.C.
371 and claims benefit of PCT Patent Application No. PCT/CA2010/000423, filed Mar. 29, 2010, which is a Continuation in Part of PCT application No. PCT/CA2009/9000351, filed on Mar. 27, 2009, which claims priority from U.S. provisional application No. 61/040,616, filed on Mar. 28, 2008. The entire contents of such prior applications are incorporated herein by reference.

FIELD OF THE INVENTION

The present invention relates to the field of mitochondrial genomics and proteomics. In one aspect, the invention relates to the identification and use of mitochondrial genome fusion transcripts and translation products, as well as probes that hybridize thereto.

BACKGROUND OF THE INVENTION

Mitochondrial Genome

The mitochondrial genome is a compact yet critical sequence of nucleic acids. Mitochondrial DNA, or "mtDNA", comprises a small genome of 16,569 nucleic acid base pairs (bp) (Anderson et al., 1981; Andrews et al., 1999) in contrast to the immense nuclear genome of 3.3 billion by (haploid). Its genetic complement is substantially smaller than that of its nuclear cell mate (0.0005%). However, individual cells carry anywhere from $10^3$ to $10^4$ mitochondria depending on specific cellular functions (Singh and Modica-Napolitano 2002). Communication or chemical signalling routinely occurs between the nuclear and mitochondrial genomes (Sherratt et al., 1997). Moreover, specific nuclear components are responsible for the maintenance and integrity of mitochondrial sequences (Croteau et al., 1999). All mtDNA genomes in a given individual are identical due to the clonal expansion of mitochondria within the ovum, once fertilization has occurred. However mutagenic events can induce sequence diversity reflected as somatic mutations. These mutations may accumulate in different tissues throughout the body in a condition known as heteroplasmy.

Mitochondrial Proteome

About 3,000 nuclear genes are required to construct, operate and maintain mitochondria, with only thirty-seven of these coded by the mitochondrial genome, indicating heavy mitochondrial dependence on nuclear loci. The mitochondrial genome codes for a complement of 24 genes, including 2 rRNAs and 22 tRNAs that ensure correct translation of the remaining 13 genes which are vital to electron transport (see FIG. 1). The mitochondrial genome is dependent on seventy nuclear encoded proteins to accomplish the oxidation and reduction reactions necessary for this vital function, in addition to the thirteen polypeptides supplied by the mitochondrial genome. Both nuclear and mitochondrial proteins form complexes spanning the inner mitochondrial membrane and collectively generate 80-90% of the chemical fuel adenosine triphosphate, or ATP, required for cellular metabolism. In addition to energy production, mitochondria play a central role in other metabolic pathways as well. A critical function of the mitochondria is mediation of cell death, or apoptosis (see Green and Kroemer, 2005). Essentially, there are signal pathways which permeabilize the outer mitochondrial membrane, or in addition, the inner mitochondrial membrane as well. When particular mitochondrial proteins are released into the cytosol, non-reversible cell death is set in motion. This process highlights the multi-functional role that some mitochondrial proteins have. These multi-tasking proteins suggest that there are other mitochondrial proteins as well which may have alternate functions.

Mitochondrial Fusion Transcriptome/Proteome

The mitochondrial genome is unusual in that it is a circular, intron-less DNA molecule. The genome is interspersed with repeat motifs which flank specific lengths of sequences. Sequences between these repeats are prone to deletion under circumstances which are not well understood. Given the number of repeats in the mitochondrial genome, there are many possible deletions. The best known example is the 4977 "common deletion." This deletion has been associated with several purported conditions and diseases and is thought to increase in frequency with aging (Dai et al., 2004; Ro et al., 2003; Barron et al., 2001; Lewis et al., 2000; Muller-Hocker, 1998; Porteous et al., 1998) (FIG. 4). The current thinking in the field of mitochondrial genomics is that mitochondrial deletions are merely deleterious by-products of damage to the mitochondrial genome by such agents as reactive oxygen species and UVR. (Krishnan et al 2008, Nature Genetics). Further, though it is recognized that high levels of mtDNA deletions can have severe consequences on the cell's ability to produce energy in the form of ATP as a result of missing gene sequences necessary for cellular respiration, it is not anticipated that these deleted mitochondrial molecules may be a component of downstream pathways, have an intended functional role, and possibly may be more aptly viewed as alternate natural forms of the recognized genes of the mitochondria.

The sequence dynamics of mtDNA are important diagnostic tools. Mutations in mtDNA are often preliminary indicators of developing disease. For example, it has been demonstrated that point mutations in the mitochondrial genome are characteristic of tumour foci in the prostate. This trend also extends to normal appearing tissue both adjacent to and distant from tumour tissue (Parr et al. 2006). This suggests that mitochondrial mutations occur early in the malignant transformation pathway.

For example, the frequency of a 3.4 kb mitochondrial deletion has excellent utility in discriminating between benign and malignant prostate tissues (Maki et al. 2008). Furthermore, an investigation of the disease associated deletions and the novel sequences, created through re-closure of the molecule identifies many open reading frames, suggesting the possibility of unique mitochondrial fusion proteins.

Mitochondrial fusion transcripts have been reported previously in the literature, first in soybeans (Morgens et al. 1984) and then later in two patients with Kearns-Sayre Syndrome, a rare neuromuscular disorder (Nakase et al 1990). Importantly, these transcripts were not found to have (or investigated regarding) association with any human cancers.

Nuclear Fusion Proteome

There is important nuclear precedence for fusion proteins and their resulting effects on cancer. Nuclear MLL gene partner translocations are well established in correlation with high risk acute leukemia and therapy-related acute myeloid leukemias following treatment with agents that target topoisomerase II (Libura et al., 2005). Currently, around 50 translocations of the human MLL gene are known to be associated with these cancers (Meyer et al., 2005). Break points for these mutations, whether partial tandem duplications or translocations, for the majority of these events, occur within nuclear specific repetitive motifs such as Alu I. Most of these mutations are reciprocal translocations (84%) and include about 40 different genes (Libura et al. 2005).

There are known functional chimeric proteins created from some of these rearrangements which affect the course of malignant disease. For example, murine cells which express the protein from MLL-ENL accelerate the prevalence of chromosome abnormalities in cells which survive exposure to etoposide (Eguchi et al., 2006). Of particular interest is MLL-SMAP1 and the reciprocal SMAP1-MLL. SMAP1 binds calcium and as such participates in cell signalling and trafficking.

Mitochondrial fusion proteins may be assumed to have similar attributes to nuclear fusion proteins, especially since mitochondria and mitochondrial proteins play similar roles in signalling and apoptosis.

SUMMARY OF THE INVENTION

An object of the present invention to provide aberrant mitochondrial DNA, associated fusion transcripts and translation products and hybridization probes therefor.

In accordance with an aspect of the invention, there is provided an isolated mitochondrial fusion transcript associated with cancer.

In accordance with another aspect of the invention, there is provided an isolated mtDNA encoding a fusion transcript of the invention.

In accordance with another aspect of the invention, there is provided a hybridization probe having a nucleic acid sequence complementary to at least a portion of a mitochondrial fusion transcript or an mtDNA of the invention.

In accordance with another aspect of the invention, there is provided a method of detecting a cancer in a mammal, the method comprising assaying a tissue sample from the mammal for the presence of at least one mitochondrial fusion transcript associated with cancer by hybridizing the sample with at least one hybridization probe having a nucleic acid sequence complementary to at least a portion of a mitochondrial fusion transcript according to the invention.

In accordance with another aspect of the invention, there is provided a method of detecting a cancer in a mammal, the method comprising assaying a tissue sample from the mammal for the presence of at least one aberrant mtDNA associated with cancer by hybridizing the sample with at least one hybridization probe having a nucleic acid sequence complementary to at least a portion of an mtDNA according to the invention.

In accordance with another aspect of the invention, there is provided a kit for conducting an assay for detecting the presence of a cancer in a mammal, said kit comprising at least one hybridization probe complementary to at least a portion of a fusion transcript or an mtDNA of the invention.

In accordance with another aspect of the invention, there is provided a mitochondrial fusion protein, the protein having an amino acid sequence resulting from the translation of a mitochondrial fusion transcript of the invention.

In accordance with another aspect of the invention, there is provided a method of detecting a cancer in a mammal, the method comprising assaying a tissue sample from the mammal for the presence of at least one mitochondrial fusion protein, the protein having an amino acid sequence resulting from the translation of a mitochondrial fusion transcript according to the invention.

BRIEF DESCRIPTION OF THE DRAWINGS

The embodiments of the invention will now be described by way of example only with reference to the appended drawings wherein:

FIGS. 18a and 18b illustrate the results for transcript 20 of the invention in the identification of testicular cancer.

FIG. 20b illustrates the wild-type CO2 protein identified in mitochondrial NA22 cell line gel slice 5 of FIG. 19 after searching the Human (SwissProt) database.

FIG. 21a illustrates the identified protein of fusion transcript P0062 based on the peptides KGPNVVGPYGLLQP-FADAMK, YDQLMHLLWK and LITTQQWLIK.

FIG. 21b illustrates the identified peptides of ND1 identified in gel slice 5 of FIG. 19 after searching the Human (SwissProt) database.

FIG. 22 illustrates the identified protein of fusion transcript P0064 based on the peptides KGPNVVGPYGLLQPFAD-AMK and WAIIEEFTK.

FIG. 23a illustrates the identified protein of fusion transcript P0176 based on the peptides KGPNVVGPYGLLQP- FADAMK, VFSWLATLHGSNMK and VLMVEEPSMN-LEWLYGCPPPYHTFEEPVYMK.

FIG. 23b illustrates the wild-type CO1 protein identified in mitochondrial NA22 cell line gel slice 4 of FIG. 19 after searching the Human (SwissProt) database.

DETAILED DESCRIPTION OF THE INVENTION

Figure 1:
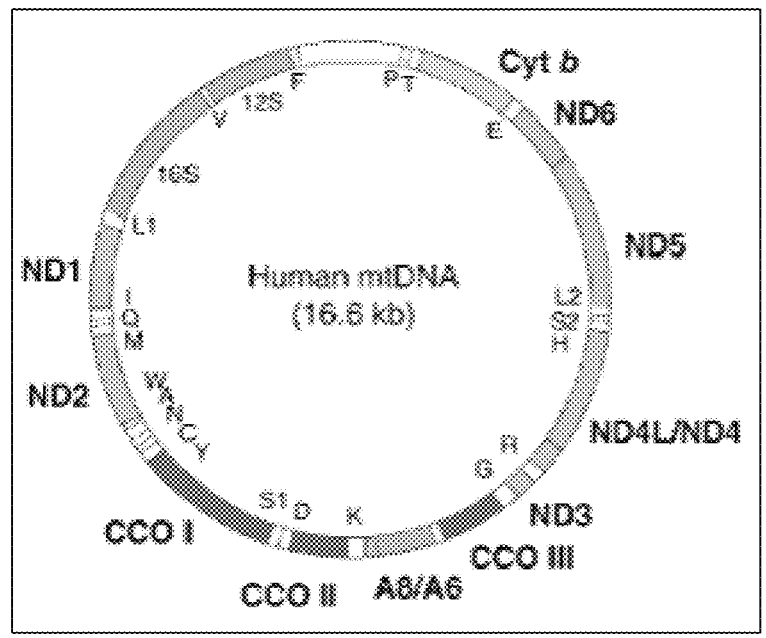
FIG. 1 is an illustration showing mitochondrial protein coding genes.

The present invention provides novel mitochondrial fusion transcripts, the parent mutated mtDNA molecules, and the resulting translation products that are useful for predicting, diagnosing and/or monitoring cancer. The invention further provides hybridization probes for the detection of fusion transcripts and associated mtDNA molecules and the use of such probes.

Definitions

Unless defined otherwise, all technical and scientific terms used herein have the same meaning as commonly understood by one of ordinary skill in the art to which this invention belongs.

The terms "comprise", "comprises", "comprised" or "comprising" may be used in the present description. As used herein (including the specification and/or the claims), these terms are to be interpreted as specifying the presence of the stated features, integers, steps or components, but not as precluding the presence of one or more other feature, integer, step, component or a group thereof as would be apparent to persons having ordinary skill in the relevant art.

As used herein, "aberration" or "mutation" encompasses any modification in the wild type mitochondrial DNA sequence that results in a fusion transcript and includes, without limitation, insertions, translocations, deletions, duplications, recombinations, rearrangements or combinations thereof.

As defined herein, "biological sample" refers to a tissue or bodily fluid containing cells from which a molecule of interest can be obtained. For example, the biological sample can be derived from tissue such as prostate, breast, colorectal, lung and skin, or from blood, saliva, cerebral spinal fluid, sputa, urine, mucous, synovial fluid, peritoneal fluid, amniotic fluid and the like. The biological sample may be a surgical specimen or a biopsy specimen. The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

A "continuous" transcript is a fusion transcript that keeps the reading frame from the beginning to the end of both spliced genes. An "end" transcript is a fusion transcript that results in a premature termination codon before the original termination codon of a second spliced gene.

As used herein, "mitochondrial DNA" or "mtDNA" is DNA present in mitochondria.

As used herein, the expression "mitochondrial fusion protein" or "fusion protein" refers to a peptide product produced by the transcription and translation of a mutated mitochondrial DNA, wherein such mutations comprise deletions or other "large-scale" mitochondrial DNA rearrangements. In addition, or alternatively, an in-frame protein may be translated from alternate initiation and termination codons within that sequence.

As used herein, the expression "mitochondrial fusion transcript" or "fusion transcript" refers to an RNA transcription product produced as a result of the transcription of a mutated mitochondrial DNA sequence wherein such mutations may comprise mitochondrial deletions and other large-scale mitochondrial DNA rearrangements.

As used herein, the expression "mitochondrial translation product" or "translation product" refers to any amino acid chain derived from a mitochondrial fusion transcript including peptides, polypeptides and proteins. It will be understood that "mitochondrial translation products" comprise "fusion proteins", as defined above.

Computer Analysis and Sequence Targeting

As discussed above, mitochondrial fusion transcripts have been reported in soybeans (Morgens et al. 1984) and in humans suffering from a rare neuromuscular disorder (Nakase et al 1990). Fusion transcripts associated with human cancer have not, however, been described.

Using the knowledge gained from mapping the large-scale deletions of the human mitochondrial genome associated with cancer, the observation of high frequencies of these deletions, and the evidence in another organism and another disease type of transcriptionally active mutated mtDNA molecules, the present inventors hypothesized that such deletions may have importance beyond the DNA molecule and the damage and repair processes as it relates to cancer. To test this hypothesis computer analysis of the mitochondrial genome was conducted, specific for repeat elements, which suggested many potential deletion sites. Following this initial step of identifying unique repeats in the mitochondrial sequence having non-adjacent or non-tandem locations, a filter was then applied to identify those repeats that upon initiating a deletion event in the DNA molecule would then likely reclose or religate to produce a fused DNA sequence having an open reading frame (ORF) and thus capable of being transcribed by the mitochondrial transcription machinery. A subset of 18 of these molecules were then selected for targeting to investigate whether: they existed in the natural biological state of humans; they were polyadenylated and thus expected to proceed to protein synthesis; they had relevance to malignancy. Results from these investigations proved positive for all three queries and are described hereinafter.

Genomic Mutations

Mitochondrial DNA (mtDNA) dynamics are an important diagnostic tool. Mutations in mtDNA are often preliminary indicators of developing disease and may act as biomarkers indicative of risk factors associated with disease onset. According to the present invention, mutations in the mitochondrial genome result in the generation of fusion transcripts associated with cancer. Thus, the use of mtDNA encoding such transcripts and probes directed thereto for the detection, diagnosis and monitoring of cancer is provided.

One of skill in the art will appreciate that the mtDNA molecules for use in the methods of the present invention may be derived through the isolation of naturally-occurring mutants or may be based on the complementary sequence of any of the fusion transcripts described herein. Exemplary mtDNA sequences and fusion transcripts are disclosed in Applicant's co-pending U.S. Application No. 61/040,616 and published PCT application no. PCT/CA2009/000351 (published as WO 2009/117811).

Detection of Mutant Genomic Sequences

Mutant mtDNA sequences according to the present invention may comprise any modification that results in the generation of a fusion transcript. Non-limiting examples of such modifications include insertions, translocations, deletions, duplications, recombinations, rearrangements or combinations thereof. While the modification or change can vary greatly in size from only a few bases to several kilobases, preferably the modification results in a substantive deletion or other large-scale genomic aberration.

Extraction of DNA to detect the presence of such mutations may take place using art-recognized methods, followed by amplification of all or a region of the mitochondrial genome, and may include sequencing of the mitochondrial genome, as described in Current Protocols in Molecular Biology.

The step of detecting the mutations can be selected from any technique known in the art. For example, analyzing mtDNA can comprise sequencing the mtDNA, amplifying mtDNA by PCR, Southern, Northern, Western South-Western blot hybridizations, denaturing HPLC, hybridization to microarrays, biochips or gene chips, molecular marker analysis, biosensors, melting temperature profiling or a combination of any of the above.

Any suitable means to sequence mitochondrial DNA may be used. Preferably, mtDNA is amplified by PCR prior to sequencing. The method of PCR is well known in the art and may be performed as described in Mullis and Faloona, 1987, Methods Enzymol., 155: 335. PCR products can be sequenced directly or cloned into a vector which is then placed into a bacterial host. Examples of DNA sequencing methods are found in Brumley, R. L. Jr. and Smith, L. M., 1991, Rapid DNA sequencing by horizontal ultrathin gel electrophoresis, Nucleic Acids Res. 19:4121-4126 and Luckey, J. A., et al, 1993, High speed DNA sequencing by capillary gel electrophoresis, Methods Enzymol. 218: 154-172. The combined use of PCR and sequencing of mtDNA is described in Hopgood, R., et al, 1992, Strategies for automated sequencing of human mtDNA directly from PCR products, Biotechniques 13:82-92 and Tanaka, M. et al, 1996, Automated sequencing of mtDNA, Methods Enzymol. 264: 407-421.

Methods of selecting appropriate sequences for preparing various primers are also known in the art. For example, the primer can be prepared using conventional solid-phase synthesis using commercially available equipment, such as that available from Applied Biosystems USA Inc. (Foster City, Calif.), DuPont, (Wilmington, Del.), or Milligen (Bedford, Mass.).

According to an aspect of the invention, to determine candidate genomic sequences, a junction point of a sequence deletion is first identified. Sequence deletions are primarily identified by direct and indirect repetitive elements which flank the sequence to be deleted at the 5' and 3' end. The removal of a section of the nucleotides from the genome followed by the ligation of the genome results in the creation of a novel junction point.

Upon identification of the junction point, the nucleotides of the genes flanking the junction point are determined in order to identify a spliced gene. Typically the spliced gene comprises the initiation codon from the first gene and the termination codon of the second gene, and may be expressed as a continuous transcript, i.e. one that keeps the reading frame from the beginning to the end of both spliced genes. Some known mitochondrial deletions discovered to have an open reading frame (ORF) when the rearranged sequences are rejoined at the splice site are provided in Table 1.

Exemplary mtDNA molecules for use in the methods of the present invention are provided below. These mtDNAs are based on modifications of the known mitochondrial genome (SEQ ID NO: 1) and have been assigned a fusion or "FUS" designation, wherein A:B represents the junction point between the last mitochondrial nucleotide of the first spliced gene and the first mitochondrial nucleotide of the second spliced gene. The identification of the spliced genes is provided in parentheses followed by the corresponding sequence identifier. Where provided below, (AltMet) and (OrigMet) refer to alternate and original translation start sites, respectively.

FUS 8469:13447 (AltMet) (ATP synthase F0 subunit 8 to NADH dehydrogenase subunit) (SEQ ID No: 2)

FUS 10744:14124 (NADH dehydrogenase subunit 4L (ND4L) to NADH dehydrogenase subunit 5 (ND5)) (SEQ ID No: 3)

FUS 7974:15496 (Cytochrome c oxidase subunit II (COII) to Cytochrome b (Cytb)) (SEQ ID No: 4)

FUS 7992:15730 (Cytochrome c oxidase subunit II (COII) to Cytochrome b (Cytb)) (SEQ ID No: 5)

FUS 8210:15339 (Cytochrome c oxidase subunit II (COII) to Cytochrome b (Cytb)) (SEQ ID No: 6)

FUS 8828:14896 (ATP synthase F0 subunit 6 (ATPase6) to Cytochrome b (Cytb)) (SEQ ID No: 7)

FUS 10665:14856 (NADH dehydrogenase subunit 4L (ND4L) to Cytochrome b (Cytb)) (SEQ ID No: 8)

FUS 6075:13799 (Cytochrome c oxidase subunit I (COI) to NADH de hydrogenase subunit 5 (ND5)) (SEQ ID No: 9)

FUS 6325:13989 (Cytochrome c oxidase subunit I (COI) to NADH dehydrogenase subunit 5 (ND5)) (SEQ ID No: 10)

FUS 7438:13476 (Cytochrome c oxidase subunit I (COI) to NADH dehydrogenase subunit 5 (ND5)) (SEQ ID No: 11)

FUS 7775:13532 (Cytochrome c oxidase subunit II (COII) to NADH dehydrogenase subunit 5 (ND5)) (SEQ ID No: 12)

FUS 8213:13991 (Cytochrome c oxidase subunit II (COII) to NADH dehydrogenase subunit 5 (ND5)) (SEQ ID No: 13)

FUS 9191:12909 (ATP synthase F0 subunit 6 (ATPase6) to NADH dehydrogenase subunit 5 (ND5)) (SEQ ID No: 14)

FUS 9574:12972 (Cytochrome c oxidase subunit III (COIII) to NADH dehydrogenase subunit 5 (ND5)) (SEQ ID No: 15)

FUS 10367:12829 (NADH dehydrogenase subunit 3 (ND3) to NADH dehydrogenase subunit 5 (ND5)) (SEQ ID No: 16)

FUS 11232:13980 (NADH dehydrogenase subunit 4 (ND4) to NADH dehydrogenase subunit 5 (ND5) (SEQ ID No: 17)

FUS 8469:13447 (OrigMet) (ATP synthase F0 subunit 8 to NADH dehydrogenase subunit) (SEQ ID No: 18)

FUS 9144:13816 ((ATP synthase F0 subunit 6 (ATPase6) to NADH dehydrogenase subunit 5 (ND5)) (SEQ ID No: 54)

The present invention also provides the use of variants or fragments of these sequences for predicting, diagnosing and/or monitoring cancer.

"Variant", as used herein, refers to a nucleic acid differing from an mtDNA sequence of the present invention, but retaining essential properties thereof. Generally, variants are overall closely similar, and, in many regions, identical to a select mtDNA sequence. Specifically, the variants of the present invention comprise at least one of the nucleotides of the junction point of the spliced genes, and may further comprise one or more nucleotides adjacent thereto. In one embodiment of the invention, the variant sequence is at least 80%, 85%, 90%, 95%, 96%, 97%, 98% or 99% identical to any one of the mtDNA sequences of the invention, or the complementary strand thereto.

In the present invention, "fragment" refers to a short nucleic acid sequence which is a portion of that contained in the disclosed genomic sequences, or the complementary strand thereto. This portion includes at least one of the nucleotides comprising the junction point of the spliced genes, and may further comprise one or more nucleotides adjacent thereto. The fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases of any one of the mtDNA sequences listed above. In this context "about" includes the particularly recited value, a value larger or smaller by several (5, 4, 3, 2, or 1) nucleotides, at either terminus or at both termini. These fragments have uses that include, but are not limited to, as diagnostic probes and primers as discussed herein. Of course, larger fragments (e.g., 50, 150, 500, 600, 2000 nucleotides) are also contemplated.

Thus, in specific embodiments of the invention, the mtDNA sequences are selected from the group consisting of:
SEQ ID NO: 2 (FUS 8469:13447; AltMet)
SEQ ID NO: 3 (FUS 10744:14124)
SEQ ID NO: 4 (FUS 7974:15496)
SEQ ID NO: 5 (FUS 7992:15730)
SEQ ID NO: 6 (FUS 8210:15339)
SEQ ID NO: 7 (FUS 8828:14896)
SEQ ID NO: 8 (FUS 10665:14856)
SEQ ID NO: 9 (FUS 6075:13799)
SEQ ID NO: 10 (FUS 6325:13989)
SEQ ID NO: 11 (FUS 7438:13476)
SEQ ID NO: 12 (FUS 7775:13532)
SEQ ID NO: 13 (FUS 8213:13991)
SEQ ID NO: 14 (FUS 9191:12909)
SEQ ID NO: 15 (FUS 9574:12972)
SEQ ID NO: 16 (FUS 10367:12829)
SEQ ID NO: 17 (FUS 11232:13980)
SEQ ID NO: 18 (FUS 8469:13447; OrigMet)
SEQ ID NO: 54 (FUS 9144:13816),
and fragments or variants thereof.

Probes

Another aspect of the invention is to provide a hybridization probe capable of recognizing an aberrant mtDNA sequence of the invention. As used herein, the term "probe" refers to an oligonucleotide which forms a duplex structure with a sequence in the target nucleic acid, due to complementarity of at least one sequence in the probe with a sequence in the target region. The probe may be labeled, according to methods known in the art.

Once aberrant mtDNA associated with particular disease is identified, hybridization of mtDNA to, for example, an array of oligonucleotides can be used to identify particular mutations, however, any known method of hybridization may be used.

As with the primers of the present invention, probes may be generated directly against exemplary mtDNA fusion molecules of the invention, or to a fragment or variant thereof. For instance, the sequences set forth in SEQ ID NOs: 2-18 and 54 and those disclosed in Table 1 can be used to design primers or probes that will detect a nucleic acid sequence comprising a fusion sequence of interest. As would be understood by those of skill in the art, primers or probes which hybridize to these nucleic acid molecules may do so under highly stringent hybridization conditions or lower stringency conditions, such conditions known to those skilled in the art and found, for example, in Current Protocols in Molecular Biology (John Wiley & Sons, New York (1989)), 6.3.1-6.3.6.

In specific embodiments of the invention, the probes of the invention contain a sequence complementary to at least a portion of the aberrant mtDNA comprising the junction point of the spliced genes. This portion includes at least one of the nucleotides involved in the junction point A:B, and may further comprise one or more nucleotides adjacent thereto. In this regard, the present invention encompasses any suitable targeting mechanism that will select an mtDNA molecule using the nucleotides involved and/or adjacent to the junction point A:B.

Various types of probes known in the art are contemplated by the present invention. For example, the probe may be a hybridization probe, the binding of which to a target nucleotide sequence can be detected using a general DNA binding dye such as ethidium bromide, SYBR® Green, SYBR® Gold and the like. Alternatively, the probe can incorporate one or more detectable labels. Detectable labels are molecules or moieties a property or characteristic of which can be detected directly or indirectly and are chosen such that the ability of the probe to hybridize with its target sequence is not affected. Methods of labelling nucleic acid sequences are well-known in the art (see, for example, Ausubel et al., (1997 & updates) *Current Protocols in Molecular Biology*, Wiley & Sons, New York).

Labels suitable for use with the probes of the present invention include those that can be directly detected, such as radio-isotopes, fluorophores, chemiluminophores, enzymes, colloidal particles, fluorescent microparticles, and the like. One skilled in the art will understand that directly detectable labels may require additional components, such as substrates, triggering reagents, light, and the like to enable detection of the label. The present invention also contemplates the use of labels that are detected indirectly.

The probes of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A probe of "at least 20 nt in length," for example, is intended to include 20 or more contiguous bases that are complementary to an mtDNA sequence of the invention. Of course, larger probes (e.g., 50, 150, 500, 600, 2000 nucleotides) may be preferable.

The probes of the invention will also hybridize to nucleic acid molecules in biological samples, thereby enabling the methods of the invention. Accordingly, in one aspect of the invention, there is provided a hybridization probe for use in the detection of cancer, wherein the probe is complementary to at least a portion of an aberrant mtDNA molecule. In another aspect the present invention provides probes and a use of (or a method of using) such probes for the detection of colorectal cancer, lung cancer, breast cancer, ovarian cancer, testicular, cancer, prostate cancer and/or melanoma skin cancer.

Assays

Measuring the level of aberrant mtDNA in a biological sample can determine the presence of one or more cancers in a subject. The present invention, therefore, encompasses methods for predicting, diagnosing or monitoring cancer, comprising obtaining one or more biological samples, extracting mtDNA from the samples, and assaying the samples for aberrant mtDNA by: quantifying the amount of one or more aberrant mtDNA sequences in the sample and comparing the quantity detected with a reference value. As would be understood by those of skill in the art, the reference value is based on whether the method seeks to predict, diagnose or monitor cancer. Accordingly, the reference value may relate to mtDNA data collected from one or more known non-cancerous biological samples, from one or more known cancerous biological samples, and/or from one or more biological samples taken over time.

In one aspect, the invention provides a method of detecting cancer in a mammal, the method comprising assaying a tissue sample from the mammal for the presence of an aberrant mitochondrial DNA described above. The present invention also provides for methods comprising assaying a tissue sample from the mammal by hybridizing the sample with at least one hybridization probe. The probe may be generated against a mutant mitochondrial DNA sequence of the invention as described herein.

In another aspect, the invention provides a method as above, wherein the assay comprises:
a) conducting a hybridization reaction using at least one of the probes to allow the at least one probe to hybridize to a complementary aberrant mitochondrial DNA sequence;
b) quantifying the amount of the at least one aberrant mitochondrial DNA sequence in the sample by quantifying the amount of the mitochondrial DNA hybridized to the at least one probe; and,
c) comparing the amount of the mitochondrial DNA in the sample to at least one known reference value.

Also included in the present invention are methods for predicting, diagnosing or monitoring cancer comprising diagnostic imaging assays as described below. The diagnostic assays of the invention can be readily adapted for high-throughput. High-throughput assays provide the advantage of processing many samples simultaneously and significantly decrease the time required to screen a large number of samples. The present invention, therefore, contemplates the use of the nucleotides of the present invention in high-throughput screening or assays to detect and/or quantitate target nucleotide sequences in a plurality of test samples.

Fusion Transcripts

The present invention further provides the identification of fusion transcripts and associated hybridization probes useful in methods for predicting, diagnosing and/or monitoring cancer. One of skill in the art will appreciate that such molecules may be derived through the isolation of naturally-occurring transcripts or, alternatively, by the recombinant expression of mtDNAs isolated according to the methods of the invention. As discussed, such mtDNAs typically comprise a spliced gene having the initiation codon from the first gene and the termination codon of the second gene. Accordingly, fusion transcripts derived therefrom comprise a junction point associated with the spliced genes.

Detection of Fusion Transcripts

Naturally occurring fusion transcripts can be extracted from a biological sample and identified according to any suitable method known in the art, or may be conducted according to the methods described in the examples. In one embodiment of the invention, stable polyadenylated fusion transcripts are identified using Oligo(dT) primers that target transcripts with poly-A tails, followed by RT-PCR using primer pairs designed against the target transcript.

The following exemplary fusion transcripts were detected using such methods and found useful in predicting, diagnosing and/or monitoring cancer as indicated in the examples. Likewise, fusion transcripts derived from the ORF sequences identified in Table 1 may be useful in predicting, diagnosing and/or monitoring cancer.

SEQ ID NO: 19 (Transcript 1; 8469:13447; AltMet)
SEQ ID NO: 20 (Transcript 2; 10744:14124)
SEQ ID NO: 21 (Transcript 3; 7974:15496)
SEQ ID NO: 22 (Transcript 4; 7992:15730)
SEQ ID NO: 23 (Transcript 5; 8210:15339)
SEQ ID NO: 24 (Transcript 6; 8828:14896)
SEQ ID NO: 25 (Transcript 7; 10665:14856)
SEQ ID NO: 26 (Transcript 8; 6075:13799)
SEQ ID NO: 27 (Transcript 9; 6325:13989)
SEQ ID NO: 28 (Transcript 10; 7438:13476)
SEQ ID NO: 29 (Transcript 11; 7775:13532)
SEQ ID NO: 30 (Transcript 12; 8213:13991)
SEQ ID NO: 31 (Transcript 14; 9191:12909)
SEQ ID NO: 32 (Transcript 15; 9574:12972)
SEQ ID NO: 33 (Transcript 16; 10367:12829)
SEQ ID NO: 34 (Transcript 17; 11232:13980)
SEQ ID NO: 35 (Transcript 20; 8469:13447; OrigMet)
SEQ ID NO: 53 (Transcript 13; 9144:13816)

Fusion transcripts can also be produced by recombinant techniques known in the art. Typically this involves transformation (including transfection, transduction, or infection) of a suitable host cell with an expression vector comprising an mtDNA sequence of interest.

Variants or fragments of the fusion transcripts identified herein are also provided. Such sequences may adhere to the size limitations and percent identities described above with respect to genomic variants and fragments, or as determined suitable by a skilled technician.

Probes

Once a fusion transcript has been characterized, primers or probes can be developed to target the transcript in a biological sample. Such primers and probes may be prepared using any known method (as described above) or as set out in the examples provided below. A probe may, for example, be generated for the fusion transcript, and detection technologies, such as QuantiGene 2.0™ by Panomics™, used to detect the presence of the transcript in a sample. Primers and probes may be generated directly against exemplary fusion transcripts of the invention, or to a fragment or variant thereof. For instance, the sequences set forth in SEQ ID NOs: 19-35 and 53, as well as those disclosed in Table 1, can be used to design probes that will detect a nucleic acid sequence comprising a fusion sequence of interest.

As would be understood by those skilled in the art, probes designed to hybridize to the fusion transcripts of the invention contain a sequence complementary to at least a portion of the transcript expressing the junction point of the spliced genes. This portion includes at least one of the nucleotides complementary to the expressed junction point, and may further comprise one or more complementary nucleotides adjacent thereto. In this regard, the present invention encompasses any suitable targeting mechanism that will select a fusion transcript that uses the nucleotides involved and adjacent to the junction point of the spliced genes.

Various types of probes and methods of labelling known in the art are contemplated for the preparation of transcript probes. Such types and methods have been described above with respect to the detection of genomic sequences. The transcript probes of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A probe of "at least 20 nt in length," for example, is intended to include 20 or more contiguous bases that are complementary to an mtDNA sequence of the invention. Of course, larger probes (e.g., 50, 150, 500, 600, 2000 nucleotides) may be preferable.

In one aspect, the invention provides a hybridization probe for use in the detection of cancer, wherein the probe is complementary to at least a portion of a mitochondrial fusion transcript provided above.

In another aspect, the present invention provides probes and a use of (or a method of using) such probes for the detection of colorectal cancer, lung cancer, breast cancer, ovarian cancer, testicular cancer, prostate cancer or melanoma skin cancer.

Assays

Measuring the level of mitochondrial fusion transcripts in a biological sample can determine the presence of one or more cancers in a subject. The present invention, therefore, provides methods for predicting, diagnosing or monitoring cancer, comprising obtaining one or more biological samples, extracting mitochondrial RNA from the samples, and assaying the samples for fusion transcripts by: quantifying the amount of one or more fusion transcripts in the sample and comparing the quantity detected with a reference value. As would be understood by those of skill in the art, the reference value is based on whether the method seeks to predict, diagnose or monitor cancer. Accordingly, the reference value may relate to transcript data collected from one or more known non-cancerous biological samples, from one or more known cancerous biological samples, and/or from one or more biological samples taken over time.

In one aspect, the invention provides a method of detecting a cancer in a mammal, the method comprising assaying a tissue sample from said mammal for the presence of at least one fusion transcript of the invention by hybridizing said sample with at least one hybridization probe having a nucleic acid sequence complementary to at least a portion of the mitochondrial fusion transcript.

In another aspect, the invention provides a method as above, wherein the assay comprises:
a) conducting a hybridization reaction using at least one of the above-noted probes to allow the at least one probe to hybridize to a complementary mitochondrial fusion transcript;
b) quantifying the amount of the at least one mitochondrial fusion transcript in the sample by quantifying the amount of the transcript hybridized to the at least one probe; and,
c) comparing the amount of the mitochondrial fusion transcript in the sample to at least one known reference value.

As discussed above, the diagnostic assays of the invention may also comprise diagnostic imaging methods as described herein and can be readily adapted for high-throughput. The present invention, therefore, contemplates the use of the fusion transcripts and associated probes of the present invention in high-throughput screening or assays to detect and/or quantitate target nucleotide sequences in a plurality of test samples.

Translation Products

To date, mitochondrial fusion proteins have not been detected or isolated. However, the levels of mitochondrial fusion transcripts observed from the examples provided below and the indications that they are polyadenylated provide further evidence supporting the existence of such mitochondrial fusion proteins. Accordingly, the present invention provides the identification of fusion proteins for predicting, diagnosing, and/or monitoring of cancer.

Fusion proteins contemplated for use in the disclosed methods may be derived through the isolation of naturally-occurring polypeptides or through gene expression. Such polypeptides can be prepared by methods known in the art, such as purification from cell extracts or the use of recombinant techniques.

Putative protein sequences corresponding to transcripts 1-17 and 20 are provided below along with their respective sequence identifier. These, as well as the putative protein sequences corresponding to the deletion sequences disclosed in Table 1, are herein contemplated for use in the methods of the present invention.

SEQ ID NO: 36 (Transcripts 1)
SEQ ID NO: 37 (Transcript 2)
SEQ ID NO: 38 (Transcript 3)
SEQ ID NO: 39 (Transcript 4)
SEQ ID NO: 40 (Transcript 5)
SEQ ID NO: 41 (Transcript 6)
SEQ ID NO: 42 (Transcript 7)
SEQ ID NO: 43 (Transcript 8)
SEQ ID NO: 44 (Transcript 9)
SEQ ID NO: 45 (Transcript 10)
SEQ ID NO: 46 (Transcript 11)
SEQ ID NO: 47 (Transcript 12)
SEQ ID NO: 48 (Transcript 14)
SEQ ID NO: 49 (Transcript 15)
SEQ ID NO: 50 (Transcript 16)
SEQ ID NO: 51 (Transcript 17)
SEQ ID NO: 52 (Transcripts 20)
SEQ ID NO: 55 (Transcript 13)

Detection of Fusion Proteins

Fusion proteins of the invention can be recovered and purified from a biological sample by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Most preferably, high performance liquid chromatography ("HPLC") is employed for purification.

Assaying fusion protein levels in a biological sample can occur using a variety of techniques. For example, protein expression in tissues can be studied with classical immunohistological methods (Jalkanen et al., J. Cell. Biol. 101:976-985 (1985); Jalkanen, M., et al., J. Cell. Biol. 105:3087-3096 (1987)). Other methods useful for detecting protein expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($<125>$I, $<121>$I), carbon ($<14>$C), sulfur ($<35>$S), tritium ($<3>$H), indium ($<112>$In), and technetium ($<99m>$Tc), and fluorescent labels, such as fluorescein and rhodamine, and biotin.

The polypeptides of the invention can also be produced by recombinant techniques known in the art. Typically this involves transformation (including transfection, transduction, or infection) of a suitable host cell with an expression vector comprising a polynucleotide encoding the protein or polypeptide of interest.

Antibodies

Protein specific antibodies for use in the assays of the present invention can be raised against the wild-type or expressed mitochondrial fusion proteins of the invention or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments, or antigen-binding fragments, thereof (such as, for example, Fab and F(ab')2 fragments) which are capable of specifically binding to, or having "specificity to", a mitochondrial fusion protein. Fab and F(ab')2 fragments lack the Fc fragment of intact antibody, clear more rapidly from the circulation, and may have less non-specific tissue binding of an intact antibody (Wahl et al., J. Nucl. Med. 24:316-325 (1983)). Thus, these fragments are preferred.

The antibodies of the present invention may be prepared by any of a variety of methods. For example, cells expressing the mitochondrial fusion protein or an antigenic fragment thereof can be administered to an animal in order to induce the production of sera containing polyclonal antibodies. In one method, a preparation of mitochondrial fusion protein is prepared and purified to render it substantially free of natural contaminants. Such a preparation is then introduced into an animal in order to produce polyclonal antisera of greater specific activity.

In a related method, the antibodies of the present invention are monoclonal antibodies. Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., (1981) pp. 563-681). In general, such procedures involve immunizing an animal (preferably a mouse) with a mitochondrial fusion protein antigen or with a mitochondrial fusion protein-expressing cell.

The present invention comprises immunological assays using antibodies or antigen-binding fragments having specificity to the fusion proteins described herein. Such immunological assays may be facilitated by kits containing the antibodies or antigen-binding fragments along with any other necessary reagents, test strips, materials, instructions etc.

Assays

Measuring the level of a translation product such as a fusion protein in a biological sample can determine the presence of one or more cancers in a subject. The present invention, therefore, provides methods for predicting, diagnosing or monitoring cancer, comprising obtaining one or more biological samples, extracting mitochondrial fusion proteins from the samples, and assaying the samples for such molecules by: quantifying the amount of one or more molecules in the sample and comparing the quantity detected with a reference value. As would be understood by those of skill in the art, the reference value is based on whether the method seeks to predict, diagnose or monitor cancer. Accordingly, the reference value may relate to protein data collected from one or more known non-cancerous biological samples, from one or more known cancerous biological samples, and/or from one or more biological samples taken over time.

Techniques for quantifying proteins in a sample are well known in the art and include, for instance, classical immunohistological methods (Jalkanen et al., J. Cell. Biol. 101:976-985 (1985); Jalkanen, M., et al., J. Cell. Biol. 105:3087-3096 (1987)). Additional methods useful for detecting protein expression include immunoassays such as the radioimmunoassay (RIA) and the enzyme linked immunosorbent assay (ELISA).

In one aspect, the invention provides a method of detecting a cancer in a mammal, the method comprising assaying a tissue sample from the mammal for the presence of at least one mitochondrial fusion protein. In another aspect, the present invention provides for the detection of mitochondrial fusion proteins in the diagnosis of colorectal cancer, lung cancer, breast cancer, ovarian cancer, testicular cancer, prostate cancer and/or melanoma skin cancer.

Diagnostic Imaging

Diagnostic Devices

The invention includes diagnostic devices such as biochips, gene chips or microarrays used to diagnose specific diseases or identify specific mutations. All sequenced mitochondrial genomes are assessed to create a consensus structure of the base pair arrangement and are assigned a prohibiting index for proportion of base pair deletions and mutations associated with a particular disease or disorder. The diagnostic arrangement is then used to create biochips, gene chips, or microarrays.

Once sequences associated with particular diseases, disease states or disorders are identified, hybridization of a mitochondrial nucleotide sample to an array of oligonucleotides can be used to identify particular mutations. Any known method of hybridization may be used. Preferably, an array is used, which has oligonucleotide probes matching the wild type or mutated region, and a control probe. Commercially available arrays such as microarrays or gene chips are suitable. These arrays contain thousands of matched and control pairs of probes on a slide or microchip, and are capable of sequencing the entire genome very quickly. Review articles describing the use of microarrays in genome and DNA sequence analysis are available on-line.

Microarray

Polynucleotide arrays provide a high throughput technique that can assay a large number of polynucleotides in a sample comprising one or more target nucleic acid sequences. The arrays of the invention are useful for gene expression analysis, diagnosis of disease and prognosis of disease (e.g., monitoring a patient's response to therapy, and the like).

Any combination of the polynucleotide sequences of mtDNA indicative of disease, or disease progression are used for the construction of a microarray.

The target nucleic acid samples to be analyzed using a microarray are derived from any human tissue or fluid which contains adequate amounts of mtDNA, as previously described. The target nucleic acid samples are contacted with polynucleotide members under hybridization conditions sufficient to produce a hybridization pattern of complementary nucleic acid members/target complexes.

Construction of a Microarray

The microarray comprises a plurality of unique polynucleotides attached to one surface of a solid support, wherein each of the polynucleotides is attached to the surface of the solid support in a non-identical preselected region. Each associated sample on the array comprises a polynucleotide composition, of known identity, usually of known sequence, as described in greater detail below. Any conceivable substrate may be employed in the invention.

The array is constructed using any known means. The nucleic acid members may be produced using established techniques such as polymerase chain reaction (PCR) and reverse transcription (RT). These methods are similar to those currently known in the art (see e.g. PCR Strategies, Michael A. Innis (Editor), et al. (1995) and PCR: Introduction to Biotechniques Series, C. R. Newton, A. Graham (1997)). Amplified polynucleotides are purified by methods well known in the art (e.g., column purification). A polynucleotide is considered pure when it has been isolated so as to be substantially free of primers and incomplete products produced during the synthesis of the desired polynucleotide. Preferably, a purified polynucleotide will also be substantially free of contaminants which may hinder or otherwise mask the binding activity of the molecule.

In the arrays of the invention, the polynucleotide compositions are stably associated with the surface of a solid support, wherein the support may be a flexible or rigid solid support.

Any solid support to which a nucleic acid member may be attached may be used in the invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Due to their flat surface, probe and hybridization reagents are minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides.

The particular material selected as the solid support is not essential to the invention, as long as it provides the described function. Normally, those who make or use the invention will select the best commercially available material based upon the economics of cost and availability, the expected application requirements of the final product, and the demands of the overall manufacturing process.

Numerous methods are used for attachment of the nucleic acid members of the invention to the substrate (a process referred as spotting). For example, polynucleotides are attached using the techniques of, for example U.S. Pat. No. 5,807,522, which is incorporated herein by reference for teaching methods of polymer attachment. Alternatively, spotting is carried out using contact printing technology.

The amount of polynucleotide present in each composition will be sufficient to provide for adequate hybridization and detection of target polynucleotide sequences during the assay in which the array is employed. Generally, the amount of each nucleic acid member stably associated with the solid support of the array is at least about 0.1 ng, preferably at least about 0.5 ng and more preferably at least about 1 ng, where the amount may be as high as 1000 ng or higher, but will usually not exceed about 20 ng.

Control polynucleotides may be spotted on the array and used as target expression control polynucleotides and mismatch control nucleotides to monitor non-specific binding or cross-hybridization to a polynucleotide in the sample other than the target to which the probe is directed. Mismatch probes thus indicate whether a hybridization is specific or not. For example, if the target is present the perfectly matched probes should be consistently brighter than the mismatched probes. In addition, if all central mismatches are present, the mismatch probes are used to detect a mutation.

Target Preparation

The targets for the microarrays, may be derived from one or more biological samples. It may be desirable to amplify the target nucleic acid sample prior to hybridization. One of skill in the art will appreciate that whatever amplification method is used, if a quantitative result is desired, care must be taken to use a method that maintains or controls for the relative frequencies of the amplified polynucleotides. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified polynucleotide. Detailed protocols for quantitative PCR are provided in PCR Protocols, A Guide to Methods and Applications, Innis et al., Academic Press, Inc. N.Y., (1990). Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

The invention provides for labeled target or labeled probe as described above. For the microarrays, any analytically detectable marker that is attached to or incorporated into a molecule may be used in the invention. An analytically detectable marker refers to any molecule, moiety or atom which is analytically detected and quantified. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™) fluorescent dyes (e.g., fluorescein, texas red, rhodamine, green fluorescent protein, and the like), radiolabels (e.g., $3H$, $125I$, $35S$, $14C$, or $32P$), enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in a preferred embodiment, the label is simultaneously incorporated during the amplification step in the preparation of the sample polynucleotides. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed polynucleotides. Alternatively, a label may be added directly to the original polynucleotide sample (e.g., mRNA, polyA mRNA, cDNA, etc.) or to the amplification product after the amplification is completed. Means of attaching labels to polynucleotides are well known to those of skill in the art and include, for example nick translation or end-labeling (e.g. with a labeled RNA) by kinasing of the polynucleotide and subsequent attachment (ligation) of a polynucleotide linker joining the sample polynucleotide to a label (e.g., a fluorophore).

In a preferred embodiment, the target will include one or more control molecules which hybridize to control probes on the microarray to normalize signals generated from the microarray. Labeled normalization targets are polynucleotide sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays.

Image Acquisition and Data Analysis

Following hybridization and any washing step(s) and/or subsequent treatments of a conventional nature, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target polynucleotides to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test polynucleotides from the remaining data. The resulting data is displayed as an image with the intensity in each region varying according to the binding affinity between associated oligonucleotides and/or polynucleotides and the test polynucleotides.

Diagnostic Tests

Following detection or visualization, the hybridization pattern is used to determine quantitative information about the genetic profile of the labeled target polynucleotide sample that was contacted with the array to generate the hybridization pattern, as well as the state or condition of the tissue, fluid, organs, cell, etc. from which the sample was derived. In this regard, the invention further provides for diagnostic tests for detecting cancer. The invention also provides for monitoring a patient's condition. According to the method of the invention, the presence of cancer is detected by obtaining a biological sample from a patient. A test sample comprising nucleic acid is prepared from the biological sample. The nucleic acid extracted from the sample is hybridized to an array comprising a solid substrate and a plurality of nucleic acid members, wherein each member is indicative of the presence of disease or a predisposition to cancer. According to this diagnostic test, hybridization of the sample comprising nucleic acid to one or more nucleic acid members on the array is indicative of cancer or a predisposition to a cancer.

Diagnostic Monitoring

The methods of the present invention may further comprise the step of recommending a monitoring regime or course of therapy based on the outcome of one or more assays. This allows clinicians to practice personalized medicine; e.g. cancer therapy, by monitoring the progression of the patient's cancer (such as by recognizing when an initial or subsequent mutation occurs) or treatment (such as by recognizing when a mutation is stabilized).

With knowledge of the boundaries of the sequence variation in hand, the information can be used to diagnose a precancerous condition or existing cancer condition. Further, by quantitating the amount of aberrant mtDNA in successive samples over time, the progression of a cancer condition can be monitored. For example, data provided by assaying the patient's tissues at one point in time to detect a first set of mutations from wild-type could be compared against data provided from a subsequent assay, to determine if changes in the aberration have occurred.

Where a mutation is found in an individual who has not yet developed symptoms of cancer, the mutation may be indicative of a genetic susceptibility to develop a cancer condition. A determination of susceptibility to disease or diagnosis of its presence can further be evaluated on a qualitative basis based on information concerning the prevalence, if any, of the cancer condition in the patient's family history and the presence of other risk factors, such as exposure to environmental factors and whether the patient's cells also carry a mutation of another sort.

Biological Sample

The present invention provides for diagnostic tests which involve obtaining or collecting one or more biological samples. In the context of the present invention, "biological sample" refers to a tissue or bodily fluid containing cells from which mtDNA, mtRNA and translation products or fusion proteins can be obtained. For example, the biological sample can be derived from tissue including, but not limited to, skin, lung, breast, prostate, nervous, muscle, heart, stomach, colon, rectal tissue and the like; or from blood, saliva, cerebral spinal fluid, sputa, urine, mucous, synovial fluid, peritoneal fluid, amniotic fluid and the like. The biological sample may be obtained from a cancerous or non-cancerous tissue and may be, but is not limited to, a surgical specimen or a biopsy specimen.

The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

One skilled in the art will understand that more than one sample type may be assayed at a single time (i.e. for the detection of more than one cancer). Furthermore, where a course of collections are required, for example, for the monitoring of cancer over time, a given sample may be diagnosed alone or together with other samples taken throughout a test period. In this regard, biological samples may be taken once only, or at regular intervals such as biweekly, monthly, semiannually or annually.

Kits

The present invention provides diagnostic/screening kits for detecting cancer in a clinical environment. Such kits may include one or more sampling means, in combination with one or more probes according to the present invention. Alternatively, or in addition thereto, the kit may comprise means for detecting a translation product of the invention.

The kits can optionally include reagents required to conduct a diagnostic assay, such as buffers, salts, detection reagents, and the like. Other components, such as buffers and solutions for the isolation and/or treatment of a biological sample, may also be included in the kit. One or more of the components of the kit may be lyophilised and the kit may further comprise reagents suitable for the reconstitution of the lyophilised components.

Where appropriate, the kit may also contain reaction vessels, mixing vessels and other components that facilitate the preparation of the test sample. The kit may also optionally include instructions for use, which may be provided in paper form or in computer-readable form, such as a disc, CD, DVD or the like.

In one embodiment of the invention there is provided a kit for diagnosing cancer comprising sampling means and a hybridization probe of the invention.

In another embodiment, the kits of the present invention may comprise an immunological assay. In such case, the kits may comprise antibodies or antigen-binding fragments having specificity towards the fusion proteins described herein. It will be understood that various other reagents, test strips etc. required for such immunological assay will be contained in the kits as will the required instructions to users.

EXAMPLES

Various aspects of the invention will be described by illustration using the following examples. The examples provided herein serve only to illustrate certain specific embodiments of the invention and are not intended to limit the scope of the invention in any way.

Example 1

Detection of Mitochondrial Fusion Transcripts

Figure 2:
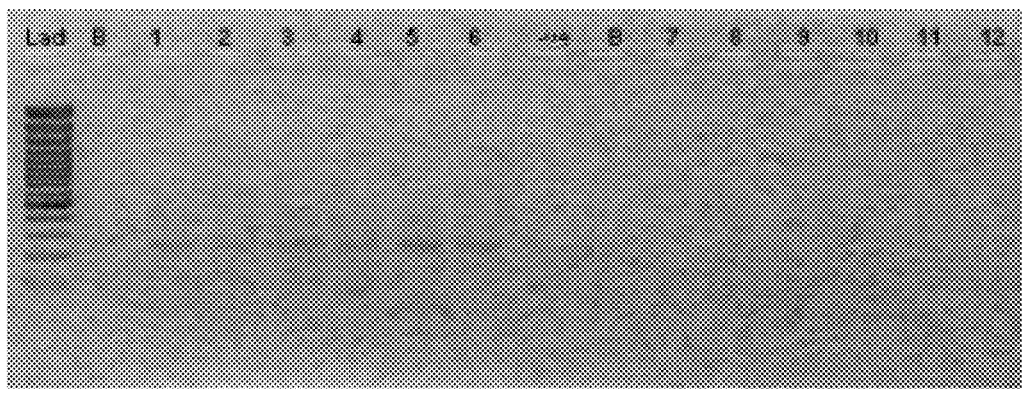
FIG. 2 shows polyadenalated fusion transcripts in prostate samples invoked by the loss of the 3.4 kb deletion.
Figure 3:
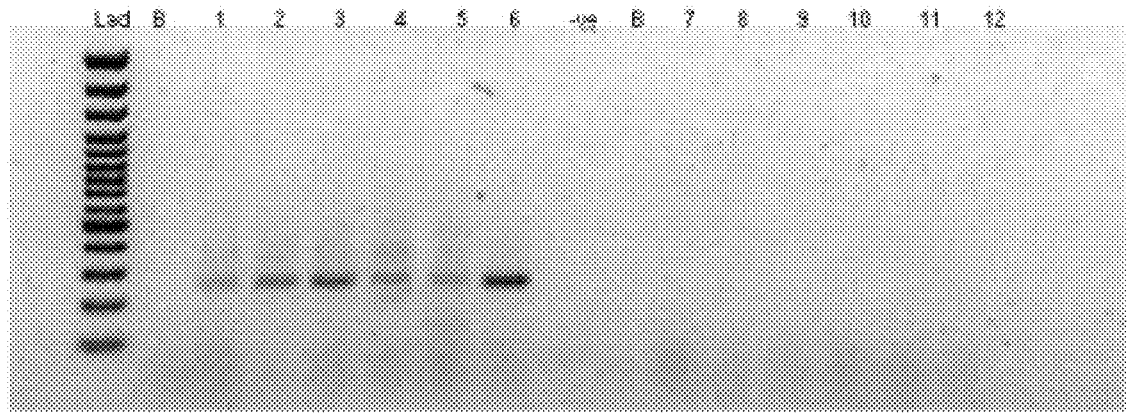
FIG. 3 shows polyadenalated fusion transcripts in prostate samples invoked by the loss of the 4977 kb common deletion.
Figure 4:
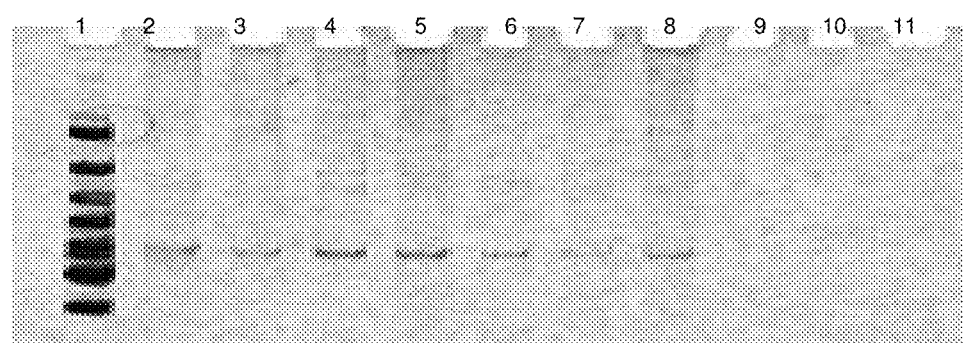
FIG. 4 shows polyadenalated fusion transcripts in breast samples invoked by the loss of the 3.4 kb segment from the mtgenome.

The mitochondrial 4977 "common deletion" and a 3.4 kb deletion previously identified by the present Applicant in PCT application no. PCT/CA2007/001711 (published under number WO 2009/039601, the entire contents of which are incorporated by reference) result in unique open reading frames having active transcripts as identified by oligo-dT selection in prostate tissue (FIGS. 2 and 3). Examination of breast tissue samples also reveals the presence of a stable polyadenylated fusion transcript resulting from the 3.4 kb deletion (FIG. 4).

Reverse Transcriptase-PCR Protocol for Deletion Transcript Detection

RNA Isolation cDNA Synthesis

Total RNA was isolated from snap frozen prostate and breast tissue samples (both malignant and normal samples adjacent to tumours) using the Aurum™ Total RNA Fatty and Fibrous Tissue kit (Bio-Rad, Hercules, Calif.) following the manufacturer's instructions. Since in this experiment, genomic DNA contamination was to be avoided, a DNase I treatment step was included, using methods as commonly known in the art. RNA quantity and quality were determined with an ND-1000 spectrophotometer (NanoDrop® technologies). From a starting material of about 100 g, total RNA concentrations varied from 100-100 ng/ul with a 260/280 ratio between 1.89-2.10. RNA concentrations were adjusted to 100 ng/ul and 2 ul of each template were used for first strand DNA synthesis with SuperScript™ First-Strand Synthesis System for RT-PCR (Invitrogen) following the manufacturer's instructions. In order to identify stable polyadenylated fusion transcripts, Oligo(dT) primers that target transcripts with poly-A tails were used.

PCR

Real time PCR was performed using 5 ul of each cDNA template with the iQ™ SYBR® Green Supermix (Bio-Rad, Hercules, Calif.) on DNA Engine Opticon® 2 Continuous Fluorescence Detection System (Bio-Rad, Hercules, Calif.). The primer pairs targeting the 4977 bp deletion are; 8416F 5'-CCTTACACTATTCCTCATCAC-3', 13637R 5'-TGAC-CTGTTAGGGTGAGAAG-3', and those for the 3.4 kb deletion are; ND4LF 5'-TCGCTCACACCTCATATCCTC-3', ND5R 5'-TGTGATTAGGAGTAGGGTTAGG-3'. The reaction cocktail included: 2×SYBR® Green Supermix (100 mM KCL, 40 mM Tris-HCl, pH 8.4, 0.4 mM of each dNTP [dATP, dCTP, dGTP, and dTTP], iTaq™ DNA polymerase, 50 units/ml, 6 mM $MgCl_2$, SYBR® Green 1, 20 nM flourescein, and stabilizers), 250 nM each of primers, and $ddH_2O$. PCR cycling parameters were as follows; (1) 95° C. for 2 min, (2) 95° C. for 30 sec, (3) 55° C. (for the 4977 bp deletion) and 63° C. (for the 3.4 kb deletion) for 30 sec, (4) 72° C. for 45 sec, (5) plate read, followed by 39 cycles of steps 3 to 5, and final incubation at 4° C. Apart from cycling threshold and melting curve analysis, samples were run on agarose gels for specific visualization of amplification products (see FIGS. 2 to 4).

FIG. 2 is an agarose gel showing polyadenalated fusion transcripts in prostate samples invoked by the loss of 3.4 kb from the mitochondrial genome. Legend for FIG. 2: B-blank, Lanes 1-6 transcripts detected in cDNA; lanes 7-12 no reverse transcriptase (RT) controls for samples in lanes 1-6.

FIG. 3 shows polyadenalated fusion transcripts in prostate samples invoked by the loss of the 4977 kb common deletion. Legend for FIG. 3: B-blank, Lanes 1-6 transcripts detected in cDNA; lanes 7-12 no RT controls for samples in lanes 1-6.

FIG. 4 shows polyadenalated fusion transcripts in breast samples invoked by the loss of 3.4 kb from the mtgenome. Legend for FIG. 4: Lanes 2-8 transcripts from breast cDNAs; lane 9 negative (water) control; lanes 10 and 11, negative, no RT, controls for samples in lanes 2 and 3.

These results demonstrate the existence of stable mitochondrial fusion transcripts.

Example 2

Identification and Targeting of Fusion Products

Various hybridization probes were designed to detect, and further demonstrate the presence of novel transcripts resulting from mutated mitochondrial genomes, such as the 3.4 kb deletion. For this purpose, a single-plex branched DNA platform for quantitative gene expression analysis (QuantiGene 2.0™, Panomics™) was utilized. The specific deletions and sequences listed in this example are based on their relative positions with the entire mtDNA genome, which is recited in SEQ ID NO: 1. The nucleic acid sequences of the four transcripts to which the probes were designed in this example are identified herein as follows: Transcript 1 (SEQ ID NO: 19), Transcript 2 (SEQ ID NO: 20), Transcript 3 (SEQ ID NO: 21) and Transcript 4 (SEQ ID NO: 22).

An example of a continuous transcript from the 3.4 kb mitochondrial genome deletion occurs with the genes ND4L (NADH dehydrogenase subunit 4L) and ND5 (NADH dehydrogenase subunit 5). A probe having a complementary sequence to SEQ ID NO: 20, was used to detect transcript 2. The repetitive elements occur at positions 10745-10754 in ND4L and 14124-14133 in ND5.

Figure 5A:
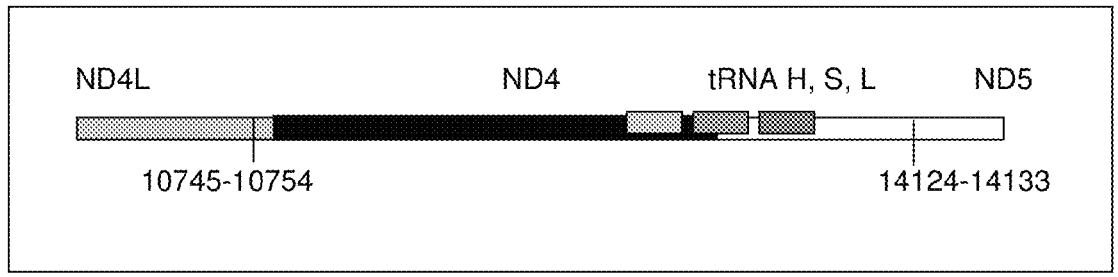
FIGS. 5a and 5b show an example of a mitochondrial DNA region before and after splicing of genes.
Figure 5B:
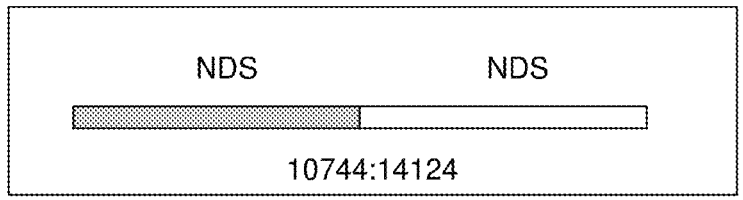
Figure 6A:
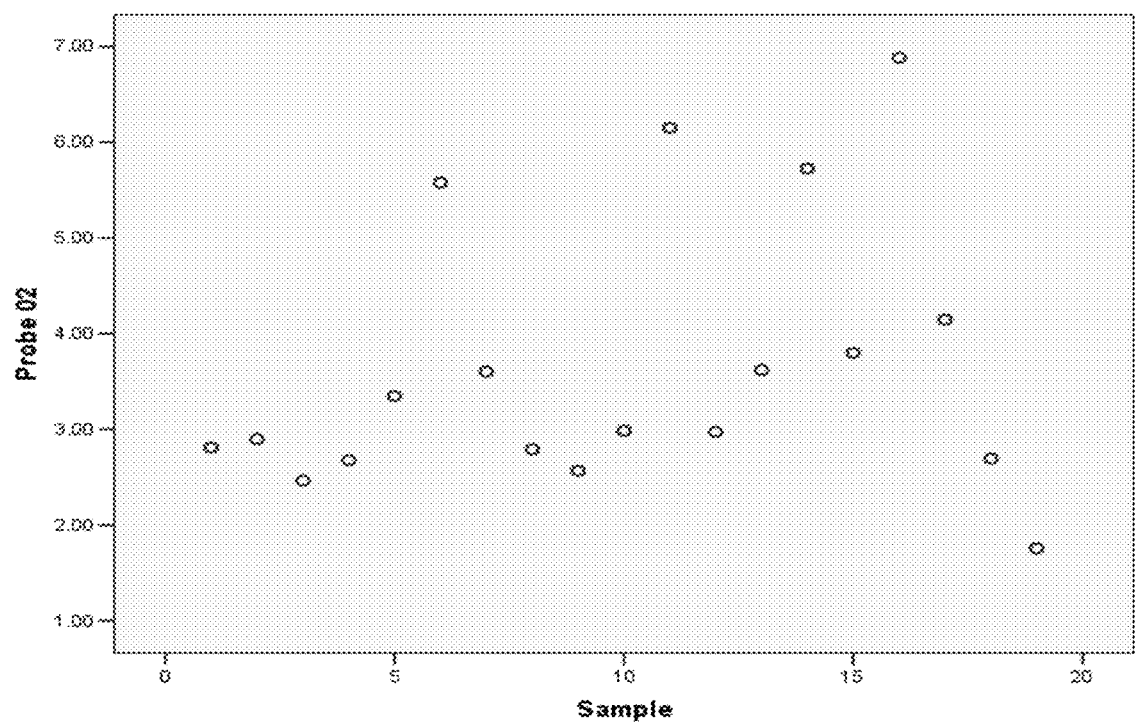
FIGS. 6a to 6g illustrate the results for transcripts 2, 3, 8, 9, 10, 11 and 12 of the invention in the identification of colorectal cancer tumours.
Figure 6A:
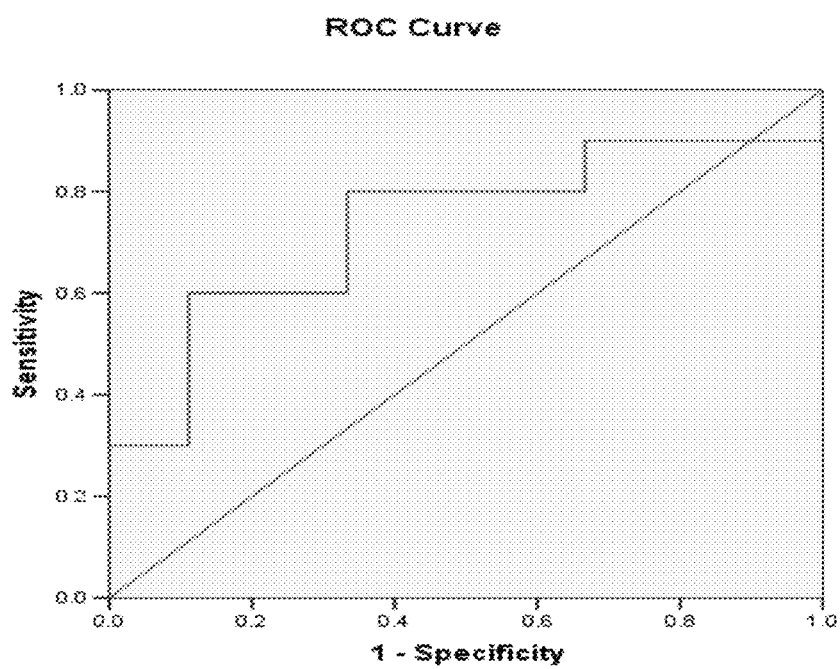
Figure 6B:
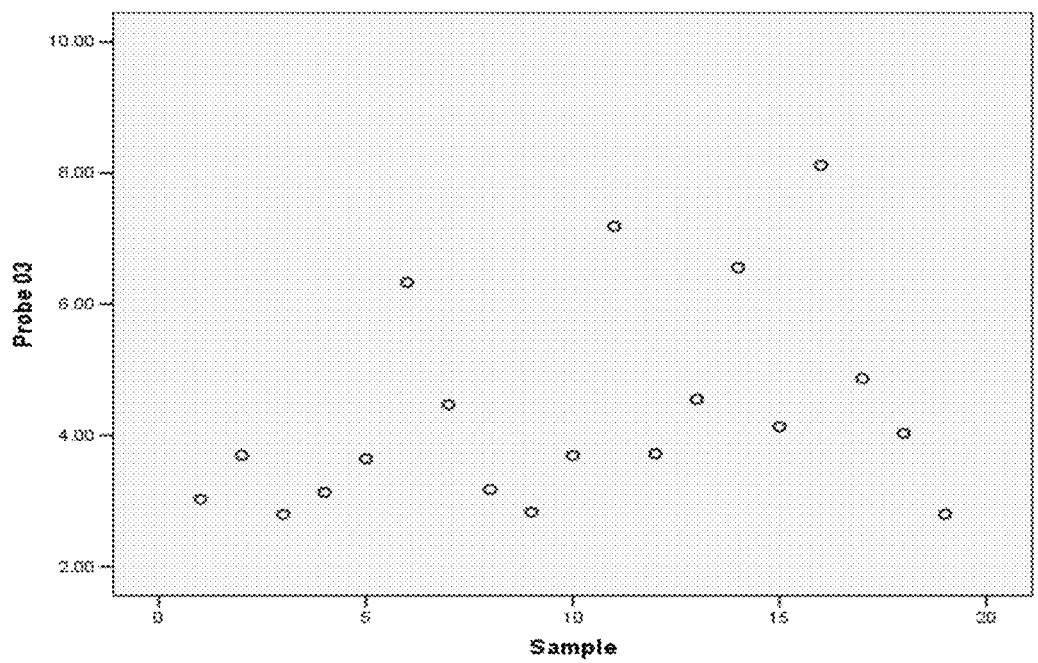
Figure 6B:
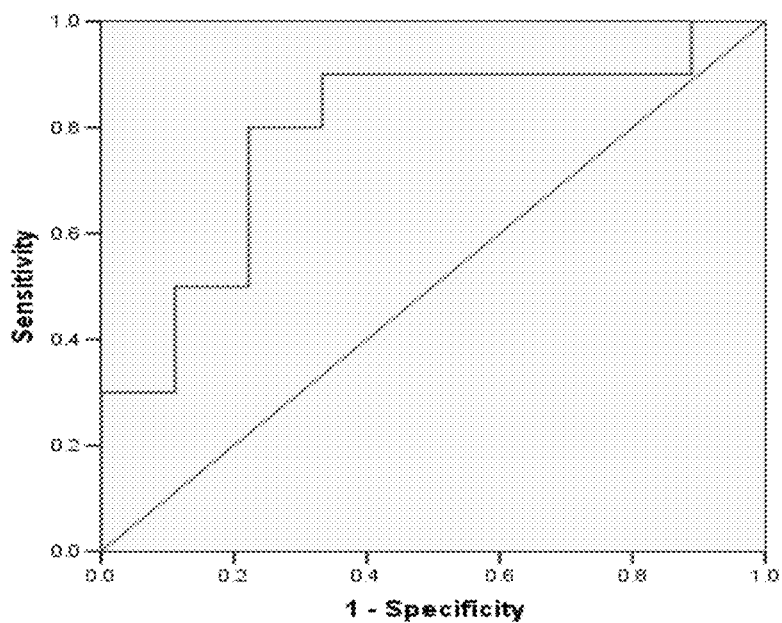
Figure 6C:
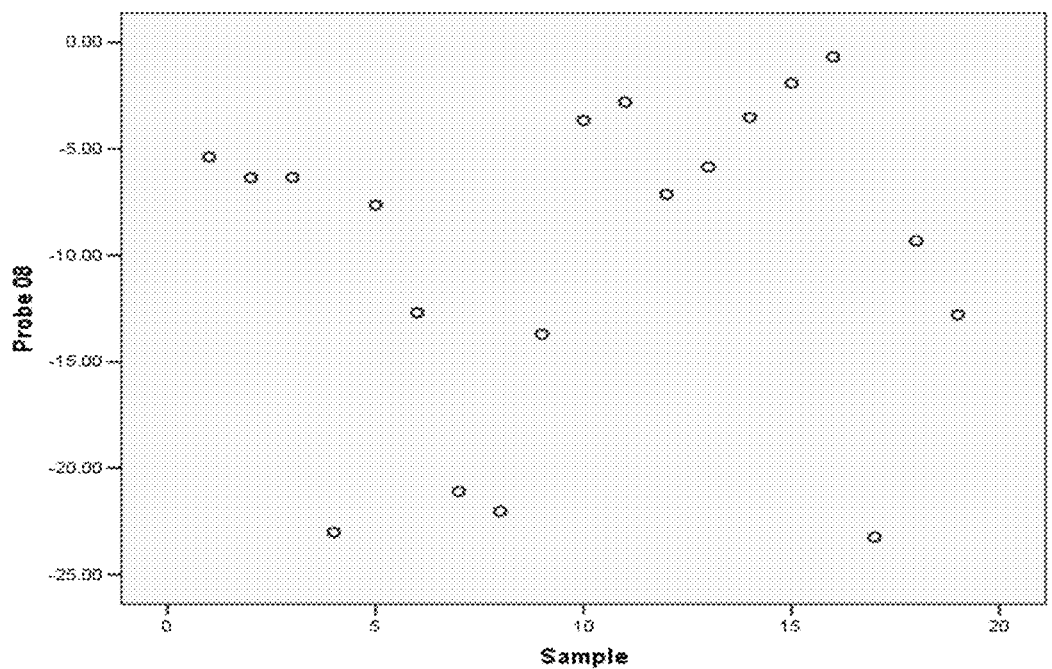
Figure 6C:
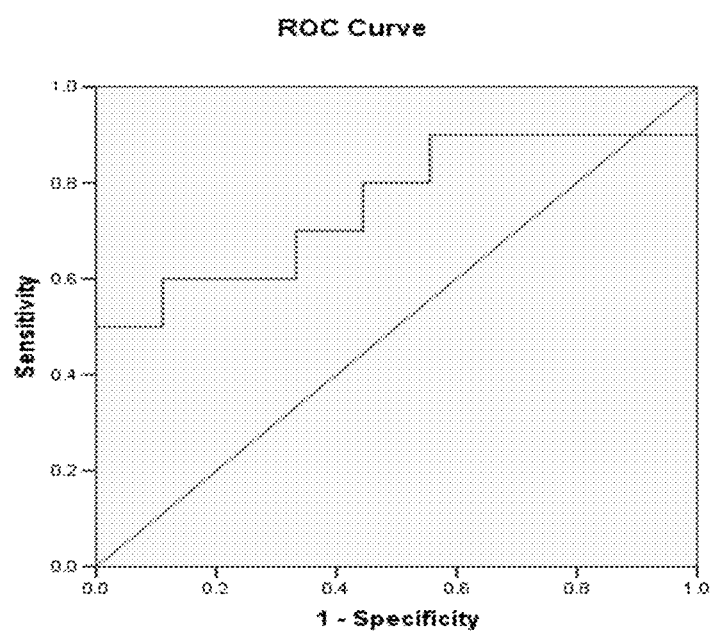
Figure 6D:
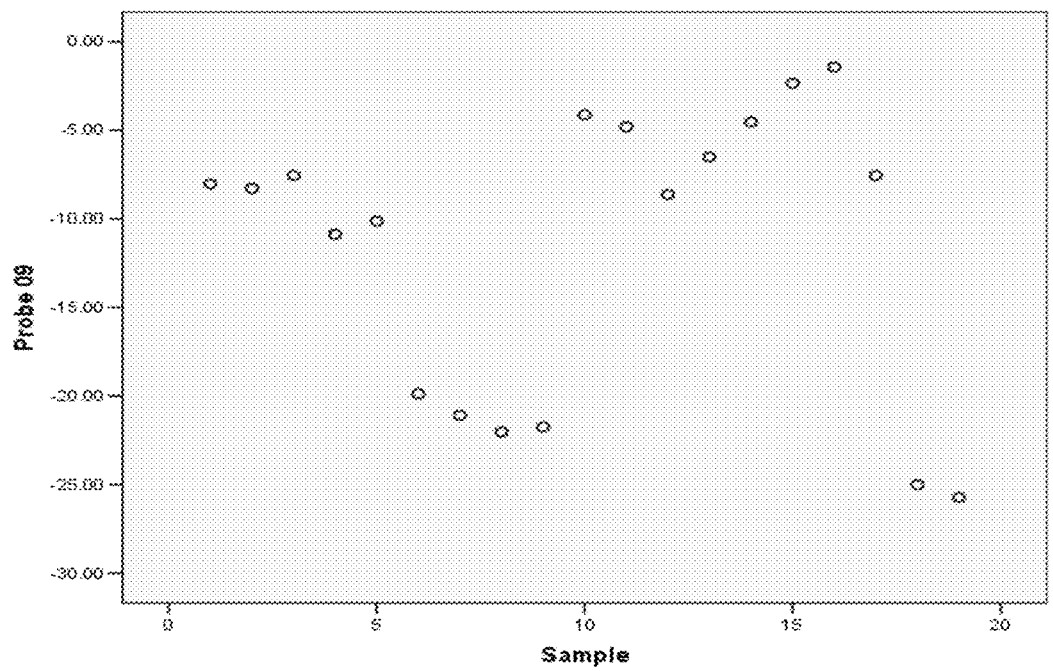
Figure 6D:
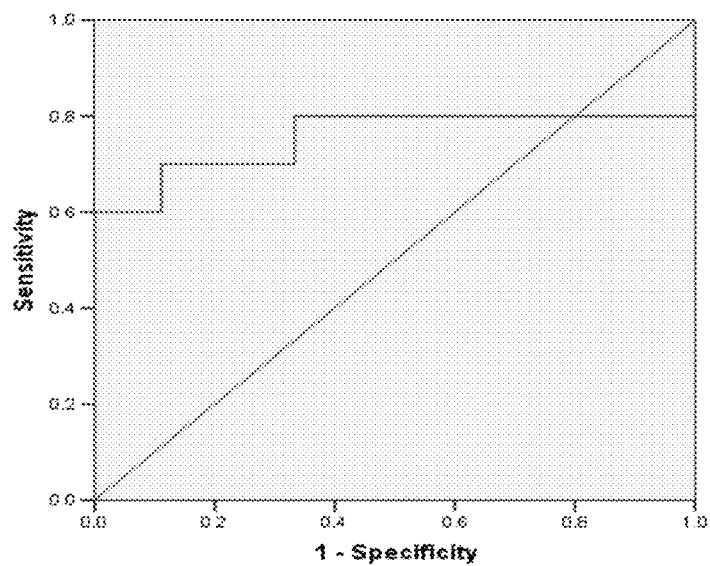
Figure 6E:
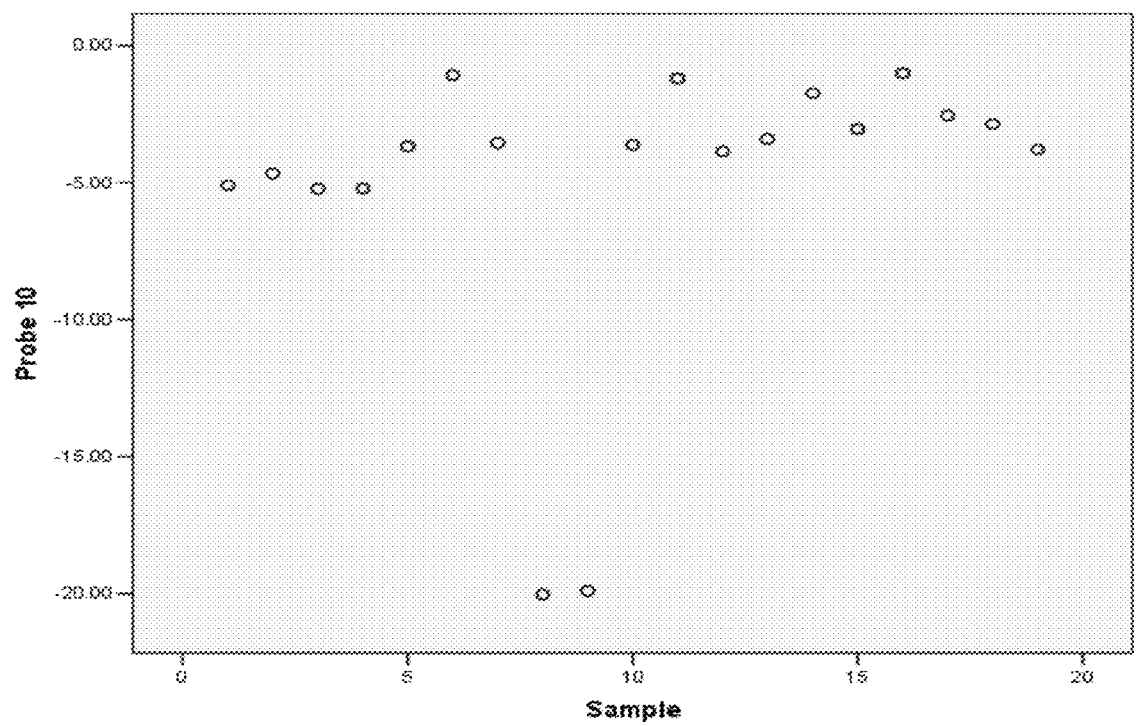
Figure 6E:
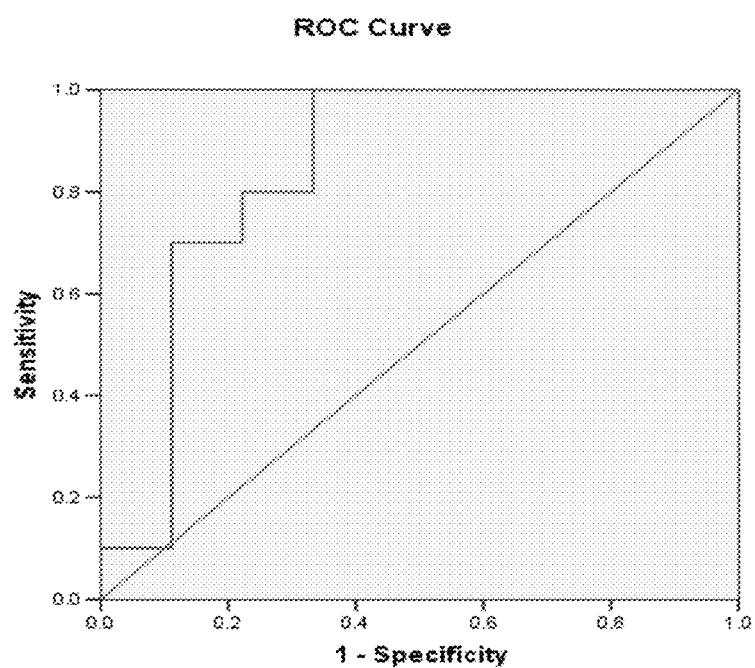
Figure 6F:
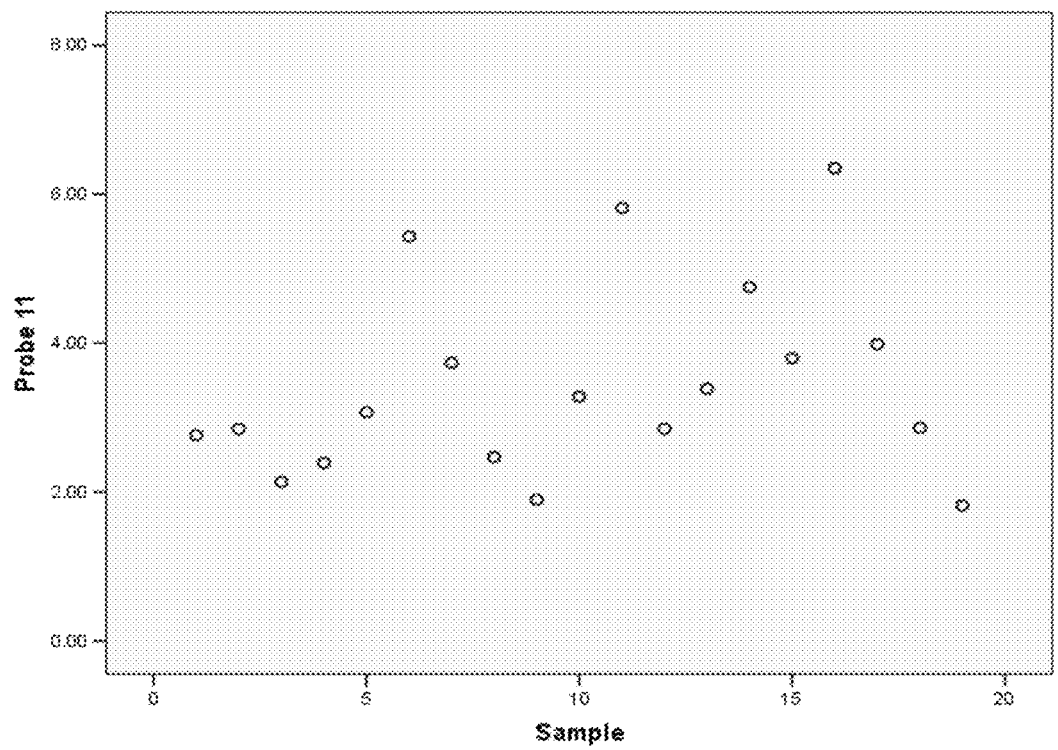
Figure 6F:
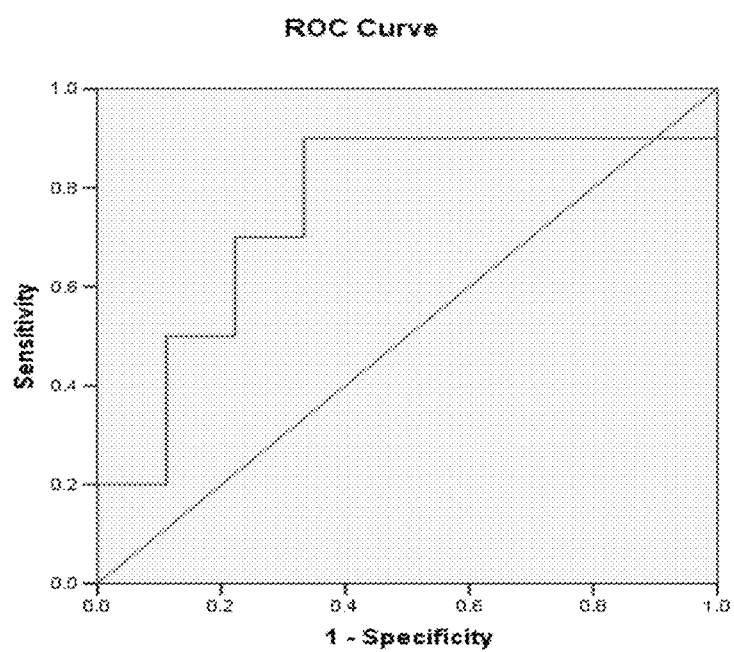
Figure 6G:
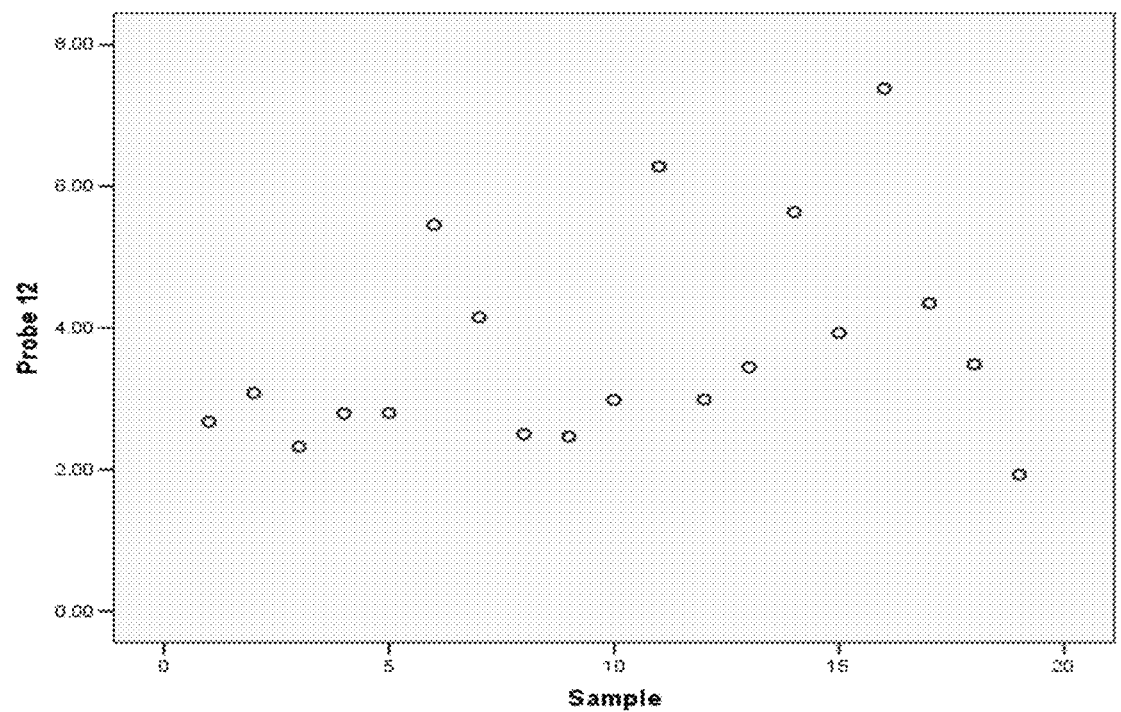
Figure 6G:
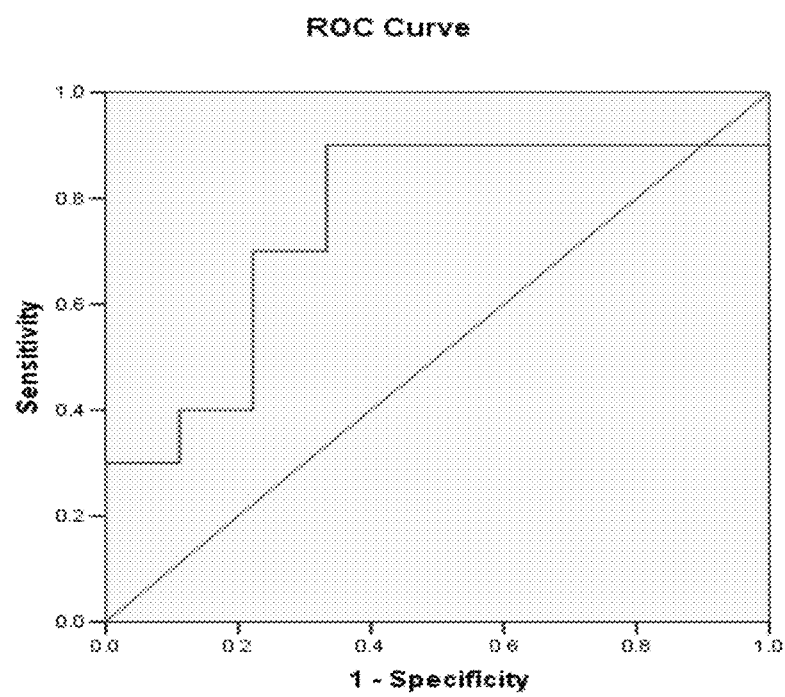
Figure 7A:
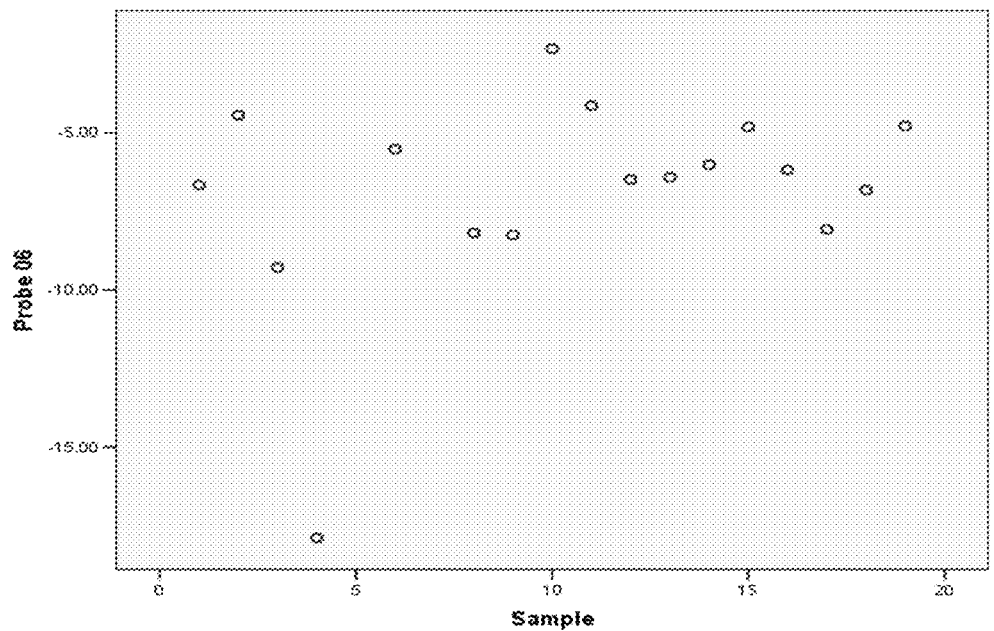
FIGS. 7a to 7d illustrate the results for transcripts 6, 8, 10 and 20 of the invention in the identification of lung cancer tumours.
Figure 7A:
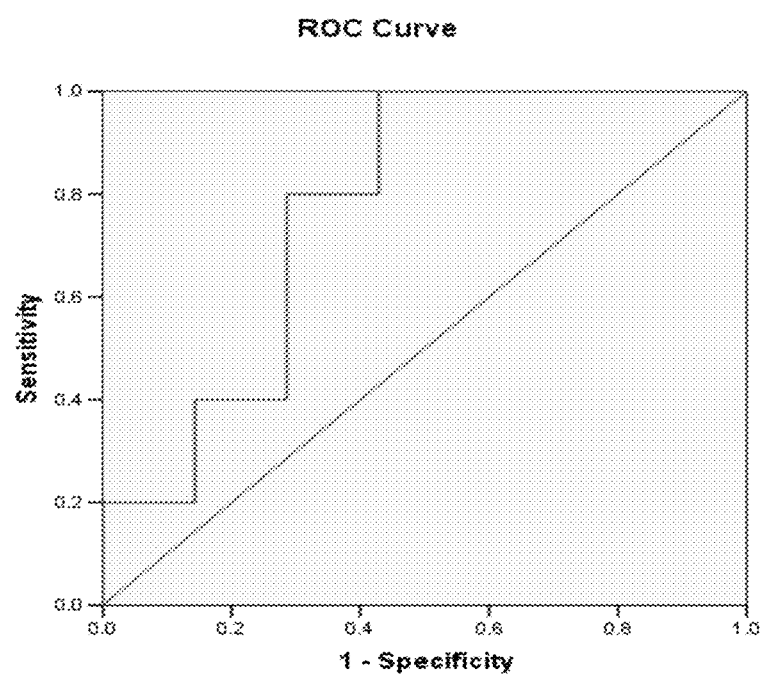
Figure 7B:
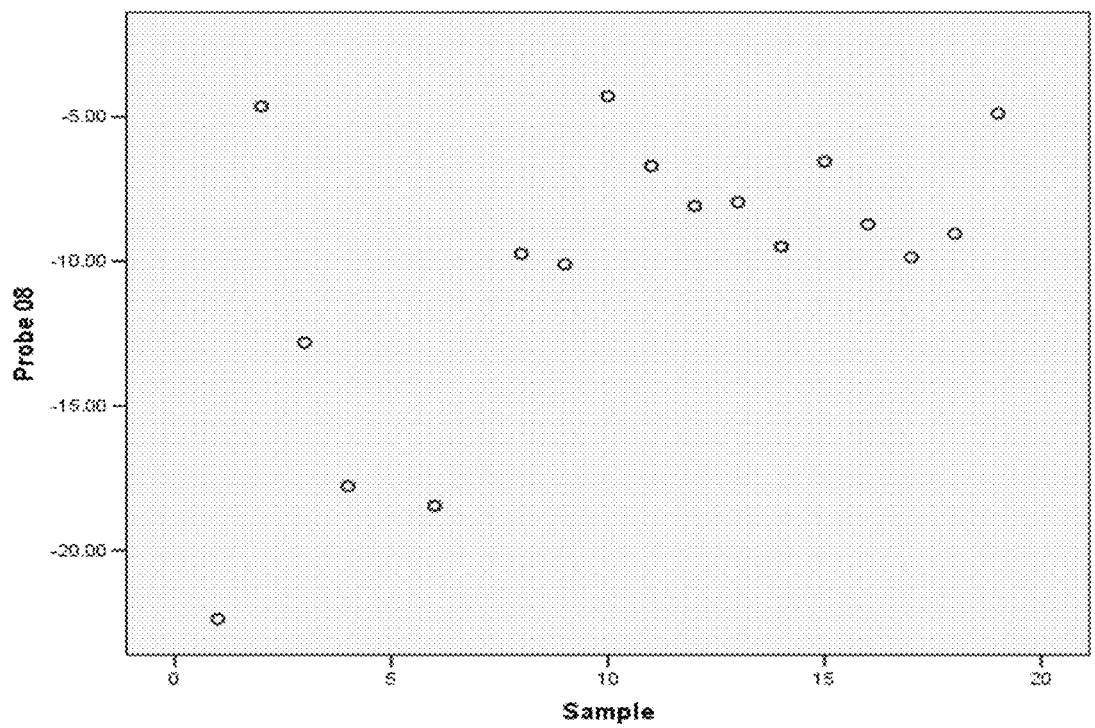
Figure 7B:
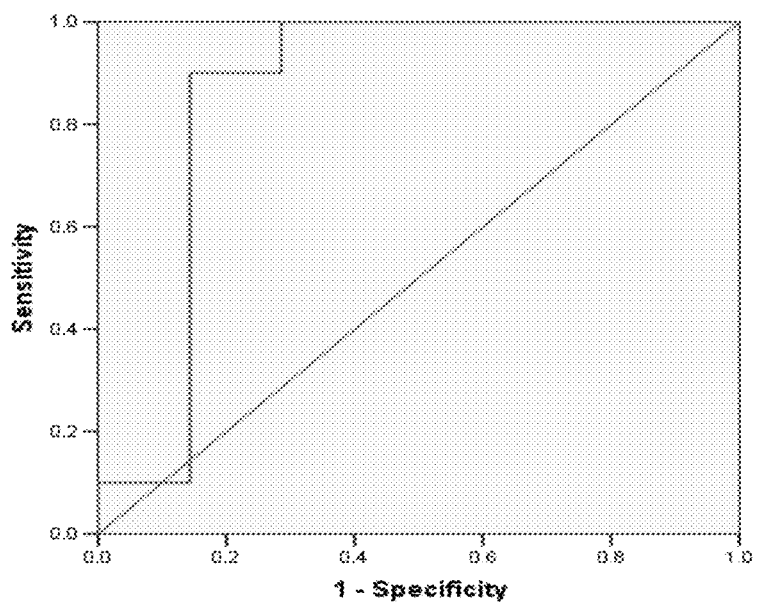
Figure 7C:
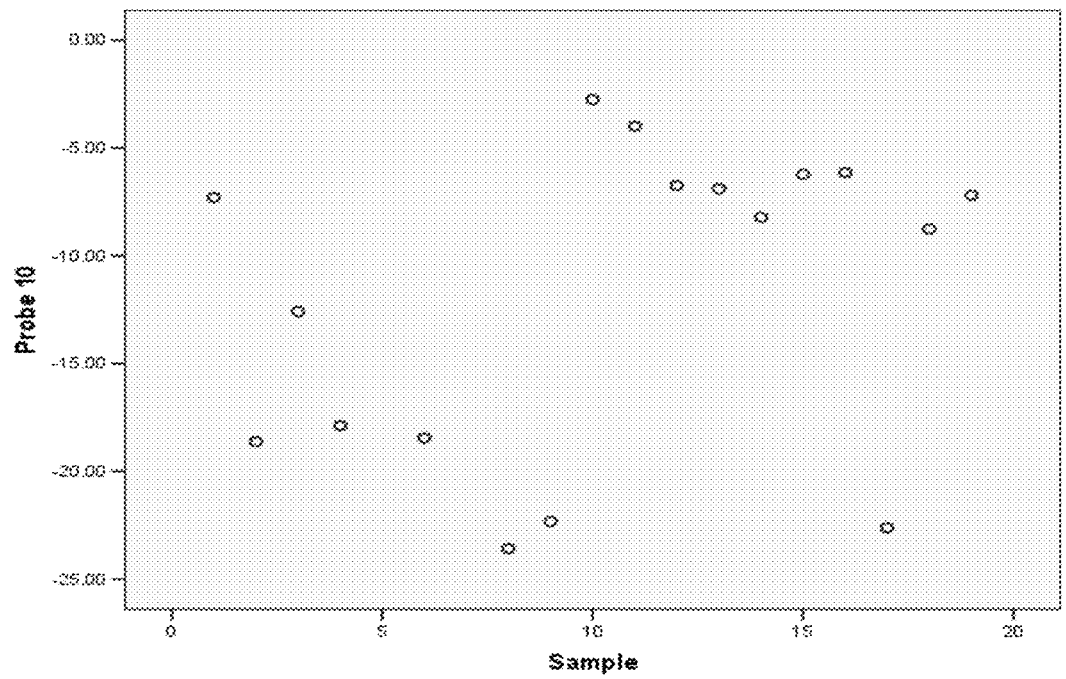
Figure 7C:
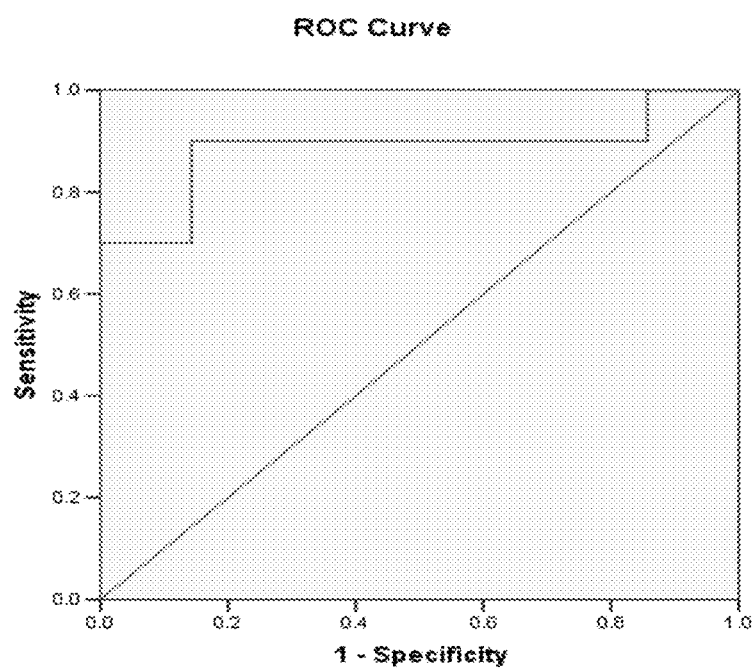
Figure 7D:
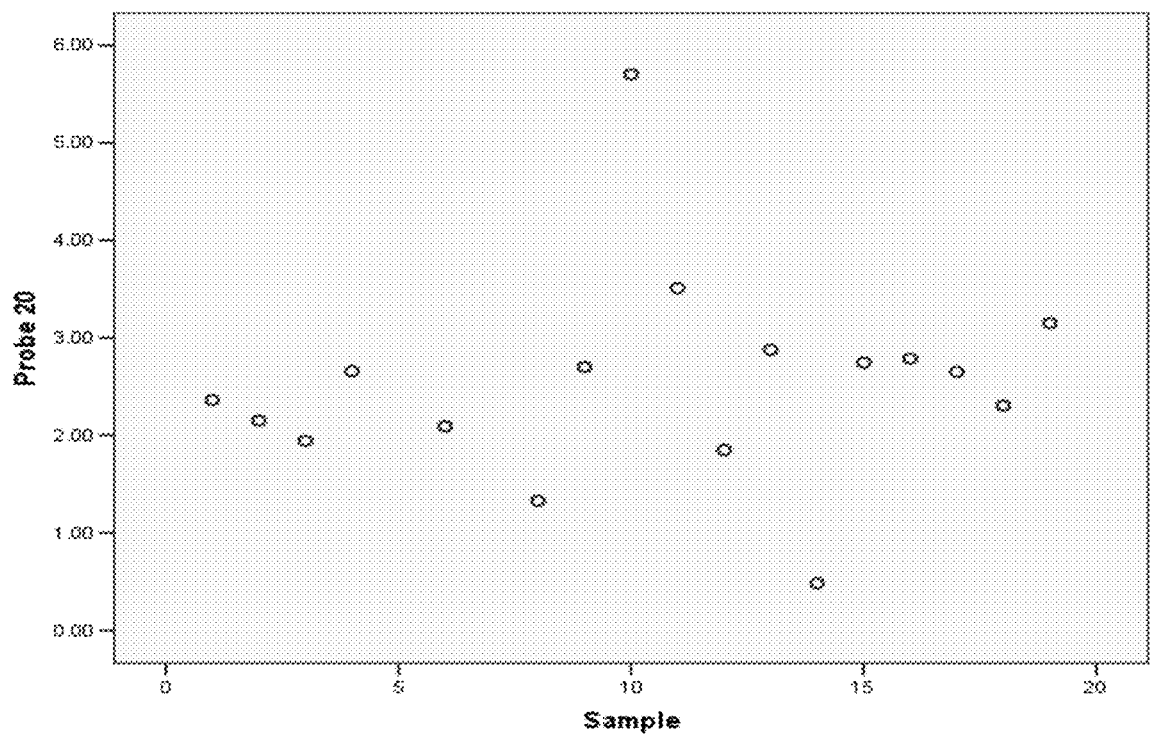
Figure 7D:
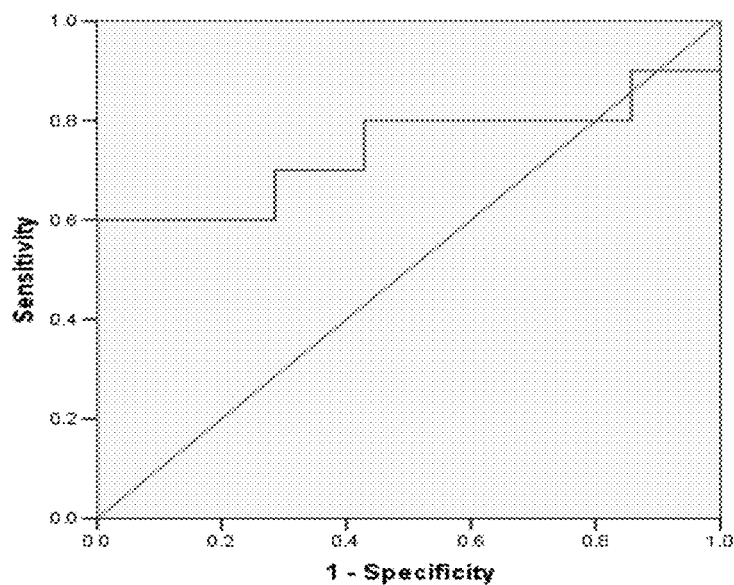
Figure 8A:
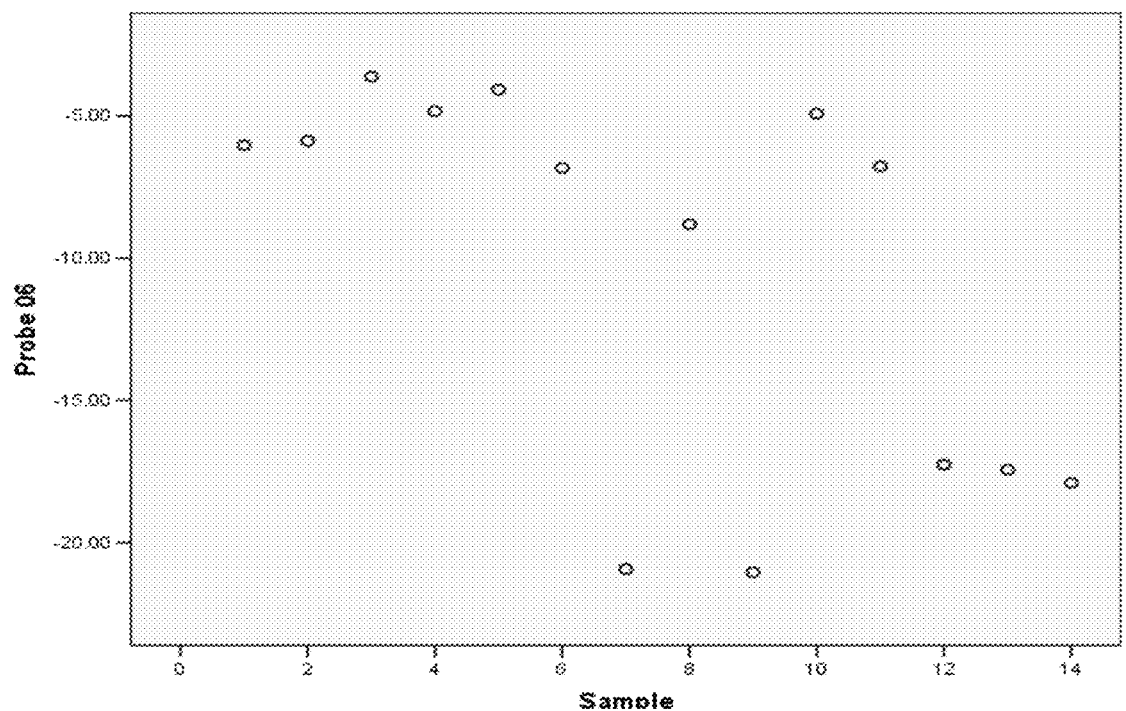
FIGS. 8a to 8g illustrate the results for transcripts 6, 10, 11, 14, 15, 16 and 20 of the invention in the identification of melanomas.
Figure 8A:
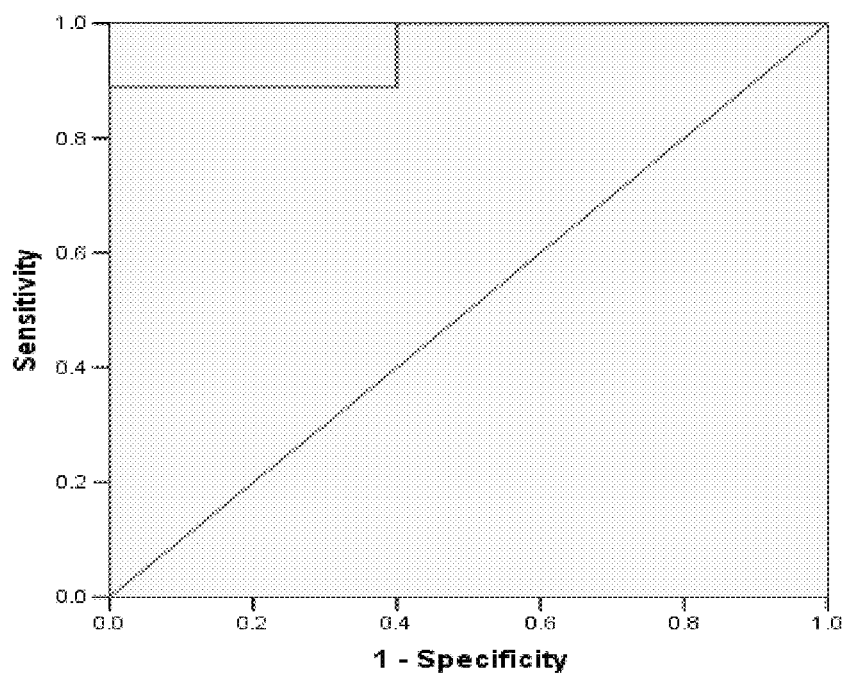
Figure 8B:
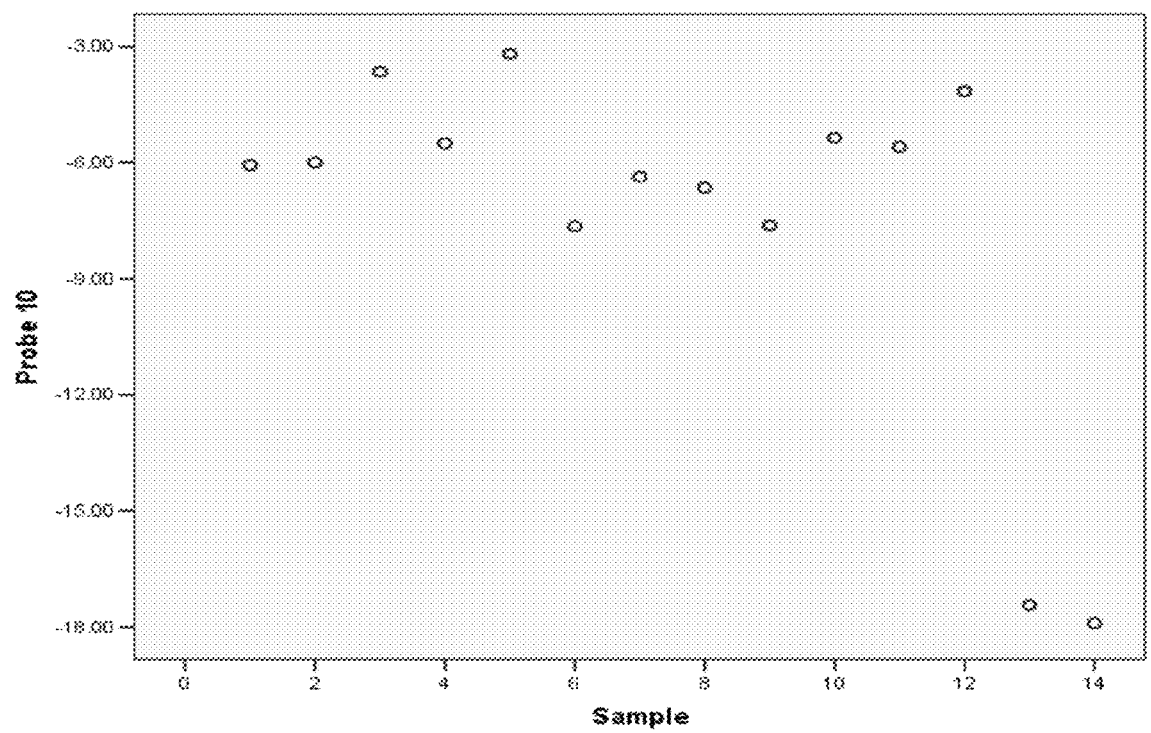
Figure 8B:
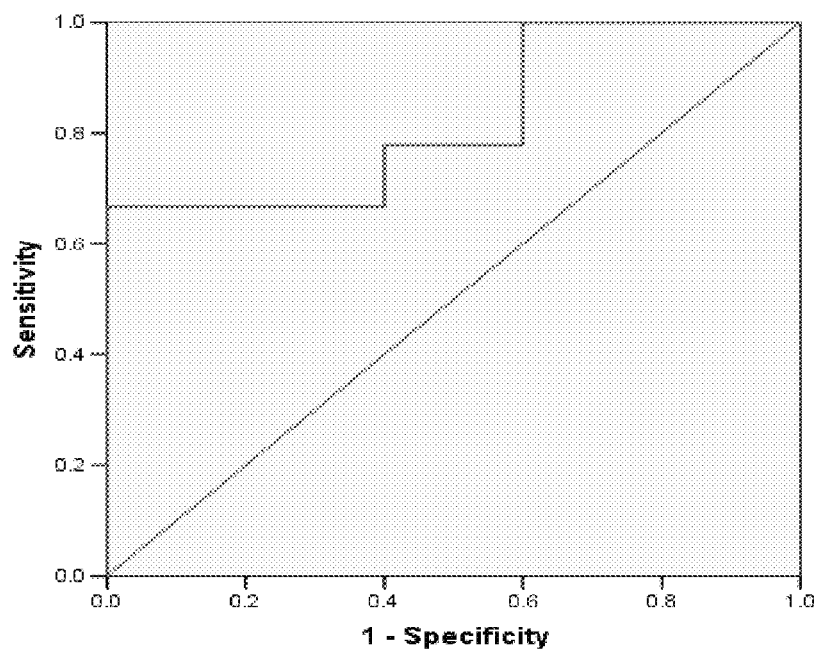
Figure 8C:
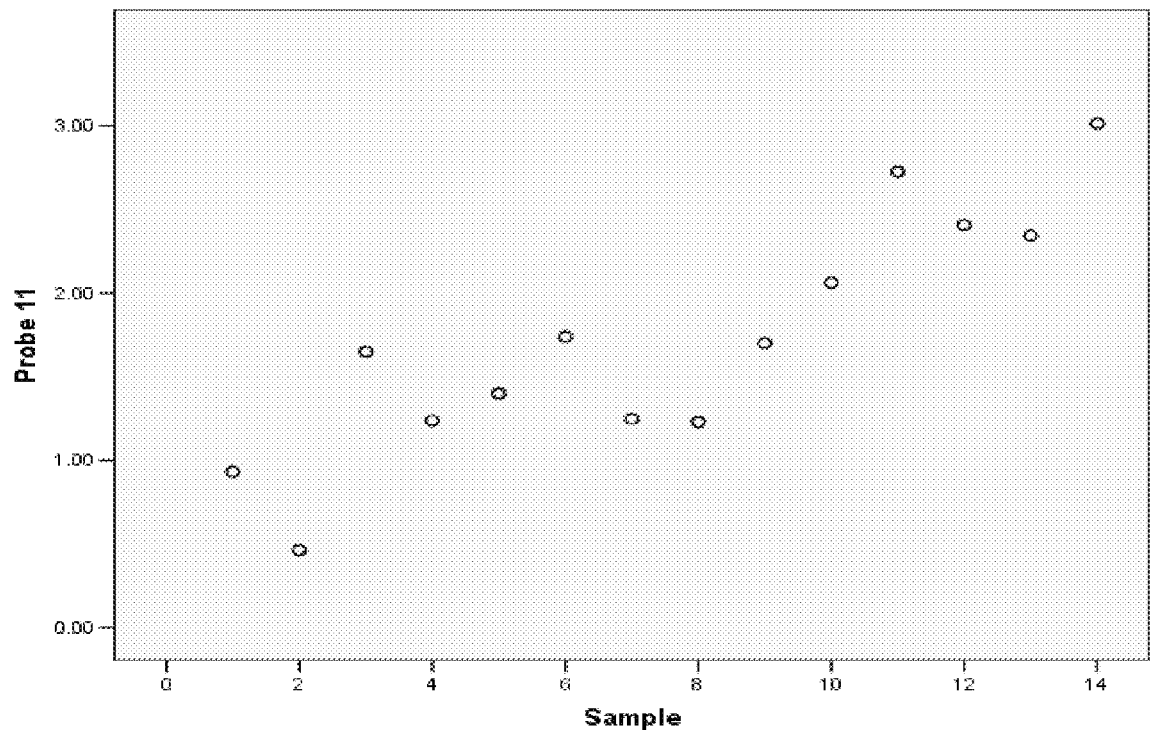
Figure 8C:
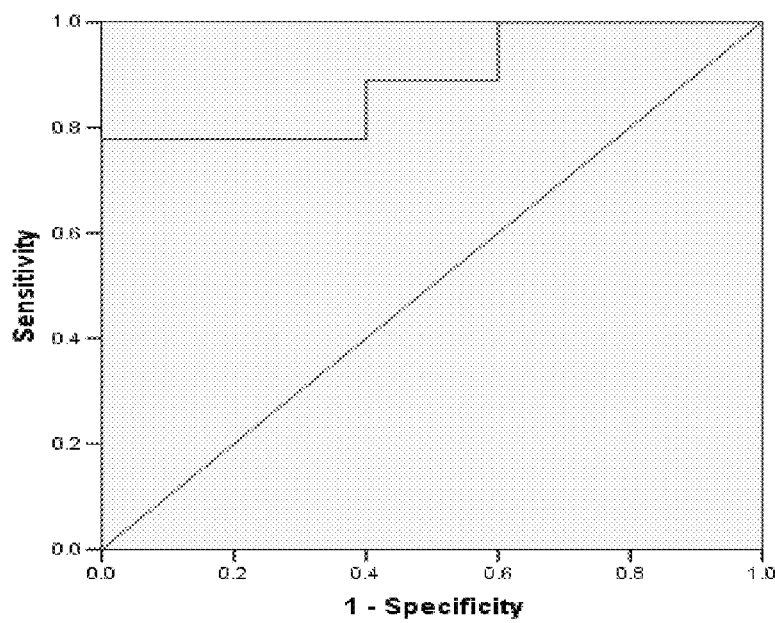
Figure 8D:
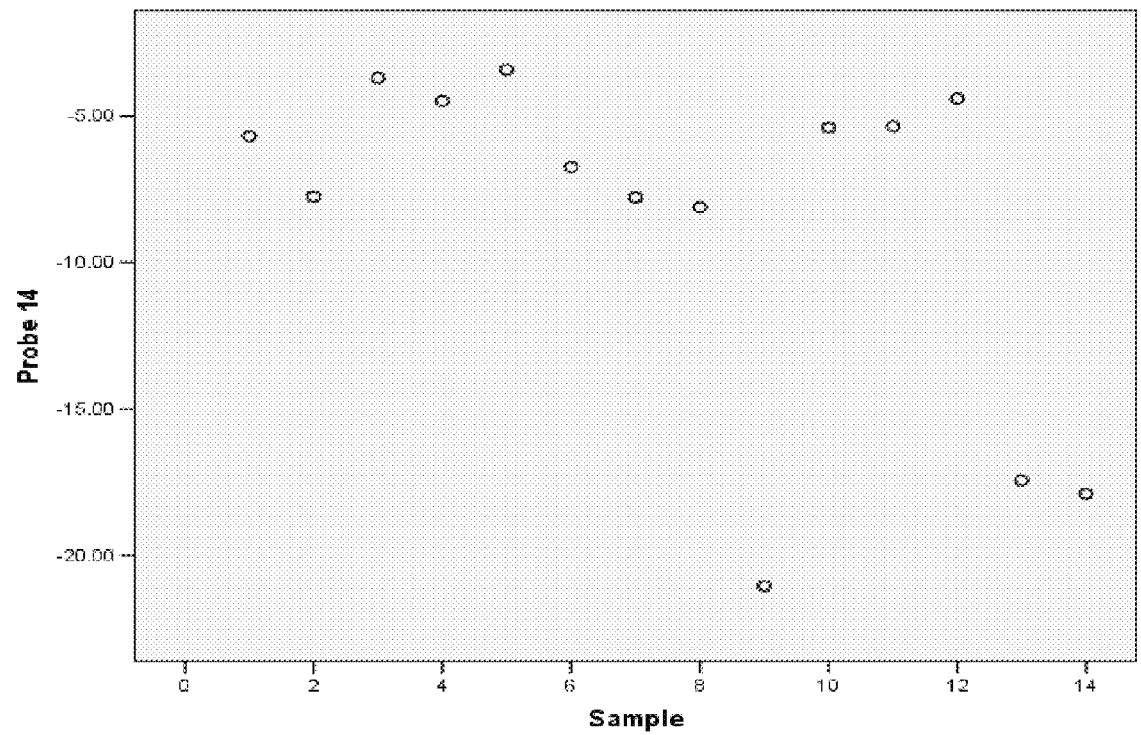
Figure 8D:
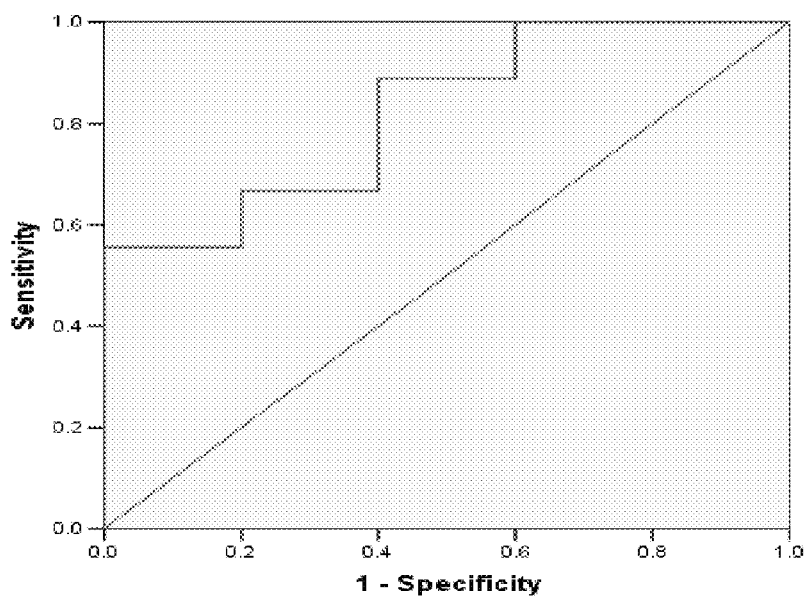
Figure 8E:
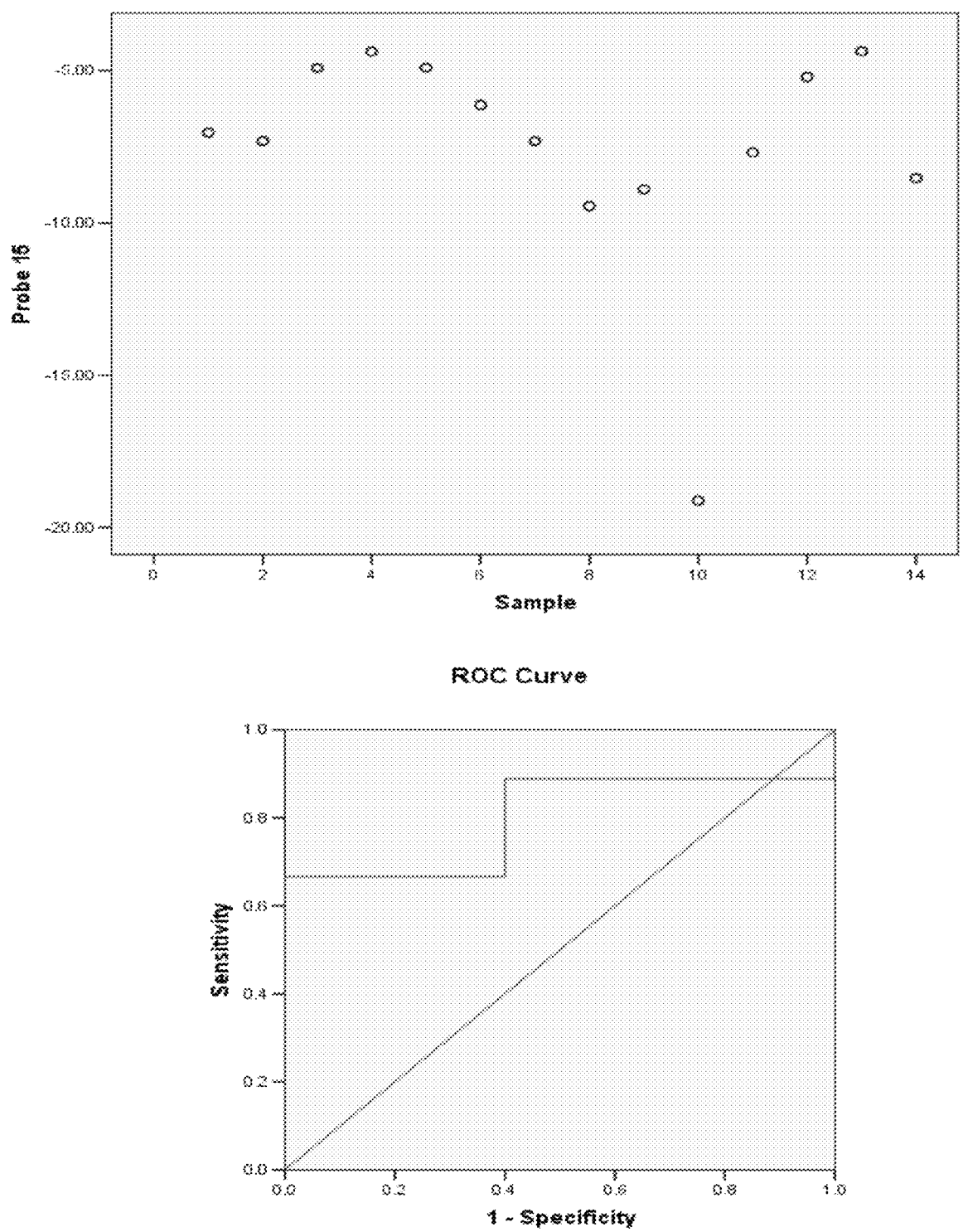
Figure 8F:
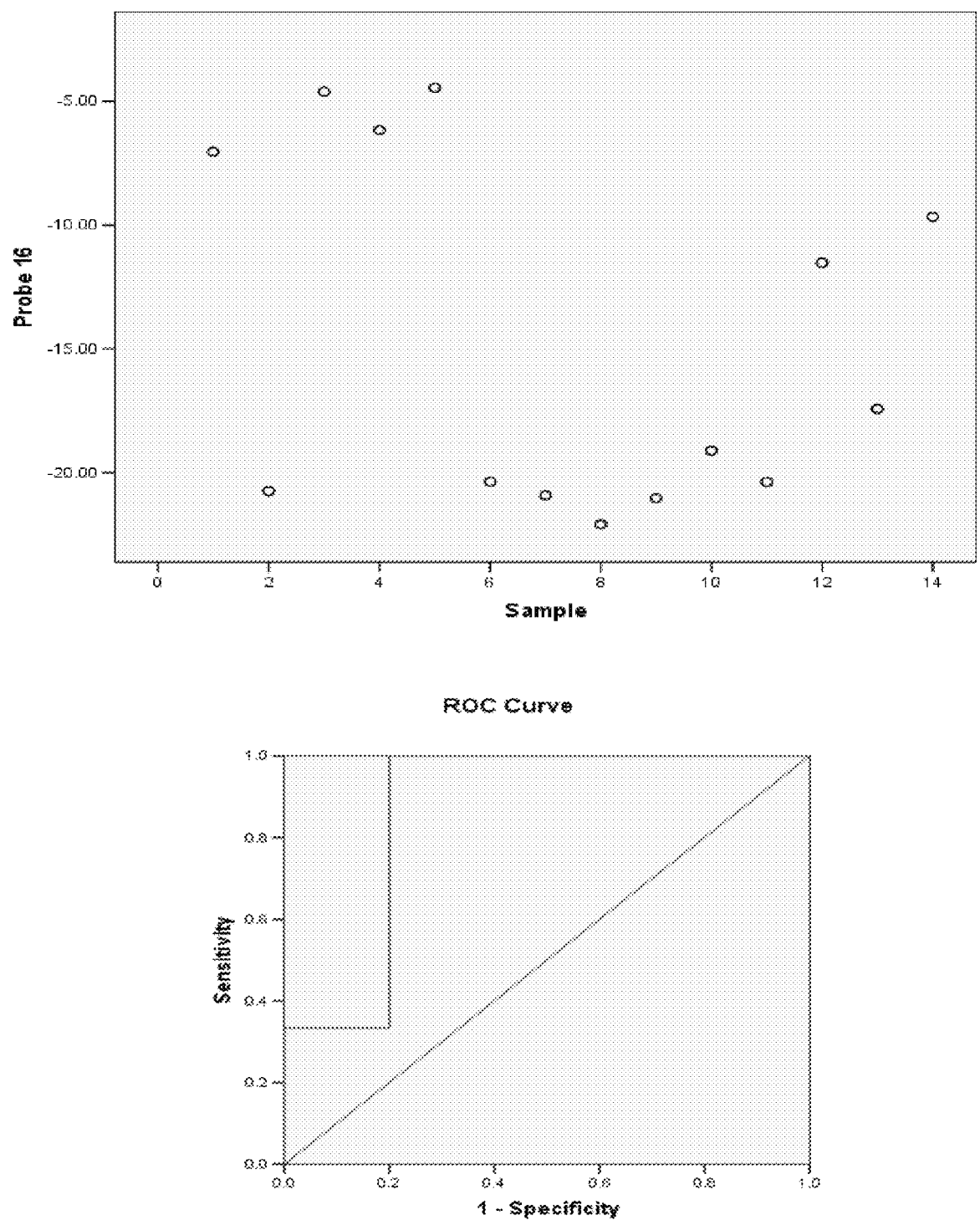
Figure 8G:
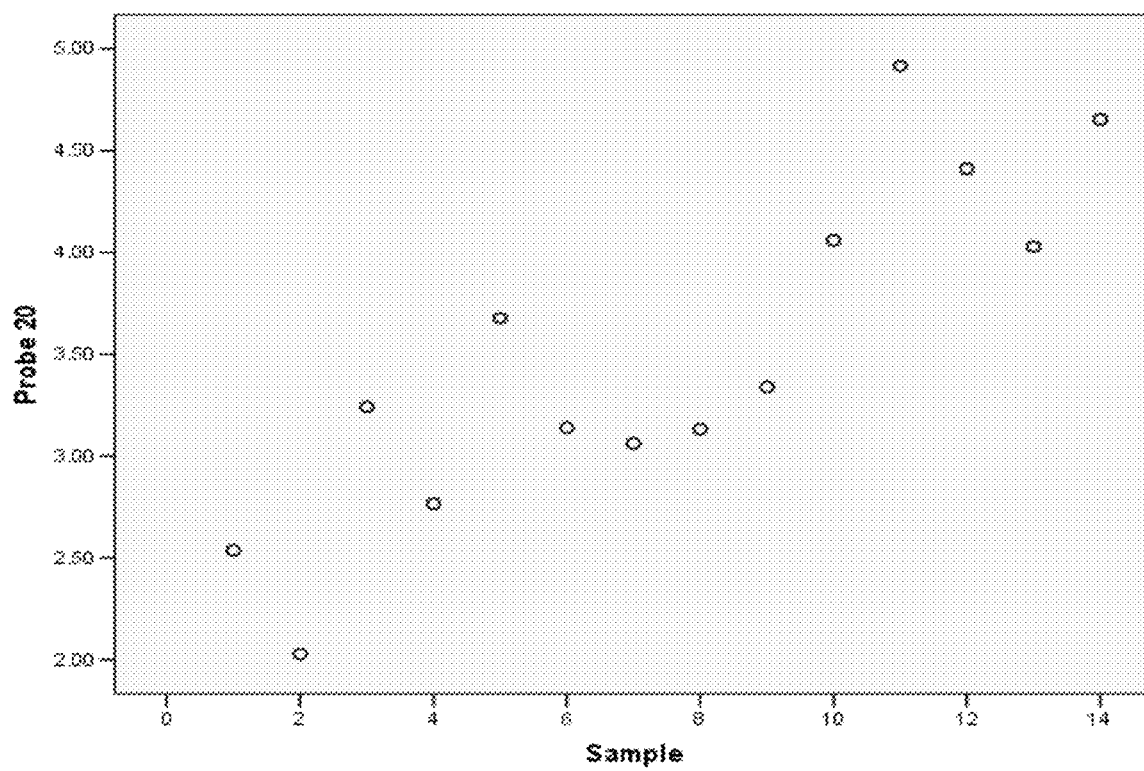
Figure 8G:
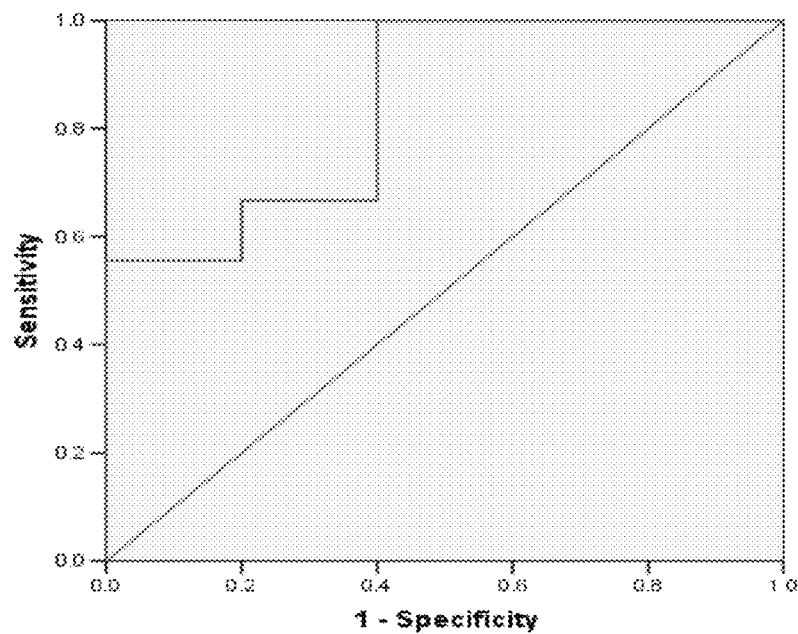
Figure 9A:
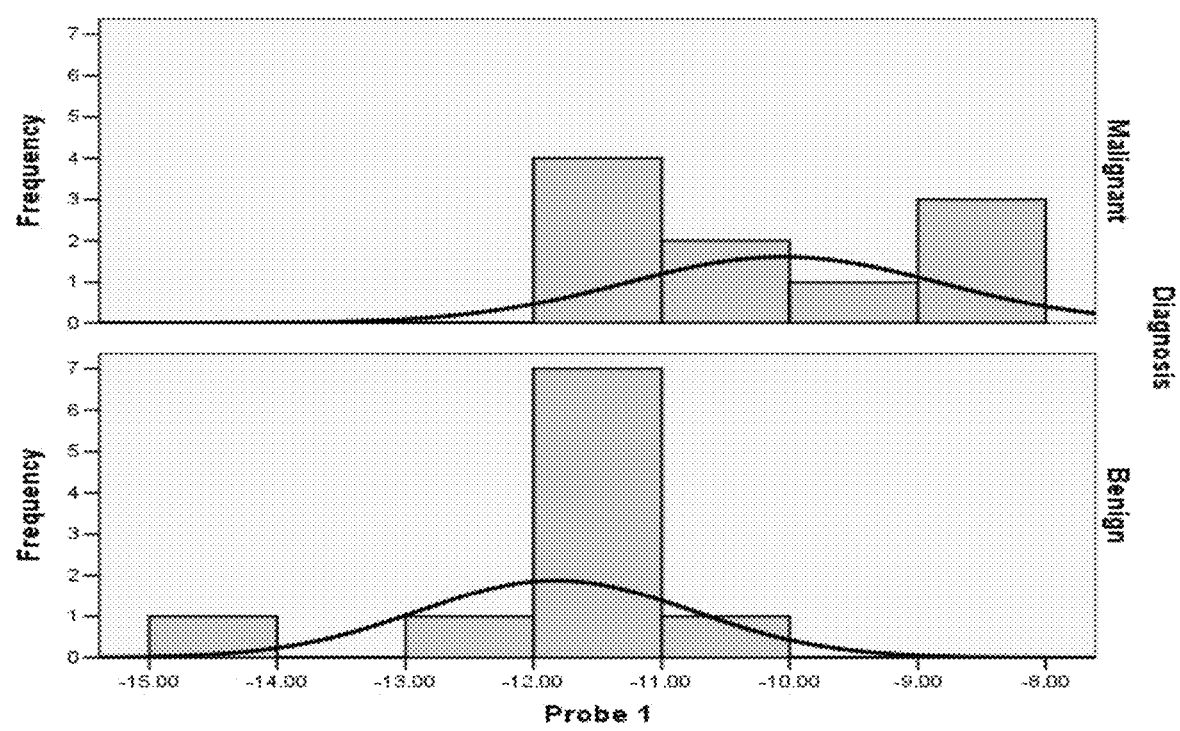
FIGS. 9a to 9h illustrate the results for transcripts 1, 2, 3, 6, 11, 12, 15 and 20 of the invention in the identification of ovarian cancer.
Figure 9A:
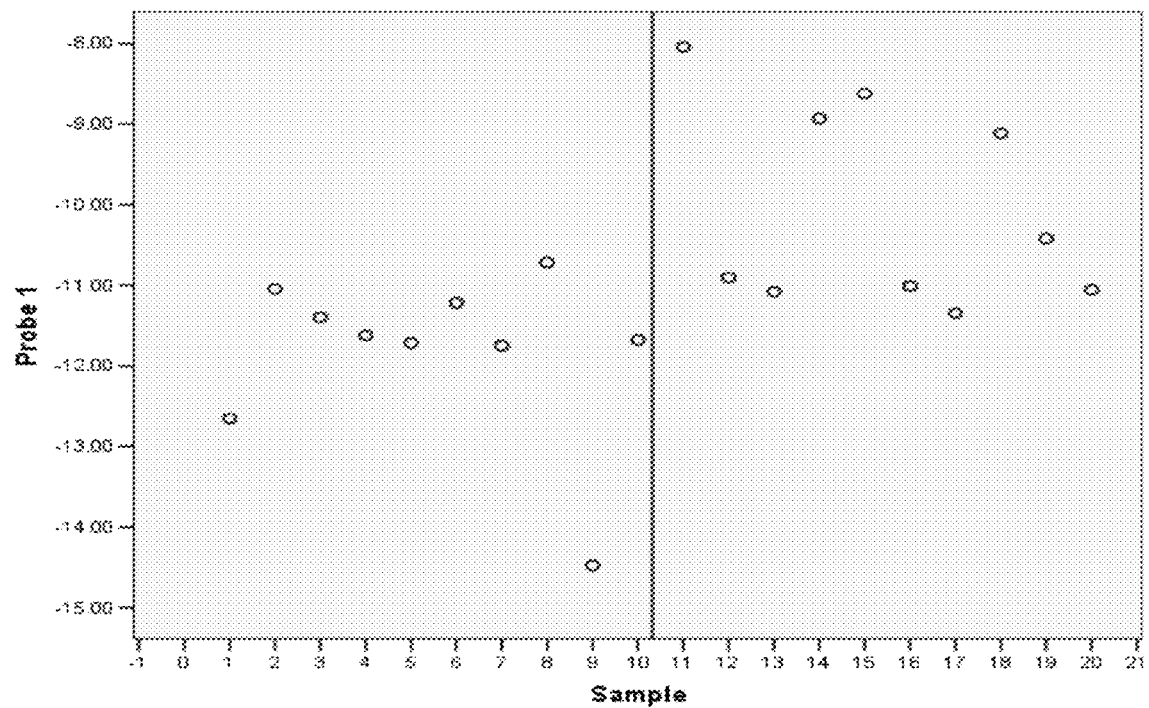
Figure 9A:
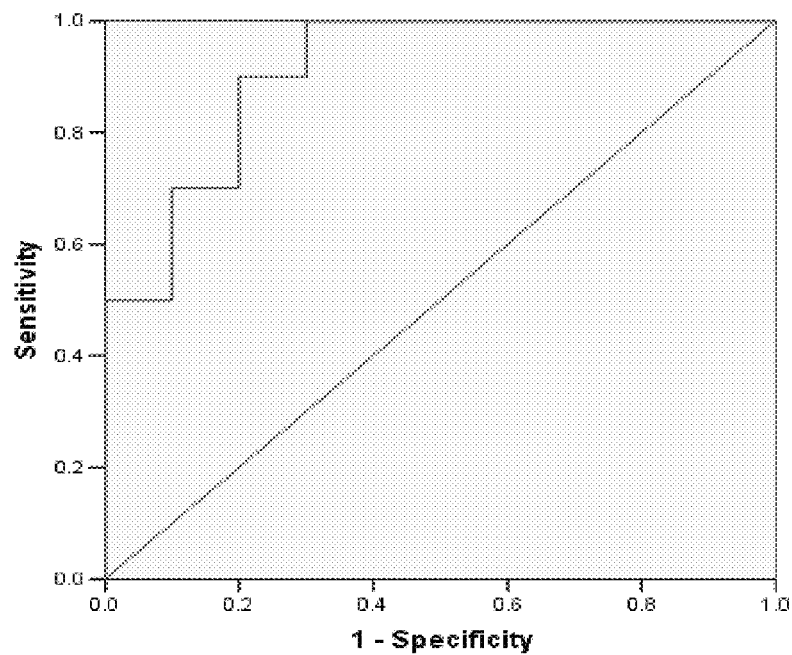
Figure 9B:
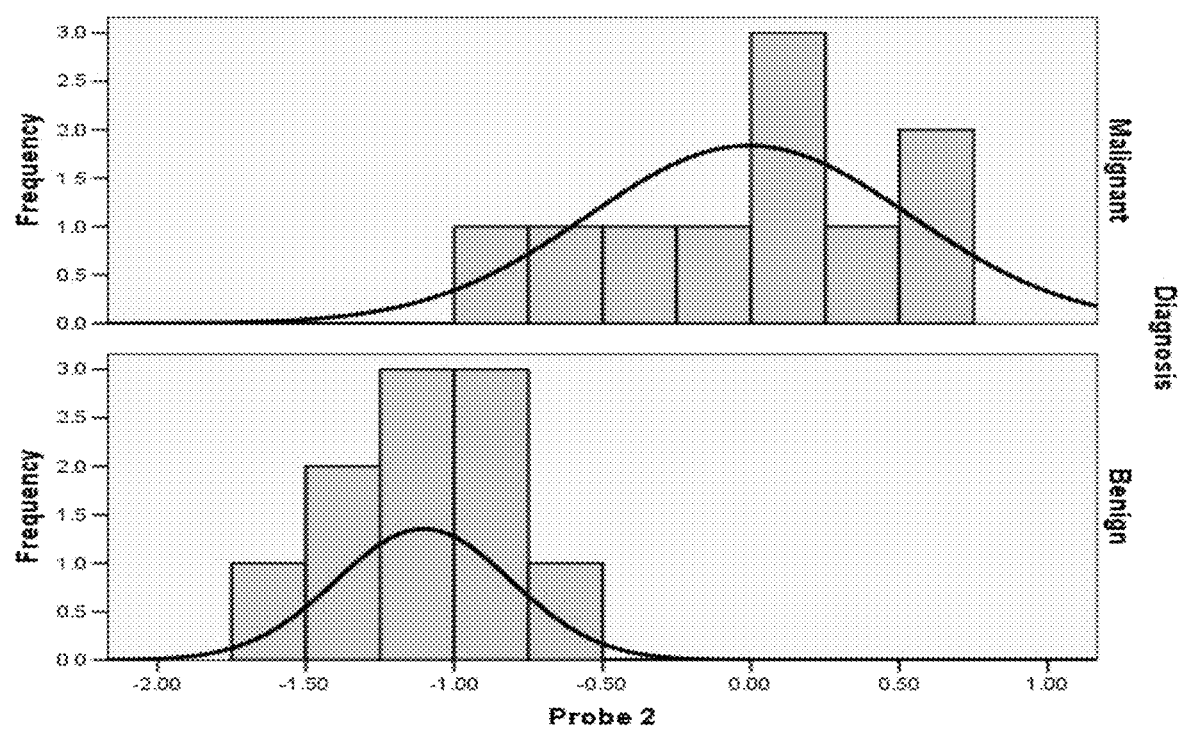
Figure 9B:
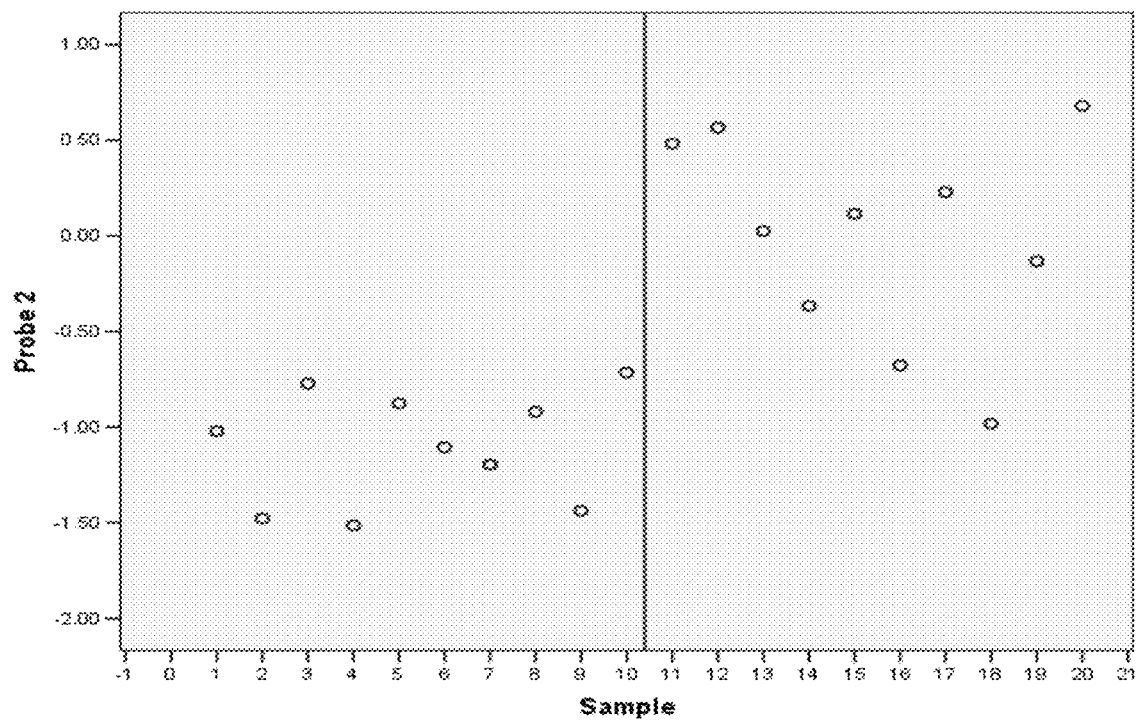
Figure 9B:
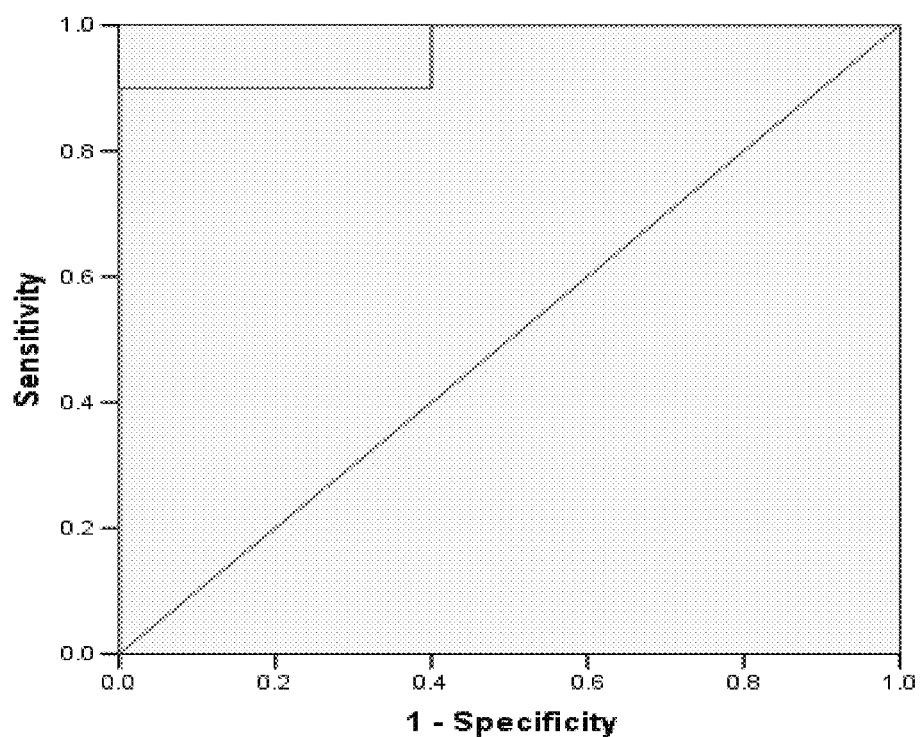
Figure 9C:
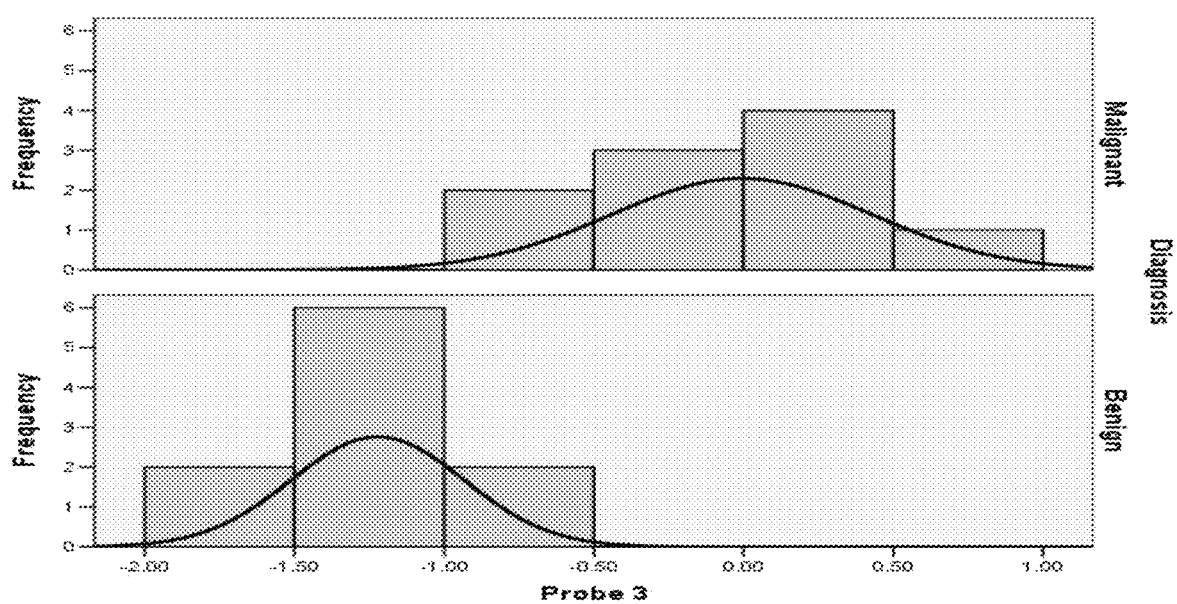
Figure 9C:
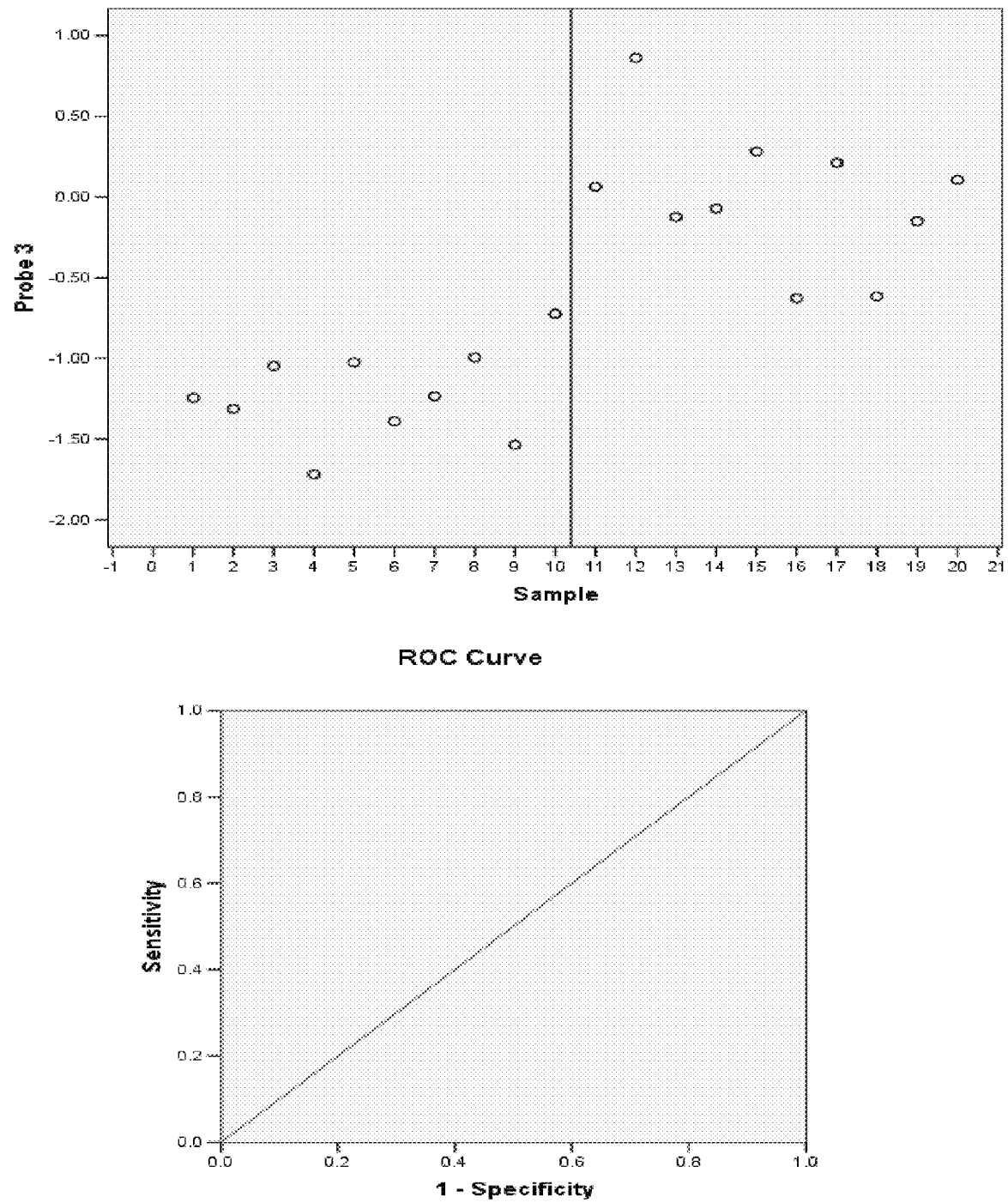
Figure 9D:
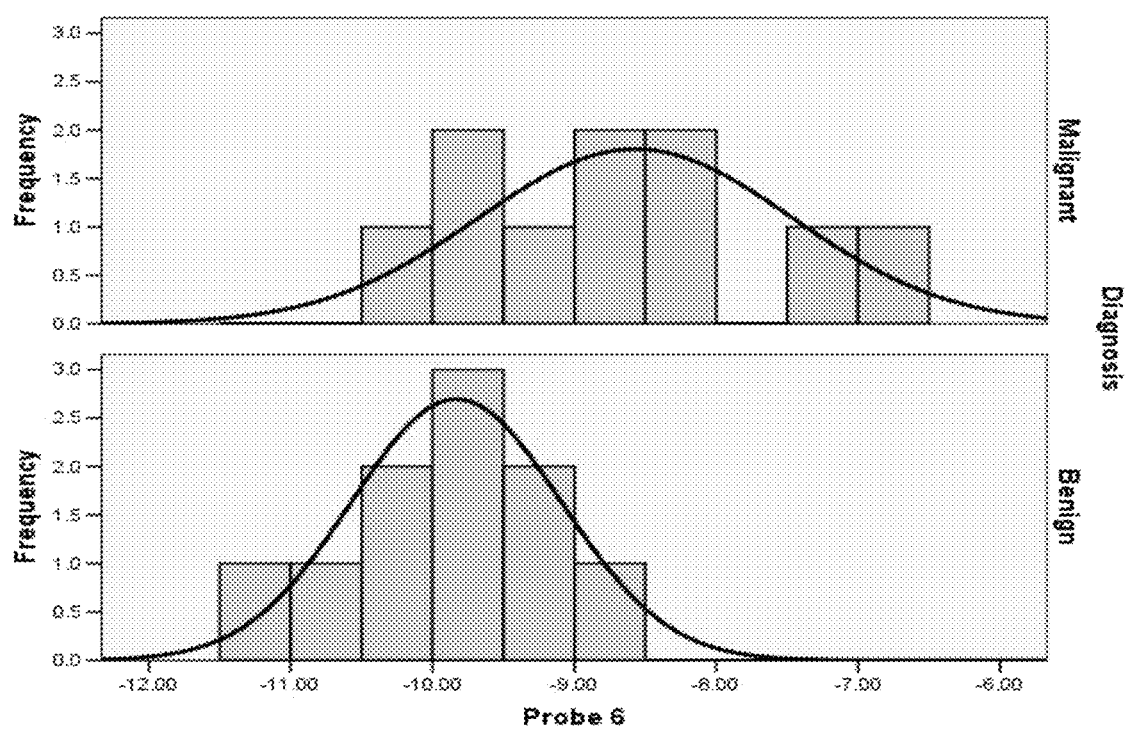
Figure 9D:
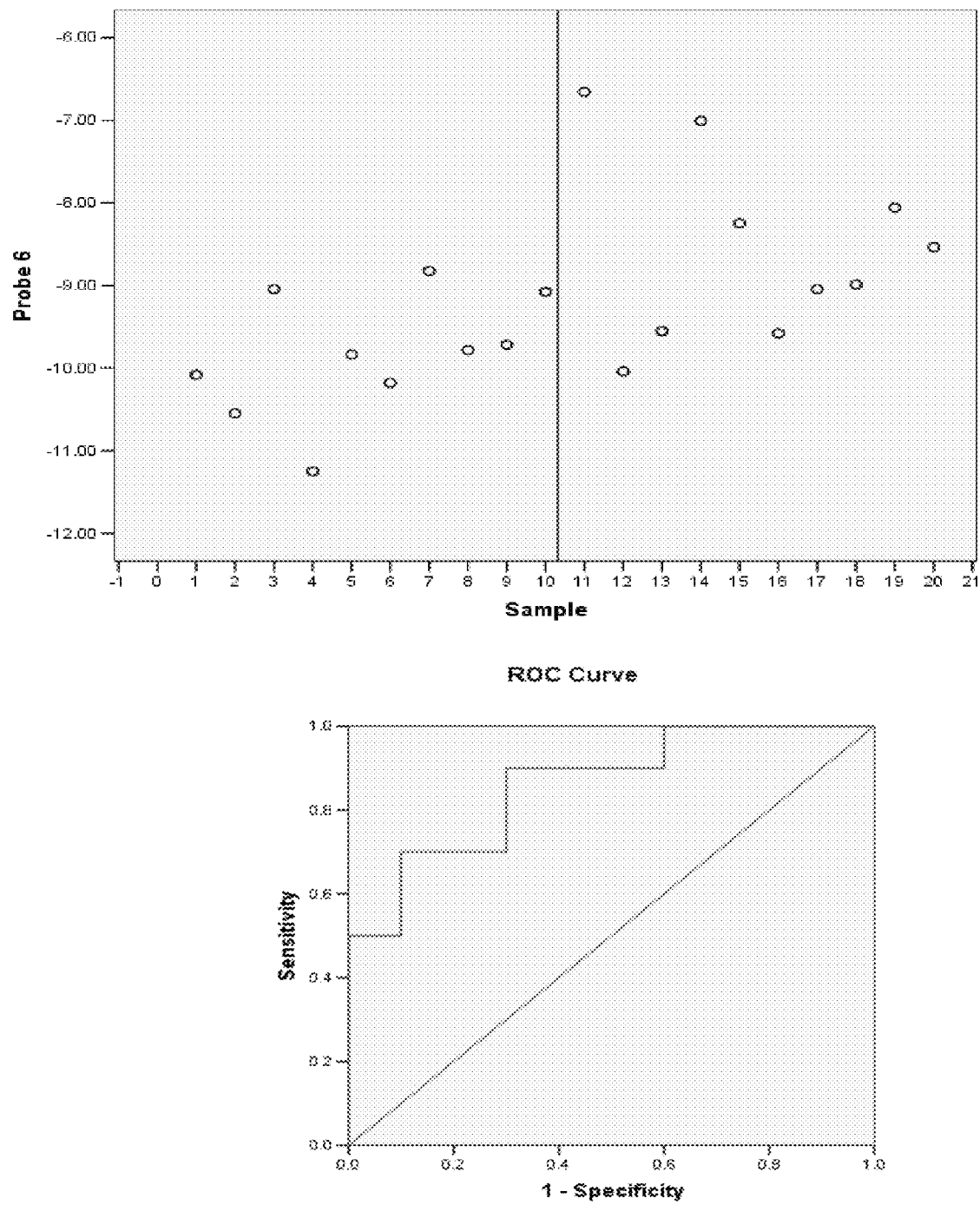
Figure 9E:
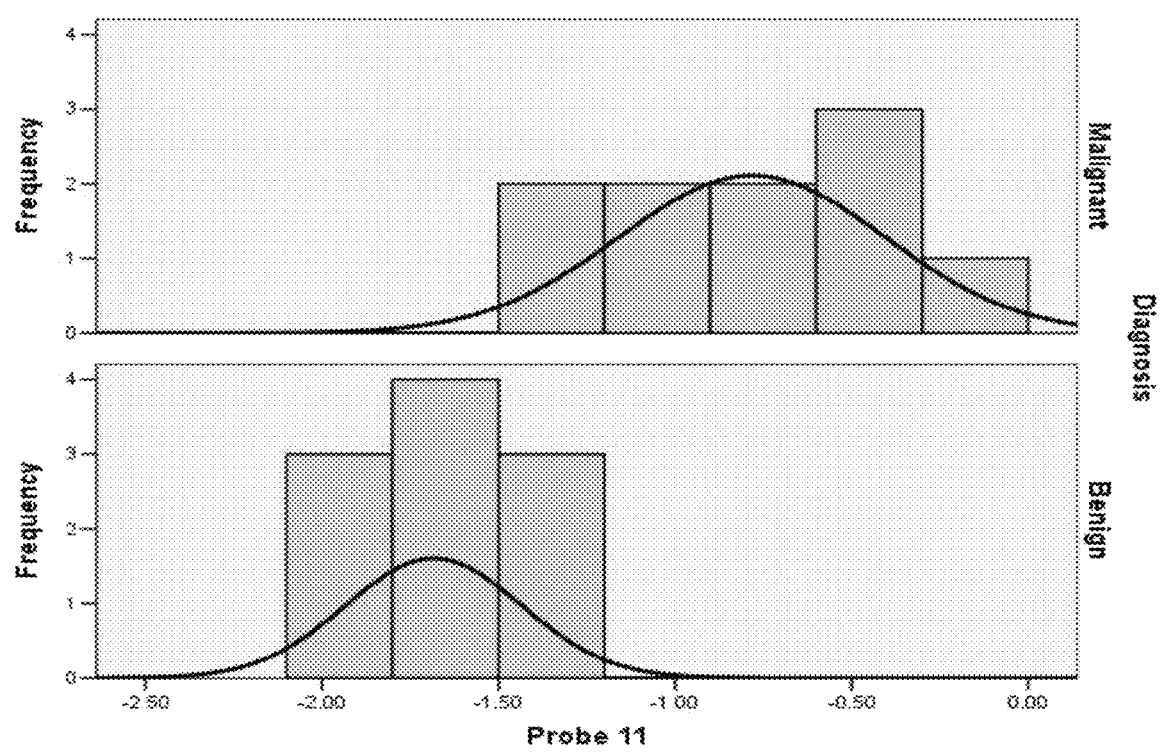
Figure 9E:
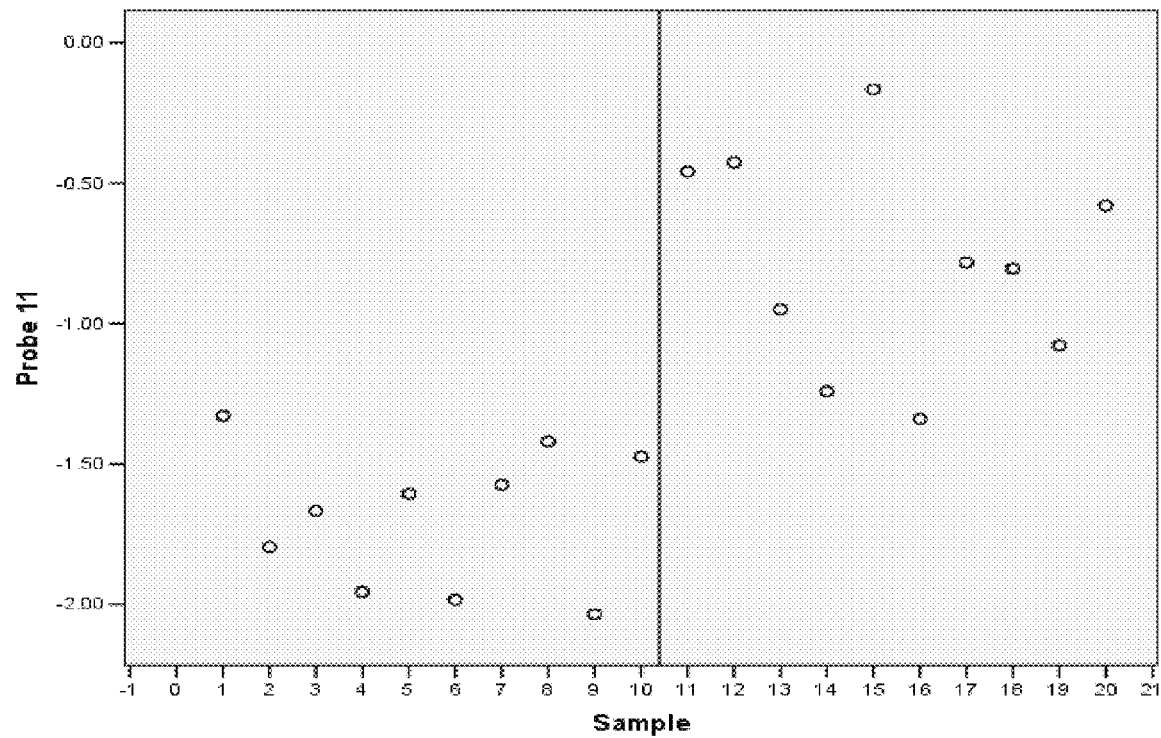
Figure 9E:
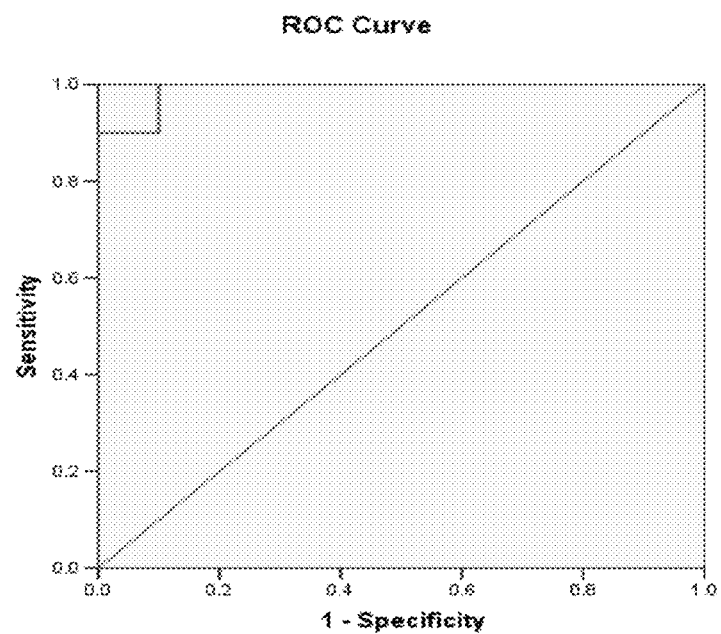
Figure 9F:
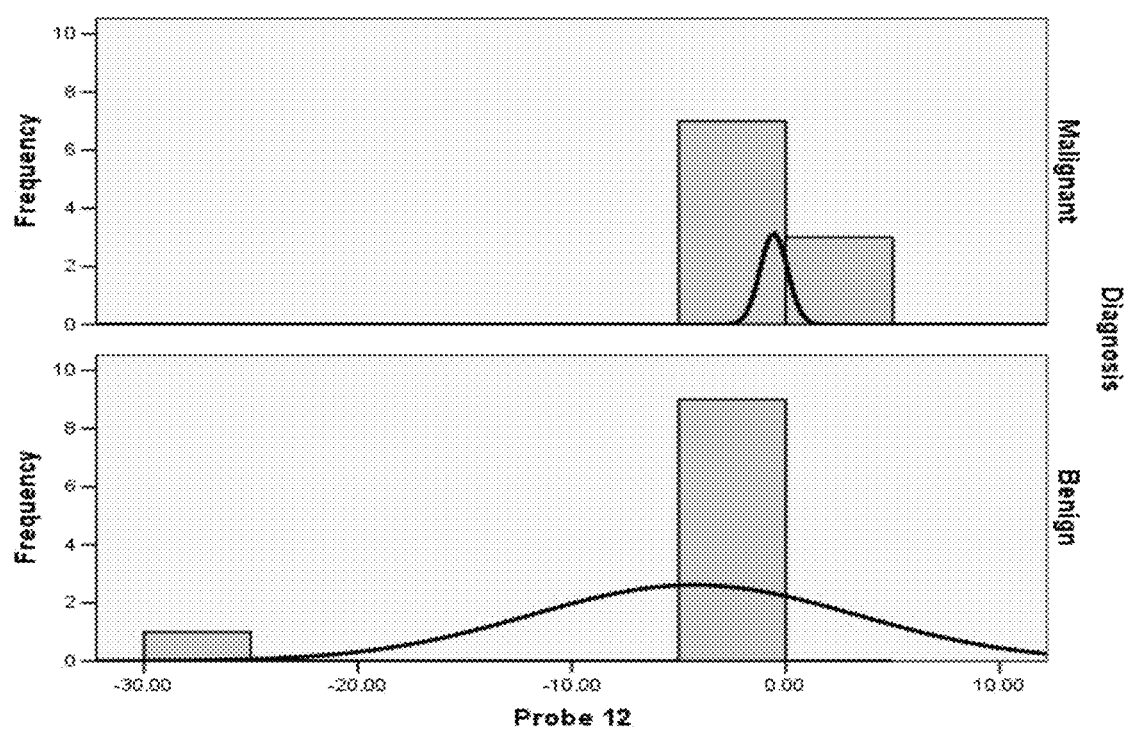
Figure 9F:
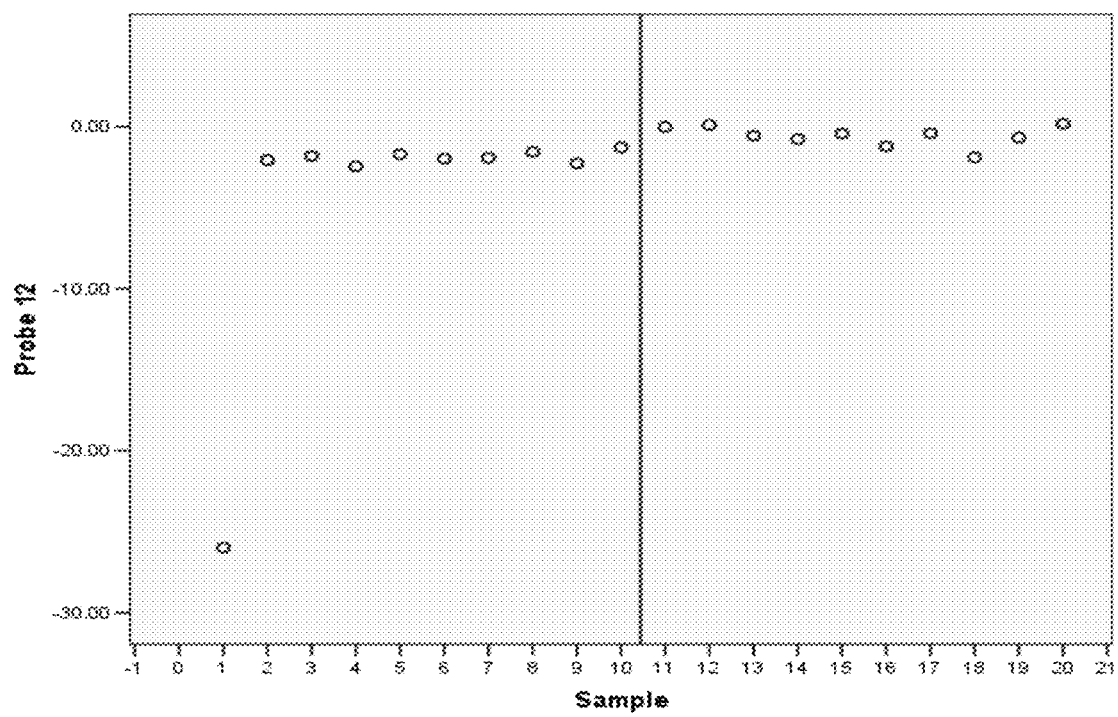
Figure 9F:
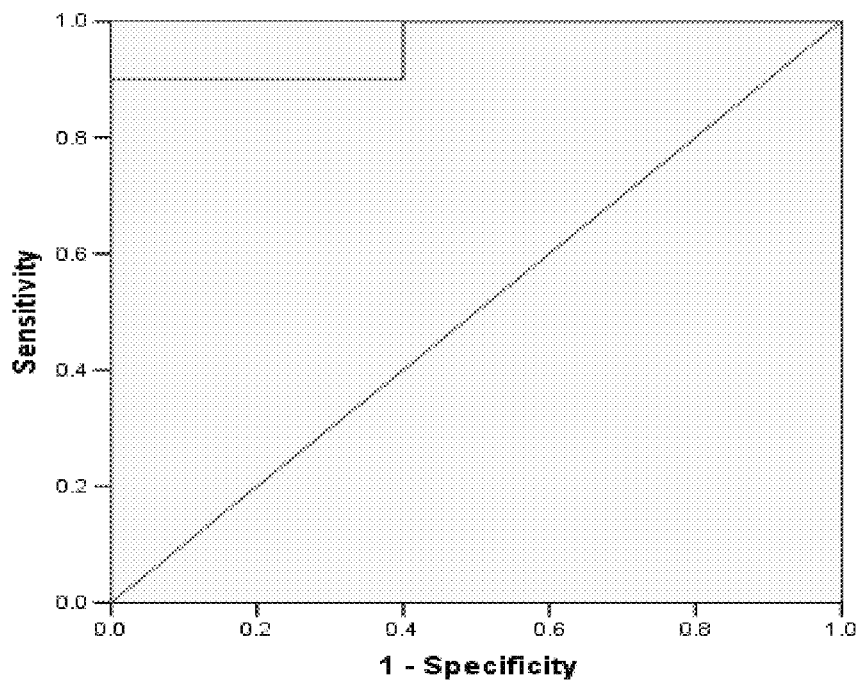
Figure 9G:
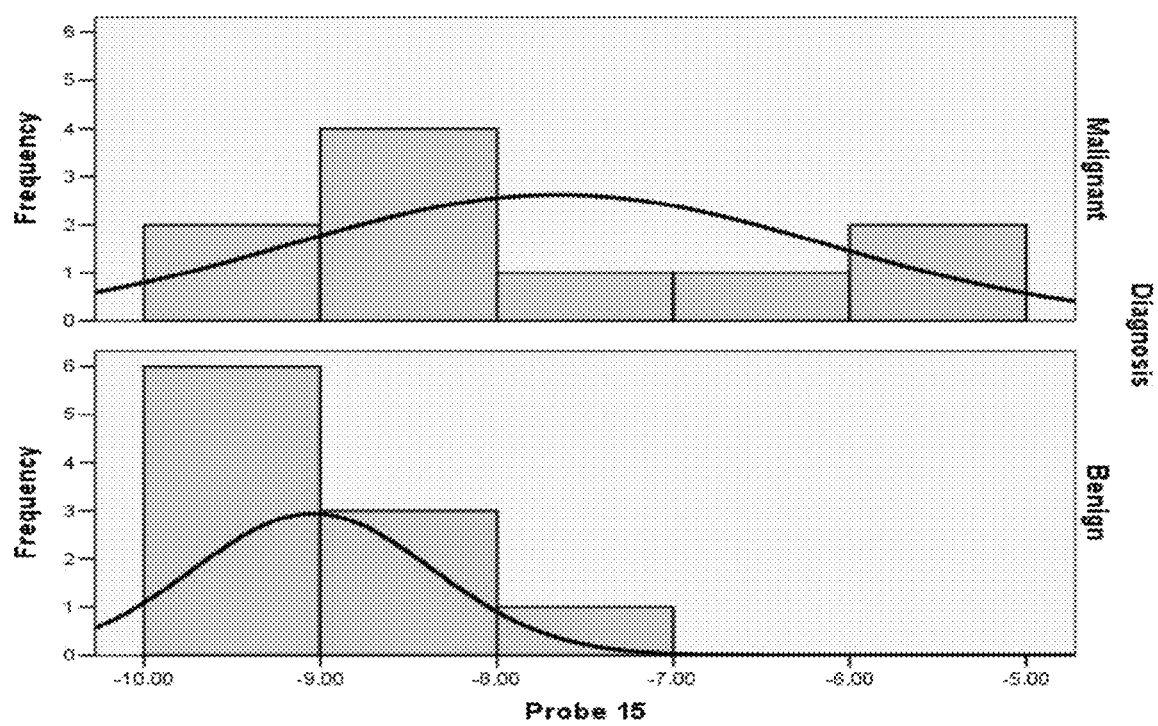
Figure 9G:
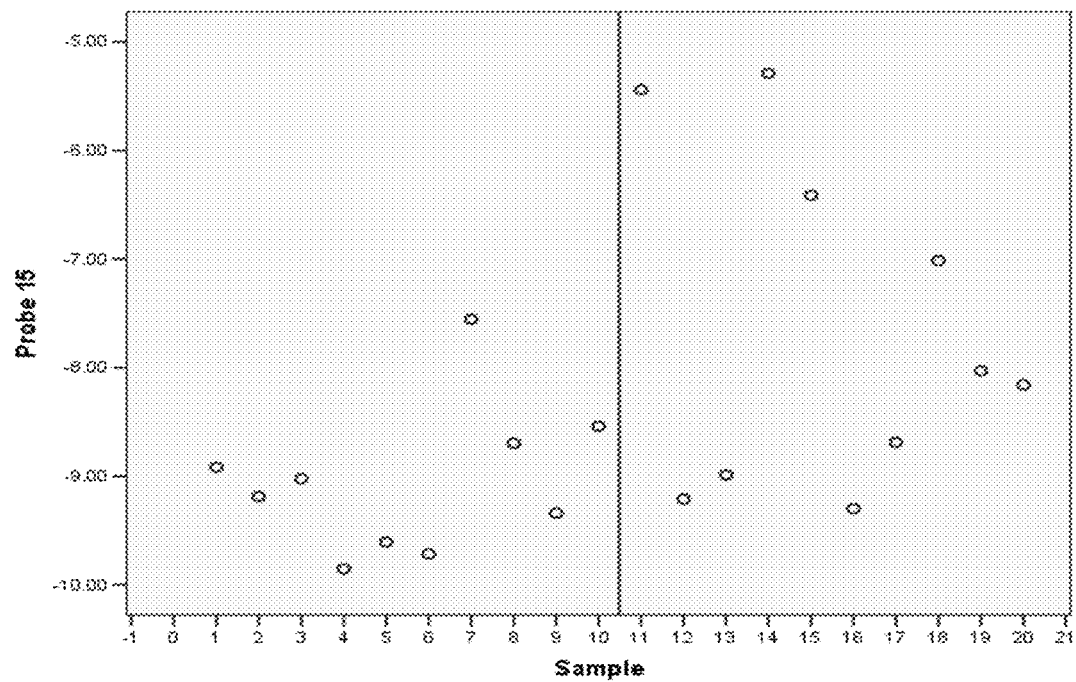
Figure 9G:
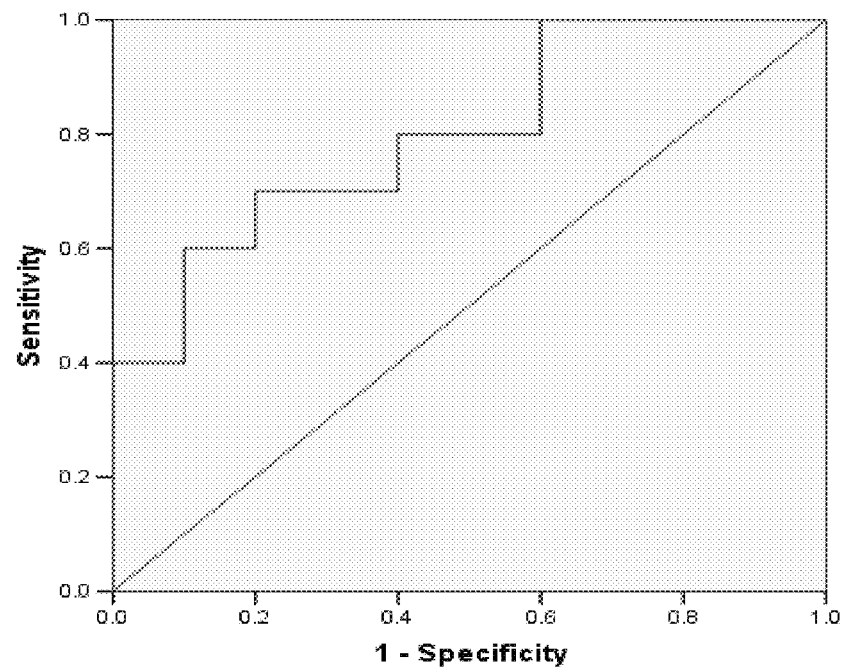
Figure 9H:
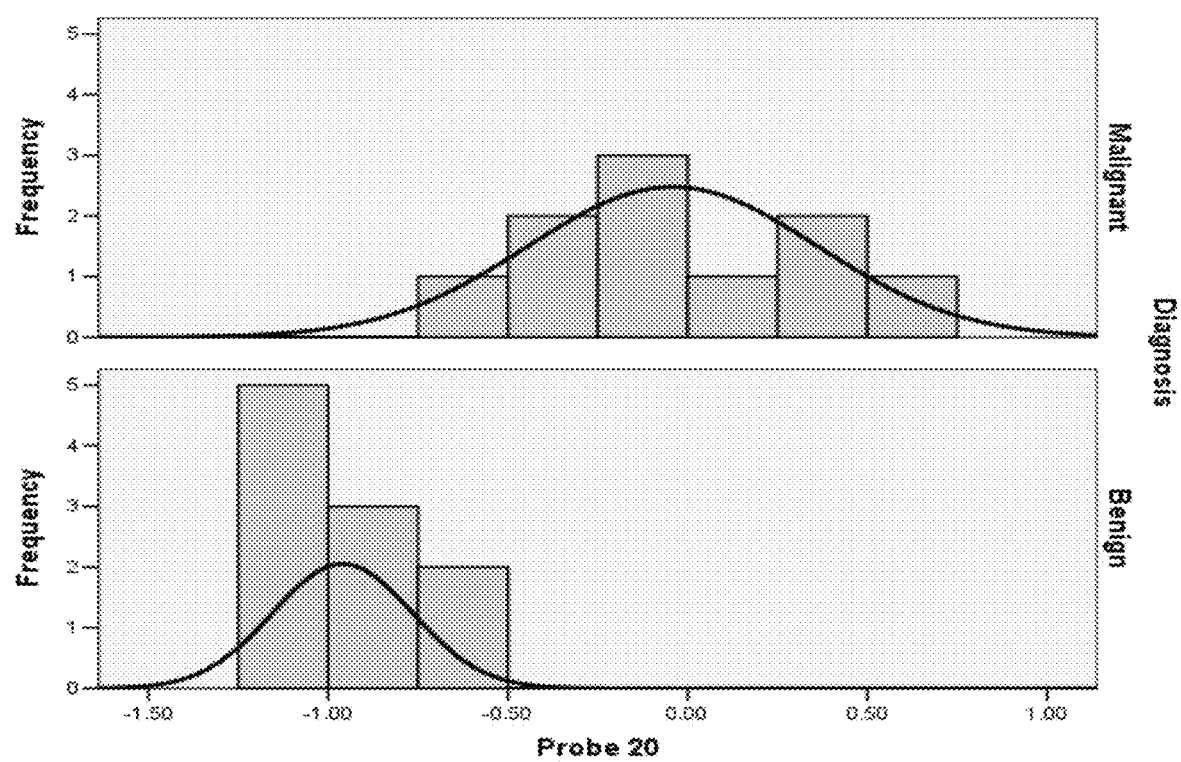
Figure 9H:
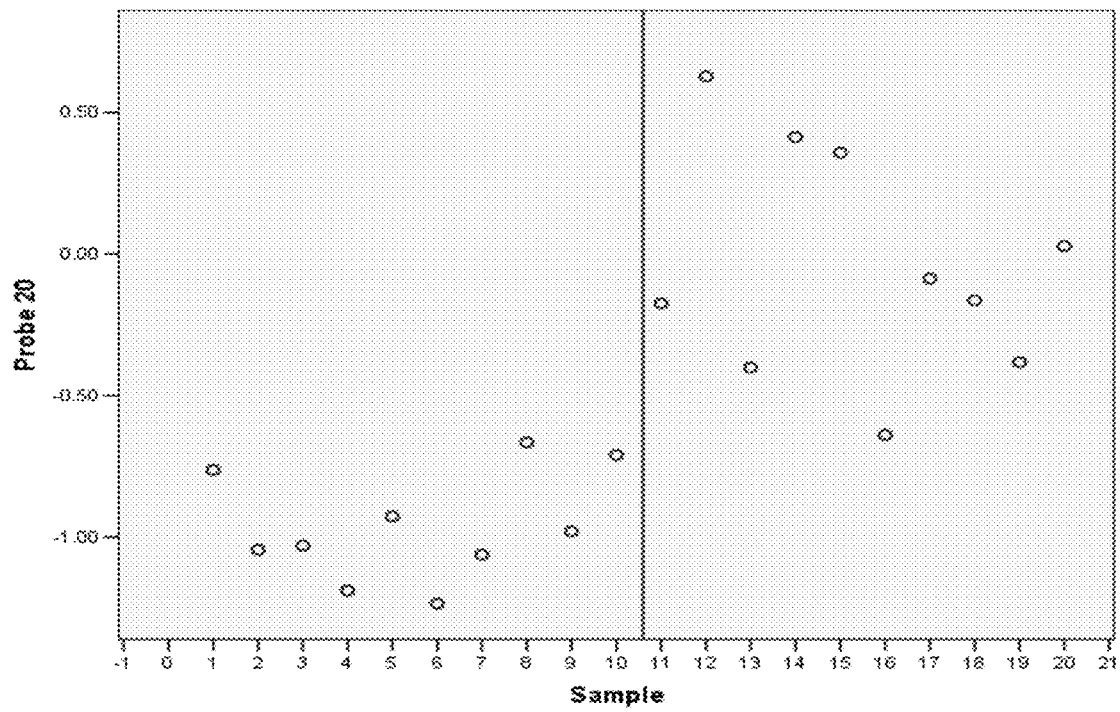
Figure 9H:
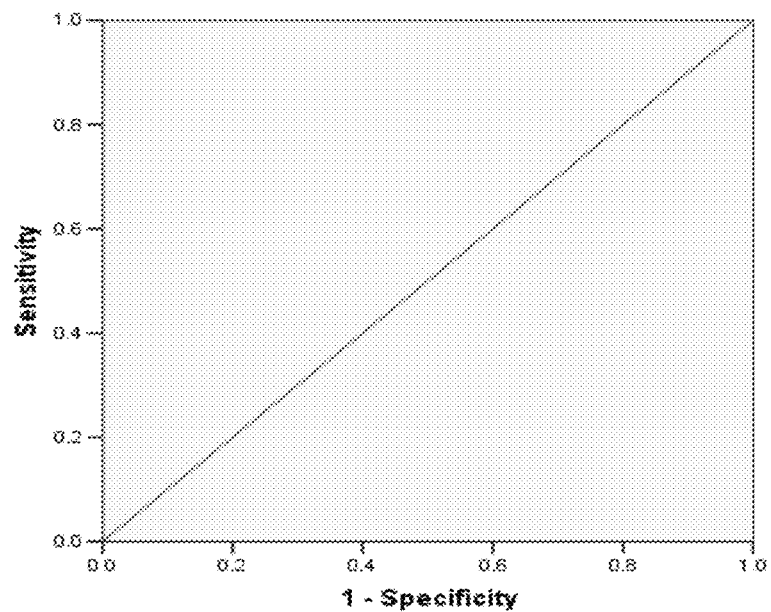
Figure 10A:
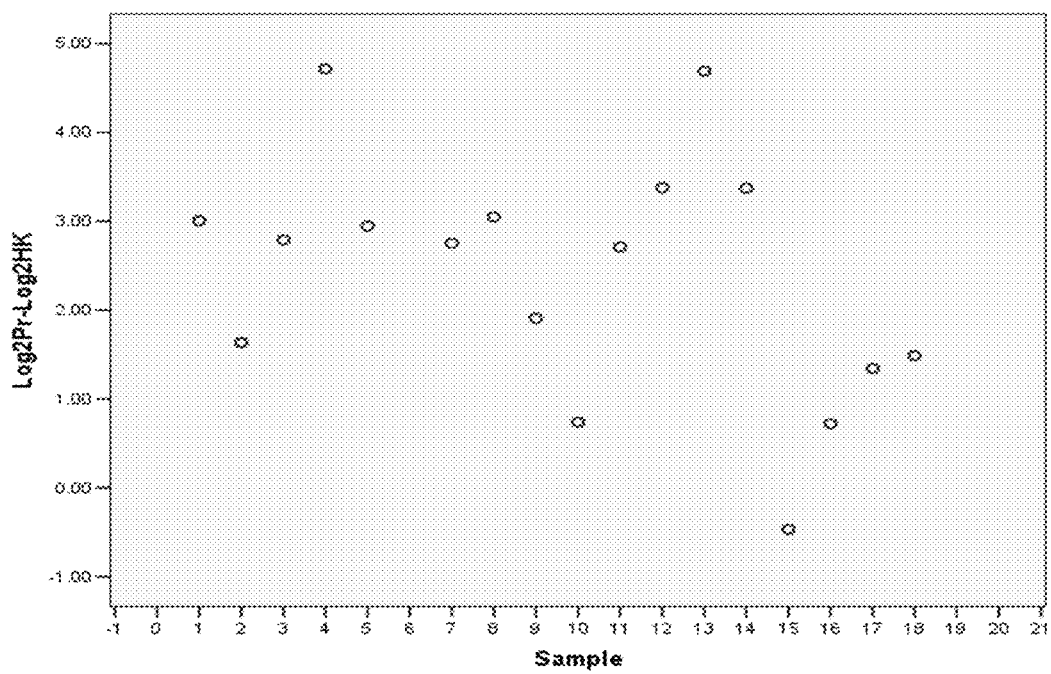
FIGS. 10a and 10b illustrate the results for transcript 2 of the invention in the identification of testicular cancer.
Figure 10A:
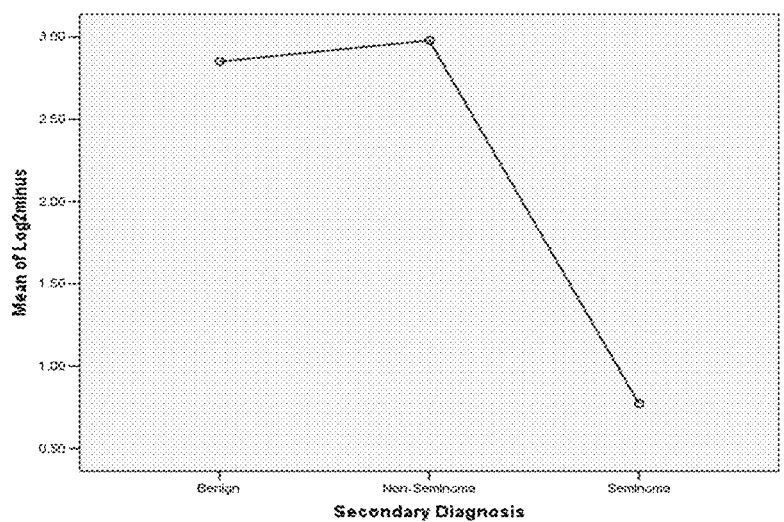
Figure 10B:
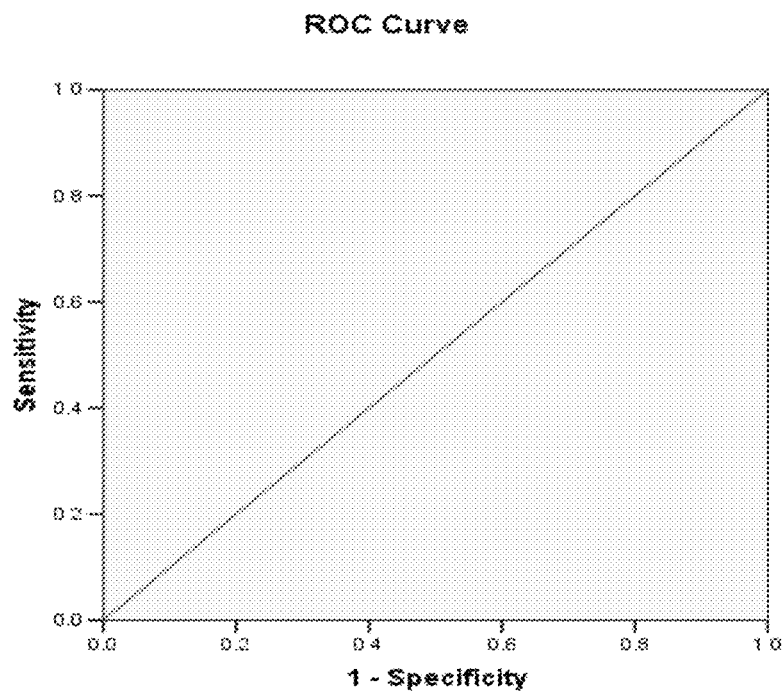
Figure 10B:
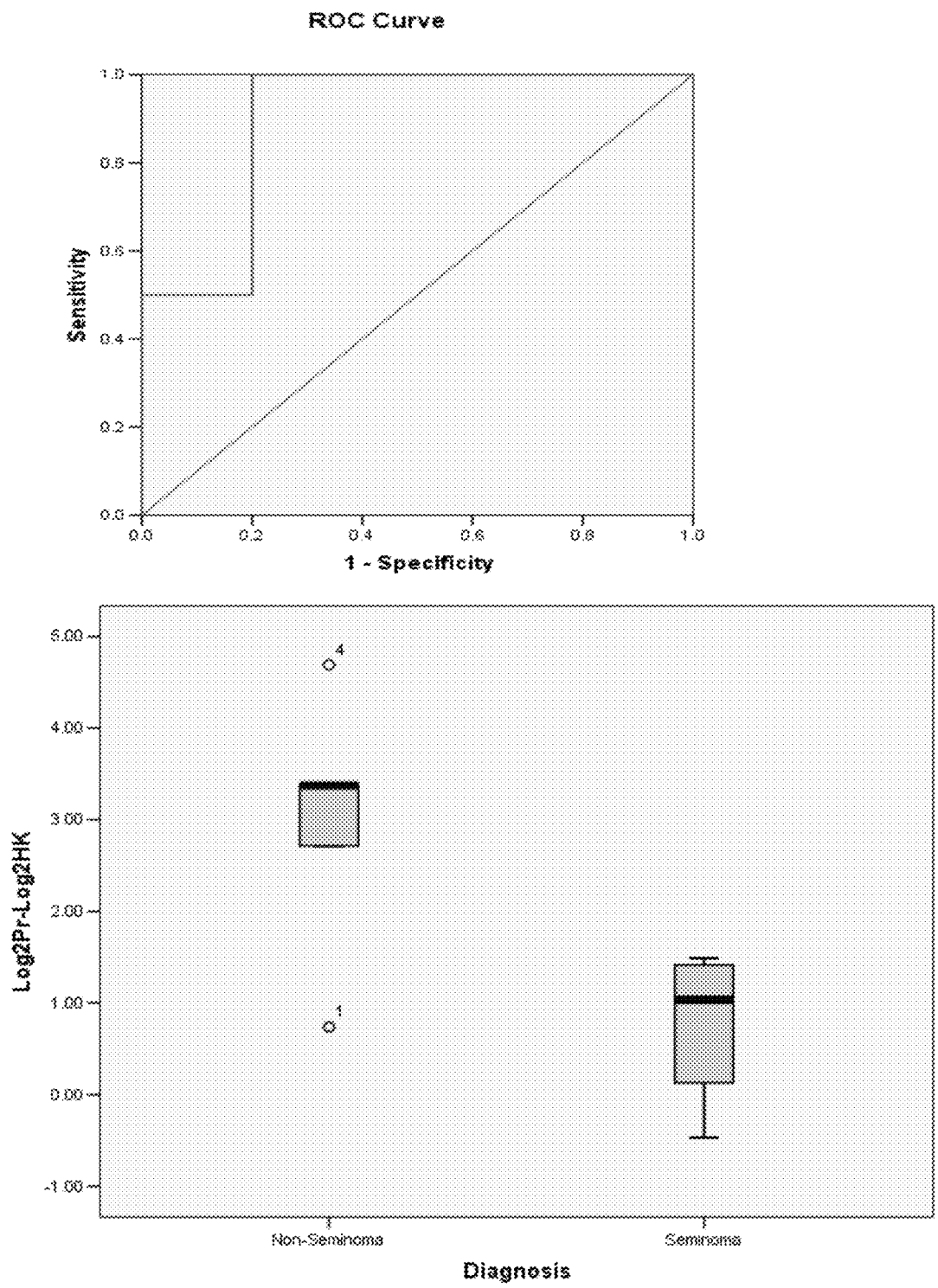
Figure 11A:
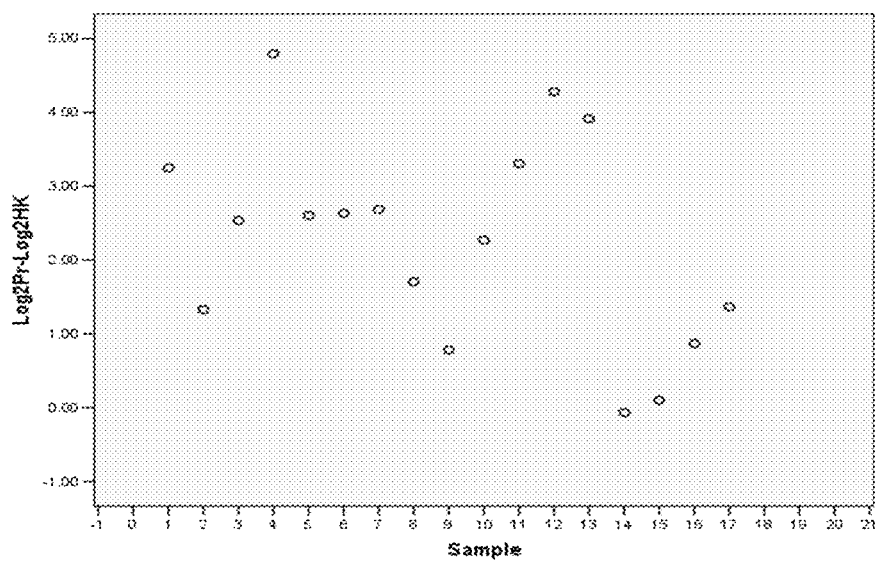
FIGS. 11a and 11b illustrate the results for transcript 3 of the invention in the identification of testicular cancer.
Figure 11A:
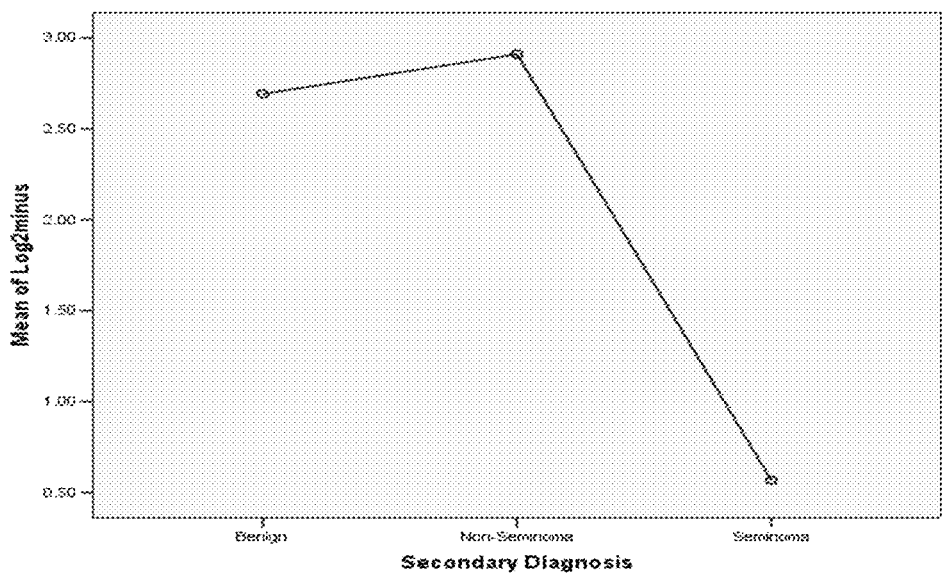
Figure 11B:
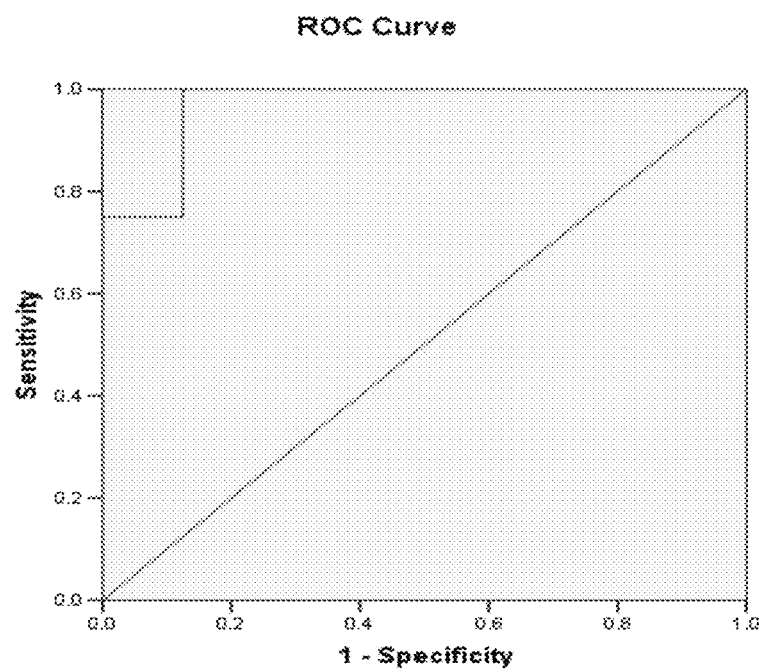
Figure 11B:
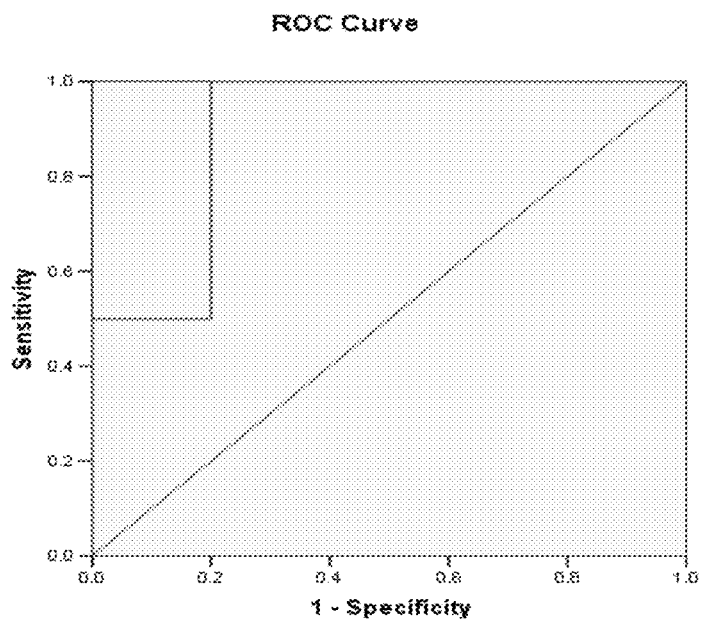
Figure 12:
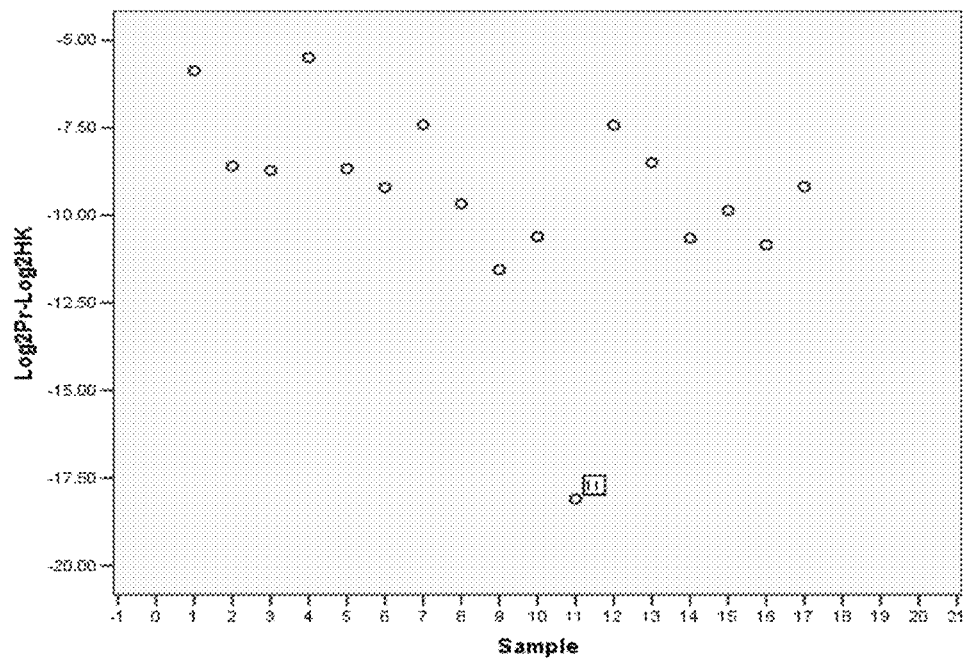
FIG. 12 illustrates the results for transcript 4 of the invention in the identification of testicular cancer.
Figure 12:
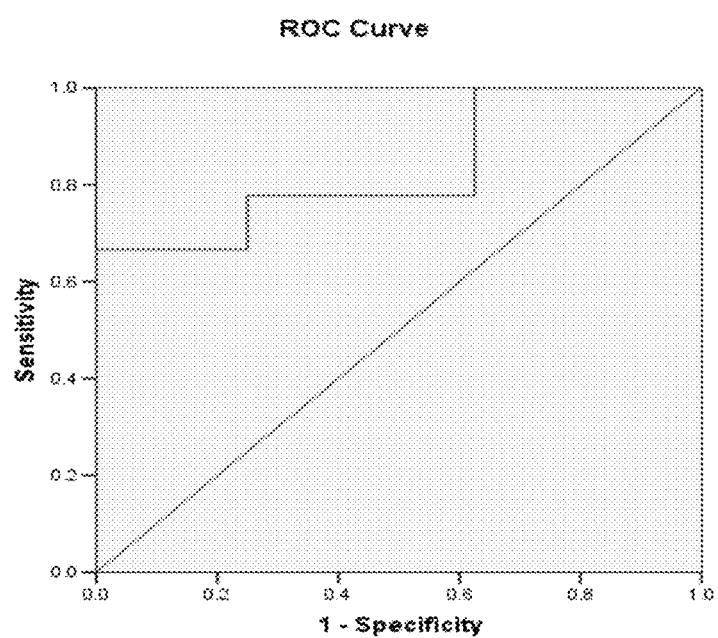
Figure 13A:
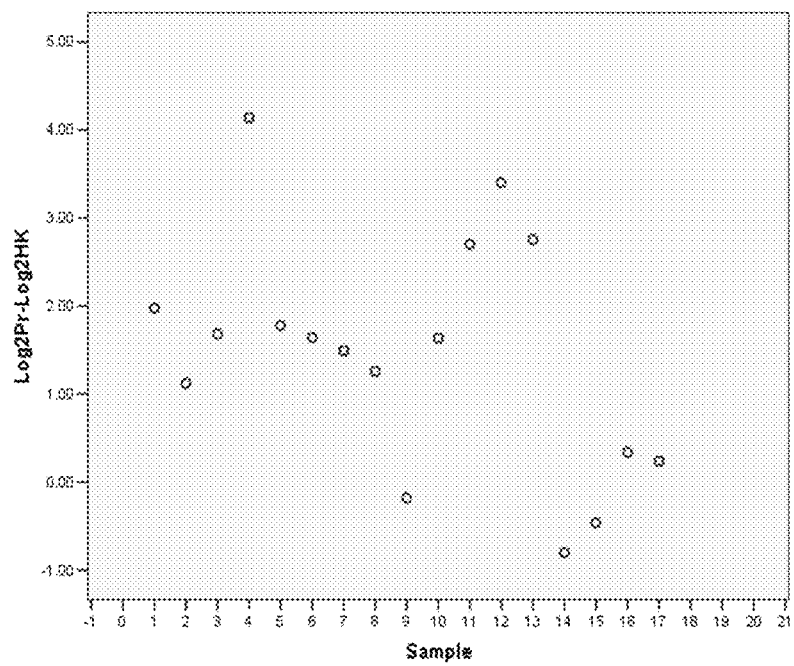
FIGS. 13a and 13b illustrate the results for transcript 11 of the invention in the identification of testicular cancer.
Figure 13A:
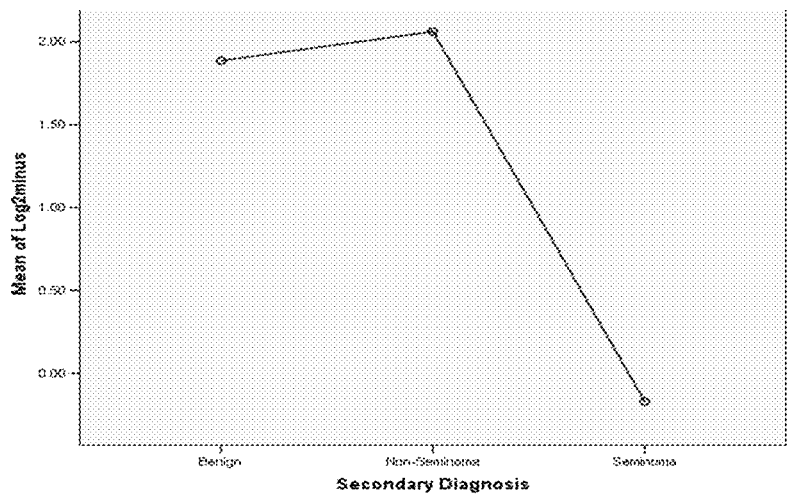
Figure 13B:
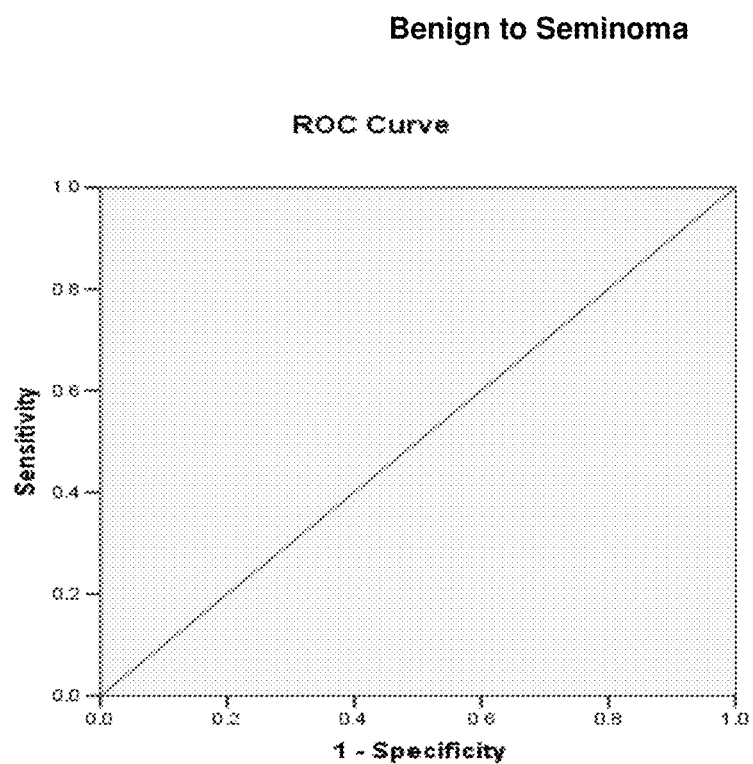
Figure 13B:
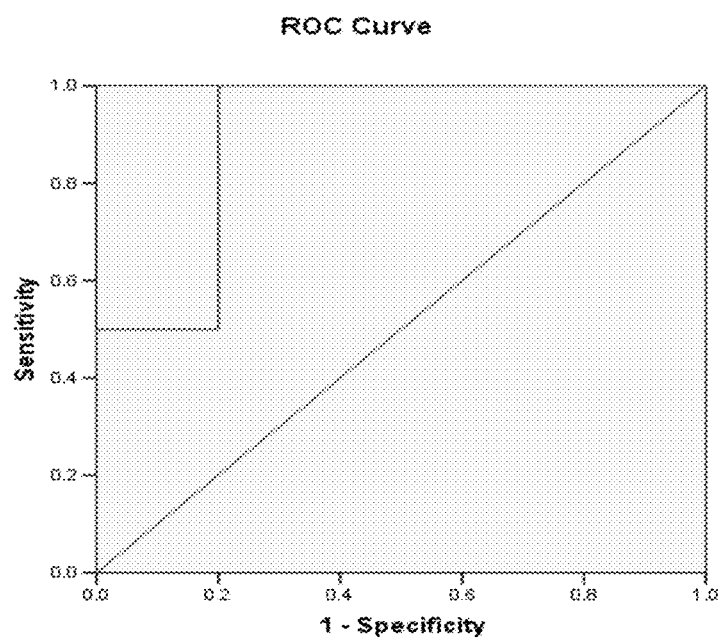
Figure 14A:
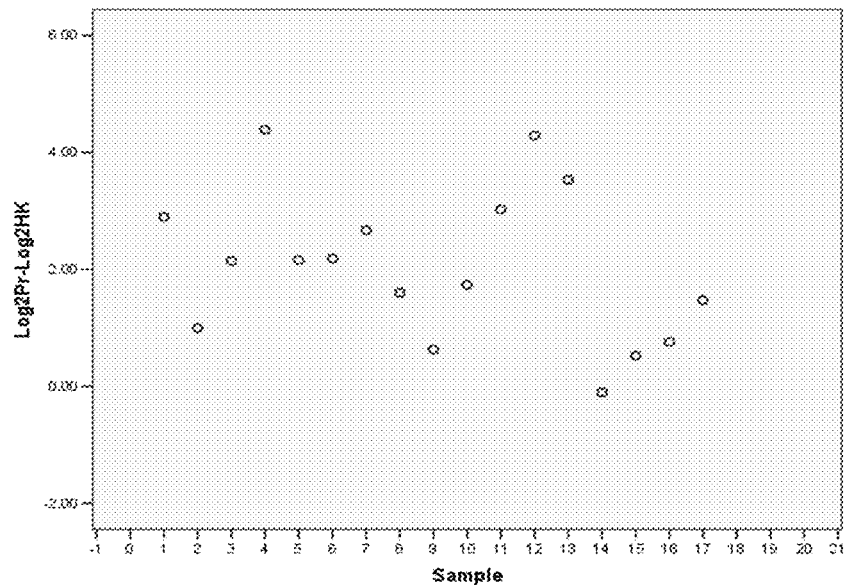
FIGS. 14a and 14b illustrate the results for transcript 12 of the invention in the identification of testicular cancer.
Figure 14A:
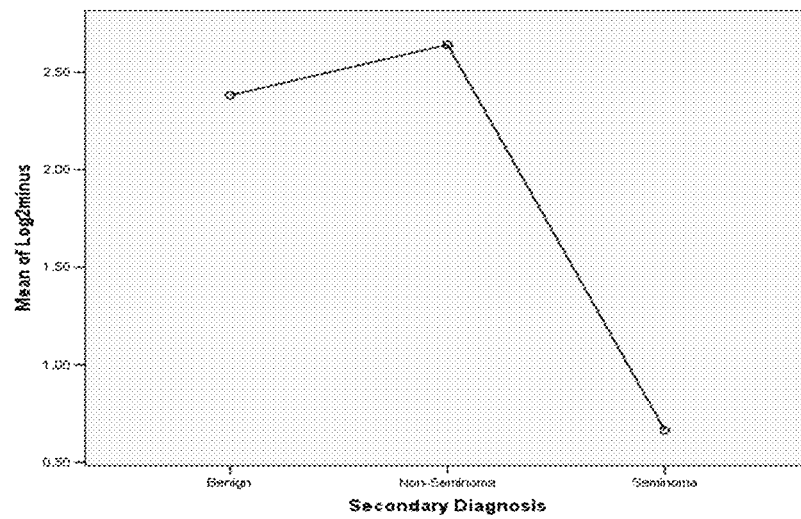
Figure 14B:
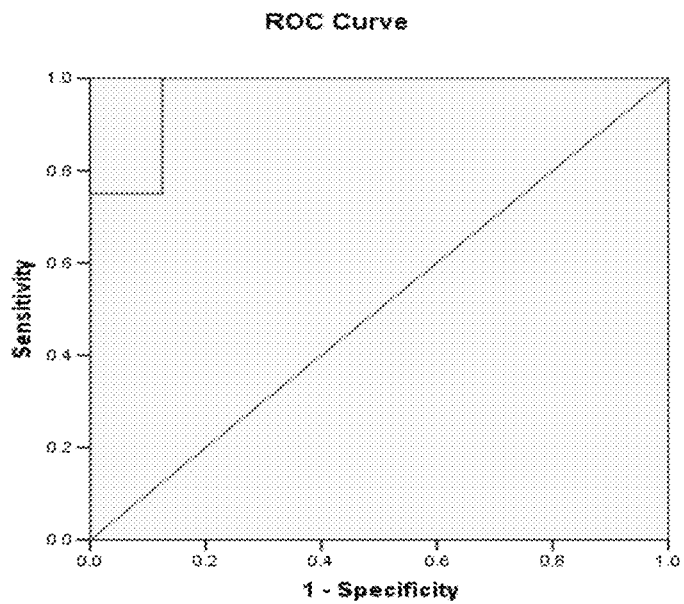
Figure 14B:
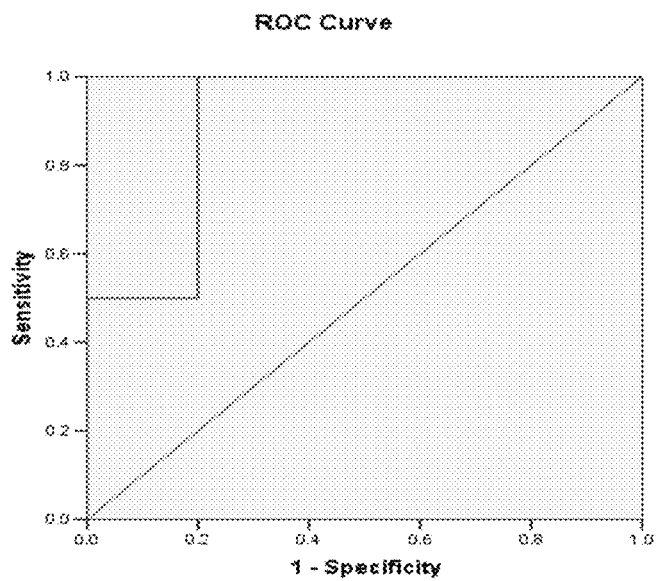
Figure 15A:
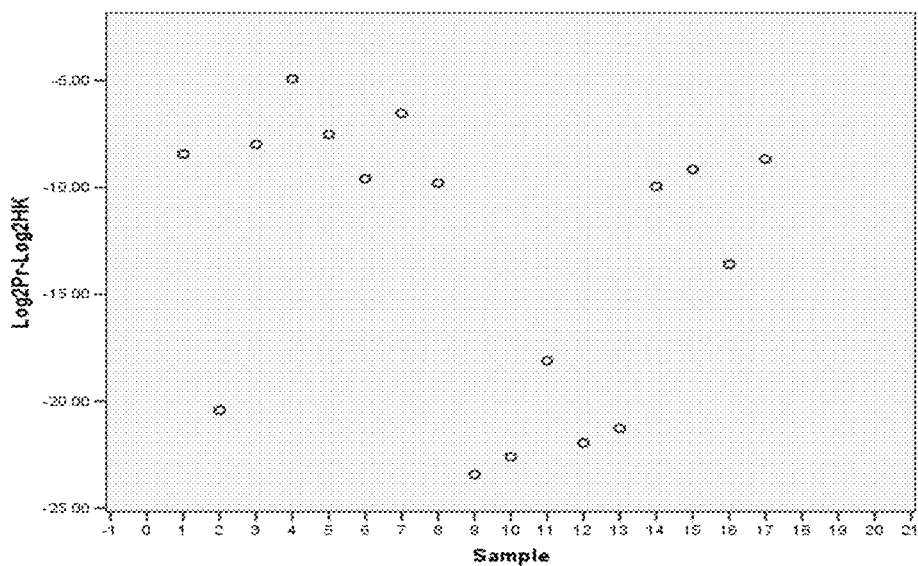
FIGS. 15a and 15b illustrate the results for transcript 13 of the invention in the identification of testicular cancer.
Figure 15A:
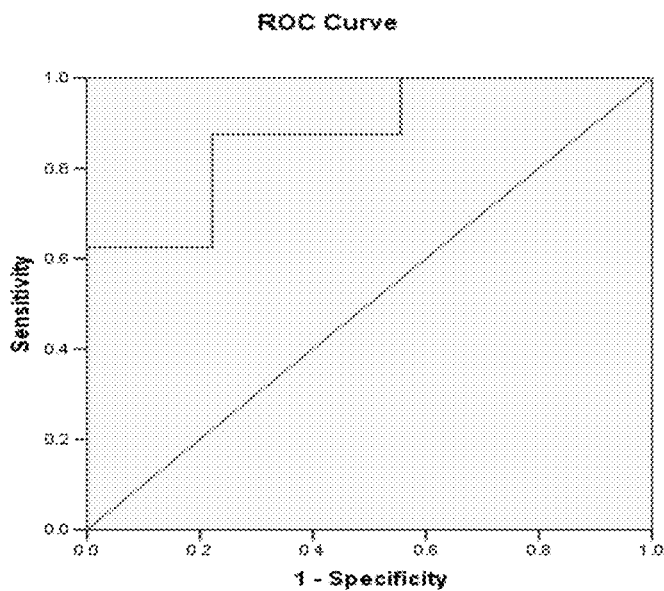
Figure 15A:
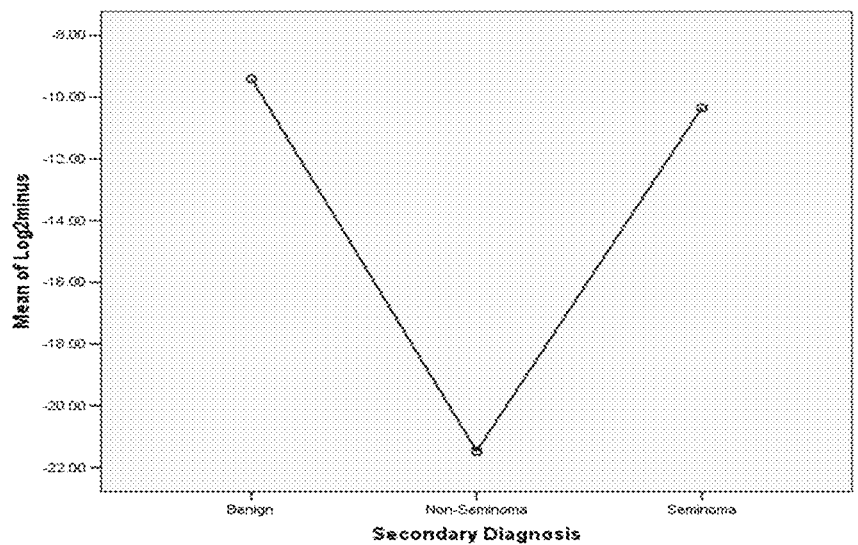
Figure 15B:
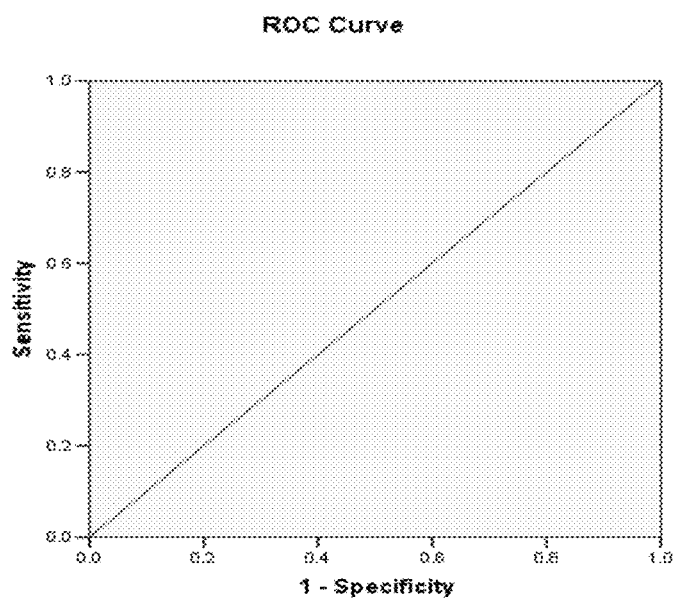
Figure 15B:
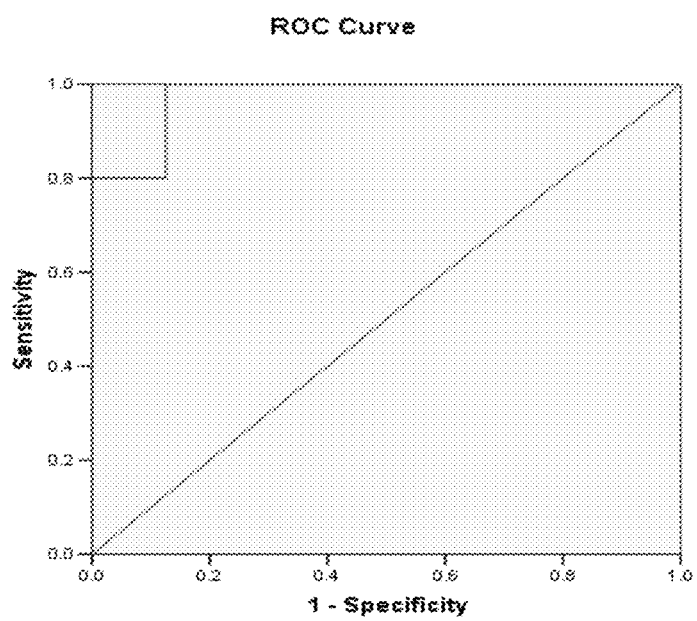
Figure 16:
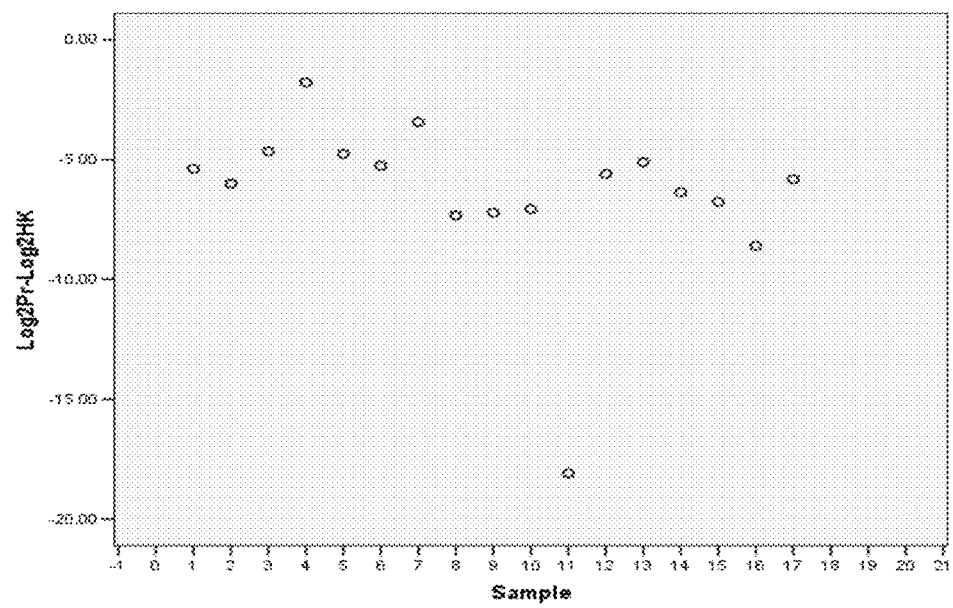
FIG. 16 illustrates the results for transcript 15 of the invention in the identification of testicular cancer.
Figure 16:
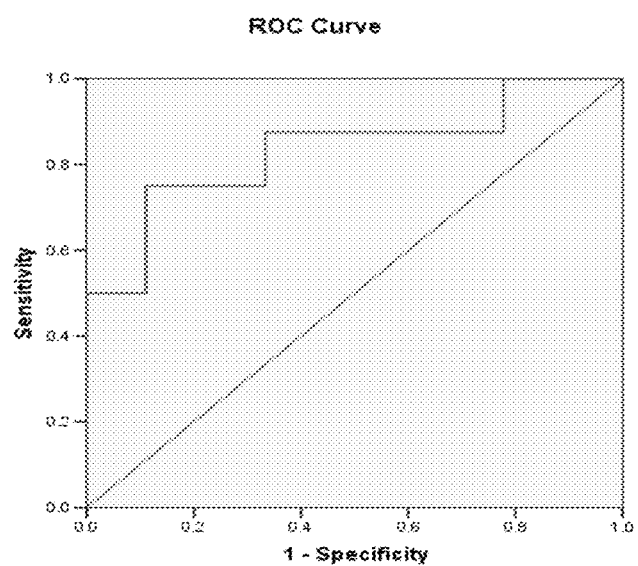
Figure 17A:
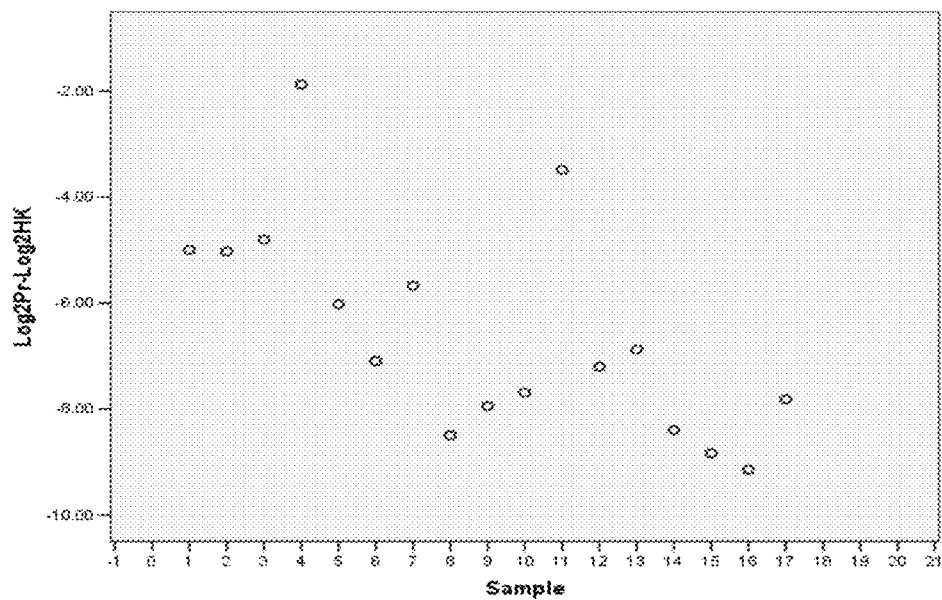
FIGS. 17a and 17b illustrate the results for transcript 16 of the invention in the identification of testicular cancer.
Figure 17A:
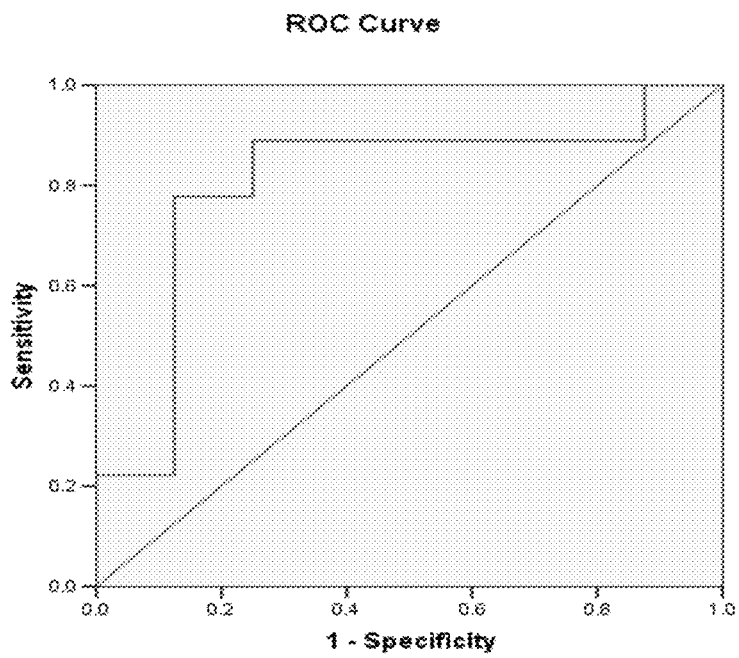
Figure 17A:
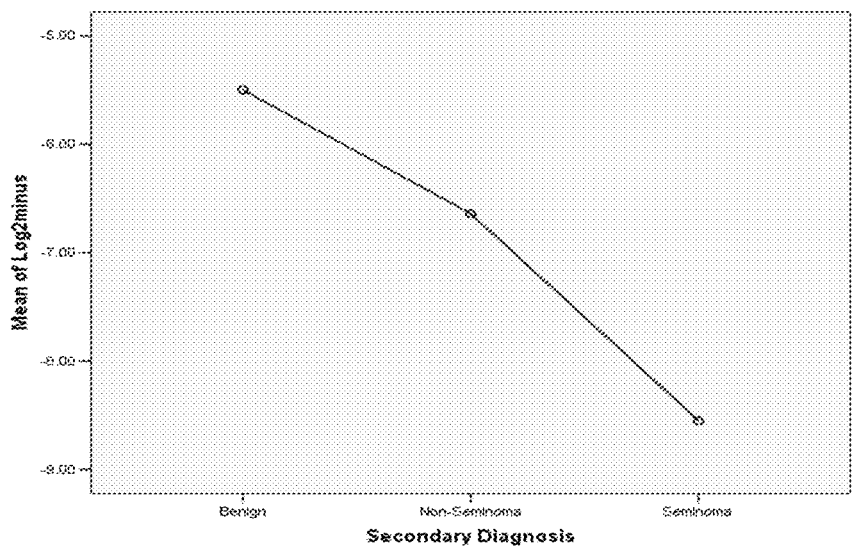
Figure 17B:
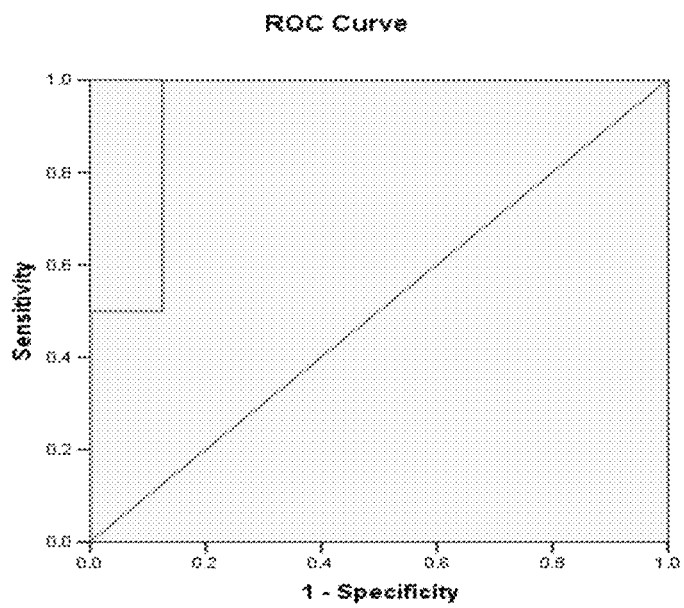
Figure 18B:
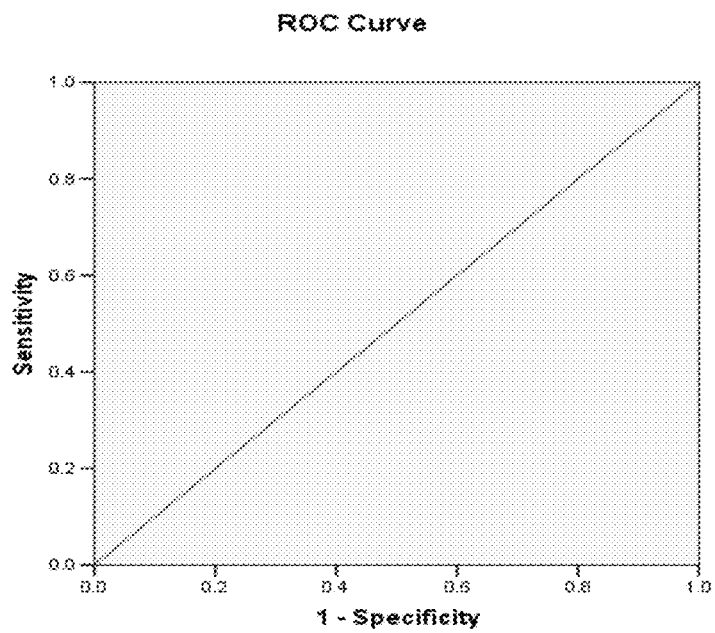
Figure 18B:
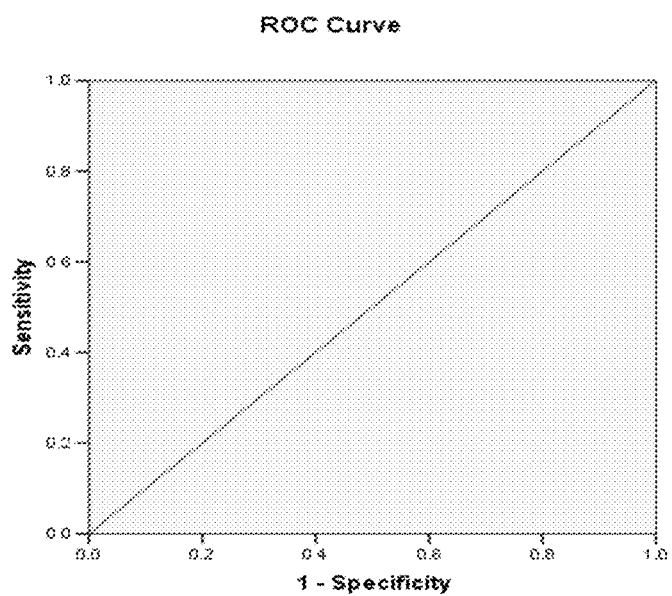

The 3.4 kb deletion results in the removal of the 3' end of ND4L, the full ND4 gene, tRNA histidine, tRNA serine2, tRNA leucine2, and the majority of the 5' end of ND5 (see FIG. 5a), resulting in a gene splice of ND4L and ND5 with a junction point of 10744(ND4L):14124(ND5) (FIG. 5b).

By starting at the original initiation codon of the first gene, ND4L, the amino acid sequence was translated until a termination codon occurs. In this example the termination codon is the original termination codon of ND5. Therefore, despite splicing two genes together, the reading frame is kept intact resulting in a hypothetical or predicted transcript that is 100 amino acids (or 300 bp) in length. This fusion protein transcript product is identified herein as SEQ ID NO: 37. The nucleotide sequence (SEQ ID NO: 3) encoding such protein corresponds to the mitochondrial genome positions of 10470-10744:14124-14148. SEQ ID NO: 3 is the complementary DNA sequence to the RNA transcript (SEQ ID NO: 20) detected in the manner described above.

Similarly, transcript 1 is a fusion transcript between ATPase 8 and ND5 associated with positions 8469:13447

(SEQ ID NO: 19). Transcripts 3 and 4 (SEQ ID NO: 21 and SEQ ID NO: 22, respectively) are fusion transcripts between COII and Cytb associated with nucleotide positions 7974: 15496 and 7992:15730 respectively. Table 3 provides a summary of the relationships between the various sequences used in this example. Table 3 includes the detected fusion transcript, the DNA sequence complementary to the fusion transcript detected and hypothetical translation products for each transcript.

Example 3

Application to Prostate Cancer

Using the four fusion transcripts, i.e. transcripts 1 to 4, discussed above, two prostate tissue samples from one patient were analyzed to assess the quantitative difference of the novel predicted fusion transcripts. The results of the experiment are provided in Table 2 below, wherein "Homog 1" refers to the homogenate of frozen prostate tumour tissue from a patient and "Homog 2" refers to the homogenate of frozen normal prostate tissue adjacent to the tumour of the patient. These samples were processed according to the manufacturer's protocol (*QuantiGene® Sample Processing Kit for Fresh or Frozen Animal Tissues*; and QuantiGene® *2.0 Reagent System User Manual*) starting with 25.8 mg of Homog 1 and 28.9 mg of Homog 2 (the assay setup is shown in Tables 5a and 5b).

Clearly demonstrated is an increased presence of mitochondrial fusion transcripts in prostate cancer tissue compared to normal adjacent prostate tissue. The fusion transcript is present in the normal tissue, although at much lower levels. The relative luminescence units (RLU) generated by hybridization of a probe to a target transcript are directly proportional to the abundance of each transcript. Table 2 also indicates the coefficients of variation, CV, expressed as a percentage, of the readings taken for the samples. The CV comprises the Standard deviation divided by the average of the values. The significance of such stably transcribed mitochondrial gene products in cancer tissue has implications in disease evolution and progression.

Example 4

Application to Breast Cancer

Using the same protocol from Example 3 but focusing only on Transcript 2, the novel fusion transcript associated with the 3.4 kb mtgenome deletion, analyses were conducted on two samples of breast tumour tissue and two samples of tumour-free tissues adjacent to those tumours, as well as three samples of prostate tumour tissue, one sample comprising adjacent tumour-free tissue. Results for this example are provided in Table 4. The prostate tumour tissue sample having a corresponding normal tissue section demonstrated a similar pattern to the prostate sample analyzed in Example 3 in that the tumour tissue had approximately 2 times the amount of the fusion transcript than did the normal adjacent tissue. The breast tumour samples demonstrated a marked increase in the fusion transcript levels when compared to the adjacent non-tumour tissues. A 1:100 dilution of the homogenate was used for this analysis as it performed most reproducibly in the experiment cited in Example 3.

Thus, the above discussed results illustrate the application of the transcripts of the invention in the detection of tumours of both prostate and breast tissue.

Example 5

Application to Colorectal Cancer

This study sought to determine the effectiveness of several transcripts of the invention in detecting colorectal cancer. A total of 19 samples were prepared comprising nine control (benign) tissue samples (samples 1 to 9) and ten tumour (malignant) tissue samples (samples 10 to 19). The samples were homogenized according to the manufacturer's recommendations (Quantigene® Sample Processing Kit for Fresh or Frozen Animal Tissues; and Quantigene 2.0 Reagent System User Manual). Seven target transcripts and one housekeeper transcript were prepared in the manner as outlined above in previous examples. The characteristics of the transcripts are summarized as follows:

TABLE 7

Characteristics of Breast Cancer Transcripts

| Transcript ID | Junction Site | Gene Junction |
|---|---|---|
| 2 | 10744:14124 | ND4L:ND5 |
| 3 | 7974:15496 | COII:Cytb |
| 10 | 7438:13476 | COI:ND5 |
| 11 | 7775:13532 | COII:ND5 |
| 12 | 8213:13991 | COII:ND5 |
| Peptidylpropyl isomerase B (PPIB) ("housekeeper") | N/A | N/A |

It is noted that transcripts 2 and 3 are the same as those discussed above with respect to Examples 3 and 4.

Homogenates were prepared using approximately 25 mg of tissue from OCT blocks and diluted 1:1 for transcripts 2 and 4, and 1:8 for transcripts 10 and 11. The quantity of the transcripts was measured in Relative Luminescence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2 a$ RLU-$\log_2 h$ RLU where a is the target fusion transcript and h is the housekeeper transcript.

The analysis of the data comprised the following steps:
a) Establish CV's (coefficients of variation) for triplicate assays; acceptable if ≤15%.
b) Establish average RLU value for triplicate assays of target fusion transcript (a) and housekeeper transcript (h).
c) Establish lower limit from triplicate value of background RLU (I).
d) Subtract lower limit (I) from (a).
e) Calculate log 2 a RLU-log 2 h RLU.

Summary of Results:

The results of the above analysis are illustrated in FIGS. 6a to 6g, which comprise plots of the $\log_2 a$ RLU-$\log_2 h$ RLU against sample number. Also illustrated are the respective ROC (Receiver Operating Characteristic) curves determined from the results for each transcript.

Transcript 2: There exists a statistically significant difference between the means (p<0.10) of the normal and malignant groups (p>0.09), using a cutoff value of 3.6129 as demonstrated by the ROC curve results in a sensitivity of 60% and specificity of 89% and the area under the curve is 0.73 indicating fair test accuracy. The threshold value chosen may be adjusted to increase either the specificity or sensitivity of the test for a particular application.

Transcript 3: There exists a statistically significant difference between the means (p<0.05) of the normal and malignant groups (p=0.03), using a cutoff value of 4.0813 as demonstrated by the ROC curve results in a sensitivity of 60% and specificity of 78% and the area under the curve is 0.79 indicating fair to good test accuracy. The threshold value chosen may be adjusted to increase either the specificity or sensitivity of the test for a particular application.

Transcript 8: There exists a statistically significant difference between the means (p<0.1) of the normal and malignant groups (p=0.06). Using a cutoff value of −6.0975 as demonstrated by the ROC curve results in a sensitivity of 60% and specificity of 89% and the area under the curve is 0.76 indicating fair test accuracy. The threshold value chosen may be adjusted to increase either the specificity or sensitivity of the test for a particular application.

Transcript 9: There exists a statistically significant difference between the means (p<0.1) of the normal and malignant groups (p=0.06). Using a cutoff value of −7.5555 as demonstrated by the ROC curve results in a sensitivity of 60% and specificity of 89% and the area under the curve is 0.76 indicating fair to good test accuracy. The threshold value chosen may be adjusted to increase either the specificity or sensitivity of the test for a particular application.

Transcript 10: There is a statistically significant difference between the means (p≤0.01) of the normal and malignant groups (p=0.01). Using a cutoff value of −3.8272 as demonstrated by the ROC curve results in a sensitivity of 90% and specificity of 67% and the area under the curve is 0.84, indicating good test accuracy. The threshold value chosen may be adjusted to increase either the specificity or sensitivity of the test for a particular application.

Transcript 11: There exists a statistically significant difference between the means (p<0.1) of the normal and malignant groups (p=0.06), using a cutoff value of 3.1753 as demonstrated by the ROC curve results in a sensitivity of 70% and specificity of 78% and the area under the curve is 0.76 indicating fair to good test accuracy. The threshold value chosen may be adjusted to increase either the specificity or sensitivity of the test for a particular application.

Transcript 12: There exists a statistically significant difference between the means (p<0.1) of the normal and malignant groups (p=0.06), using a cut-off value of 3.2626 as demonstrated by the ROC curve results in a sensitivity of 70% and specificity of 78% and the area under the curve is 0.76 indicating fair to good test accuracy. The threshold value chosen may be adjusted to increase either the specificity or sensitivity of the test for a particular application.

Conclusions:

The above results illustrate the utility of transcripts 2, 3, 8, 9, 10, 11, and 12 in the detection of colorectal cancer and in distinguishing malignant from normal colorectal tissue. As indicated above, transcripts 2 and 3 were also found to have utility in the detection of prostate cancer. Transcript 2 was also found to have utility in the detection of breast cancer. Transcript 11 was also found to have utility in the detection of melanoma skin cancer. Transcript 10 was also found to have utility in the detection of lung cancer and melanoma. Transcript 8 was also found to have utility in the detection of lung cancer. Any of the 7 transcripts listed may be used individually or in combination as a tool for the detection of characterization of colorectal cancer in a clinical setting.

Example 6

Application to Lung Cancer

This study sought to determine the effectiveness of several transcripts of the invention in the detection of lung cancer. As in Example 5, nine control (benign) tissue samples (samples 1 to 9) and ten tumour (malignant) tissue samples (samples 10 to 19) were homogenized according to the manufacturer's recommendations (Quantigene® Sample Processing Kit for Fresh or Frozen Animal Tissues; and Quantigene 2.0 Reagent System User Manual). Homogenates were diluted 1:8 and the quantity of 4 target transcripts and 1 housekeeper transcript was measured in Relative Luminescence Units RLU on a Glomax™ Multi Detection System (Promega). All samples were assayed in triplicate for each transcript. Background measurements (no template) were done in triplicate as well.

The following transcripts were prepared for this example:

TABLE 8

Characteristics of Lung Cancer Transcripts

| Transcript ID | Junction Site | Gene Junction |
|---|---|---|
| 6 | 8828:14896 | ATPase6:Cytb |
| 8 | 6075:13799 | COI:ND5 |
| 10 | 7438:13476 | COI:ND5 |
| 20 | 8469:13447 | ATPase8:ND5 |
| Peptidylpropyl isomerase B (PPIB) ("housekeeper") | N/A | N/A |

The tissue samples used in this example had the following characteristics:

TABLE 9

Characteristics of Lung Cancer Samples

| Sample | Malignant | Comments (source of tissue) |
|---|---|---|
| 1 | NO | interstitial lung disease |
| 2 | NO | emphysema |
| 3 | NO | aneurysm |
| 4 | NO | bronchopneumonia, COPD |
| 5 | NO | malignant neoplasm in liver, origin unknown, calcified granulomas in lung |
| 6 | NO | 12 hours post mortem, mild emphysema |
| 7 | NO | 12 hours post mortem, large B cell lymphoma, pulmonary edema, pneumonia |
| 8 | NO | pneumonia, edema, alveolar damage |
| 9 | NO | congestion and edema |
| 10 | YES | adenocarcinoma, non-small cell |
| 11 | YES | small cell |
| 12 | YES | squamous cell carcinoma, NSC, emphysema |
| 13 | YES | adenocarcinoma, lung cancer, nsc, metastatic |
| 14 | YES | squamous cell carcinoma, non-small cell |
| 15 | YES | mixed squamous and adenocarcinoma |
| 16 | YES | non-small cell carcinoma, squamous |
| 17 | YES | small cell carcinoma |
| 18 | YES | adenocarcinoma, lung cancer, nsc |
| 19 | YES | adenocarcinoma, lung cancer, nsc, metastatic |

The analysis of data was performed according to the method described in Example 5. The results are illustrated in FIGS. 7a, 7b, 7c and 7d.

Summary of Results:

Transcript 6: There exists a statistically significant difference between the means (p<0.1) of the normal (benign) and malignant groups (p=0.06), using a cutoff value of −6.5691 as demonstrated by the ROC curve results in a sensitivity of 80% and specificity of 71% and the area under the curve is 0.77, indicating fair test accuracy. The threshold value chosen may be adjusted to increase either the specificity or sensitivity of the test for a particular application.

Transcript 8: The difference between the means of the normal and malignant groups is statistically significant, p<0.05 (p=0.02). Using a cutoff value of −9.6166 as demonstrated by the ROC curve results in a sensitivity of 90% and specificity of 86% and the area under the curve is 0.86 indicating good test accuracy. The threshold value chosen may be adjusted to increase either the specificity or sensitivity of the test for a particular application.

Transcript 10: The difference between the means of the normal and malignant groups is statistically significant, $p\leq0.01$ (p=0.01). Using a cutoff value of −10.6717 as demonstrated by the ROC curve results in a sensitivity of 90% and specificity of 86% and the area under the curve is 0.89 indicating good test accuracy. The threshold value chosen may be adjusted to increase either the specificity or sensitivity of the test for a particular application.

Transcript 20: The difference between the means of the normal and malignant groups is statistically significant, $p\leq0.1$ (p=0.1). Using a cutoff value of 2.5071 as demonstrated by the ROC curve results in a sensitivity of 70% and specificity of 71% and the area under the curve is 0.74 indicating fair test accuracy. The threshold value chosen may be adjusted to increase either the specificity or sensitivity of the test for a particular application.

Conclusions:

The results from example 6 illustrate the utility of transcripts 6, 8, 10, and 20 of the invention in the detection of lung cancer tumours and the distinction between malignant and normal lung tissues. Any of these three transcripts may be used for the detection or characterization of lung cancer in a clinical setting.

Example 7

Application to Melanoma

This study sought to determine the effectiveness of several transcripts of the invention in the detection of melanomas. In this study a total of 14 samples were used, comprising five control (benign) tissue samples and nine malignant tissue samples. All samples were formalin fixed, paraffin embedded (FFPE). The FFPE tissue samples were sectioned into tubes and homogenized according to the manufacturer's recommendations (Quantigene® 2.0 Sample Processing Kit for FFPE Samples; and Quantigene 2.0 Reagent System User Manual) such that each sample approximated 20 microns prior to homogenization. Homogenates were diluted 1:4 and the quantity of 7 target transcripts and 1 housekeeper transcript was measured in Relative Luminescence Units RLU on a Glomax™ Multi Detection System (Promega). All samples were assayed in triplicate for each transcript. Background measurements (no template) were done in triplicate as well.

The 14 tissue samples used in this example had the following characteristics:

TABLE 10

Characteristics of Melanoma Cancer Samples

| Sample | Malignant | Comments (source of tissue) |
|---|---|---|
| 1 | NO | breast reduction tissue (skin) |
| 2 | NO | breast reduction tissue (skin) |
| 3 | NO | breast reduction tissue (skin) |
| 4 | NO | breast reduction tissue (skin) |
| 5 | NO | breast reduction tissue (skin) |
| 6 | YES | lentigo maligna, (melanoma in situ) invasive melanoma not present |
| 7 | YES | invasive malignant melanoma |
| 8 | YES | nodular melanoma, pT3b, associated features of lentigo maligna |
| 9 | YES | residual superficial spreading invasive malignant melanoma, Clark's level II |
| 10 | YES | superficial spreading malignant melanoma, Clark's Level II |
| 11 | YES | nodular malignant melanoma, Clark's level IV |
| 12 | YES | superficial spreading malignant melanoma in situ, no evidence of invasion |
| 13 | YES | superficial spreading malignant melanoma, Clark's level II, focally present vertical phase |
| 14 | YES | superficial spreading malignant melanoma in situ, Clark's level I |

The following transcripts were prepared for this example:

TABLE 11

Characteristics of Melanoma Cancer Transcripts

| Transcript ID | Junction Site | Gene Junction |
|---|---|---|
| 6 | 8828:4896 | ATPase6:Cytb |
| 10 | 7438:13476 | COI:ND5 |
| 11 | 7775:13532 | COII:ND5 |
| 14 | 9191:12909 | ATPase6:ND5 |
| 15 | 9574:12972 | COIII:ND5 |
| 16 | 10367:12829 | ND3:ND5 |
| 20 | 8469:13447 | ATPase8:ND5 |
| Peptidylpropyl isomerase B (PPIB) ("housekeeper") | N/A | N/A |

As indicated, transcripts 10 and 11 were also used in Example 5. The analysis of data was performed according to the method described in Example 5. The results are illustrated in FIGS. 8a-8g.

Summary of Results:

Transcript 6: There exists a statistically significant difference between the means ($p\leq0.01$) of the normal and malignant groups (p=0.01). Further, using a cutoff value of −5.9531 as demonstrated by the ROC curve results in a sensitivity of 89% and specificity of 80% and the area under the curve is 0.96, indicating very good test accuracy. The threshold value chosen may be adjusted to increase either the specificity or sensitivity of the test for a particular application.

Transcript 10: There exists a statistically significant difference between the means ($p\leq00.05$) of the normal and malignant groups (p=0.05), using a cutoff value of −4.7572 as demonstrated by the ROC curve results in a sensitivity of 89% and specificity of 40% and the area under the curve is 0.82, indicating good test accuracy. The threshold value chosen may be adjusted to increase either the specificity or sensitivity of the test for a particular application.

Transcript 11: There exists a statistically significant difference between the means ($p<0.05$) of the normal and malignant groups (p=0.02). Further, using a cutoff value of 1.6762 as demonstrated by the ROC curve results in a sensitivity of 78% and specificity of 100% and the area under the curve is 0.89, indicating good test accuracy. The threshold value chosen may be adjusted to increase either the specificity or sensitivity of the test for a particular application.

Transcript 14: There exists a statistically significant difference between the means ($p\leq0.05$) of the normal and malignant groups (p=0.05). Further, using a cutoff value of −4.9118 as demonstrated by the ROC curve results in a sensitivity of 89% and specificity of 60% and the area under the curve is 0.82, indicating good test accuracy. The threshold value chosen may be adjusted to increase either the specificity or sensitivity of the test for a particular application.

Transcript 15: There exists a statistically significant difference between the means (p<0.1) of the normal and malignant groups (p=0.07), using a cutoff value of −7.3107 as demonstrated by the ROC curve results in a sensitivity of 100% and specificity of 67% and the area under the curve is 0.80, indicating good test accuracy. The threshold value chosen may be adjusted to increase either the specificity or sensitivity of the test for a particular application.

Transcript 16: There exists a statistically significant difference between the means (p<0.05) of the normal and malignant groups (p=0.03). Further, using a cutoff value of −10.5963 as demonstrated by the ROC curve results in a sensitivity of 89% and specificity of 80% and the area under the curve is 0.878, indicating good test accuracy. The threshold value chosen may be adjusted to increase either the specificity or sensitivity of the test for a particular application.

Transcript 20: There exists a statistically significant difference between the means (p<0.05) of the normal and malignant groups (p=0.04). Further, using a cutoff value of −8.3543 as demonstrated by the ROC curve results in a sensitivity of 100% and specificity of 80% and the area under the curve is 0.89, indicating good test accuracy. The threshold value chosen may be adjusted to increase either the specificity or sensitivity of the test for a particular application.

Conclusions:

The results from example 7 illustrate the utility of transcripts 6, 10, 11, 14, 15, 16 and 20 of the invention in the detection of malignant melanomas. As indicated above, transcripts 10 and 11 were also found have utility in detecting colorectal cancer while transcript 6 has utility in the detection of lung cancer. A transcript summary by disease is provided at Table 6.

Example 8

Application to Ovarian Cancer

This study sought to determine the effectiveness of several transcripts of the invention in detecting ovarian cancer. A total of 20 samples were prepared comprising ten control (benign) tissue samples (samples 1 to 10) and ten tumour (malignant) tissue samples (samples 11 to 20). The samples were homogenized according to the manufacturer's recommendations (Quantigene® Sample Processing Kit for Fresh or Frozen Animal Tissues; and Quantigene 2.0 Reagent System User Manual). Eight target transcripts and one housekeeper transcript were prepared in the manner as outlined above in previous examples.

The 20 tissue samples used in this example had the following characteristics:

TABLE 12

Characteristics of Ovarian Cancer Samples

| Sample | Diagnosis | Comments |
| --- | --- | --- |
| 1 | Normal | follicular cyst |
| 2 | Normal | fibroma |
| 3 | Normal | No pathological change in ovaries |
| 4 | Normal | follicular cysts |
| 5 | Normal | cellular fibroma |
| 6 | Normal | benign follicular and simple cysts |
| 7 | Normal | leiomyomata, corpora albicantia |
| 8 | Normal | copora albicantia and an epithelial inclusions cysts |
| 9 | Normal | corpora albicantia |
| 10 | Normal | corpora albicantia, surface inclusion cysts, follicullar cysts |
| 11 | Malignant | high grade poorly differentiated papillary serous carcinoma involving omentum |
| 12 | Malignant | endometrioid adenocarcinoma, well to moderately differentiated with focal serous differentiation |
| 13 | Malignant | papillary serous carcinoma |
| 14 | Malignant | mixed epithelial carcinoma predominantly papillary serous carcinoma |
| 15 | Malignant | High grade: serous carcinoma, papillary and solid growth patterns |
| 16 | Malignant | High Grade (3/3) Papillary serous carcinoma |
| 17 | Malignant | papillary serous carcinoma, high nuclear grade |
| 18 | Malignant | Papillary serous cystadenocarcinomas Grade:III |
| 19 | Malignant | poorly differentiated papillary serous carcinoma |
| 20 | Malignant | Well-differentiated adnocarcinoma, Endometrioid type, Grade 1 |

The characteristics of the transcripts are summarized as follows:

TABLE 13

Characteristics of Ovarian Cancer Transcripts

| Transcript ID | Junction Site | Gene Junction |
| --- | --- | --- |
| 1 | 8469:13447 | ATPase8:ND5 |
| 2 | 10744:14124 | ND4L:ND5 |
| 3 | 7974:15496 | COII:Cytb |
| 6 | 8828:14896 | ATPase6:Cytb |
| 11 | 7775:13532 | COII:ND5 |
| 12 | 8213:13991 | COII:ND5 |
| 15 | 9574:12972 | COIII:ND5 |
| 20 | 8469:13447 | ATPase8:ND5 |
| Ribosomal Protein Large PO (LRP) Housekeeper | N/A | N/A |

It is noted that transcripts 1, 2, 3, 6, 11, 12, 15 and 20 are the same as those discussed above with respect to Examples 3-7.

Homogenates were prepared using approximately 25 mg of frozen tissue and diluted 1:4. The quantity of the transcripts was measured in Relative Luminescence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2$ a RLU-$\log_2$ h RLU where a is the target fusion transcript and h is the housekeeper transcript.

The analysis of the data comprised the following steps:
a) Establish CV's (coefficients of variation) for triplicate assays; acceptable if ≤15%.
b) Establish average RLU value for triplicate assays of target fusion transcript (a) and housekeeper transcript (h).
c) Establish lower limit from triplicate value of background RLU (I).
d) Subtract lower limit (I) from (a).
e) Calculate $\log_2$ a RLU-$\log_2$ h RLU.

Summary of Results:

The results of the above analysis are illustrated in FIGS. 9a to 9h, which comprise plots of the $\log_2$ a RLU-$\log_2$ h RLU against sample number. Also illustrated are the respective ROC (Receiver Operating Characteristic) curves determined from the results for each transcript.

Transcript 1: There exists a statistically significant difference between the means (p<0.05) of the normal and malignant groups (p=0.002). Using a cutoff value of −11.1503 as demonstrated by the ROC curve results in a sensitivity of 90% and specificity of 80% and the area under the curve is 0.91 indicating very good test accuracy. The threshold value chosen may be adjusted to increase either the specificity or sensitivity of the test for a particular application.

Transcript 2: There exists a statistically significant difference between the means (p<0.01) of the normal and malignant groups (p=0.001). Using a cutoff value of 0.6962 as demonstrated by the ROC curve results in a sensitivity of 90% and specificity of 100% and the area under the curve is 0.96 indicating very good test accuracy. The threshold value chosen may be adjusted to increase either the specificity or sensitivity of the test for a particular application.

Transcript 3: There exists a statistically significant difference between the means (p<0.01) of the normal and malignant groups (p=0.000). Using a cutoff value of 0.6754 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Transcript 6: There exists a statistically significant difference between the means (p<0.01) of the normal and malignant groups (p=0.007). Using a cutoff value of −9.6479 as demonstrated by the ROC curve results in a sensitivity of 90% and specificity of 70% and the area under the curve is 0.86 indicating good test accuracy. The threshold value chosen may be adjusted to increase either the specificity or sensitivity of the test for a particular application.

Transcript 11: There is a statistically significant difference between the means (p<0.01) of the normal and malignant groups (p=0.000). Using a cutoff value of −1.3794 demonstrated by the ROC curve results in a sensitivity of 100% and specificity of 90% and the area under the curve is 0.99, indicating excellent test accuracy. The threshold value chosen may be adjusted to increase either the specificity or sensitivity of the test for a particular application.

Transcript 12: There exists a statistically significant difference between the means (p<0.01) of the normal and malignant groups (p=0.001). Using a cutoff value of −1.2379 as demonstrated by the ROC curve results in a sensitivity of 90% and specificity of 100% and the area under the curve is 0.96 indicating excellent test accuracy. The threshold value chosen may be adjusted to increase either the specificity or sensitivity of the test for a particular application.

Transcript 15: There exists a statistically significant difference between the means (p<0.05) of the normal and malignant groups (p=0.023). Using a cut-off value of −8.6926 as demonstrated by the ROC curve results in a sensitivity of 70% and specificity of 80% and the area under the curve is 0.80 indicating good test accuracy. The threshold value chosen may be adjusted to increase either the specificity or sensitivity of the test for a particular application.

Transcript 20: There exists a statistically significant difference between the means (p<0.01) of the normal and malignant groups (p=0.000). Using a cut-off value of 0.6521 as demonstrated by the ROC curve results in a sensitivity of 100% and specificity of 100% and the area under the curve is 0.76 indicating fair to good test accuracy. The threshold value chosen may be adjusted to increase either the specificity or sensitivity of the test for a particular application.

Conclusions:
The above results illustrate the utility of transcripts 1, 2, 3, 6, 11, 12, 15, and 20 in the detection of ovarian cancer and in distinguishing malignant from normal ovarian tissue. Transcripts 1, 2 and 3 were also found to have utility in the detection of prostate cancer. Transcript 6 was also found to have utility in the detection of melanoma and lung cancer. Transcript 11 was also found to have utility in the detection of melanoma skin cancer, colorectal cancer and testicular cancer. Transcript 12 was also found to have utility in the detection of colorectal cancer and testicular cancer. Transcript 15 was also found to have utility in the detection of melanoma and testicular cancer. Transcript 20 was also found to have utility in the detection of colorectal cancer, melanoma, and testicular cancer. Any of the 8 transcripts listed may be used individually or in combination as a tool for the detection or characterization of ovarian cancer in a clinical setting.

Example 9

Application to Testicular Cancer

This study sought to determine the effectiveness of several transcripts of the invention in detecting testicular cancer. A total of 17 samples were prepared comprising eight control (benign) tissue samples (samples 1 to 8) and 9 tumour (malignant) tissue samples (samples 9 to 17), 5 of the malignant samples were non-seminomas (samples 9-13) and 4 were seminomas (samples 14-17). The samples were homogenized according to the manufacturer's recommendations (Quantigene® Sample Processing Kit for Fresh or Frozen Animal Tissues; and Quantigene 2.0 Reagent System User Manual). 10 target transcripts and one housekeeper transcript were prepared in the manner as outlined above in previous examples.

The 17 tissue samples used in this example had the following characteristics:

TABLE 14

Characteristics of Testicular Cancer Samples

| Sample | General Diagnosis | Stratified Malignant Diagnosis |
|---|---|---|
| 1 | Benign | Benign |
| 2 | Benign | Benign |
| 3 | Benign | Benign |
| 4 | Benign | Benign |
| 5 | Benign | Benign |
| 6 | Benign | Benign |
| 7 | Benign | Benign |
| 8 | Benign | Benign |
| 9 | Malignant | Non-Seminoma |
| 10 | Malignant | Non-Seminoma |
| 11 | Malignant | Non-Seminoma |
| 12 | Malignant | Non-Seminoma |
| 13 | Malignant | Non-Seminoma |
| 14 | Malignant | Seminoma |
| 15 | Malignant | Seminoma |
| 16 | Malignant | Seminoma |
| 17 | Malignant | Seminoma |

The characteristics of the transcripts are summarized as follows:

TABLE 15

Characteristics of Testicular Cancer Transcripts

| Transcript ID | Junction Site | Gene Junction |
| --- | --- | --- |
| 2 | 10744:14124 | ND4L:ND5 |
| 3 | 7974:15496 | COII:Cytb |
| 4 | 7992:15730 | COII:Cytb |
| 11 | 7775:13532 | COII:ND5 |
| 12 | 8213:13991 | COII:ND5 |
| 13 | 9144:13816 | ATPase6:ND5 |
| 15 | 9574:12972 | COIII:ND5 |
| 16 | 10367:12829 | ND3:ND5 |
| 20 | 8469:13447 | ATPase8:ND5 |
| Peptidylpropyl isomerase B (PPIB) | N/A | N/A |

It is noted that transcripts 2, 3, 4, 11, 12, 15, 16 and 20 are the same as those discussed above with respect to Examples 3-8.

Homogenates were prepared using approximately 25 mg of frozen tissue and diluted 1:4. The quantity of the transcripts was measured in Relative Luminescence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2$ a RLU-$\log_2$ h RLU where a is the target fusion transcript and h is the housekeeper transcript.

The analysis of the data comprised the following steps:

a) Establish CV's (coefficients of variation) for triplicate assays; acceptable if ≤15%.

b) Establish average RLU value for triplicate assays of target fusion transcript (a) and housekeeper transcript (h).

c) Establish lower limit from triplicate value of background RLU (I).

d) Subtract lower limit (I) from (a).

e) Calculate $\log_2$ a RLU-$\log_2$ h RLU.

Summary of Results:

The results of the above analysis are illustrated in FIGS. 10 to 18, which comprise plots of the $\log_2$ a RLU-$\log_2$ h RLU against sample number. Also illustrated are the respective ROC (Receiver Operating Characteristic) curves determined from the results for each transcript.

While some transcripts distinguish between benign and malignant testicular tissue, others demonstrate distinction between the tumour subtypes of seminoma and non-seminoma and/or benign testicular tissue. It is therefore anticipated that combining transcripts from each class will facilitate not only detection of testicular cancer but also classification into subtype of seminoma or non-seminomas.

Transcript 2: There exists a statistically significant difference between the means ($p<0.05$) of the normal group and the malignant seminomas ($p=0.02$). Using a cutoff value of 1.5621 as demonstrated by the ROC curve results in a sensitivity of 100% and specificity of 100% and the area under the curve is 1.00 indicating excellent test accuracy. There also exists a statistically significant difference between the means ($p<0.05$) of the malignant seminomas and the malignant non-seminomas ($p=0.024$). Using a cutoff value of 2.1006 as demonstrated by the ROC curve results in a sensitivity of 100% and specificity of 80% and the area under the curve is 0.90 indicating excellent test accuracy. The threshold value chosen may be adjusted to increase either the specificity or sensitivity of the test for a particular application.

Transcript 3: There exists a statistically significant difference between the means ($p<0.05$) of the normal group and the malignant seminomas ($p=0.018$). Using a cutoff value of 0.969 as demonstrated by the ROC curve results in a sensitivity of 100% and specificity of 87.5% and the area under the curve is 0.969 indicating excellent accuracy. There also exists a statistically significant difference between the means ($p<0.05$) of the malignant seminomas and the malignant non-seminomas ($p=0.017$). Using a cutoff value of 1.8181 as demonstrated by the ROC curve results in a sensitivity of 100% and specificity of 80% and the area under the curve is 0.9 indicating excellent test accuracy. The threshold value chosen may be adjusted to increase either the specificity or sensitivity of the test for a particular application.

Transcript 4: There exists a statistically significant difference between the means ($p<0.05$) of the normal and malignant groups ($p=0.034$). Using a cutoff value of −9.7628 as demonstrated by the ROC curve results in a sensitivity of 67% and specificity of 100% and the area under the curve is 0.833 indicating good test accuracy. The threshold value chosen may be adjusted to increase either the specificity or sensitivity of the test for a particular application.

Transcript 11: There exists a statistically significant difference between the means ($p<0.05$) of the normal group and the malignant seminomas ($p=0.016$). Using a cutoff value of 0.732 as demonstrated by the ROC curve results in a sensitivity of 100% and specificity of 100% and the area under the curve is 1.00 indicating excellent test accuracy. There also exists a statistically significant difference between the means ($p<0.05$) of the malignant seminomas and the malignant non-seminomas ($p=0.016$). Using a cutoff value of 0.9884 as demonstrated by the ROC curve results in a sensitivity of 100% and specificity of 80% and the area under the curve is 0.90 indicating excellent test accuracy. The threshold value chosen may be adjusted to increase either the specificity or sensitivity of the test for a particular application.

Transcript 12: There exists a statistically significant difference between the means ($p<0.1$) of the normal group and the malignant seminomas ($p=0.056$). Using a cutoff value of 1.5361 as demonstrated by the ROC curve results in a sensitivity of 100% and specificity of 87.5% and the area under the curve is 0.969 indicating excellent test accuracy. There also exists a statistically significant difference between the means ($p<0.05$) of the malignant seminomas and the malignant non-seminomas ($p=0.044$). Using a cutoff value of 1.6039 as demonstrated by the ROC curve results in a sensitivity of 100% and specificity of 80% and the area under the curve is 0.9 indicating excellent test accuracy. The threshold value chosen may be adjusted to increase either the specificity or sensitivity of the test for a particular application.

Transcript 13: There exists a statistically significant difference between the means ($p<0.05$) of the normal group and the malignant group ($p=0.019$). Using a cutoff value of −9.8751 as demonstrated by the ROC curve results in a sensitivity of 87.5% and specificity of 78% and the area under the curve is 0.875 indicating very good test accuracy. There also exists a statistically significant difference between the means ($p<0.01$) of the malignant non-seminomas and the benign group ($p=0.000$). Using a cutoff value of −13.9519 as demonstrated by the ROC curve results in a sensitivity of 100% and specificity of 87.5% and the area under the curve is 0.975 indicating excellent test accuracy. There also exists a statistically significant difference between the means ($p<0.01$) of the malignant seminomas and the malignant non-seminomas ($p=0.001$). Using a cutoff value of −15.8501 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Transcript 15: There exists a statistically significant difference between the means (p<0.1) of the normal and malignant groups (p=0.065). Using a cut-off value of −5.4916 as demonstrated by the ROC curve results in a sensitivity of 75% and specificity of 89% and the area under the curve is 0.833 indicating good test accuracy. The threshold value chosen may be adjusted to increase either the specificity or sensitivity of the test for a particular application.

Transcript 16: There exists a statistically significant difference between the means (p<0.05) of the normal and malignant groups including both seminomas and non-seminomas (p=0.037). Using a cut-off value of −6.448 as demonstrated by the ROC curve results in a sensitivity of 89% and specificity of 75% and the area under the curve is 0.806 indicating good test accuracy. There also exists a statistically significant difference between the means (p<0.05) of the normal and malignant seminomas (p=0.037). Using a cut-off value of −7.4575 as demonstrated by the ROC curve results in a sensitivity of 100% and specificity of 87.5% and the area under the curve is 0.938 indicating excellent test accuracy. The threshold value chosen may be adjusted to increase either the specificity or sensitivity of the test for a particular application.

Transcript 20: There exists a statistically significant difference between the means (p<0.01) of the normal group and the malignant seminomas (p=0.006). Using a cutoff value of 1.8364 as demonstrated by the ROC curve results in a sensitivity of 100% and specificity of 100% and the area under the curve is 1.00 indicating excellent test accuracy. There also exists a statistically significant difference between the means (p<0.01) of the malignant seminomas and the malignant non-seminomas (p=0.004). Using a cutoff value of 1.6065 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Conclusions:

The above results illustrate the utility of transcripts 2, 3, 4, 11, 12, 13, 15, 16, and 20 in the detection of testicular cancer, and testicular cancer subtypes, and in distinguishing malignant from normal testicular tissue. Transcript 2 was also found to have utility in the detection of prostate, breast, colorectal and ovarian cancer. Transcript 3 was also found to have utility in the detection of prostate, breast, melanoma, colorectal, and ovarian cancers. Transcript 4 was also found to have utility in the detection of prostate and colorectal cancers. Transcript 11 was also found to have utility in the detection of colorectal, melanoma, and ovarian cancers. Transcript 12 was also found to have utility in the detection of colorectal and ovarian cancers. Transcript 15 was also found to have utility in the detection of melanoma and ovarian cancers. Transcript 16 was also found to have utility in the detection of melanoma skin cancer. Transcript 20 was also found to have utility in the detection of colorectal cancer, melanoma, and ovarian cancer. Any of the 9 transcripts listed may be used individually or in combination as a tool for the detection or characterization of ovarian cancer in a clinical setting.

In one aspect, the invention provides a kit for conducting an assay for determining the presence of cancer in a tissue sample. The kit includes the required reagents for conducting the assay as described above. In particular, the kit includes one or more containers containing one or more hybridization probes corresponding to transcripts 1 to 17, and 20 described above. As will be understood, the reagents for conducting the assay may include any necessary buffers, salts, detection reagents etc. Further, the kit may include any necessary sample collection devices, containers etc. for obtaining the needed tissue samples, reagents or materials to prepare the tissue samples for example by homogenization or nucleic acid extraction, and for conducting the subject assay or assays. The kit may also include control tissues or samples to establish or validate acceptable values for diseased or non-diseased tissues.

Example 10

Detection of Fusion Protein

Cell Lines

The presence of fusion proteins was investigated in two human prostate cell lines. Firstly the normal prostate cell line RWPE-1 (ATCC Cat# CRL-11609), these cells are non tumourigenic in nude mice and were established by infection with human papilloma virus 18 of histologically normal adult human prostate cells. Secondly a tumorigenic cell line WPE1-NA22 were examined (ATCC Cat# CRL-2849). These cells were derived from the RWPE-1 cells following exposure to N-methyl-N-nitrosourea. These cells are tumourogenic in nude mice unlike it's parent cell line RWPE-1.

Both cell lines were grown in Keratinicyte Serum Free Medium (Invitrogen Cat#17005-042), medium is supplemented with bovine pituitary extract and human recombinant epidermal growth factor. Cells were grown to 90% confluence then trypsinised using TrypLE Select (Invitrogen Cat#12563029). Cells were then counted using an automated counting system (Invitrogen Countess Cat#C10227), aliquots were then snap frozen and stored at −80° C.

Protein Extraction

Cell fractions were extracted from both RWPE1 and WPE1-NA22 cell lines using the Qproteome Mitochondria Isolation Kit (Qiagen Cat#37612). Both mitochondrial and cytoplasmic fractions were extracted from $1 \times 10^7$ cells. Protein concentration was then calculated using a fluorescent protein assay (Quant-IT Protein, Invitrogen Cat#Q33211) measured on a Qubit fluorometer (Invitrogen Cat#Q32857).

SDS-Page Gel Electrophoresis

Figure 19:
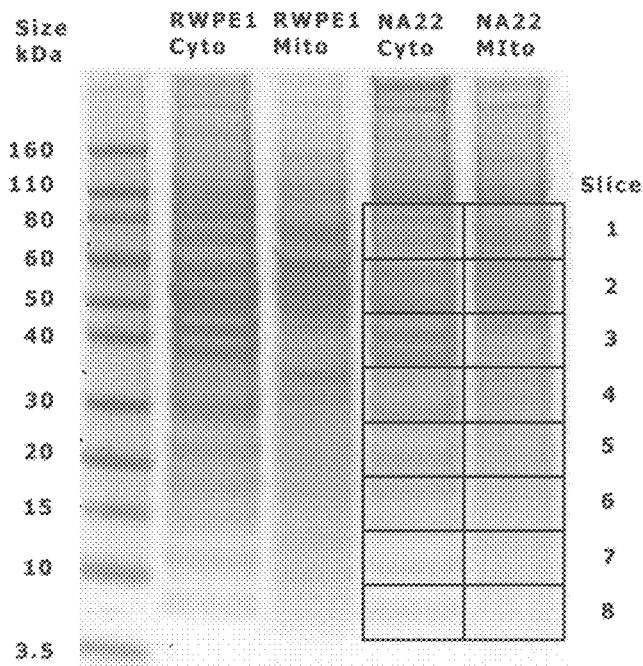
FIG. 19 illustrates the SDS PAGE gel of cytosolic and mitochondrial fractions of RWPE1 and WPE1-NA22 cell lines conducted during the fusion protein discovery phase.

SDS-Page electrophoresis was carried out on mitochondrial and cytosolic fractions prepared using the Qproteome mitochondrial isolation kit. 20 μg of protein was run in each lane on a 4-12% precast (invitrogen Nupage Cat#NP0321) bis-tris gel reducing gel, using a MES running buffer (Invitrogen Cat# NP00020). The gel was stained overnight with colloidal blue gel stain (Invitrogen Cat# LC6025). The results are illustrated in FIG. 19. The approximate size (kD) range of proteins predicted to be contained in each of the 8 gel slices illustrated in FIG. 19 are as follows:

| 1 | 60-80 |
|---|-------|
| 2 | 50-60 |
| 3 | 40-50 |
| 4 | 30-40 |
| 5 | 20-30 |
| 6 | 15-20 |
| 7 | 10-15 |
| 8 | 3.5-10 |

LCMS

Eight gel slices were cut out from each lane of a colloidal blue stained 1D SDS-PAGE (FIG. 19) and in gel digested with trypsin following standard procedures.

The digestion products were eluted form the gel and evaporated. An aliquot was injected onto an LCMS system (Dionex/LC Packings Ultimate3000 coupled online to a Thermo LTQ XL orbitrap) and separated on a 25 cm (75 um ID) PepMap (Dionex) column at a flow rate of 300 ml/min with formic acid as a ion pairing agent and a linear gradient starting at 5% MeCN going to 40% MeCN over 110 min. MS spectra were collected in the orbitrap at a resolution of 60000 (400 Da) and MSMS spectra in the linear ion trap at low resolution.

Data were processed using Thermo Proteome Discoverer to generate .mgf (mascot generic format) peak list files, which were submitted in house to X!Tandem, searching a custom database comprised of the human proteome (ensembl) and predicted fusion proteins based on the fusion transcripts described previously. To calculate a false discovery rate (FDR), the searched database also included the reverse sequence of all proteins.

Protein Complexes Analysis

Upon completion of the X!Tandem custom database search all identified proteins and fusion transcripts were returned. The proteins were scored by their $\log(e)^+$ values and classified as significant when the $\log(e)^+$ was less than negative one, with preference given to proteins with a $\log(e)^+$ less than negative three. Fusion proteins were identified by the presence of at least one peptide from each of the contributing genes of the fusion transcript present in the same gel slice. Protein sequence coverage from the identified peptides by the LC/MS-MS are displayed in red. The sequence of the protein which may be difficult to observe a peptide due to experimental conditions are indicated in green. Finally, protein sequence that is displayed in black represents a neutral possibility of identifying a peptide.

Examples of Identified Fusion Proteins

Many mitochondrial fusion proteins were identified using this methodology. Four of such fusion proteins are described below as representative examples.

Example Fusion Protein 1

Figure 20A:
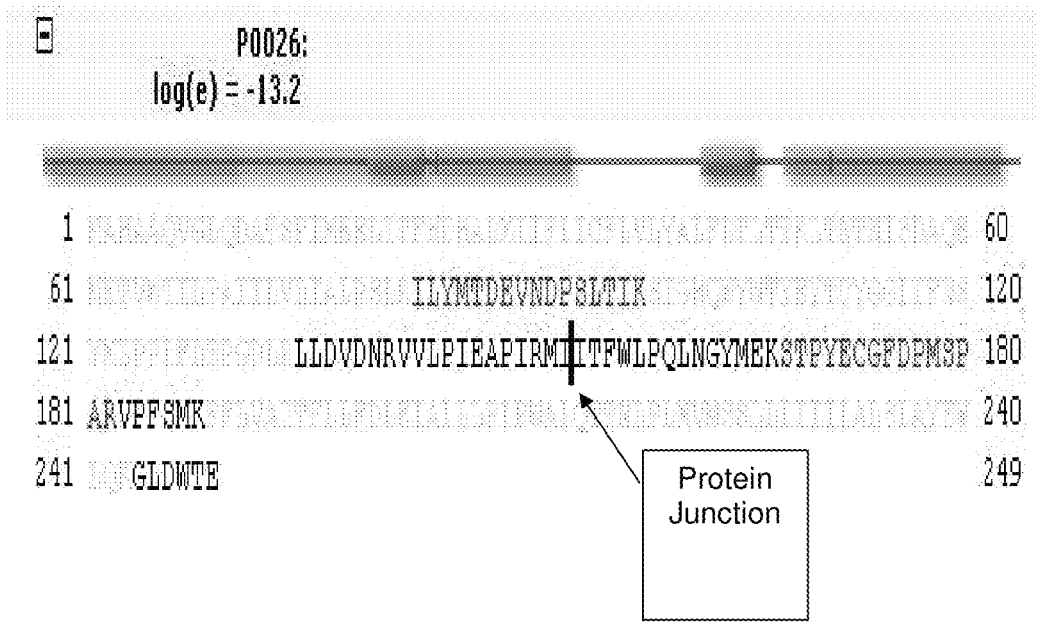
FIG. 20a illustrates the identified protein of fusion transcript P0026 based on the peptides ILYMTDEVNDPSLTIK and STPYECGFDPMSP.
Figure 24A:
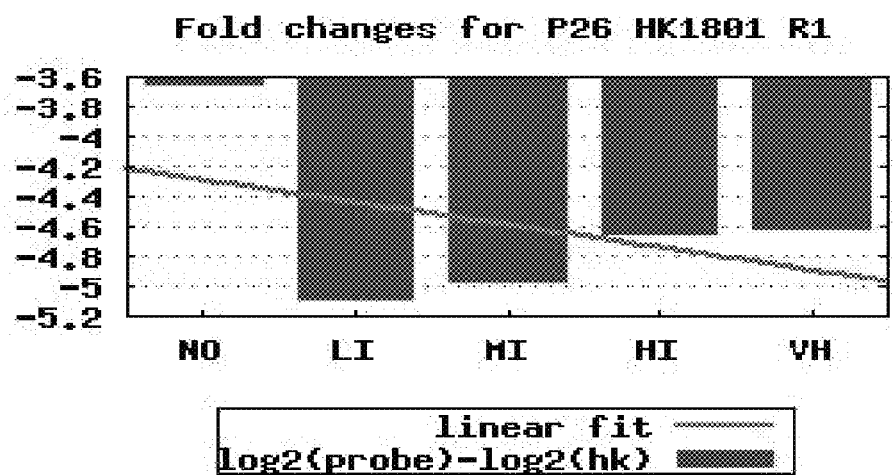
FIGS. 24a to 24d illustrate the results of quantitative measurements of fusion transcripts P0026, P0062, P0064 and P0176, respectively.
Figure 24B:
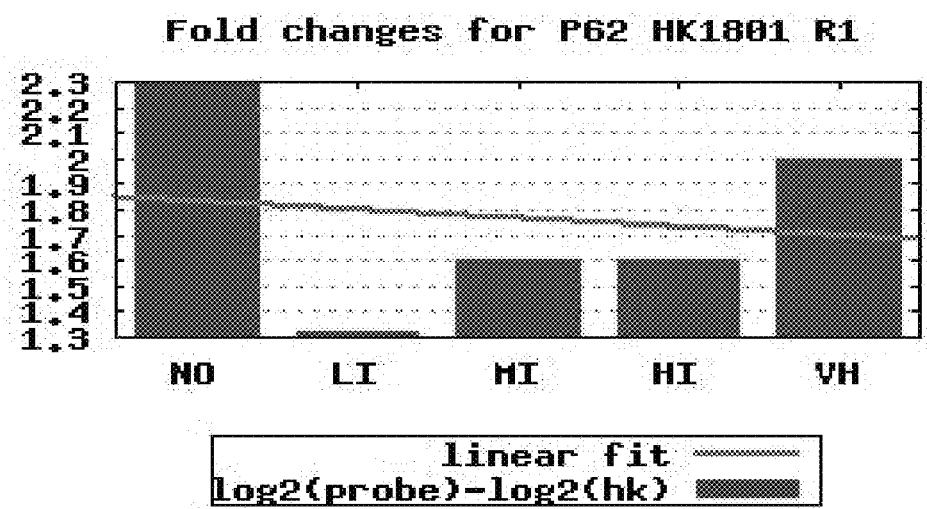
Figure 24C:
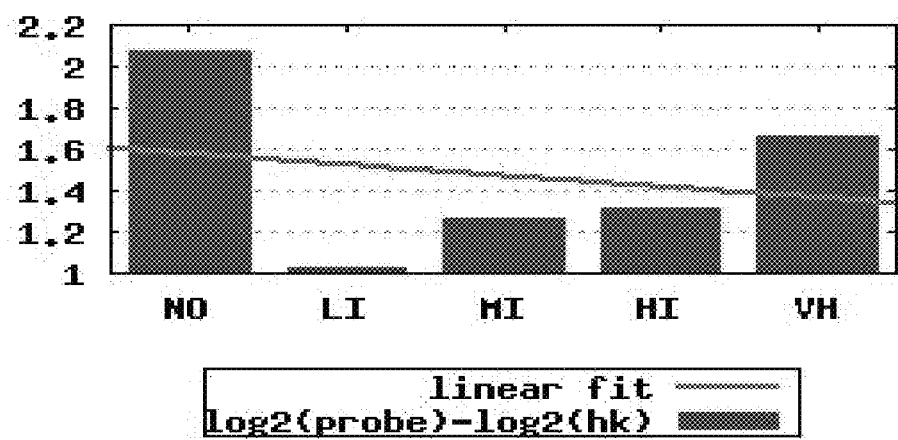
Figure 24D:
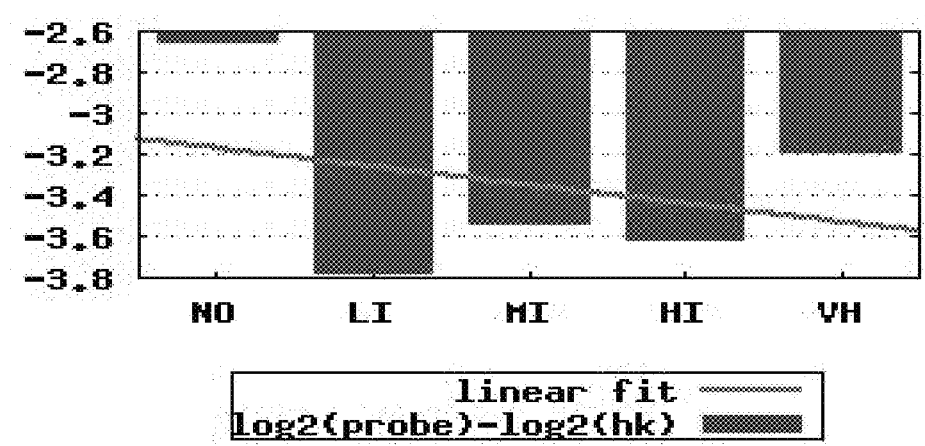

FIGS. 20a illustrates the amino acid sequence of the fusion protein corresponding to the fusion transcript identified as P0026, which was identified ($\log(e)^+=-13.2$) in slice 7 of the mitochondrial NA22 cell line (FIG. 19) from the presence of the Cytochrome c oxidase subunit 2 (CO2) N-terminus peptide ILYMTDEVNDPSLTIK and the NADH-ubiquinone oxidoreductase chain 3 (ND3) C-terminus peptide STPYECGFDPMSP (FIG. 20a).

The most C-terminus tryptic peptide of wild-type CO2, IFEMGPVFTL, was searched against all mitochondrial NA22 cell line gel slices .xml data. This peptide was only observed in gel slice 5 (FIG. 19). This was further confirmed by identifying CO2 wild-type ($\log(e)^+=-42.9$) (FIG. 20b) in mitochondrial NA22 cell line gel slice 5 only after searching the Human (SwissProt) database (no fusion transcripts) with all gel slices.

Cytochrome c oxidase subunit 2 peptide ILYMTDEVNDPSLTIK was observed in gel slices 5 and 7. This indicates that wild type CO2, with a molecular weight of ~25 kDa is present in the 20-30 kDa gel slice 5, and a fragment of CO2 N-terminus exists in gel slice 7. The tryptic peptide STPYECGFDPMSP from ND3 is only identified in gel slice 7 (10-15 kDa), which identifies the wild-type gene (13 kDa) and the C-terminus of P0026.

The sequences for the fusion transcript P0026, the mutant DNA from which it is derived and the resulting protein are provided herein, respectively, as SEQ ID NO: 56, SEQ ID NO: 57 and SEQ ID NO: 58.

Example Fusion Protein 2

FIG. 21a illustrates the amino acid sequence of the fusion protein corresponding to fusion transcript P0062, which was identified ($\log(e)^+=-41.2$) in slice 5 (20-30 kDa), shown in FIG. 19, of the mitochondrial NA22 cell line from the presence of the NADH dehydrogenase subunit 1 (ND1) N-terminus peptides KGPNVVGPYGLLQPFADAMK and YDQLMHLLWK and the ATP synthase subunit 6 C-terminus peptide LITTQQWLIK. All three peptides were identified in the mitochondrial NA22 cell line gel slice 5 (FIG. 19) but due to the most C-terminus peptide of ND1 (YDQLMHLLWK) being present only in gel slice 5, the presence of both wild-type (FIG. 21b) and the fusion protein corresponding to fusion transcript P0062 is possible.

The sequences for the fusion transcript P0062, the mutant DNA from which it is derived and the resulting protein are provided herein, respectively, as SEQ ID NO: 59, SEQ ID NO: 60 and SEQ ID NO: 61.

Example Fusion Protein 3

FIG. 22 illustrates the amino acid sequence of the fusion protein corresponding to fusion transcript P0064, which was identified in slice 4 ($\log(e)+=-22$), shown in FIG. 19, of the mitochondrial NA22 cell line with the peptide KGPNVVGPYGLLQPFADAMK from the N-terminus of ND1 and the NADH dehydrogenase subunit 2 (ND2) C-terminus peptide WAIIEEFTK. The ND1 C-terminus peptide YDQLMHLLWK was not observed in gel slice 4, and based on the expected sizes of P0064 and ND2 it is suggested that gel slice 4 contains P0064 and ND2.

The sequences for the fusion transcript P0064, the mutant DNA from which it is derived and the resulting protein are provided herein, respectively, as SEQ ID NO: 62, SEQ ID NO: 63 and SEQ ID NO: 64.

Example Fusion Protein 4

FIG. 23a illustrates the amino acid sequence of the fusion protein corresponding to fusion transcript P0176, which was identified in slice 4 ($\log(e)+=-33.8$), shown in FIG. 19, of the mitochondrial NA22 cell line with the peptide KGPNVVGPYGLLQPFADAMK from the N-terminus of ND1 and the Cytochrome c oxidase subunit 1 (CO1) C-terminus peptides VFSWLATLHGSNMK and VLMVEEPSMNLEWLYGCPPPYHTFEEPVYMK. Both of the CO1 peptides were only observed together in gel slice 4 (30-40 kDa) of the mitochondrial NA22 cell line despite an expected size of 55 kDa. This was further confirmed by identifying CO1 wild-type ($\log(e)^+=-14.6$) (FIG. 23b) in mitochondrial NA22 cell line gel slice 4 only after searching the Human (SwissProt) database (no fusion transcripts) with all gel slices.

The only ND1 peptide observed in gel slice 4 was KGPNVVGPYGLLQPFADAMK. Since the ND1 C-terminus peptide YDQLMHLLWK was not present, wild-type ND1 is not present in the slice, which supports the presence of P0176.

The sequences for the fusion transcript P0176, the mutant DNA from which it is derived and the resulting protein are provided herein, respectively, as SEQ ID NO: 65, SEQ ID NO: 66 and SEQ ID NO: 67.

Corresponding Fusion Transcripts

Quantitative measurements of the fusion transcripts associated with each of these four fusion proteins were conducted in a series of cell lines of which two were those used in the LC-MS/MS experiment, specifically RWPE-1 and WPE1-NA22, which is a malignant cell line with low invasive potential. The results of these measurements is illustrated in FIGS.

24a-24d, corresponding to the four proteins discussed above. In FIGS. 24a-d, cell line RWPE-1 is indicated as NO and cell line WPE1-NA22 is indicated as LI. The additional cell lines included in this experiment represent a continued progression of malignancy with moderate invasive potential (MI), high invasive potential (HI), and very high invasive potential (VH).

The cells were lysed and assayed using custom probes specific to each of the fusion transcripts on the branching DNA platform as described herein or previously in PCT application no. PCT/CA2009/000351 (published under number WO 2009/117811), the entire contents of which are incorporated herein by reference. Results indicated high levels of expression (with RLU values ranging from $10^6$–$10^8$). A general trend was observed in the quantity of each fusion transcript in that the initial transformation from normal cells to malignant cells (NO-LI) was punctuated by a marked change in quantity of the transcript, followed by either a continued increase or continued decrease in the quantity as malignant progression proceeds from LI to VH).

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference in their entirety.

Bibliography

The following references, amongst others, were cited in the foregoing description. The entire contents of these references are incorporated herein by way of reference thereto.

| Author | Journal | Title | Volume | Date |
| --- | --- | --- | --- | --- |
| Anderson et al | Nature | Sequence and Organization of the Human Mitochondrial Genome | 290(5806): 457-65 | 1981 |
| Andrews et al | Nat Genet | Reanalysis and revision of the Cambridge reference sequence for human mitochondrial DNA. | 23(2): 147 | 1999 |
| Modica-Napolitano et al | Expert Rev Mol Med | Mitochondria as targets for detection and treatment of cancer | 4: 1-19 | 2002 |
| Sherratt et al | Clin Sci (Lond) | Mitochondrial DNA defects: a widening clinical spectrum of disorders. | 92(3): 225-35 | 1997 |
| Croteau et al | Mutat Res | Mitochondrial DNA repair pathways. | 434(3): 137-48 | 1999 |
| Green and Kroemer | J Clin Invest | Pharmacological manipulation of cell death: clinical applications in sight? | 115(10): 2610-2617 | 2005 |
| Dai et al | Acta Otolaryngol | Correlation of cochlear blood supply with mitochondrial DNA common deletion in presbyacusis. | 24(2): 130-6 | 2004 |
| Ro et al | Muscle Nerve | Deleted 4977-bp mitochondrial DNA mutation is associated with sporadic amyotrophic lateral sclerosis: a hospital-based case-control study. | 28(6): 737-43 | 2003 |
| Barron et al | Invest Ophthalmol Vis Sci | Mitochondrial abnormalities in ageing macular photoreceptors. | 42(12): 3016-22 | 2001 |
| Lewis et al | J Pathol | Detection of damage to the mitochondrial genome in the oncocytic cells of Warthin's tumour. | 191(3): 274-81 | 2000 |
| Muller-Hocker et al | Mod Pathol | The common 4977 base pair deletion of mitochondrial DNA preferentially accumulates in the cardiac conduction system of patients with Kearns-Sayre syndrome. | 11(3): 295-301. | 1998 |
| Porteous et al | Eur J Biochem | Bioenergetic consequences of accumulating the common 4977-bp mitochondrial DNA deletion. | 257(1): 192-201 | 1998 |
| Parr et al | J Mol Diagn | Somatic mitochondrial DNA mutations in prostate cancer and normal appearing adjacent glands in comparison to age-matched prostate samples without malignant histology. | 8(3): 312-9. | 2006 |
| Maki et al | Am J Clin Pathol | Mitochondrial genome deletion aids in the identification of false- and true-negative prostate needle core biopsy specimens. | 129(1): 57-66 | 2008 |
| Nakase et al | Am J Hum Genet | Transcription and translation of deleted mitochondrial genomes in Kearns-Sayre syndrome: implications for pathogenesis. | 46(3): 418-27. | 1990 |
| Libura et al | Blood | Therapy-related acute myeloid leukemia-like MLL rearrangements are induced by etoposide in primary human CD34+ cells and remain stable after clonal expansion. | 105(5): 2124-31 | 2005 |
| Meyer et al | Proc Natl Acad Sci USA | Diagnostic tool for the identification of MLL rearrangements including unknown partner genes. | 102(2): 449-54 | 2005 |
| Eguchi et al | Genes Chromosomes | MLL chimeric protein activation renders cells vulnerable to chromosomal damage: | 45(8): 754-60 | 2006 |

-continued

| Author | Journal | Title | Volume | Date |
|---|---|---|---|---|
| | Cancer | an explanation for the very short latency of infant leukemia. | | |
| Hayashi et al | Proc Natl Acad Sci USA | Introduction of disease-related mitochondrial DNA deletions into HeLa cells lacking mitochondrial DNA results in mitochondrial dysfunction | 88: 10614-10618 | 1991 |

TABLE 1

Known mitochondrial deletions having an ORF

| Deletion Junction (nt/nt) | Deletion Size (bp) | Repeat Location (nt/nt) | Number of Repeats | References |
|---|---|---|---|---|
| COX I-ND5 | | | | |
| 6075:13799 | −7723 | 6076-6084/13799-13807 | D, 9/9 | Mita, S., Rizzuto, R., Moraes, C.T., Shanske, S., Arnaudo, E., Fabrizi, G.M., Koga, Y., DiMauro, S., Schon, E.A. (1990) "Recombination via flanking direct repeats is a major cause of large-scale deletions of human mitochondrial DNA" Nucleic Acids Research 18(3): 561-567 |
| 6238:14103 | −7864 | 6235-6238/14099-14102 | D, 4/4 | Blok, R.B., Thorburn, D.R., Thompson, G.N., Dahl, H.H. (1995) "A topoisomerase II cleavage site is associated with a novel mitochondrial DNA deletion" Human Genetics 95 (1): 75-81 |
| 6325:13989 | −7663 | 6326-6341/13889-14004 | D, 16/17 | Larsson, N.G., Holme, E., Kristiansson, B., Oldfors, A., Tulinius, M. (1990) "Progressive Increase of the mutated mitochondrial DNA fraction in Kearns-Sayre syndrome" Pediatric Research 28 (2): 131-136 Larsson, N.G., Holme, E. (1992) "Multiple short direct repeats associated with single mtDNA deletions" Biochimica et Biophysica Acta 1139 (4): 311-314 |
| 6330:13994 | −7663 | 6331-6341/13994-14004 | D, 11/11 | Mita, S., Rizzuto, R., Moraes, C.T., Shanske, S., Arnaudo, E., Fabrizi, G.M., Koga, Y., DiMauro, S., Schon, E.A. (1990) "Recombination via flanking direct repeats is a major cause of large-scale deletions of human mitochondrial DNA" Nucleic Acids Research 18(3):561-567 |
| COX II-ND5 | | | | |
| 7829:14135 | −6305 | 7824-7829/14129-14134 | D, 6/6 | Bet, L., Moggio, M., Comi, G.P., Mariani, C., Prelle, A., Checcarelli, N., Bordoni, A., Bresolin, N., Scarpini, E., Scarlato, G. (1994) "Multiple sclerosis and mitochondrial myopathy: an unusual combination of diseases" Journal of Neurology 241 (8): 511-516 |
| 8213:13991 | −5777 | 8214-8220/13991-13997 | D, 7/7 | Hinokio, Y., Suzuki, S., Komatu., Ohtomo, M., Onoda, M., Matsumoto, M., Hirai, S., Sato, Y., Akai, H., Abe, K., Torota, T. (1995) "A new mitochondrial DNA deletion associated with diabetic amyotrophy, diabetic myoatrophy and diabetic fatty liver" Muscle and Nerve 3 (9): S142-149 |
| ATPase-ND5 | | | | |
| 8631:13513 | −4881 | 8625-8631/13506-13512 | D, 7/7 | Zhang, C., Baumer, A., Mackay, I.R., Linnane, A.W., Nagley, P. (1995) "Unusual pattern of mitochondrial DNA deletions in skeletal muscle of an adult human with chronic fatigue syndrome" Human Molecular Genetics 4 (4): 751:754 |
| 9144:13816 | −4671 | 9137-9144/13808-13815 | D, 8/8 | Ota, Y., Tanaka, S., Sato, W., Ohno, K., Yamamoto, T., Maehara, M., Negoro, T., Watanabe, K., Awaya, S., Ozawa, T. (1991) "Detection of platelet mitochondrial DNA deletions in Kearns-Sayre syndrome" Investigative Ophthalmology and Visual Science 32 (10): 2667-2675 |
| 9191:12909 | −3717 | 9189-9191/12906-12908 | D, 3/3 | Tanaka, M., Sato, W., Ohno, K., Yamamoto, T., Ozawa, T. (1989) "Direct squencing of mitochondrial DNA in myopathic patients" Biochemical and Biophysical Research Communications 164 ( ): 156-163 |
| 10190:13753 | −3562 | 10191-10198/13753-13760 | D, 8/8 | Rotig, A., Bourgeron, T., Chretien, D., Rustin, P., Munnich, A. (1995) "Spectrum of mitochondrial DNA rearrangements in the Pearson marrow-pancreas syndrome" Human Molecular Genetics 4 (8): 1327-1330 Rotig, A., Cormier, V., Koll, F., Mize, C.E., Saudabray, J. M., Veerman, A., Pearson, H.A., Munnich, A. (1991) "Site-specific deletions of the mitochondrial genome in Pearson marrow-pancreas syndrome" Genomics 10 (2): 502-504 |
| 10367:12829 | −2461 | 10365-10367/12826-12828 | D, 3/3 | Kapsa, R., Thompson, G.N., Thorburn, D.R., Dahl, H.H., Marzuki, S., Byrne, E., Blok, R.B. (1994) "A novel mtDNA deletion in an infant with Pearson syndrome" Journal of Inherited Metabolic Disease 17 (5): 521-526 |
| ND4L-ND5 | | | | |
| 10744-14124 | −3379 | 10745-10754/14124-14133 | D/ 9/10 | Cormier-Daire, V., Bonnefont, J.P., Rustin, P., Maurage, C., Ogler, H., Schmitz, J., Ricour, C., Saudabray, J.M., Munnich, A., Rotig, A. (1994) "Mitochondrial DNA rearrangements with onset as chronic diarrhea with villous atrophy" Journal of Pediatrics 124 (1): 63-70 |

TABLE 1-continued

Known mitochondrial deletions having an ORF

| Deletion Junction (nt/nt) | Deletion Size (bp) | Repeat Location (nt/nt) | Number of Repeats | References |
|---|---|---|---|---|
| ND4-ND5 | | | | |
| 11232:13980 | −2747 | 11234-11242/13981-13989 | D, 9/9 | Rotig, A., Cormier, V., Koll, F., Mize, C.E., Saudabray, J.-M., Veerman, A., Pearson, H. A., Munnich, A. (1991) "Site-specific deletions of the mitochondrial genome in Pearson marrow-pancreas syndrome" Genomics 10 (2): 502:504 Rotig, A., Cormier, V., Blanche, S., Bonnefont, J.P., Ledeist, F., Romero, N., Schmitz, J., Rustin, P., Fischer, A., Saudabray, J.M. (1990) "Pearson's marrow-pancreas syndrome. A multi-system mitochondrial disorder in infancy" Journal of Clinical Investigation 86 ( ): 1601-1608 Cormier, V., Rotig, A., Quartino, A.R., Forni, G.L., Cerone, R., Maier, M., Saudabray, J.M., Munnich, A. (1990) "Widespread multitissue deletions of the mitochondrial genome in Pearson marrow-pancreas syndrome" Journal of Pediatrics 117 (4): 599-602 Awata, T., Matsumoto, T., Iwamoto, Y., Matsuda, A., Kuzuya, T., Saito, T. (1993) "Japanese case of diabetes mellitus and deafness with mutations in mitochondrial tRNALeu(UUR) gene [letter]" Lancet 341 (8855): 1291-1292 |

TABLE 2

Prostate Cancer Detection with Novel Mitochondrial Fusion Transcripts

| Transcript | | RNA Transcript 1 | Homog 1 Transcript 1 | Homog 2 Transcript 1 | RNA Transcript 2 | Homog 1 Transcript 2 | Homog 2 Transcript 2 | RNA Transcript 3 | Homog 1 Transcript 3 | Homog 2 Transcript 3 | RNA Transcript 4 | Homog 1 Transcript 4 | Homog 2 Transcript 4 |
|---|---|---|---|---|---|---|---|---|---|---|---|---|---|
| | | 1 | 2 | 3 | 4 | 5 | 6 | 7 | 8 | 9 | 10 | 11 | 12 |
| No dilution | A | 2957 | 353 | 233 | 144838 | 75374 | 17192 | 348424 | 333189 | 213844 | 509 | 565 | 207 |
| Replicate A | B | 3174 | 475 | 298 | 202793 | 100062 | 31750 | 320877 | 278137 | 210265 | 401 | 676 | 250 |
| 1:10 dilution | C | 1041 | 262 | 114 | 106195 | 98403 | 36191 | 238467 | 248677 | 123497 | 181 | 486 | 168 |
| Replicate C | D | 1040 | 272 | 176 | 120308 | 116930 | 50323 | 239231 | 262520 | 129778 | 153 | 467 | 149 |
| 1:100 dilution | E | 318 | 170 | 110 | 25155 | 64823 | 27725 | 100345 | 164606 | 85287 | 72 | 265 | 119 |
| Replicate E | F | 287 | 150 | 109 | 23500 | 50524 | 24629 | 100856 | 178527 | 84731 | 83 | 251 | 120 |
| 1:1000 dilution | G | 100 | 76 | 123 | 3002 | 12960 | 252 | 29203 | 102309 | 137 | 31 | 143 | 66 |
| Replicate G | H | 94 | 83 | 91 | 1263 | 5796 | 285 | 29092 | 97257 | 96 | 45 | 110 | 94 |
| %CV A | | 5.0 | 20.9 | 17.3 | 23.6 | 19.9 | 42.1 | 5.8 | 12.7 | 1.2 | 16.9 | 12.7 | 13.3 |
| %CV C | | 0.1 | 2.5 | 30.1 | 8.8 | 12.2 | 23.1 | 0.2 | 3.8 | 3.5 | 12.0 | 2.8 | 8.3 |
| %CV E | | 7.1 | 9.0 | 0.6 | 4.8 | 17.5 | 8.4 | 0.4 | 5.7 | 0.5 | 9.8 | 3.8 | 0.6 |
| %CV G | | 4.7 | 6.0 | 20.8 | 57.7 | 54.0 | 8.8 | 0.3 | 3.6 | 25.0 | 27.0 | 18.2 | 24.9 |

\* unit results in table are RLU (relative luminescence units); Data read on Glorunner ™

%CV = Coefficient of variation (as %).

Legend:

Homog = homogenate.

Homog 1: Prostate tumour tissue sample from patient;

Homog 2: Histologically normal tissue adjacent to tumour from patient.

RNA: Control: Total RNA from prostate tissue (Ambion p/n 7988).

Shading: Background measurement.

TABLE 3

Deletion/Transcript/Hypothetical translation product relationships

| Deletion | RNA transcript | DNA sequence with deletion complementary to RNA transcript | Transcript No. | Hypothetical Fusion Protein |
|---|---|---|---|---|
| ATP synthase F0 subunit 8 to NADH dehydrogenase subunit mitochondrial positions 8366-14148 (with reference to SEQ ID NO: 1). Translated sequence begins at position 8389 | SEQ ID NO: 19 | SEQ ID NO: 2 | 1 | SEQ ID NO: 36 |
| NADH dehydrogenase subunit 4L (ND4L) to NADH dehydrogenase subunit 5 (ND5); Mitochondrial positions 10470-14148 (with reference to SEQ ID NO: 1) | SEQ ID NO: 20 | SEQ ID NO: 3 | 2 | SEQ ID NO: 37 |
| Cytochrome c oxidase subunit II (COII) to Cytochrome b (Cytb); Mitochondrial positions 7586-15887 (with reference to SEQ ID NO: 1) | SEQ ID NO: 21 | SEQ ID NO: 4 | 3 | SEQ ID NO: 38 |
| Cytochrome c oxidase subunit II (COII) to Cytochrome b (Cytb); Mitochondrial positions 7586-15887 (with reference to SEQ ID NO: 1) | SEQ ID NO: 22 | SEQ ID NO: 5 | 4 | SEQ ID NO: 39 |

TABLE 4

Breast and Prostate Cancer Detection

| | | Breast Tumour 1 / 1 | Normal adjacent Breast Tumour 1 / 2 | Breast Tumour 2 / 3 | Normal Adjacent to Breast Tumour 2 / 4 | Prostate Tumour 3 / 5 | Prostate Tumour 4 / 6 | Prostate Tumour 5 / 7 | Normal Adjacent to Prostate Tumour 5 / 8 |
|---|---|---|---|---|---|---|---|---|---|
| 1:100 dilution | E | 68920 | 2971 | 49108 | 1245 | 46723 | 56679 | 99836 | 35504 |
| 1:100 dilution replicate | F | 92409 | 3017 | 60637 | 1512 | 53940 | 56155 | 100582 | 44221 |
| | G | 420 | 3 | 31 | 6 | 26 | 25 | 44 | 23 |
| | H | 518 | 3 | 4 | 5 | 5 | 3 | 4 | 2 |
| | % CV | 20.6 | 1.1 | 14.9 | 13.7 | 10.1 | 0.7 | 0.5 | 15.5 | unit results in table are RLU (relative luminescence units)
background G1, H1
empty well G2-G8, H2- H8

TABLE 5a

Assay Conditions

| | Template for the assay | | | | | | | | | | | |
|---|---|---|---|---|---|---|---|---|---|---|---|---|
| | RNA Transcript 1 / 1 | Homogen 1 Transcript 1 / 2 | Homogen 2 Transcript 1 / 3 | RNA Transcript 2 / 4 | Homogen 1 Transcript 2 / 5 | Homogen 2 Transcript 2 / 6 | RNA Transcript 3 / 7 | Homogen 1 Transcript 3 / 8 | Homogen 2 Transcript 3 / 9 | RNA Transcript 4 / 10 | Homogen 1 Transcript 4 / 11 | Homogen 2 Transcript 4 / 12 |
| A | RNA | Homog 1 | Homog 2 | RNA | Homog 1 | Homog 2 | RNA | Homog 1 | Homog 2 | RNA | Homog 1 | Homog 2 |
| B | Dil 1 | Dil 1 | Dil 1 | Dil 1 | Dil 1 | Dil 1 | Dil 1 | Dil 1 | Dil 1 | Dil 1 | Dil 1 | Dil 1 |
| C | RNA | Homog 1 | Homog 2 | RNA | Homog 1 | Homog 2 | RNA | Homog 1 | Homog 2 | RNA | Homog 1 | Homog 2 |
| D | Dil 2 | Dil 2 | Dil 2 | Dil 2 | Dil 2 | Dil 2 | Dil 2 | Dil 2 | Dil 2 | Dil 2 | Dil 2 | Dil 2 |
| E | RNA | Homog 1 | Homog 2 | RNA | Homog 1 | Homog 2 | RNA | Homog 1 | Homog 2 | RNA | Homog 1 | Homog 2 |
| F | Dil 3 | Dil 3 | Dil 3 | Dil 3 | Dil 3 | Dil 3 | Dil 3 | Dil 3 | Dil 3 | Dil 3 | Dil 3 | Dil 3 |

TABLE 5a-continued

Assay Conditions

| | Template for the assay | | | | | | | | | | | |
|---|---|---|---|---|---|---|---|---|---|---|---|---|
| | RNA Transcript 1 1 | Homogen 1 Transcript 1 2 | Homogen 2 Transcript 1 3 | RNA Transcript 2 4 | Homogen 1 Transcript 2 5 | Homogen 2 Transcript 2 6 | RNA Transcript 3 7 | Homogen 1 Transcript 3 8 | Homogen 2 Transcript 3 9 | RNA Transcript 4 10 | Homogen 1 Transcript 4 11 | Homogen 2 Transcript 4 12 |
| G | RNA Dil 4 | Homog 1 Dil 4 | Transcript 1 Background | RNA Dil 4 | Homog 1 Dil 4 | Transcript 1 Background | RNA Dil 4 | Homog 1 Dil 4 | Transcript 1 Background | RNA Dil 4 | Homog 1 Dil 4 | Transcript 1 Background |
| H | | | | | | | | | | | | |

Homogenate1 - Used 26 mg of tissue to homogenize in 700 ul H soln with Proteinase K (PK). Used Qiagen TissueRuptor. Used 40 ul homogenate supernatant, 20, 10 and 5 ul for dilution
Homogenate1 = Tumour tissue from the tumorous Prostate
Homogenate2 - Used 29 mg of tissue to homogenize in 700 ul H soln with PK. Used Qiagen TissueRuptor. Used 40 ul homogenate supernatant, 20, 10 and 5 ul for dilution
Homogenate2 = Normal tissue from the tumorous Prostate
RNA dilution was made as below. RNA was from Prostate Normal from Ambion.
Assay was done in duplicates.

TABLE 5b

RNA dilution

| RNA Dilution | | ng/ul |
|---|---|---|
| | Dil 1 | 3000 |
| 1:3 dil | Dil 2 | 1000 |
| Serial dil | Dil 3 | 333 |
| | Dil 4 | 111 |

TABLE 6

Transcript Summary by Disease

| Probe | Prostate Cancer | Breast Cancer | Colorectal Cancer | Melanoma Skin Cancer | Lung Cancer | Ovarian Cancer | Testicular Cancer |
|---|---|---|---|---|---|---|---|
| 1 | • | | | | | • | |
| 2 | • | • | | • | | • | • |
| 3 | • | | • | • | | • | • |
| 4 | • | | • | | | | • |
| 5 | | | | • | | | |
| 6 | | | | • | • | • | |
| 7 | | | • | • | | | |
| 8 | | | | | • | | |
| 9 | | | | • | | | |
| 10 | | | • | | • | | |
| 11 | | | • | • | | • | • |
| 12 | | | • | | | • | • |
| 13 | | | | | | • | |
| 14 | | | | • | | | |
| 15 | | | | • | | • | • |
| 16 | | | • | | | • | • |
| 17 | | | | • | | | |
| 20 | | • | • | | • | | • |

We claim:

1. A method of detecting a cancer in a mammal, the method comprising assaying a biological sample from the mammal for the presence of at least one mitochondrial fusion protein, the protein having an amino acid sequence resulting from the translation of a mitochondrial fusion transcript corresponding to a mutation in mitochondrial DNA, wherein the amino acid sequence is set forth in SEQ ID NO: 58.

2. The method of claim 1, wherein the cancer is prostate cancer, testicular cancer, ovarian cancer, breast cancer, colorectal cancer, lung cancer or melanoma skin cancer.

3. The method of claim 1, wherein said assay comprises an immunological assay.

4. The method of claim 3, wherein said assay is conducted using an antibody or antigen-binding fragment thereof having a specificity to an isolated mitochondrial fusion protein having an amino acid sequence as set forth in SEQ ID NO: 58.

5. The method of claim 1, wherein the biological sample is obtained from a subject suspected of having one of prostate cancer, testicular cancer, ovarian cancer, breast cancer, colorectal cancer, lung cancer or melanoma skin cancer.

6. The method of claim 5, wherein the biological sample is a tissue or fluid.

7. The method of claim 6, wherein the tissue is skin, lung, breast, prostate, nervous, muscle, heart, stomach, colon or rectal tissue.

8. The method of claim 6, wherein the fluid is blood, saliva, cerebral spinal fluid, sputa, urine, mucous, synovial fluid, peritoneal fluid or amniotic fluid.

9. The method of claim 1, wherein the cancer is prostate cancer.

10. The method of claim 1, wherein the biological sample is prostate tissue.

* * * * *

SEQUENCE LISTING

<160> NUMBER OF SEQ ID NOS: 67

<210> SEQ ID NO 1
<211> LENGTH: 16568
<212> TYPE: DNA
<213> ORGANISM: Human

<400> SEQUENCE: 1
gatcacaggt ctatcaccct attaaccact cacgggagct ctccatgcat ttggtatttt     60

```
cgtctggggg gtatgcacgc gatagcattg cgagacgctg gagccggagc accctatgtc    120
gcagtatctg tctttgattc ctgcctcatc ctattattta tcgcacctac gttcaatatt    180
acaggcgaac atacttacta aagtgtgtta attaattaat gcttgtagga cataataata    240
acaattgaat gtctgcacag ccactttcca cacagacatc ataacaaaaa atttccacca    300
aaccccccct ccccgcttc tggccacagc acttaaacac atctctgcca aaccccaaaa     360
acaaagaacc ctaacaccag cctaaccaga tttcaaattt tatcttttgg cggtatgcac    420
ttttaacagt cacccccaa ctaacacatt attttcccct cccactccca tactactaat     480
ctcatcaata caaccccgc ccatcctacc cagcacacac acaccgctgc taaccccata     540
ccccgaacca accaaacccc aaagacaccc ccacagttt atgtagctta cctcctcaaa     600
gcaatacact gaaaatgttt agacgggctc acatcacccc ataaacaaat aggtttggtc    660
ctagcctttc tattagctct tagtaagatt acacatgcaa gcatcccgt tccagtgagt     720
tcaccctcta aatcaccacg atcaaaagga caagcatca agcacgcagc aatgcagctc     780
aaaacgctta gcctagccac accccacgg gaaacagcag tgattaaccct ttagcaataa    840
acgaaagttt aactaagcta tactaacccc agggttggtc aatttcgtgc cagccaccgc    900
ggtcacacga ttaacccaag tcaatagaag ccggcgtaaa gagtgtttta gatcaccccc    960
tccccaataa agctaaaact cacctgagtt gtaaaaaact ccagttgaca caaaatagac   1020
tacgaaagtg gctttaacat atctgaacac acaatagcta agacccaaac tgggattaga   1080
taccccacta tgcttagccc taaacctcaa cagttaaatc aacaaaactg ctcgccagaa   1140
cactacgagc cacagcttaa aactcaaagg acctggcggt gcttcatatc cctctagagg   1200
agcctgttct gtaatcgata aaccccgatc aacctcacca cctcttgctc agcctatata   1260
ccgccatctt cagcaaaccc tgatgaaggc tacaaagtaa gcgcaagtac cacgtaaag    1320
acgttaggtc aaggtgtagc ccatgaggtg gcaagaaatg gctacatttt ctaccccag    1380
aaaactacga tagcccttat gaaacttaag ggtcgaaggt ggatttagca gtaaactaag   1440
agtagagtgc ttagttgaac agggccctga agcgcgtaca caccgcccgt cacccctcctc  1500
aagtatactt caaaggacat ttaactaaaa cccctacgca tttatataga ggagacaagt   1560
cgtaacatgg taagtgtact ggaaagtgca cttggacgaa ccagagtgta gcttaacaca   1620
aagcacccaa cttacactta ggagatttca acttaacttg accgctctga gctaaaccta   1680
gccccaaacc cactccacct tactaccaga caaccttagc caaaccatttt acccaaataa   1740
agtataggcg atagaaattg aaacctggcg caatagatat agtaccgcaa gggaaagatg   1800
aaaaattata accaagcata atatagcaag gactaaccccc tataccttct gcataatgaa   1860
ttaactagaa ataactttgc aaggagagcc aaagctaaga ccccgaaac cagacgagct    1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaactta aatttgccca cagaaccctc taaatcccct tgtaaattta actgttagtc     2100
caaagaggaa cagctctttg gacactagga aaaaccttg tagagagagt aaaaaattta    2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
```

```
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tactttaac cagtgaaatt gacctgcccg tgaagaggcg   2700
ggcataacac agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggtttct atctacttca aattcctccc   3120
tgtacgaaag gacaagagaa ataaggccta cttcacaaag cgccttcccc cgtaaatgat   3180
atcatctcaa cttagtatta tacccacacc cacccaagaa cagggtttgt taagatggca   3240
gagcccggta atcgcataaa acttaaaact ttacagtcag aggttcaatt cctcttctta   3300
acaacatacc catggccaac ctcctactcc tcattgtacc cattctaatc gcaatggcat   3360
tcctaatgct taccgaacga aaaattctag gctatataca actacgcaaa ggccccaacg   3420
ttgtaggccc ctacgggcta ctacaaccct tcgctgacgc cataaaactc ttcaccaaag   3480 agccctaaa acccgccaca tctaccatca ccctctacat caccgccccg accttagctc   3540
tcaccatcgc tcttctacta tgaacccccc tccccatacc caacccctg gtcaacctca   3600 acctaggcct cctatttatt ctagccacct ctagcctagc cgtttactca atcctctgat   3660
cagggtgagc atcaaactca aactacgccc tgatcggcgc actgcgagca gtagcccaaa   3720
caatctcata tgaagtcacc ctagccatca ttctactatc aacattacta ataagtggct   3780
cctttaacct ctccaccctt atcacaacac aagaacacct ctgattactc ctgccatcat   3840
gacccttggc cataatatga tttatctcca cactagcaga gaccaaccga acccccttcg   3900
accttgccga aggggagtcc gaactagtct caggcttcaa catcgaatac gccgcaggcc   3960
ccttcgccct attcttcata gccgaataca caaacattat tataataaac accctcacca   4020
ctacaatctt cctaggaaca acatatgacg cactctcccc tgaactctac acaacatatt   4080
ttgtcaccaa gaccctactt ctaacctccc tgttcttatg aattcgaaca gcatacccccc   4140 gattccgcta cgaccaactc atacacctcc tatgaaaaaa cttcctacca ctcaccctag   4200
cattacttat atgatatgtc tccatacca ttacaatctc cagcattccc cctcaaacct   4260
aagaaatatg tctgataaaa gagttacttt gatagagtaa ataataggag cttaaacccc   4320
cttatttcta ggactatgag aatcgaaccc atccctgaga atccaaaatt ctccgtgcca   4380
cctatcacac cccatcctaa agtaaggtca gctaaataag ctatcgggcc cataccccga   4440
aaatgttggt tataccccttc ccgtactaat taatcccctg gcccaacccg tcatctactc   4500
taccatcttt gcaggcacac tcatcacagc gctaagctcg cactgatttt ttacctgagt   4560
aggcctagaa ataaacatgc tagcttttat tccagttcta accaaaaaaa taaaccctcg   4620
ttccacagaa gctgccatca agtatttcct cacgcaagca accgcatcca taatccttct   4680
aatagctatc ctcttcaaca atatactctc cggacaatga accataacca atactaccaa   4740
tcaatactca tcattaataa tcataatagc tatagcaata aaactaggaa tagcccccttt   4800 tcacttctga gtcccagagg ttacccaagg cacccctctg acatccggcc tgcttcttct   4860
```

```
cacatgacaa aaactagccc ccatctcaat catataccaa atctctccct cactaaacgt    4920
aagccttctc ctcactctct caatcttatc catcatagca ggcagttgag gtggattaaa    4980
ccaaacccag ctacgcaaaa tcttagcata ctcctcaatt acccacatag gatgaataat    5040
agcagttcta ccgtacaacc ctaacataac cattcttaat ttaactattt atattatcct    5100
aactactacc gcattcctac tactcaactt aaactccagc accacgaccc tactactatc    5160
tcgcacctga aacaagctaa catgactaac acccttaatt ccatccaccc tcctctccct    5220
aggaggcctg cccccgctaa ccggcttttt gcccaaatgg gccattatcg aagaattcac    5280
aaaaaacaat agcctcatca tccccaccat catagccacc atcaccctcc ttaacctcta    5340
cttctaccta cgcctaatct actccacctc aatcacacta ctccccatat ctaacaacgt    5400
aaaaataaaa tgacagtttg aacatacaaa acccaccccca ttcctcccca cactcatcgc    5460
ccttaccacg ctactcctac ctatctcccc ttttatacta ataatcttat agaaatttag    5520
gttaaataca gaccaagagc cttcaaagcc ctcagtaagt tgcaatactt aatttctgta    5580
acagctaagg actgcaaaac cccactctgc atcaactgaa cgcaaatcag ccactttaat    5640
taagctaagc ccttactaga ccaatgggac ttaaacccac aaaacttag ttaacagcta    5700 agcaccctaa tcaactggct tcaatctact tctcccgccg ccgggaaaaa aggcgggaga    5760
agccccggca ggtttgaagc tgcttcttcg aatttgcaat tcaatatgaa aatcacctcg    5820
gagctggtaa aaagaggcct aaccctgtc tttagattta cagtccaatg cttcactcag    5880
ccattttacc tcaccccac tgatgttcgc cgaccgttga ctattctcta caaaccacaa    5940
agacattgga acactatacc tattattcgg cgcatgagct ggagtcctag gcacagctct    6000
aagcctcctt attcgagccg agctgggcca gccaggcaac cttctaggta acgaccacat    6060
ctacaacgtt atcgtcacag cccatgcatt tgtaataatc ttcttcatag taatacccat    6120
cataatcgga ggctttggca actgactagt tcccctaata atcggtgccc ccgatatggc    6180
gtttccccgc ataaacaaca taagcttctg actcttacct ccctctctcc tactcctgct    6240
cgcatctgct atagtggagg ccggagcagg aacaggttga acagtctacc ctcccttagc    6300
agggaactac tcccaccctg gagcctccgt agacctaacc atcttctcct tacacctagc    6360
aggtgtctcc tctatcttag gggccatcaa tttcatcaca acaattatca atataaaacc    6420
ccctgccata acccaatacc aaacgcccct cttcgtctga tccgtcctaa tcacagcagt    6480
cctacttctc ctatctctcc cagtcctagc tgctggcatc actatactac taacagaccg    6540
caacctcaac accaccttct tcgacccccgc cggaggagga gaccccattc tataccaaca    6600
cctattctga tttttcggtc accctgaagt ttatattctt atcctaccag gcttcggaat    6660
aatctcccat attgtaactt actactccgg aaaaaaagaa ccatttggat acataggtat    6720
ggtctgagct atgatatcaa ttggcttcct agggtttatc gtgtgagcac accatatatt    6780
tacagtagga atagacgtag acacacgagc atatttcacc tccgctacca taatcatcgc    6840
tatccccacc ggcgtcaaag tatttagctg actcgccaca ctccacgaa gcaatatgaa    6900 atgatctgct gcagtgctct gagccctagg attcatcttt cttttcaccg taggtggcct    6960
gactggcatt gtattagcaa actcatcact agacatcgta ctacacgaca cgtactacgt    7020
tgtagcccac ttccactatg tcctatcaat aggagctgta tttgccatca taggaggctt    7080
cattcactga tttcccctat tctcaggcta caccctagac caaacctacg ccaaaatcca    7140
tttcactatc atattcatcg gcgtaaatct aactttcttc ccacaacact ttctcggcct    7200
atccggaatg ccccgacgtt actcggacta ccccgatgca tacaccacat gaaacatcct    7260
```

-continued

```
atcatctgta ggctcattca tttctctaac agcagtaata ttaataattt tcatgatttg    7320
agaagccttc gcttcgaagc gaaaagtcct aatagtagaa gaaccctcca taaacctgga    7380
gtgactatat ggatgccccc caccctacca cacattcgaa gaacccgtat acataaaatc    7440
tagacaaaaa aggaaggaat cgaaccccccc aaagctggtt tcaagccaac cccatggcct   7500
ccatgacttt ttcaaaaagg tattagaaaa accatttcat aactttgtca agttaaatt    7560 ataggctaaa tcctatatat cttaatggca catgcagcgc aagtaggtct acaagacgct    7620 acttcccta tcatagaaga gcttatcacc tttcatgatc acgccctcat aatcattttc     7680
cttatctgct tcctagtcct gtatgccctt ttcctaacac tcacaacaaa actaactaat    7740
actaacatct cagacgctca ggaaatagaa accgtctgaa ctatcctgcc cgccatcatc    7800
ctagtcctca tcgccctccc atccctacgc atcctttaca taacagacga ggtcaacgat    7860 ccctcccta ccatcaaatc aattggccac caatggtact gaacctacga gtacaccgac     7920
tacggcggac taatcttcaa ctcctacata cttcccccat tattcctaga accaggcgac    7980
ctgcgactcc ttgacgttga caatcgagta gtactcccga ttgaagcccc cattcgtata    8040
ataattacat cacaagacgt cttgcactca tgagctgtcc ccacattagg cttaaaaaca    8100
gatgcaattc ccggacgtct aaaccaaacc actttcaccg ctacacgacc gggggtatac    8160
tacggtcaat gctctgaaat ctgtggagca accacagtt tcatgcccat cgtcctagaa     8220
ttaattcccc taaaaatctt tgaaataggg cccgtattta ccctatagca cccctctac    8280 cccctctaga gcccactgta aagctaactt agcattaacc ttttaagtta agattaaga    8340 gaaccaacac ctctttacag tgaaatgccc caactaaata ctaccgtatg gcccaccata   8400 attacccca tactccttac actattcctc atcacccaac taaaaatatt aaacacaaac     8460
taccacctac ctccctcacc aaagcccata aaaataaaaa attataacaa accctgagaa    8520
ccaaaatgaa cgaaaatctg ttcgcttcat tcattgcccc cacaatccta ggcctacccg    8580
ccgcagtact gatcattcta tttcccctc tattgatccc cacctccaaa tatctcatca    8640
acaaccgact aatcaccacc caacaatgac taatcaaact aacctcaaaa caaatgataa    8700
ccatacacaa cactaaagga cgaacctgat ctcttatact agtatcctta atcattttta    8760
ttgccacaac taacctcctc ggactcctgc ctcactcatt tacaccaacc acccaactat    8820
ctataaacct agccatggcc atccccttat gagcgggcac agtgattata ggctttcgct    8880
ctaagattaa aaatgcccta gcccacttct taccacaagg cacacctaca ccccttatcc    8940
ccatactagt tattatcgaa accatcagcc tactcattca accaatagcc ctggccgtac    9000
gcctaaccgc taacattact gcaggccacc tactcatgca cctaattgga agcgccaccc    9060
tagcaatatc aaccattaac cttccctcta cacttatcat cttcacaatt ctaattctac   9120
tgactatcct agaaatcgct gtcgccttaa tccaagccta cgttttcaca cttctagtaa    9180
gcctctacct gcacgacaac acataatgac ccaccaatca catgcctatc atatagtaaa    9240
acccagccca tgacccctaa caggggccct ctcagccctc ctaatgacct ccggcctagc   9300
catgtgattt cacttccact ccataacgct cctcatacta ggcctactaa ccaacacact    9360
aaccatatac caatgatggc gcgatgtaac acgagaaagc ataccaag gccaccacac     9420 accacctgtc caaaaaggcc ttcgatacgg gataatccta tttattacct cagaagtttt    9480
tttcttcgca ggattttttct gagccttta ccactccagc ctagcccta cccccaatt     9540 aggagggcac tggcccccaa caggcatcac ccgctaaat ccctagaag tcccactcct     9600 aaacacatcc gtattactcg catcaggagt atcaatcacc tgagctcacc atagtctaat    9660
```

```
agaaaacaac cgaaaccaaa taattcaagc actgcttatt acaattttac tgggtctcta   9720
ttttaccctc ctacaagcct cagagtactt cgagtctccc ttcaccattt ccgacggcat   9780
ctacggctca acattttttg tagccacagg cttccacgga cttcacgtca ttattggctc   9840
aactttcctc actatctgct tcatccgcca actaatattt cactttacat ccaaacatca   9900
ctttggcttc gaagccgccg cctgatactg gcattttgta gatgtggttt gactatttct   9960
gtatgtctcc atctattgat gagggtctta ctcttttagt ataaatagta ccgttaactt  10020
ccaattaact agttttgaca acattcaaaa aagagtaata aacttcgcct taatttaat   10080
aatcaacacc ctcctagcct tactactaat aattattaca ttttgactac cacaactcaa  10140
cggctacata gaaaaatcca ccccttacga gtgcggcttc gaccctatat cccccgcccg  10200
cgtccctttc tccataaaat tcttcttagt agctattacc ttcttattat ttgatctaga  10260
aattgccctc cttttacccc taccatgagc cctacaaaca actaacctgc cactaatagt  10320
tatgtcatcc ctcttattaa tcatcatcct agccctaagt ctggcctatg agtgactaca  10380
aaaaggatta gactgaaccg aattggtata tagtttaaac aaaacgaatg atttcgactc  10440
attaaattat gataatcata tttaccaaat gcccctcatt tacataaata ttatactagc  10500
atttaccatc tcacttctag gaatactagt atatcgctca cacctcatat cctccctact  10560
atgcctagaa ggaataatac tatcgctgtt cattatagct actctcataa ccctcaacac  10620
ccactccctc ttagccaata ttgtgcctat tgccatacta gtctttgccg cctgcgaagc  10680
agcggtgggc ctagccctac tagtctcaat ctccaacaca tatggcctag actacgtaca  10740
taacctaaac ctactccaat gctaaaacta atcgtcccaa caattatatt actaccactg  10800
acatgacttt ccaaaaaaca cataatttga atcaacacaa ccacccacag cctaattatt  10860
agcatcatcc ctctactatt ttttaaccaa atcaacaaca acctatttag ctgttcccca  10920
accttttcct ccgacccccct aacaaccccc ctcctaatac taactacctg actcctaccc  10980
ctcacaatca tggcaagcca acgccactta tccagtgaac cactatcacg aaaaaaactc  11040
tacctctcta tactaatctc cctacaaatc tccttaatta taacattcac agccacagaa  11100
ctaatcatat tttatatctt cttcgaaacc acacttatcc caccttggc tatcatcacc  11160
cgatgaggca accagccaga acgcctgaac gcaggcacat acttcctatt ctacacccta  11220
gtaggctccc ttcccctact catcgcacta atttacactc acaacaccct aggctcacta  11280
aacattctac tactcactct cactgcccaa gaactatcaa actcctgagc caacaactta  11340
atatgactag cttacacaat agcttttata gtaaagatac ctctttacgg actccactta  11400
tgactcccta aagcccatgt cgaagccccc atcgctgggt caatagtact tgccgcagta  11460
ctcttaaaac taggcggcta tggtataata cgcctcacac tcattctcaa cccctgaca   11520
aaacacatag cctaccccct tccttgtacta tccctatgag gcataattat aacaagctcc  11580
atctgcctac gacaaacaga cctaaaatcg ctcattgcat actcttcaat cagccacata  11640
gccctcgtag taacagccat tctcatccaa ccccctgaa gcttcaccgg cgcagtcatt  11700
ctcataatcg cccacgggct tacatcctca ttactattct gcctagcaaa ctcaaactac  11760
gaacgcactc acagtcgcat cataatcctc tctcaaggac ttcaaactct actcccacta  11820
atagcttttt gatgacttct agcaagcctc gctaacctcg ccttaccccc cactattaac  11880
ctactgggag aactctctgt gctagtaacc acgttctcct gatcaaatat cactctccta  11940
cttacaggac tcaacatact agtcacagcc ctatactccc tctacatatt taccacaaca  12000
caatggggct cactcaccca ccacattaac aacataaaac cctcattcac acgagaaaac  12060
```

```
accctcatgt tcatacacct atccccatt ctcctcctat ccctcaaccc cgacatcatt   12120
accgggtttt cctcttgtaa atatagttta accaaaacat cagattgtga atctgacaac   12180
agaggcttac gacccttat ttaccgagaa agctcacaag aactgctaac tcatgccccc     12240
atgtctaaca acatggcttt ctcaactttt aaaggataac agctatccat tggtcttagg   12300
ccccaaaaat tttggtgcaa ctccaaataa aagtaataac catgcacact actataacca   12360
ccctaaccct gacttcccta attccccca tccttaccac cctcgttaac cctaacaaaa     12420
aaaactcata ccccattat gtaaaatcca ttgtcgcatc caccttatt atcagtctct      12480 tccccacaac aatattcatg tgcctagacc aagaagttat tatctcgaac tgacactgag   12540
ccacaaccca acaacccag ctctccctaa gcttcaaact agactacttc tccataatat    12600
tcatccctgt agcattgttc gttacatggt ccatcataga attctcactg tgatatataa   12660
actcagaccc aaacattaat cagttcttca aatatctact catcttccta attaccatac   12720
taatcttagt taccgctaac aacctattcc aactgttcat cggctgagag ggcgtaggaa    12780
ttatatcctt cttgctcatc agttgatgat acgcccgagc agatgccaac acagcagcca    12840
ttcaagcaat cctatacaac cgtatcggcg atatcggttt catcctcgcc ttagcatgat    12900
ttatcctaca ctccaactca tgagacccac aacaaatagc ccttctaaac gctaatccaa   12960
gcctcacccc actactaggc ctcctcctag cagcagcagg caaatcagcc caattaggtc    13020
tccacccctg actcccctca gccatagaag gccccacccc agtctcagcc ctactccact    13080
caagcactat agttgtagca ggaatcttct tactcatccg cttccacccc ctagcagaaa   13140
atagcccact aatccaaact ctaacactat gcttaggcgc tatcaccact ctgttcgcag   13200
cagtctgcgc ccttacacaa aatgacatca aaaaaatcgt agccttctcc acttcaagtc    13260
aactaggact cataatagtt acaatcggca tcaaccaacc acacctagca ttcctgcaca    13320
tctgtaccca cgccttcttc aaagccatac tatttatgtg ctccgggtcc atcatccaca    13380
accttaacaa tgaacaagat attcgaaaaa taggaggact actcaaaacc atacctctca    13440
cttcaacctc cctcaccatt ggcagcctag cattagcagg aatacctttc ctcacaggtt   13500
tctactccaa agaccacatc atcgaaaccg caaacatatc atacacaaac gcctgagccc    13560
tatctattac tctcatcgct acctccctga caagcgccta tagcactcga ataattcttc   13620
tcaccctaac aggtcaacct cgcttcccca cccttactaa cattaacgaa aataacccca   13680
ccctactaaa ccccattaaa cgcctggcag ccggaagcct attcgcagga tttctcatta   13740
ctaacaacat ttccccgca tcccccttcc aaacaacaat cccctctac ctaaaactca     13800 cagccctcgc tgtcactttc ctaggacttc taacagccct agacctcaac tacctaacca   13860
acaaacttaa aataaaatcc ccactatgca catttatttt ctccaacata ctcggattct    13920
accctagcat cacacaccgc acaatcccct atctaggcct tcttacgagc caaaacctgc    13980
ccctactcct cctagaccta acctgactag aaaagctatt acctaaaaca atttcacagc   14040
accaaatctc cacctccatc atcacctcaa cccaaaaagg cataattaaa ctttacttcc    14100
tctctttctt cttcccactc atcctaaccc tactcctaat cacataacct attccccga   14160 gcaatctcaa ttacaatata tacaccaaca acaatgttc aaccagtaac tactactaat   14220
caacgcccat aatcatacaa agcccccgca ccaataggat cctcccgaat caaccctgac   14280
ccctctcctt cataaattat tcagcttcct acactattaa agtttaccac aaccaccacc   14340
ccatcatact ctttcacccca cagcaccaat cctacctcca tcgctaaccc cactaaaaca    14400
ctcaccaaga cctcaacccc tgaccccat gcctcaggat actcctcaat agccatcgct   14460
```

```
gtagtatatc caaagacaac catcattccc cctaaataaa ttaaaaaaac tattaaaccc    14520
atataacctc ccccaaaatt cagaataata acacacccga ccacaccgct aacaatcaat    14580
actaaacccc cataaatagg agaaggctta gaagaaaacc ccacaaaccc cattactaaa    14640
cccacactca acagaaacaa agcatacatc attattctcg cacggactac aaccacgacc    14700
aatgatatga aaaccatcg ttgtatttca actacaagaa caccaatgac cccaatacgc     14760
aaaactaacc ccctaataaa attaattaac cactcattca tcgacctccc caccccatcc    14820
aacatctccg catgatgaaa cttcggctca ctccttggcg cctgcctgat cctccaaatc    14880
accacaggac tattcctagc catgcactac tcaccagacg cctcaaccgc cttttcatca    14940
atcgcccaca tcactcgaga cgtaaattat ggctgaatca tccgctacct tcacgccaat    15000
ggcgcctcaa tattctttat ctgcctcttc ctacacatcg ggcgaggcct atattacgga    15060
tcatttctct actcagaaac ctgaaacatc ggcattatcc tcctgcttgc aactatagca    15120
acagccttca taggctatgt cctcccgtga ggccaaatat cattctgagg ggccacagta    15180
attacaaact tactatccgc catcccatac attgggacag acctagttca atgaatctga    15240
ggaggctact cagtagacag tcccaccctc acacgattct ttacctttca cttcatcttg    15300
cccttcatta ttgcagccct agcaacactc cacctcctat tcttgcacga acgggatca    15360 aacaaccccc taggaatcac ctcccattcc gataaaatca ccttccaccc ttactacaca    15420
atcaaagacg ccctcggctt acttctcttc cttctctcct taatgacatt aacactattc    15480
tcaccagacc tcctaggcga cccagacaat tataccctag ccaaccccctt aaacacccct    15540 ccccacatca agcccgaatg atatttccta ttcgcctaca caattctccg atccgtccct    15600
aacaaactag gaggcgtcct tgccctatta ctatccatcc tcatcctagc aataatcccc    15660
atcctccata tatccaaaca caaagcata atatttcgcc cactaagcca atcactttat    15720
tgactcctag ccgcagacct cctcattcta acctgaatcg gaggacaacc agtaagctac    15780 cctttttacca tcattggaca agtagcatcc gtactatact tcacaacaat cctaatccta    15840
ataccaacta tctccctaat tgaaaacaaa atactcaaat gggcctgtcc ttgtagtata    15900
aactaataca ccagtcttgt aaaccggaga tgaaaacctt tttccaagga caaatcagag    15960
aaaaagtctt taactccacc attagcaccc aaagctaaga ttctaattta aactattctc    16020
tgttctttca tggggaagca gatttgggta ccacccaagt attgactcac ccatcaacaa    16080
ccgctatgta tttcgtacat tactgccagc caccatgaat attgtacggt accataaata    16140
cttgaccacc tgtagtacat aaaaacccaa tccacatcaa aaccccctcc ccatgcttac    16200
aagcaagtac agcaatcaac cctcaactat cacacatcaa ctgcaactcc aaagccaccc    16260
ctcacccact aggataccaa caaacctacc cacccttaac agtacatagt acataaagcc    16320
atttaccgta catagcacat acagtcaaa tcccttctcg tccccatgga tgacccccct    16380 cagataggg tcccttgacc accatcctcc gtgaaatcaa tatcccgcac aagagtgcta    16440
ctctcctcgc tccgggccca taacacttgg gggtagctaa agtgaactgt atccgacatc    16500
tggttcctac ttcagggtca taaagcctaa atagcccaca cgttcccctt aaataagaca    16560
tcacgatg                                                            16568
```

<210> SEQ ID NO 2
<211> LENGTH: 783
<212> TYPE: DNA
<213> ORGANISM: Artificial
<220> FEATURE:
<223> OTHER INFORMATION: cDNA

<400> SEQUENCE: 2

| | | | | | |
|---|---|---|---|---|---|
| atggcccacc | ataattaccc | ccatactcct | tacactattc | ctcatcaccc | aactaaaaat | 60 |
| attaaacaca | aactaccacc | tacctccctc | accattggca | gcctagcatt | agcaggaata | 120 |
| cctttcctca | caggtttcta | ctccaaagac | cacatcatcg | aaaccgcaaa | catatcatac | 180 |
| acaaacgcct | gagccctatc | tattactctc | atcgctacct | ccctgacaag | cgcctatagc | 240 |
| actcgaataa | ttcttctcac | cctaacaggt | caacctcgct | tccccaccct | tactaacatt | 300 |
| aacgaaaata | accccaccct | actaaacccc | attaaacgcc | tggcagccgg | aagcctattc | 360 |
| gcaggatttc | tcattactaa | caacatttcc | cccgcatccc | ccttccaaac | aacaatcccc | 420 |
| ctctacctaa | aactcacagc | cctcgctgtc | actttcctag | gacttctaac | agccctagac | 480 |
| ctcaactacc | taaccaacaa | acttaaaata | aaatccccac | tatgcacatt | ttatttctcc | 540 |
| aacatactcg | gattctaccc | tagcatcaca | caccgcacaa | tcccctatct | aggccttctt | 600 |
| acgagccaaa | acctgcccct | actcctccta | gacctaacct | gactagaaaa | gctattacct | 660 |
| aaaacaattt | cacagcacca | aatctccacc | tccatcatca | cctcaaccca | aaaaggcata | 720 |
| attaaacttt | acttcctctc | tttcttcttc | ccactcatcc | taaccctact | cctaatcaca | 780 |
| taa | | | | | | 783 |

<210> SEQ ID NO 3
<211> LENGTH: 300
<212> TYPE: DNA
<213> ORGANISM: Artificial
<220> FEATURE:
<223> OTHER INFORMATION: cDNA

<400> SEQUENCE: 3

| | | | | | |
|---|---|---|---|---|---|
| atgcccctca | tttacataaa | tattatacta | gcatttacca | tctcacttct | aggaatacta | 60 |
| gtatatcgct | cacacctcat | atcctcccta | ctatgcctag | aaggaataat | actatcgctg | 120 |
| ttcattatag | ctactctcat | aaccctcaac | acccactccc | tcttagccaa | tattgtgcct | 180 |
| attgccatac | tagtctttgc | cgcctgcgaa | gcagcggtgg | gcctagccct | actagtctca | 240 |
| atctccaaca | catatggcct | agactacgta | cataacctaa | ccctactcct | aatcacataa | 300 |

<210> SEQ ID NO 4
<211> LENGTH: 781
<212> TYPE: DNA
<213> ORGANISM: Artificial
<220> FEATURE:
<223> OTHER INFORMATION: cDNA

<400> SEQUENCE: 4

| | | | | | |
|---|---|---|---|---|---|
| atggcacatg | cagcgcaagt | aggtctacaa | gacgctactt | cccctatcat | agaagagctt | 60 |
| atcacctttc | atgatcacgc | cctcataatc | attttcctta | tctgcttcct | agtcctgtat | 120 |
| gcccttttcc | taacactcac | aacaaaacta | actaatacta | acatctcaga | cgctcaggaa | 180 |
| atagaaaccg | tctgaactat | cctgcccgcc | atcatcctag | tcctcatcgc | cctcccatcc | 240 |
| ctacgcatcc | tttacataac | agacgaggtc | aacgatccct | cccttaccat | caaatcaatt | 300 |
| ggccaccaat | ggtactgaac | ctacgagtac | accgactacg | cggactaat | cttcaactcc | 360 |
| tacatacttc | cccattatt | cctagaacca | ggcgacccga | caattatac | cctagccaac | 420 |
| cccttaaaca | cccctcccca | catcaagccc | gaatgatatt | tcctattcgc | ctacacaatt | 480 |
| ctccgatccg | tccctaacaa | actaggaggc | gtccttgccc | tattactatc | catcctcatc | 540 |
| ctagcaataa | tccccatcct | ccatatatcc | aaacaacaaa | gcataatatt | tcgcccacta | 600 |

| | |
|---|---|
| agccaatcac tttattgact cctagccgca gacctcctca ttctaacctg aatcggagga | 660 |
| caaccagtaa gctacccttt taccatcatt ggacaagtag catccgtact atacttcaca | 720 |
| acaatcctaa tcctaatacc aactatctcc ctaattgaaa acaaaatact caaatgggcc | 780 |
| t | 781 |

<210> SEQ ID NO 5
<211> LENGTH: 565
<212> TYPE: DNA
<213> ORGANISM: Artificial
<220> FEATURE:
<223> OTHER INFORMATION: cDNA

<400> SEQUENCE: 5

| | |
|---|---|
| atggcacatg cagcgcaagt aggtctacaa gacgctactt cccctatcat agaagagctt | 60 |
| atcacctttc atgatcacgc cctcataatc attttcctta tctgcttcct agtcctgtat | 120 |
| gccctttttcc taacactcac aacaaaacta actaatacta acatctcaga cgctcaggaa | 180 |
| atagaaaccg tctgaactat cctgcccgcc atcatcctag tcctcatcgc cctcccatcc | 240 |
| ctacgcatcc tttacataac agacgaggtc aacgatccct cccttaccat caaatcaatt | 300 |
| ggccaccaat ggtactgaac ctacgagtac accgactacg gcggactaat cttcaactcc | 360 |
| tacatacttc ccccattatt cctagaacca ggcgacctgc gactcctagc cgcagacctc | 420 |
| ctcattctaa cctgaatcgg aggacaacca gtaagctacc cttttaccat cattggacaa | 480 |
| gtagcatccg tactatactt cacaacaatc ctaatcctaa taccaactat ctccctaatt | 540 |
| gaaaacaaaa tactcaaatg ggcct | 565 |

<210> SEQ ID NO 6
<211> LENGTH: 1174
<212> TYPE: DNA
<213> ORGANISM: Artificial
<220> FEATURE:
<223> OTHER INFORMATION: cDNA

<400> SEQUENCE: 6

| | |
|---|---|
| atggcacatg cagcgcaagt aggtctacaa gacgctactt cccctatcat agaagagctt | 60 |
| atcacctttc atgatcacgc cctcataatc attttcctta tctgcttcct agtcctgtat | 120 |
| gccctttttcc taacactcac aacaaaacta actaatacta acatctcaga cgctcaggaa | 180 |
| atagaaaccg tctgaactat cctgcccgcc atcatcctag tcctcatcgc cctcccatcc | 240 |
| ctacgcatcc tttacataac agacgaggtc aacgatccct cccttaccat caaatcaatt | 300 |
| ggccaccaat ggtactgaac ctacgagtac accgactacg gcggactaat cttcaactcc | 360 |
| tacatacttc ccccattatt cctagaacca ggcgacctgc gactccttga cgttgacaat | 420 |
| cgagtagtac tcccgattga agcccccatt cgtataataa ttacatcaca agacgtcttg | 480 |
| cactcatgag ctgtccccac attaggctta aaaacagatg caattcccgg acgtctaaac | 540 |
| caaaccactt tcaccgctac acgaccgggg gtatactacg gtcaatgctc tgaaatctgt | 600 |
| ggagcaaacc acagtttcat gcccatattc ttgcacgaaa cgggatcaaa caccccccta | 660 |
| ggaatcacct cccattccga taaaatcacc ttccacccctt actacacaat caaagacgcc | 720 |
| ctcggcttac ttctcttcct tctctcctta atgacattaa cactattctc accagacctc | 780 |
| ctaggcgacc cagacaatta taccctagcc aaccccttaa acaccctcc ccacatcaag | 840 |
| cccgaatgat atttcctatt cgcctacaca attctccgat ccgtccctaa caaactagga | 900 |
| ggcgtccttg ccctattact atccatcctc atcctagcaa taatccccat cctccatata | 960 |

| | |
|---|---:|
| tccaaacaac aaagcataat atttcgccca ctaagccaat cactttattg actcctagcc | 1020 |
| gcagacctcc tcattctaac ctgaatcgga ggacaaccag taagctaccc ttttaccatc | 1080 |
| attggacaag tagcatccgt actatacttc acaacaatcc taatcctaat accaactatc | 1140 |
| tccctaattg aaaacaaaat actcaaatgg gcct | 1174 |

<210> SEQ ID NO 7
<211> LENGTH: 1294
<212> TYPE: DNA
<213> ORGANISM: Artificial
<220> FEATURE:
<223> OTHER INFORMATION: cDNA

<400> SEQUENCE: 7

| | |
|---|---:|
| atgaacgaaa atctgttcgc ttcattcatt gcccccacaa tcctaggcct accgccgca | 60 |
| gtactgatca ttctatttcc ccctctattg atcccacct ccaaatatct catcaacaac | 120 |
| cgactaatca ccacccaaca atgactaatc aaactaacct caaaacaaat gataaccata | 180 |
| cacaacacta aaggacgaac ctgatctctt atactagtat ccttaatcat ttttattgcc | 240 |
| acaactaacc tcctcggact cctgcctcac tcatttacac caaccaccca actatctata | 300 |
| aacctagcca tgcactactc accagacgcc tcaaccgcct tttcatcaat cgcccacatc | 360 |
| actcgagacg taaattatgg ctgaatcatc cgctaccttc acgccaatgg cgcctcaata | 420 |
| ttctttatct gcctcttcct acacatcggg cgaggcctat attacggatc atttctctac | 480 |
| tcagaaacct gaaacatcgg cattatcctc ctgcttgcaa ctatagcaac agccttcata | 540 |
| ggctatgtcc tcccgtgagg ccaaatatca ttctgagggg ccacagtaat tacaaactta | 600 |
| ctatccgcca tcccatacat tgggacagac ctagttcaat gaatctgagg aggctactca | 660 |
| gtagacagtc ccaccctcac acgattcttt acctttcact tcatcttgcc cttcattatt | 720 |
| gcagccctag caaacactcca cctcctattc ttgcacgaaa cgggatcaaa caacccccta | 780 |
| ggaatcacct cccattccga taaaatcacc ttccacccct actacacaat caaagacgcc | 840 |
| ctcggcttac ttctcttcct tctctcctta atgacattaa cactattctc accagacctc | 900 |
| ctaggcgacc cagacaatta taccctagcc aacccttaa acaccctcc ccacatcaag | 960 |
| cccgaatgat atttcctatt cgcctacaca attctccgat ccgtccctaa caaactagga | 1020 |
| ggcgtccttg ccctattact atccatcctc atcctagcaa taatccccat cctccatata | 1080 |
| tccaaacaac aaagcataat atttcgccca ctaagccaat cactttattg actcctagcc | 1140 |
| gcagacctcc tcattctaac ctgaatcgga ggacaaccag taagctaccc ttttaccatc | 1200 |
| attggacaag tagcatccgt actatacttc acaacaatcc taatcctaat accaactatc | 1260 |
| tccctaattg aaaacaaaat actcaaatgg gcct | 1294 |

<210> SEQ ID NO 8
<211> LENGTH: 1228
<212> TYPE: DNA
<213> ORGANISM: Artificial
<220> FEATURE:
<223> OTHER INFORMATION: cDNA

<400> SEQUENCE: 8

| | |
|---|---:|
| atgcccctca tttacataaa tattatacta gcatttacca tctcacttct aggaatacta | 60 |
| gtatatcgct cacacctcat atcctccta ctatgcctag aaggaataat actatcgctg | 120 |
| ttcattatag ctactctcat aaccctcaac acccactccc tcttagccaa tattgtgcct | 180 |
| attgccatac tagtctttgg cgcctgcctg atcctccaaa tcaccacagg actattccta | 240 |

```
gccatgcact actcaccaga cgcctcaacc gccttttcat caatcgccca catcactcga      300
gacgtaaatt atggctgaat catccgctac cttcacgcca atggcgcctc aatattcttt      360
atctgcctct tcctacacat cgggcgaggc ctatattacg gatcatttct ctactcagaa      420
acctgaaaca tcggcattat cctcctgctt gcaactatag caacagcctt cataggctat      480
gtcctcccgt gaggccaaat atcattctga ggggccacag taattacaaa cttactatcc      540
gccatcccat acattgggac agacctagtt caatgaatct gaggaggcta ctcagtagac      600
agtcccaccc tcacacgatt ctttacctttt cacttcatct tgcccttcat tattgcagcc      660
ctagcaacac tccacctcct attcttgcac gaaacgggat caaacaaccc cctaggaatc      720
acctcccatt ccgataaaat caccttccac ccttactaca caatcaaaga cgccctcggc      780
ttacttctct tccttctctc cttaatgaca ttaacactat tctcaccaga cctcctaggc      840
gacccagaca attataccct agccaacccc ttaaacaccc ctccccacat caagcccgaa      900
tgatatttcc tattcgccta cacaattctc cgatccgtcc ctaacaaact aggaggcgtc      960
cttgccctat tactatccat cctcatccta gcaataatcc ccatcctcca tatatccaaa     1020
caacaaagca taatatttcg cccactaagc caatcacttt attgactcct agccgcagac     1080
ctcctcattc taacctgaat cggaggacaa ccagtaagct acccttttac catcattgga     1140
caagtagcat ccgtactata cttcacaaca atcctaatcc taataccaac tatctcccta     1200
attgaaaaca aaatactcaa atgggcct                                         1228
```

<210> SEQ ID NO 9
<211> LENGTH: 522
<212> TYPE: DNA
<213> ORGANISM: Artificial
<220> FEATURE:
<223> OTHER INFORMATION: cDNA

<400> SEQUENCE: 9

```
atgttcgccg accgttgact attctctaca aaccacaaag acattggaac actataccta       60
ttattcggcg catgagctgg agtcctaggc acagctctaa gcctccttat tcgagccgag      120
ctgggccagc caggcaacct tctaggtaac gaccacatct acaacgttat cgtcacagcc      180
ctcgctgtca ctttcctagg acttctaaca gccctagacc tcaactacct aaccaacaaa      240
cttaaaataa aatcccccact atgcacattt tatttctcca acatactcgg attctaccct      300
agcatcacac accgcacaat ccctatctat ggccttctta cgagccaaaa cctgccccta      360
ctcctcctag acctaacctg actagaaaag ctattaccta aaacaatttc acagcaccaa      420
atctccacct ccatcatcac ctcaacccaa aaaggcataa ttaaactttta cttcctctct      480 ttcttcttcc cactcatcct aaccctactc ctaatcacat aa                         522
```

<210> SEQ ID NO 10
<211> LENGTH: 582
<212> TYPE: DNA
<213> ORGANISM: Artificial
<220> FEATURE:
<223> OTHER INFORMATION: cDNA

<400> SEQUENCE: 10

```
atgttcgccg accgttgact attctctaca aaccacaaag acattggaac actataccta       60
ttattcggcg catgagctgg agtcctaggc acagctctaa gcctccttat tcgagccgag      120
ctgggccagc caggcaacct tctaggtaac gaccacatct acaacgttat cgtcacagcc      180
catgcatttg taataatctt cttcatagta ataccatca taatcggagg ctttggcaac      240
```

| | |
|---|---|
| tgactagttc ccctaataat cggtgccccc gatatggcgt ttccccgcat aaacaacata | 300 |
| agcttctgac tcttacctcc ctctctccta ctcctgctcg catctgctat agtggaggcc | 360 |
| ggagcaggaa caggttgaac agtctaccct cccttagcag ggaactactc ccaccctgga | 420 |
| gccctcctag acctaacctg actagaaaag ctattaccta aaacaatttc acagcaccaa | 480 |
| atctccacct ccatcatcac ctcaacccaa aaaggcataa ttaaacttta cttcctctct | 540 |
| ttcttcttcc cactcatcct aaccctactc ctaatcacat aa | 582 |

<210> SEQ ID NO 11
<211> LENGTH: 2208
<212> TYPE: DNA
<213> ORGANISM: Artificial
<220> FEATURE:
<223> OTHER INFORMATION: cDNA

<400> SEQUENCE: 11

| | |
|---|---|
| atgttcgccg accgttgact attctctaca aaccacaaag acattggaac actataccta | 60 |
| ttattcggcg catgagctgg agtcctaggc acagctctaa gcctccttat tcgagccgag | 120 |
| ctgggccagc caggcaacct tctaggtaac gaccacatct acaacgttat cgtcacagcc | 180 |
| catgcatttg taataatctt cttcatagta ataccdatca taatcggagg ctttggcaac | 240 |
| tgactagttc ccctaataat cggtgccccc gatatggcgt ttccccgcat aaacaacata | 300 |
| agcttctgac tcttacctcc ctctctccta ctcctgctcg catctgctat agtggaggcc | 360 |
| ggagcaggaa caggttgaac agtctaccct cccttagcag ggaactactc ccaccctgga | 420 |
| gcctccgtag acctaaccat cttctcctta cacctagcag gtgtctcctc tatcttaggg | 480 |
| gccatcaatt tcatcacaac aattatcaat ataaaacccc ctgccataac ccaataccaa | 540 |
| acgcccctct tcgtctgatc cgtcctaatc acagcagtcc tacttctcct atctctccca | 600 |
| gtcctagctg ctggcatcac tatactacta acagaccgca acctcaacac caccttcttc | 660 |
| gaccccgccg gaggaggaga ccccattcta taccaacacc tattctgatt tttcggtcac | 720 |
| cctgaagttt atattcttat cctaccaggc ttcggaataa tctcccatat tgtaacttac | 780 |
| tactccggaa aaaagaacc atttggatac ataggtatgg tctgagctat gatatcaatt | 840 |
| ggcttcctag ggtttatcgt gtgagcacac catatattta cagtaggaat agacgtagac | 900 |
| acacgagcat atttcacctc cgctaccata atcatcgcta tccccaccgg cgtcaaagta | 960 |
| tttagctgac tcgccacact ccacggaagc aatatgaaat gatctgctgc agtgctctga | 1020 |
| gccctaggat tcatctttct tttcaccgta ggtggcctga ctggcattgt attagcaaac | 1080 |
| tcatcactag acatcgtact acacgacacg tactacgttg tagcccactt ccactatgtc | 1140 |
| ctatcaatag gagctgtatt tgccatcata ggaggcttca ttcactgatt tcccctattc | 1200 |
| tcaggctaca ccctagacca aacctacgcc aaaatccatt tcactatcat attcatcggc | 1260 |
| gtaaatctaa cttttcttccc acaacacttt ctcggcctat ccggaatgcc ccgacgttac | 1320 |
| tcggactacc ccgatgcata caccacatga aacatcctat catctgtagg ctcattcatt | 1380 |
| tctctaacag cagtaatatt aataattttc atgatttgag aagccttcgc ttcgaagcga | 1440 |
| aaagtcctaa tagtagaaga accctccata aacctggagt gactatatgg atgcccccca | 1500 |
| ccctaccaca cattcgaaga acccgtatac ataaaagcag gaataccttt cctcacaggt | 1560 |
| ttctactcca agaccacat catcgaaacc gcaaacatat catacacaaa cgcctgagcc | 1620 |
| ctatctatta ctctcatcgc tacctccctg acaagcgcct atagcactcg aataattctt | 1680 |
| ctcaccctaa caggtcaacc tcgcttcccc acccttacta acattaacga aataaccccc | 1740 |

```
accctactaa accccattaa acgcctggca gccggaagcc tattcgcagg atttctcatt      1800
actaacaaca tttcccccgc atccccttc caaacaacaa tcccctcta cctaaaactc       1860 acagccctcg ctgtcacttt cctaggactt ctaacagccc tagacctcaa ctacctaacc    1920
aacaaactta aaataaaatc cccactatgc acattttatt tctccaacat actcggattc    1980
taccctagca tcacacaccg cacaatcccc tatctaggcc ttcttacgag ccaaaacctg    2040 ccccctactcc tcctagacct aacctgacta gaaaagctat acctaaaac aatttcacag    2100 caccaaatct ccacctccat catcacctca acccaaaaag gcataattaa actttacttc    2160
ctctctttct tcttcccact catcctaacc ctactcctaa tcacataa                 2208

<210> SEQ ID NO 12
<211> LENGTH: 807
<212> TYPE: DNA
<213> ORGANISM: Artificial
<220> FEATURE:
<223> OTHER INFORMATION: cDNA

<400> SEQUENCE: 12
atggcacatg cagcgcaagt aggtctacaa gacgctactt cccctatcat agaagagctt      60
atcacctttc atgatcacgc cctcataatc attttcctta tctgcttcct agtcctgtat    120
gcccttttcc taacactcac aacaaaacta actaatacta acatctcaga cgctcaggaa    180
atagaaaccg caaacatatc atacacaaac gcctgagccc tatctattac tctcatcgct    240
acctccctga caagcgccta tagcactcga ataattcttc tcaccctaac aggtcaacct    300
cgcttcccca cccttactaa cattaacgaa ataaccccca cctactaaa ccccattaaa    360 cgcctggcag ccggaagcct attcgcagga tttctcatta ctaacaacat tccccccgca    420 tccccttcc aaacaacaat cccctctac ctaaaactca gccctcgc tgtcactttc       480 ctaggacttc taacagccct agacctcaac tacctaacca caaacttaa aataaaatcc    540 ccactatgca cattttattt ctccaacata ctcggattct accctagcat cacacaccgc    600
acaatcccct atctaggcct tcttacgagc caaaacctgc ccctactcct cctagaccta    660
acctgactag aaaagctatt acctaaaaca atttcacagc accaaatctc cacctccatc    720
atcacctcaa cccaaaaagg cataattaaa ctttacttcc tctctttctt cttcccactc    780
atcctaaccc tactcctaat cacataa                                       807

<210> SEQ ID NO 13
<211> LENGTH: 786
<212> TYPE: DNA
<213> ORGANISM: Artificial
<220> FEATURE:
<223> OTHER INFORMATION: cDNA

<400> SEQUENCE: 13
atggcacatg cagcgcaagt aggtctacaa gacgctactt cccctatcat agaagagctt      60
atcacctttc atgatcacgc cctcataatc attttcctta tctgcttcct agtcctgtat    120
gcccttttcc taacactcac aacaaaacta actaatacta acatctcaga cgctcaggaa    180
atagaaaccg tctgaactat cctgcccgcc atcatcctag tcctcatcgc cctcccatcc    240
ctacgcatcc tttacataac agacgaggtc aacgatccct ccttaccat caaatcaatt    300 ggccaccaat ggtactgaac ctacgagtac accgactacg cggactaat cttcaactcc    360 tacatacttc ccccattatt cctagaacca ggcgacctgc gactccttga cgttgacaat    420
cgagtagtac tcccgattga agccccccatt cgtataataa ttacatcaca agacgtcttg    480
```

| | |
|---|---:|
| cactcatgag ctgtccccac attaggctta aaaacagatg caattcccgg acgtctaaac | 540 |
| caaaccactt tcaccgctac acgaccgggg gtatactacg gtcaatgctc tgaaatctgt | 600 |
| ggagcaaacc acagtttcat gcccatcgtc ctagacctaa cctgactaga aaagctatta | 660 |
| cctaaaacaa tttcacagca ccaaatctcc acctccatca tcacctcaac ccaaaaaggc | 720 |
| ataattaaac tttacttcct ctctttcttc ttcccactca tcctaaccct actcctaatc | 780 |
| acataa | 786 |

<210> SEQ ID NO 14
<211> LENGTH: 1905
<212> TYPE: DNA
<213> ORGANISM: Artificial
<220> FEATURE:
<223> OTHER INFORMATION: cDNA

<400> SEQUENCE: 14

| | |
|---|---:|
| atgaacgaaa atctgttcgc ttcattcatt gcccccacaa tcctaggcct acccgccgca | 60 |
| gtactgatca ttctatttcc ccctctattg atccccacct ccaaatatct catcaacaac | 120 |
| cgactaatca ccacccaaca atgactaatc aaactaacct caaaacaaat gataaccata | 180 |
| cacaacacta aaggacgaac ctgatctctt atactagtat ccttaatcat ttttattgcc | 240 |
| acaactaacc tcctcggact cctgcctcac tcatttacac caaccaccca actatctata | 300 |
| aacctagcca tggccatccc cttatgagcg ggcacagtga ttataggctt cgctctaag | 360 |
| attaaaaatg ccctagccca cttcttacca caaggcacac ctacacccct tatccccata | 420 |
| ctagttatta tcgaaaccat cagcctactc attcaaccaa tagccctggc cgtacgccta | 480 |
| accgctaaca ttactgcagg ccacctactc atgcacctaa ttggaagcgc cacccctagca | 540 |
| atatcaacca ttaaccttcc ctctacactt atcatcttca caattctaat tctactgact | 600 |
| atcctagaaa tcgctgtcgc cttaatccaa gcctacgttt tcacacttct agtaagcctc | 660 |
| tacctacact ccaactcatg agacccacaa caaatagccc ttctaaacgc taatccaagc | 720 |
| ctcaccccac tactaggcct cctcctagca gcagcaggca aatcagccca attaggtctc | 780 |
| caccctgac tccctcagc catagaaggc cccacccag tctcagccct actccactca | 840 |
| agcactatag ttgtagcagg aatcttctta ctcatccgct tccaccccct agcagaaaat | 900 |
| agcccactaa tccaaactct aacactatgc ttaggcgcta tcaccactct gttcgcagca | 960 |
| gtctgcgccc ttacacaaaa tgacatcaaa aaaatcgtag ccttctccac ttcaagtcaa | 1020 |
| ctaggactca taatagttac aatcggcatc aaccaaccac acctagcatt cctgcacatc | 1080 |
| tgtacccacg ccttcttcaa agccatacta tttatgtgct ccgggtccat catccacaac | 1140 |
| cttaacaatg aacaagatat tcgaaaaata ggaggactac tcaaaaccat acctctcact | 1200 |
| tcaacctccc tcaccattgg cagcctagca ttagcaggaa tacctttcct cacaggtttc | 1260 |
| tactccaaag accacatcat cgaaaccgca acatatcat acacaaacgc ctgagcccta | 1320 |
| tctattactc tcatcgctac ctccctgaca agcgcctata gcactcgaat aattcttctc | 1380 |
| accctaacag gtcaacctcg cttccccacc cttactaaca ttaacgaaaa taaccccacc | 1440 |
| ctactaaaacc ccattaaacg cctggcagcc ggaagcctat tcgcaggatt tctcattact | 1500 |
| aacaacattt ccccgcatc ccccttccaa caacaatcc cctctacct aaaactcaca | 1560 |
| gccctcgctg tcactttcct aggacttcta acagccctag acctcaacta cctaaccaac | 1620 |
| aaacttaaaa taaatccccc actatgcaca ttttatttct ccaacatact cggattctac | 1680 |
| cctagcatca cacaccgcac aatcccctat ctaggccttc ttacgagcca aaacctgccc | 1740 |

```
ctactcctcc tagacctaac ctgactagaa aagctattac ctaaaacaat ttcacagcac    1800
caaatctcca cctccatcat cacctcaacc caaaaaggca taattaaact ttacttcctc    1860
tctttcttct tcccactcat cctaaccta ctcctaatca cataa                     1905

<210> SEQ ID NO 15
<211> LENGTH: 1545
<212> TYPE: DNA
<213> ORGANISM: Artificial
<220> FEATURE:
<223> OTHER INFORMATION: cDNA

<400> SEQUENCE: 15
atgacccacc aatcacatgc ctatcatata gtaaaaccca gcccatgacc cctaacaggg      60
gccctctcag ccctcctaat gacctccggc ctagccatgt gatttcactt ccactccata    120
acgctcctca tactaggcct actaaccaac acactaacca tataccaatg atggcgcgat    180
gtaacacgag aaagcacata ccaaggccac cacacaccac ctgtccaaaa aggccttcga    240
tacgggataa tcctatttat tacctcagaa gttttttttct tcgcaggatt tttctgagcc    300
ttttaccact ccagcctagc ccctacccc caattaggag ggcactggcc cccaacaggc    360
atcaccccac tactaggcct cctcctagca gcaggca atcagccca attaggtctc      420 caccctgac tccctcagc catagaaggc cccaccccag tctcagccct actccactca    480
agcactatag ttgtagcagg aatcttctta ctcatccgct ccacccct agcagaaaat     540 agcccactaa tccaaactct aacactatgc ttaggcgcta tcaccactct gttcgcagca    600
gtctgcgccc ttacacaaaa tgacatcaaa aaaatcgtag ccttctccac ttcaagtcaa    660
ctaggactca taatagttac aatcggcatc aaccaaccac acctagcatt cctgcacatc    720
tgtacccacg cctcttcaa agccatacta tttatgtgct ccgggtccat catccacaac    780
cttaacaatg aacaagatat tcgaaaaata ggaggactca tcaaaaccat acctctcact    840
tcaacctccc tcaccattgg cagcctagca ttagcaggaa taccttttcct cacaggtttc    900 tactccaaag accacatcat cgaaaccgca aacatatcat acacaaacgc ctgagcccta    960
tctattactc tcatcgctac ctccctgaca agcgcctata gcactcgaat aattcttctc    1020
accctaacag gtcaacctcg cttccccacc cttactaaca ttaacgaaaa taaccccacc    1080
ctactaaacc ccattaaacg cctggcagcc ggaagcctat tcgcaggatt tctcattact    1140
aacaacattt cccccgcatc ccccttccaa acaacaatcc cctctacct aaaactcaca    1200 gccctcgctg tcactttcct aggacttcta acagccctag acctcaacta cctaaccaac    1260
aaacttaaaa taaatccccc actatgcaca ttttatttct ccaacatact cggattctac    1320
cctagcatca cacaccgcac aatcccctat ctaggccttc ttacgagcca aaacctgccc    1380
ctactcctcc tagacctaac ctgactagaa aagctattac ctaaaacaat ttcacagcac    1440
caaatctcca cctccatcat cacctcaacc caaaaaggca taattaaact ttacttcctc    1500
tctttcttct tcccactcat cctaaccta ctcctaatca cataa                     1545

<210> SEQ ID NO 16
<211> LENGTH: 1629
<212> TYPE: DNA
<213> ORGANISM: Artificial
<220> FEATURE:
<223> OTHER INFORMATION: cDNA

<400> SEQUENCE: 16
ataaacttcg ccttaatttt aataatcaac accctcctag ccttactact aataattatt      60
```

| | |
|---|---|
| acattttgac taccacaact caacggctac atagaaaaat ccacccctta cgagtgcggc | 120 |
| ttcgacccta tatccccgc ccgcgtccct ttctccataa aattcttctt agtagctatt | 180 |
| accttcttat tatttgatct agaaattgcc ctccttttac ccctaccatg agccctacaa | 240 |
| acaactaacc tgccactaat agttatgtca tccctcttat taatcatcat cctagccta | 300 |
| agtctggcca acacagcagc cattcaagca atcctataca accgtatcgg cgatatcggt | 360 |
| ttcatcctcg ccttagcatg atttatccta cactccaact catgagaccc acaacaaata | 420 |
| gcccttctaa acgctaatcc aagcctcacc ccactactag gcctcctcct agcagcagca | 480 |
| ggcaaatcag cccaattagg tctccacccc tgactcccct cagccataga aggccccacc | 540 |
| ccagtctcag ccctactcca ctcaagcact atagttgtag caggaatctt cttactcatc | 600 |
| cgcttccacc cctagcaga aaatagccca ctaatccaaa ctctaacact atgcttaggc | 660 |
| gctatcacca ctctgttcgc agcagtctgc gcccttacac aaaatgacat caaaaaaatc | 720 |
| gtagccttct ccacttcaag tcaactagga ctcataatag ttacaatcgg catcaaccaa | 780 |
| ccacacctag cattcctgca catctgtacc cacgccttct tcaaagccat actatttatg | 840 |
| tgctccgggt ccatcatcca aaccttaac aatgaacaag atattcgaaa ataggagga | 900 |
| ctactcaaaa ccatacctct cacttcaacc tccctcacca ttggcagcct agcattagca | 960 |
| ggaatacctt tcctcacagg tttctactcc aaagaccaca tcatcgaaac cgcaaacata | 1020 |
| tcatacacaa acgcctgagc cctatctatt actctcatcg ctacctccct gacaagcgcc | 1080 |
| tatagcactc gaataattct tctcacccta acaggtcaac ctcgcttccc caccttact | 1140 |
| aacattaacg aaaataaccc caccctacta aaccccatta aacgcctggc agccggaagc | 1200 |
| ctattcgcag gatttctcat tactaacaac atttccccg catccccctt ccaaacaaca | 1260 |
| atcccctct acctaaaact cacagccctc gctgtcactt tcctaggact tctaacagcc | 1320 |
| ctagacctca actacctaac caacaaactt aaaataaaat ccccactatg cacattttat | 1380 |
| ttctccaaca tactcggatt ctaccctagc atcacacacc gcacaatccc ctatctaggc | 1440 |
| cttcttacga gccaaaacct gcccctactc tcctagacc taacctgact agaaaagcta | 1500 |
| ttacctaaaa caatttcaca gcaccaaatc tccacctcca tcatcacctc aacccaaaaa | 1560 |
| ggcataatta aactttactt cctctctttc ttcttcccac tcatcctaac cctactccta | 1620 |
| atcacataa | 1629 |

<210> SEQ ID NO 17
<211> LENGTH: 642
<212> TYPE: DNA
<213> ORGANISM: Artificial
<220> FEATURE:
<223> OTHER INFORMATION: cDNA

<400> SEQUENCE: 17

| | |
|---|---|
| atgctaaaac taatcgtccc aacaattata ttactaccac tgacatgact ttccaaaaaa | 60 |
| cacataattt gaatcaacac aaccacccac agcctaatta ttagcatcat ccctctacta | 120 |
| ttttttaacc aaatcaacaa caacctattt agctgttccc caacctttc ctccgacccc | 180 |
| ctaacaaccc cctcctaat actaactacc tgactcctac ccctcacaat catggcaagc | 240 |
| caacgccact tatccagtga accactatca cgaaaaaaac tctacctctc tactaatc | 300 |
| tccctacaaa tctccttaat tataacattc acagccacag aactaatcat attttatatc | 360 |
| ttcttcgaaa ccacacttat ccccaccttg gctatcatca cccgatgagg caaccagcca | 420 |
| gaacgcctga acgcaggcac atacttccta ttctacaccc tagtaggctc cctgccccta | 480 |

-continued

```
ctcctcctag acctaacctg actagaaaag ctattaccta aaacaatttc acagcaccaa        540
atctccacct ccatcatcac ctcaacccaa aaaggcataa ttaaactttta cttcctctct        600 ttcttcttcc cactcatcct aaccctactc ctaatcacat aa                           642
```

```
<210> SEQ ID NO 18
<211> LENGTH: 129
<212> TYPE: DNA
<213> ORGANISM: Artificial
<220> FEATURE:
<223> OTHER INFORMATION: cDNA

<400> SEQUENCE: 18
atgccccaac taaatactac cgtatggccc accataatta ccccatact ccttacacta         60 ttcctcatca cccaactaaa aatattaaac acaaactacc acctacctcc ctcaccattg       120
gcagcctag                                                              129
```

```
<210> SEQ ID NO 19
<211> LENGTH: 783
<212> TYPE: RNA
<213> ORGANISM: Human

<400> SEQUENCE: 19
auggcccacc auaauuaccc ccauacuccu uacacuauuc cucaucaccc aacuaaaaau        60
auuaaacaca aacuaccacc uaccucccuc accauggca gccuagcauu agcaggaaua       120 ccuuccuca caggguuucua cuccaaagac cacaucaucg aaaccgcaaa cauaucauac      180
acaaacgccu gagcccuauc uauuacucuc aucgcuaccu cccugacaag cgccuauagc      240
acucgaauaa uucuucucac ccuaacaggu caaccucgcu uccccacccu acuaacauu       300 aacgaaaaua accccacccu acuaaacccc auuaaacgcc uggcagccgg aagccuauuc      360
gcaggauuuc ucauuacuaa caacauuucc ccgcaucccc ccuuccaaac aacaauccc       420 cucuaccuaa aacucacagc ccucgcuguc acuuccuag acuucuaac agcccuagac        480 cucaacuacc uaaccaacaa acuuaaaaua aauccccac uaugcacauu uuauuucucc       540
aacauacucg gauucuaccc uagcaucaca caccgcacaa uccccuaucu aggccuucuu      600
acgagccaaa accugccccu acuccuccua gaccuaaccu gacuagaaaa gcuauuaccu      660
aaaacaauuu cacagcacca aaucuccacc uccaucauca ccucaaccca aaaaggcaua     720
auuaaacuuu acuuccucuc uuucuucuuc ccacucaucc uaaccuacu ccuaaucaca     780 uaa                                                                  783
```

```
<210> SEQ ID NO 20
<211> LENGTH: 300
<212> TYPE: RNA
<213> ORGANISM: Human

<400> SEQUENCE: 20
augccccuca uuuacauaaa uauuauacua gcauuuacca ucucacuucu aggaauacua       60
guauaucgcu cacaccucau auccccccua cuaugccuag aaggaauaau acuaucgcug      120
uucauuauag cuacucucau aaccccucaac acccacuccc ucuuagccaa uauugugccu      180
auugccauac uagucuuugc cgccugcgaa gcagcggugg gccuagcccu acuagucuca      240
aucuccaaca cauauggccu agacuacgua cauaaccuaa cccuacuccu aaucacauaa      300
```

```
<210> SEQ ID NO 21
<211> LENGTH: 781
```

<212> TYPE: RNA
<213> ORGANISM: Human

<400> SEQUENCE: 21

```
auggcacaug cagcgcaagu aggucuacaa gacgcuacuu ccccuaucau agaagagcuu    60
aucaccuuuc augaucacgc ccucauaauc auuuuccuua ucugcuuccu aguccuguau   120
gcccuuuucc uaacacucac aacaaaacua acuaauacua acaucucaga cgcucaggaa   180
auagaaaccg ucugaacuau ccugcccgcc aucauccuag uccucaucgc ccucccaucc   240
cuacgcaucc uuuacauaac agacgagguc aacgaucccu cccuuaccau caaaucaauu   300
ggccaccaau gguacugaac cuacgaguac accgacuacg gcggacuaau cuucaacucc   360
uacauacuuc ccccauuauu ccuagaacca ggcgacccag acaauuauac ccuagccaac   420
cccuuaaaca ccccucccca caucaagccc gaaugauauu uccauucgc cuacacaauu   480
cuccgauccg uccuaacaa acuaggaggc guccuugccc uauuacuauc caucucauc   540
cuagcaauaa uccccauccu ccauauaucc aaacaacaaa gcauauauu cgcccacua   600
agccaaucac uuuauugacu ccuagccgca gaccuccuca uucuaaccug aaucggagga   660
caaccaguaa gcuacccuuu uaccaucauu ggacaaguag cauccguacu auacuucaca   720
acaauccuaa uccuaauacc aacuaucucc cuaauugaaa acaaaauacu caaaugggcc   780
u                                                                  781
```

<210> SEQ ID NO 22
<211> LENGTH: 565
<212> TYPE: RNA
<213> ORGANISM: Human

<400> SEQUENCE: 22

```
auggcacaug cagcgcaagu aggucuacaa gacgcuacuu ccccuaucau agaagagcuu    60
aucaccuuuc augaucacgc ccucauaauc auuuuccuua ucugcuuccu aguccuguau   120
gcccuuuucc uaacacucac aacaaaacua acuaauacua acaucucaga cgcucaggaa   180
auagaaaccg ucugaacuau ccugcccgcc aucauccuag uccucaucgc ccucccaucc   240
cuacgcaucc uuuacauaac agacgagguc aacgaucccu cccuuaccau caaaucaauu   300
ggccaccaau gguacugaac cuacgaguac accgacuacg gcggacuaau cuucaacucc   360
uacauacuuc ccccauuauu ccuagaacca ggcgaccugc gacuccuagc cgcagaccuc   420
cucauucuaa ccugaaucgg aggacaacca guaagcuacc cuuuuaccau cauuggacaa   480
guagcauccg uacuauacuu cacaacaauc cuaauccuua uaccaacuau cucccuaauu   540
gaaaacaaaa uacucaaaug ggccu                                        565
```

<210> SEQ ID NO 23
<211> LENGTH: 1174
<212> TYPE: RNA
<213> ORGANISM: Human

<400> SEQUENCE: 23

```
auggcacaug cagcgcaagu aggucuacaa gacgcuacuu ccccuaucau agaagagcuu    60
aucaccuuuc augaucacgc ccucauaauc auuuuccuua ucugcuuccu aguccuguau   120
gcccuuuucc uaacacucac aacaaaacua acuaauacua acaucucaga cgcucaggaa   180
auagaaaccg ucugaacuau ccugcccgcc aucauccuag uccucaucgc ccucccaucc   240
cuacgcaucc uuuacauaac agacgagguc aacgaucccu cccuuaccau caaaucaauu   300
ggccaccaau gguacugaac cuacgaguac accgacuacg gcggacuaau cuucaacucc   360
```

```
uacauacuuc ccccauuauu ccuagaacca ggcgaccugc gacuccuuga cguugacaau    420
cgaguaguac ucccgauuga agcccccauu cguauaauaa uuacaucaca agacgucuug    480
cacucaugag cugucccac auuaggcuua aaaacagaug caauucccgg acgucuaaac     540
caaaccacuu ucaccgcuac acgaccgggg guauacuacg gucaaugcuc ugaaaucugu    600
ggagcaaacc acaguuucau gcccauauuc uugcacgaaa cgggaucaaa caaccccua    660 ggaaucaccu cccauuccga uaaaaucacc uuccacccuu acuacacaau caaagacgcc    720
cucggcuuac uucucuuccu ucucuccuua augacauuaa cacuauucuc accagaccuc    780
cuaggcgacc cagacaauua uacccuagcc aaccccuuaa acaccccucc ccacaucaag    840
cccgaaugau auuuccuauu cgccuacaca auucuccgau ccgucccuaa caaacuagga    900
ggcguccuug cccauuuacu auccauccuc auccuagcaa uaaucccau ccuccauaua     960 uccaaacaac aaagcauaau auuucgccca cuaagccaau cacuuuauug acuccuagcc   1020
gcagaccucc ucauucuaac cugaaucgga ggacaaccag uaagcuaccc uuuuaccauc   1080
auuggacaag uagcauccgu acuauacuuc acaacaaucc uaauccuaau accaacuauc   1140
ucccuaauug aaaacaaaau acucaaaugg gccu                               1174

<210> SEQ ID NO 24
<211> LENGTH: 1294
<212> TYPE: RNA
<213> ORGANISM: Human

<400> SEQUENCE: 24
augaacgaaa aucuguucgc uucauucauu gcccccacaa uccuaggccu acccgccgca     60
guacugauca uucuauuucc cccucuauug auccccaccu ccaaauaucu caucaacaac    120
cgacuaauca ccacccaaca augacuaauc aaacuaaccu caaaacaaau gauaaccaua    180
cacaacacua aaggacgaac cugaucucuu auacuaguau ccuuaaucau uuuuauugcc    240
acaacuaacc uccucggacu ccugccucac ucauuuacac caaccaccca acuaucuaua    300
aaccuagcca ugcacuacuc accagacgcc ucaccgccu uucaucaau cgcccacauc     360 acucgagacg uaaauuaugg cugaaucauc cgcuaccuuc acgccaaugg cgccucaaua    420
uucuuuaucu gccucuuccu acacaucggg cgaggccuau auuacggauc auuucucuac    480
ucagaaaccu gaaacaucgg cauuauccuc cugcuugcaa cuauagcaac agccuucaua    540
ggcuaugucc ucccgugagg ccaaauauca uucugagggg ccacaguaau uacaaacuua    600
cuauccgcca ucccauacau ugggacagac cuaguucaau gaaucugagg aggcuacuca    660
guagacaguc ccacccucac acgauucuuu accuuacacu ucaucuugcc cuucauuauu    720
gcagcccuag caacacucca ccuccuauuc uugcacgaaa cgggaucaaa caaccccua     780 ggaaucaccu cccauuccga uaaaaucacc uuccacccuu acuacacaau caaagacgcc    840
cucggcuuac uucucuuccu ucucuccuua augacauuaa cacuauucuc accagaccuc    900
cuaggcgacc cagacaauua uacccuagcc aaccccuuaa acaccccucc ccacaucaag    960
cccgaaugau auuuccuauu cgccuacaca auucuccgau ccgucccuaa caaacuagga   1020
ggcguccuug cccauuuacu auccauccuc auccuagcaa uaaucccau ccuccauaua    1080 uccaaacaac aaagcauaau auuucgccca cuaagccaau cacuuuauug acuccuagcc   1140
gcagaccucc ucauucuaac cugaaucgga ggacaaccag uaagcuaccc uuuuaccauc   1200
auuggacaag uagcauccgu acuauacuuc acaacaaucc uaauccuaau accaacuauc   1260
ucccuaauug aaaacaaaau acucaaaugg gccu                               1294
```

<210> SEQ ID NO 25
<211> LENGTH: 1228
<212> TYPE: RNA
<213> ORGANISM: Human

<400> SEQUENCE: 25

| | | | | | |
|---|---|---|---|---|---|
| augcccuca | uuuacauaaa | uauuauacua | gcauuuacca | ucucacuucu | aggaauacua | 60 |
| guauaucgcu | cacaccucau | auccucccua | cuaugccuag | aaggaauaau | acaucgcug | 120 |
| uucauuauag | cuacucucau | aacccucaac | acccacuccc | ucuuagccaa | uauugugccu | 180 |
| auugccauac | uagucuuugg | cgccugccug | auccuccaaa | ucaccacagg | acauuuccua | 240 |
| gccaugcacu | acuccaccaga | cgccucaacc | gccuuuucau | caaucgccca | caucacucga | 300 |
| gacguaaauu | auggcugaau | cauccgcuac | cuucacgcca | auggcgccuc | aauauucuuu | 360 |
| aucugccucu | uccuacacau | cgggcgaggc | cuauauuacg | gaucauuucu | cuacucagaa | 420 |
| accugaaaca | ucggcauuau | ccuccugcuu | gcaacuauag | caacagccuu | cauaggcuau | 480 |
| guccucccgu | gaggccaaau | aucauucuga | ggggccacag | uaauuacaaa | cuuacuaucc | 540 |
| gccaucccau | acauugggac | agaccuaguu | caaugaaucu | gaggaggcua | ucaguagac | 600 |
| aguccacccc | ucacgcgauu | cuuuaccuuu | cacuucaucu | ugcccuucau | uauugcagcc | 660 |
| cuagcaacac | uccaccuccu | auuccuugcac | gaaacgggau | caaacaaccc | ccuaggaauc | 720 |
| accucccauu | ccgauaaaau | caccuuccac | ccuuacuaca | caaucaaaga | cgcccucggc | 780 |
| uuacuucucu | uccuucucuc | cuuaaugaca | uuaaacauau | ucuccagaaa | ccuccuaggc | 840 |
| gacccagaca | uuauacccu | agccaacccc | uuaaacaccc | cucccacau | caagcccgaa | 900 |
| ugauauuucc | uauucgccua | cacaauucuc | cgauccgucc | cuaacaaacu | aggaggcguc | 960 |
| cuugcccuau | uacuauccau | ccucauccua | gcaauaaucc | ccauccucca | uauaccaaa | 1020 |
| caacaaagca | uaauauuucg | cccacuaagc | caaucacuuu | auugacuccu | agccgcagac | 1080 |
| cuccucauuc | uaaccugaau | cggaggacaa | ccaguaagcu | acccuuuuac | caucauugga | 1140 |
| caaguagcau | ccguacuaua | cuucacaaca | auccuaauccc | uaauaccaac | uaucucccua | 1200 |
| auugaaaaca | aaauacucaa | augggccu | | | 1228 |

<210> SEQ ID NO 26
<211> LENGTH: 522
<212> TYPE: RNA
<213> ORGANISM: Human

<400> SEQUENCE: 26

| | | | | | |
|---|---|---|---|---|---|
| auguucgccg | accguugacu | auucucuaca | aaccacaaag | acauuggaac | acuauaccua | 60 |
| uuauucggcg | caugagcugg | aguccuaggc | acagcucuaa | gccuccuuau | ucgagccgag | 120 |
| cugggccagc | caggcaaccu | ucuagguaac | gaccacaucu | acaacguuau | cgucacagcc | 180 |
| cucgcuguca | cuuccuaggg | acuucuaaca | gcccuagacc | ucaacuaccu | aaccaacaaa | 240 |
| cuuaaaauaa | aaucccacu | augcacauuu | auuuccucca | acauacucgg | auucuacccu | 300 |
| agcaucacac | accgcacaau | ccccuaucua | ggccuucuua | cgagccaaaa | ccugccccua | 360 |
| cuccuccuag | accuaaccug | acuagaaaag | cuauuaccua | aaacaauuuc | acagcaccaa | 420 |
| aucuccaccu | ccaucaucac | cucaacccaa | aaaggcauaa | uuaaacuuua | cuuccucucu | 480 |
| uucuucuucc | cacucauccu | aacccuacuc | cuaaucacau | aa | | 522 |

<210> SEQ ID NO 27
<211> LENGTH: 582

```
<212> TYPE: RNA
<213> ORGANISM: Human

<400> SEQUENCE: 27
auguucgccg accguugacu auucucuaca aaccacaaag acauuggaac acuauaccua      60
uuauucggcg caugagcugg aguccuaggc acagcucuaa gccuccuuau ucgagccgag     120
cugggccagc caggcaaccu ucuagguaac gaccacaucu acaacguuau cgucacagcc     180
caugcauuug uaauaaucuu cuucauagua auacccauca uaaucggagg cuuuggcaac     240
ugacuaguuc cccuaauaau cggugccccc gauauggcgu uccccgcau aaacaacaua      300 agcuucugac ucuuaccucc cucucuccua ucccugcucg caucugcuau aguggaggcc     360
ggagcaggaa cagguugaac agucuacccu cccuuagcag ggaacuacuc ccacccugga     420 gccuccuag accuaaccug acuagaaaag cuauuaccaa aaacaauuuc acagcaccaa      480
aucuccaccu ccaucaucac cucaacccaa aaaggcauaa uuaaacuuua cuuccucucu     540
uucuucuucc cacucauccu aacccuacuc cuaaucacau aa                        582

<210> SEQ ID NO 28
<211> LENGTH: 2208
<212> TYPE: RNA
<213> ORGANISM: Human

<400> SEQUENCE: 28
auguucgccg accguugacu auucucuaca aaccacaaag acauuggaac acuauaccua      60
uuauucggcg caugagcugg aguccuaggc acagcucuaa gccuccuuau ucgagccgag     120
cugggccagc caggcaaccu ucuagguaac gaccacaucu acaacguuau cgucacagcc     180
caugcauuug uaauaaucuu cuucauagua auacccauca uaaucggagg cuuuggcaac     240
ugacuaguuc cccuaauaau cggugccccc gauauggcgu uccccgcau aaacaacaua      300 agcuucugac ucuuaccucc cucucuccua ucccugcucg caucugcuau aguggaggcc     360
ggagcaggaa cagguugaac agucuacccu cccuuagcag ggaacuacuc ccacccugga     420
gccuccguag accuaaccau cuucccuua caccagcag gugucccuc uaucuuaggg        480 gccaucaauu ucaucacaac aauuaucaau auaaaacccc cugccauaac ccaauaccaa     540 acgcccucu cgucugauc cguccuaauc acagcaguc uacuucccu aucucuccca         600 guccuagcug cuggcaucac uauacuacua acagaccgca accucaacac caccuucuuc     660
gaccccgccg gaggaggaga ccccauucua uaccaacacc uauucugauu uuucggucac     720
ccugaaguuu auauucuuau ccuaccaggc uucggaauaa ucucccauau uguaacuuac     780
uacuccggaa aaaagaacc auuuggauac auagguaugg ucugagcuau gauaucaauu     840
ggcuuccuag gguuuaucgu gugagcacac cauauauuua caguaggaau agacguagac     900
acacgagcau auuucaccuc cgcuaccaua ucaucgcua uccccaccgg cgucaaagua     960
uuuagcugac ucgccacacu ccacggaagc aauaugaaau gaucugcgc agugcucuga   1020 gcccuaggau ucaucuuucu uuucaccgua gguggccuga cuggcauugu auuagcaaac  1080
ucaucacuag acaucguacu acacgacacg uacuacguug uagcccacuu ccacuaugu   1140 cuaucaauag gagcuguauu ugccaucaua ggaggcuuca uucacugauu ccccuauuc    1200 ucaggcuaca cccuagacca aaccuacgcc aaaauccauu ucacuaucau auucaucggc   1260
guaaaucuaa cuuucuuccc acaacacuuu cucggccuau ccggaaugcc ccgacguuac   1320
ucggacuacc ccgaugcaua caccacauga aacauccuau caucuguagg cucauucauu   1380
ucucuaacag caguaauauu aauaauuuuc augauuugag aagccuucgc uucgaagcga  1440
```

| | |
|---|---|
| aaagaccuaa uaguagaaga acccuccaua aaccuggagu gacuauaugg augccccca | 1500 |
| cccuaccaca cauucgaaga acccguauac auaaaagcag gaauaccuuu ccucacaggu | 1560 |
| uucuacucca aagaccacau caucgaaacc gcaaacauau caucacaaa cgccugagcc | 1620 |
| cuaucuauua cucucaucgc uaccucccug acaagcgccu auagcacucg aauaauucuu | 1680 |
| cucacccuaa caggucaacc ucgcuucccc acccuuacua acauuaacga aauaacccc | 1740 |
| acccuacuaa accccauuaa acgccuggca gccggaagcc uauucgcagg auuucucauu | 1800 |
| acuaacaaca uuuccccgc aucccccuuc caaacaacaa uccccucua ccuaaaacuc | 1860 |
| acagcccucg cugucacuuu ccuaggacuu cuaacagccc uagaccucaa cuaccuaacc | 1920 |
| aacaaacuua aaauaaaauc cccacuaugc acauuuuauu ucccaacau acucggauuc | 1980 |
| uacccuagca ucacacaccg cacaaucccc uaucuaggcc uucuuacgag ccaaaaccug | 2040 |
| ccccuacucc uccuagaccu aaccugacua gaaaagcuau uaccuaaaac aauuucacag | 2100 |
| caccaaaucu ccaccuccau caucaccuca acccaaaaag gcauaauuaa acuuuacuuc | 2160 |
| cucucuuucu ucuucccacu cauccuaacc cuacuccuaa ucacauaa | 2208 |

<210> SEQ ID NO 29
<211> LENGTH: 807
<212> TYPE: RNA
<213> ORGANISM: Human

<400> SEQUENCE: 29

| | |
|---|---|
| auggcacaug cagcgcaagu aggucuacaa gacgcuacuu ccccuaucau agaagagcuu | 60 |
| aucaccuuuc augaucacgc ccucauaauc auuuuccuua ucugcuuccu aguccuguau | 120 |
| gcccuuuucc uaacacucac aacaaaacua acuaauacua acaucucaga cgcucaggaa | 180 |
| auagaaaccg caaacauauc auacacaaac gccugagccc uaucuauuac ucucaucgcu | 240 |
| accucccuga caagcgccua uagcacucga auaauucuuc acccuaaac aggucaaccu | 300 |
| cgcuucccca cccuuacuaa cauuaacgaa auaaccccca cccuacuaaa ccccauuaaa | 360 |
| cgccuggcag ccggaagccu auucgcagga uuucucauua cuaacaacau uuccccgca | 420 |
| uccccuucc aaacaacaau ccccucuac cuaaaacuca cagcccucgc ugucacuuuc | 480 |
| cuaggacuuc uaacagcccu agaccucaac uaccuaacca acaaacuuaa aauaaaaucc | 540 |
| ccacuaugca cauuuauuu ucccaacaua cucggauucu acccuagcau cacacaccgc | 600 |
| acaaucccu aucuaggccu ucuuacgagc caaaaccugc cccuaccu ccuagaccua | 660 |
| accugacuag aaaagcuauu accuaaaaca auuucacagc accaaaucuc caccuccauc | 720 |
| auccaccucaa cccaaaaagg cauaauuaaa cuuuacuucc ucucuuucuu cuucccacuc | 780 |
| auccuaaccc uacuccuaau cacauaa | 807 |

<210> SEQ ID NO 30
<211> LENGTH: 786
<212> TYPE: RNA
<213> ORGANISM: Human

<400> SEQUENCE: 30

| | |
|---|---|
| auggcacaug cagcgcaagu aggucuacaa gacgcuacuu ccccuaucau agaagagcuu | 60 |
| aucaccuuuc augaucacgc ccucauaauc auuuuccuua ucugcuuccu aguccuguau | 120 |
| gcccuuuucc uaacacucac aacaaaacua acuaauacua acaucucaga cgcucaggaa | 180 |
| auagaaaccg ucgaacuau ccugcccgcc aucaucuag uccucaucgc ccucccauc | 240 |
| cuacgcaucc uuuacauaac agacgagguc aacgaucccu cccuuaccau caaucaauu | 300 |

```
ggccaccaau gguacugaac cuacgaguac accgacuacg gcggacuaau cuucaacucc    360
uacauacuuc ccccauuauu ccuagaacca ggcgaccugc gacuccuuga cguugacaau    420
cgaguaguac ucccgauuga agccccauu cguauaauaa uuacaucaca agacgucuug    480
cacucaugag cugucccac auuaggcuua aaaacagaug caauucccgg acgucuaaac    540
caaaccacuu ucaccgcuac acgaccgggg guauacuacg gucaaugcuc ugaaaucugu    600
ggagcaaacc acaguuucau gcccaucguc cuagaccuaa ccugacuaga aaagcuauua    660
ccuaaaacaa uuucacagca ccaaaucucc accccauca ucaccucaac ccaaaaaggc    720
auaauuaaac uuuacuuccu ucuuuucuuc uucccacuca uccuaacccu acuccuaauc    780
acauaa                                                                786

<210> SEQ ID NO 31
<211> LENGTH: 1905
<212> TYPE: RNA
<213> ORGANISM: Human

<400> SEQUENCE: 31
augaacgaaa aucuguucgc uucauucauu gcccccacaa uccuaggccu acccgccgca    60
guacugauca uucuauuucc cccucuauug auccccaccu ccaaauaucu caucaacaac    120
cgacuaauca ccacccaaca augacuaauc aaacuaaccu caaaacaaau gauaaccaua    180
cacaacacua aaggacgaac cugaucucuu auacuaguau ccuuaaucau uuuuauugcc    240
acaacuaaac uccucggacu ccugccacuc auuuacac caaccacccca acuaucuaua    300 aaccuagcca uggccaucccc uuaugagcg ggcacaguga uuauaggcuu cgcucuaag    360 auuaaaaaug cccuagccca uucuuacca caaggcacac cuacacccu uaucccaua    420 cuaguuauua ucgaaaccau cagccuacuc auucaaccaa uagcccuggc cguacgccua    480
accgcuaaca uuacugcagg ccaccacuc augcaccuaa uuggaagcgc cacccuagca    540
auaucaacca uuaaccuucc cucuacacuu aucaucuuca caauucuaau cuacugacu    600 auccuagaaa ucgcugucgc cuuaauccaa gccuacguuu ucacacuucu aguaagccuc    660
uaccuacacu ccaacucaug agacccacaa caaauagccc uucaaacgc uaauccaagc    720 cucaccccac uacuaggccu ccuccuagca gcagcaggca aaucagccca auuaggucuc    780
caccccugac uccccucagc cauagaaggc cccacccag ucagcccu acuccacuca    840 agcacuauag uuguagcagg aaucuucuua cucaucgcu uccaccccu agcagaaaau    900 agcccacuaa uccaaacucu aacacuaugc uuaggcgcua ucaccacucu guucgcagca    960
gucugcgccc uuacacaaaa ugacaucaaa aaaucguag ccuucuccac uucaagucaa    1020
cuaggacuca uaauaguuac aaucggcauc aaccaaccac accuagcauu ccugcacauc    1080
uguacccacg ccuucuucaa agccauacua uuuaugugcu ccggguccau cauccacaac    1140
cuuaacaaug aacaagauau ucgaaaaaua ggaggacuac ucaaaaccau accucucacu    1200
ucaaccuccc ucaccauugg cagccuagca uuagcaggaa uaccuuuccu cacagguuuc    1260
uacuccaaag accacaucau cgaaaccgca aacauaucau acacaaacgc cugagcccua    1320
ucuauuacuc ucaucgcuac cucccugaca agcgccuaua gcacgcgaau aauucuucuc    1380
acccuaacag gucaaccucg cuuccccacc cuuacuaaca uuaacgaaaa uaaccccacc    1440
cuacuaaacc ccauuaaacg ccuggcagcc ggaagccuau ucgcaggauu ucucauuacu    1500
aacaacauuu ccccгcauc ccccuuccaa acaacaaucc cccucuaccu aaaacucaca    1560
gcccucgcug ucacuuuccu aggacuucua acagcccuag accucaacua ccuaaccaac    1620
```

| | |
|---|---|
| aaacuuaaaa uaaaauccccc acuaugcaca uuuuauuucu ccaacauacu cggauucuac | 1680 |
| ccuagcauca cacaccgcac aaucccuau cuaggccuuc uuacgagcca aaaccugccc | 1740 |
| cuacuccucc uagaccuaac cugacuagaa aagcuauuac cuaaaacaau uucacagcac | 1800 |
| caaaucucca ccuccaucau caccucaacc caaaaaggca uaauuaaacu uuacuuccuc | 1860 |
| ucuuucuucu ucccacucau ccuaacccua cuccuaauca cauaa | 1905 |

<210> SEQ ID NO 32
<211> LENGTH: 1545
<212> TYPE: RNA
<213> ORGANISM: Human

<400> SEQUENCE: 32

| | |
|---|---|
| augacccacc aaucacaugc cuaucauaua guaaaaccca gcccaugacc ccuaacaggg | 60 |
| gcccucucag cccuccuaau gaccuccggc cuagccaugu gauuucacuu ccacuccaua | 120 |
| acgcuccuca uacuaggccu acuaaccaac acacuaacca uauaccaaug auggcgcgau | 180 |
| guaacacgag aaagcacaua ccaaggccac cacacaccac cuguccaaaa aggccuucga | 240 |
| uacgggauaa uccuauuuau uaccucagaa guuuuuucu cgcaggauu uuucugagcc | 300 |
| uuuuaccacu ccagccuagc cccuaccccc caauuaggag ggcacuggcc cccaacaggc | 360 |
| aucaccccac uacuaggccu ccuccuagca gcagcaggca aaucagccca auuaggucuc | 420 |
| caccccugac uccccucagc cauagaaggc cccaccccag ucucagcccu acuccacuca | 480 |
| agcacuauag uuguagcagg aaucuucuua cucauccgcu uccacccccu agcagaaaau | 540 |
| agcccacuaa uccaaacucu aacacaugc uuaggcgcua ucaccacucu guucgcagca | 600 |
| gucugcgccc uuacacaaaa ugacaucaaa aaaaucguag ccuucccac uucaagucaa | 660 |
| cuaggacuca uaauaguuac aaucggcauc aaccaaccac accuagcauu ccugcacauc | 720 |
| uguacccacg ccuucuucaa agccauacua uuuaugugcu ccggguccau caucacaac | 780 |
| cuuaacaaug aacaagauau ucgaaaaaua ggaggacuac ucaaaaccau accucucacu | 840 |
| ucaaccuccc ucaccauugg cagccuagca uuagcaggaa uaccuuuccu cacagguuuc | 900 |
| uacuccaaag accacaucau cgaaaccgca aacauaucau acacaaacgc cugagcccua | 960 |
| ucuauuacuc ucaucgcuac cucccugaca agcgccuaua gcacucgaau aauucuucuc | 1020 |
| acccuaacag gucaaccucg cuuccccacc cuuacuaaca uuaacgaaaa uaccccaccc | 1080 |
| cuacuaaacc ccauuaaacg ccuggcagcc ggaagccuau ucgcaggauu ucucauuacu | 1140 |
| aacaacauuu ccccgcauc cccuuccaa acaacaaucc cccucuaccu aaaacucaca | 1200 |
| gcccucgcug ucacuuuccu aggacuucua acagcccuag accucaacua ccuaaccaac | 1260 |
| aaacuuaaaa uaaaauccccc acaugcaca uuuuauuucu ccaacauacu cggauucuac | 1320 |
| ccuagcauca cacaccgcac aaucccuau cuaggccuuc uuacgagcca aaaccugccc | 1380 |
| cuacuccucc uagaccuaac cugacuagaa aagcuauuac cuaaaacaau uucacagcac | 1440 |
| caaaucucca ccuccaucau caccucaacc caaaaaggca uaauuaaacu uuacuuccuc | 1500 |
| ucuuucuucu ucccacucau ccuaacccua cuccuaauca cauaa | 1545 |

<210> SEQ ID NO 33
<211> LENGTH: 1629
<212> TYPE: RNA
<213> ORGANISM: Human

<400> SEQUENCE: 33

| | |
|---|---|
| auaaacuucg ccuuaauuuu aauaaucaac acccuccuag ccuuacuacu aauaauuauu | 60 |

```
acauuuugac uaccacaacu caacggcuac auagaaaaau ccaccccuua cgagugcggc    120
uucgacccua uaucccccgc ccgcgucccu uucuccauaa aauucuucuu aguagcuauu    180
accuucuuau uauuugaucu agaaauugcc ccucuuuuac cccuaccaug agcccuacaa    240
acaacuaacc ugccacuaau aguuaugca ucccucuuau uaaucaucau ccuagcccua     300
agucuggcca acacagcagc cauucaagca auccuauaca accguaucgg cgauaucggu    360
uucauccucg ccuuagcaug auuuauccua cacuccaacu caugagaccc acaacaaaua    420
gcccuucuaa acgcuaaucc aagccucacc ccacuacuag gccucuccu agcagcagca     480 ggcaaaucag cccaauuagg ucccaccccc ugacucccu cagccauaga aggcccacc      540 ccagucucag cccuacucca cucaagcacu auaguuguag caggaaucuu cuuacucauc    600
cgcuuccacc cccuagcaga aaauagccca cuauccaaa cucuaacacu augcuuaggc     660
gcuaucacca cucuguucgc agcagucugc gcccuuacac aaaaugacau caaaaaaauc    720
guagccuucu ccacuucaag ucaacuagga cucauaauag uuacaucgg caucaaccaa     780 ccacaccuag cauuccugca caucuguacc cacgccuucu ucaaagccau acuauuuaug    840
ugcuccgggu ccaucauccca caaccuuaac aaugaacaag auauucgaaa auaggagga    900 cuacucaaaa ccauaccucu cacuucaacc cccucacca uuggcagccu agcauuagca     960 ggauauaccuu uccucacagg uuucuacucc aaagaccaca ucaucgaaac cgcaaacaua   1020
ucauacacaa acgccugagc ccuaucuauu acucucaucg cuaccucccu gacaagcgcc    1080
uauagcacuc gaauaauucu cucaccccua acaggucaac cucgcuuccc caccccuuacu   1140 aacauuaacg aaaauaaccc caccccuacua aacccauua aacgccuggc agccggaagc    1200
cuauucgcag gauuucucau uacuaacaac auuuccccg cauccccccuu ccaaacaaca    1260 aucccccucu accuaaaacu cacagcccuc gcugucacuu ccuaggacu ucuaacagcc     1320 cuagaccuca acuaccuaac caacaaacuu aaaauaaaau cccacuaug cacauuuuau     1380 uucuccaaca uacucggauu cuaccuuagc aucacacacc gcacaauccc cuaucuaggc    1440
cuucuuacga gccaaaaccu gccccuacuc uccuagacc uaaccugacu agaaaagcua     1500
uuaccuaaaa caauuucaca gcaccaaauc uccaccucca ucaucccuc aacccaaaaa    1560 ggcauaauua aacuuacuu ccucucuuuc uucuucccac ucauccuaac ccuacuccua    1620
aucacauaa                                                            1629

<210> SEQ ID NO 34
<211> LENGTH: 642
<212> TYPE: RNA
<213> ORGANISM: Human

<400> SEQUENCE: 34
augcuaaaac uaaucgucccc aacaauuaua uuacuaccac ugacaugacu uuccaaaaaa    60
cacauaauuu gaaucaacac aaccacccac agccuaauua uuagcaucau cccucuacua   120
uuuuuuaacc aaaucaacaa caaccuauuu agcuguuccc caaccuuuuc cucccgacccc   180 cuaacaaccc cccuccuaau acuaacuacc ugacuccuac cccucacaau cauggcaagc    240
caacgccacu uaccaguga ccacuauca cgaaaaaac ucuaccucuc uauacuaauc       300
ucccuacaaa ucuccuuaau auaaacauuc acagccacag aacuaaucau auuuuauauc    360
uucuucgaaa ccacacuuau ccccaccuug gcuaucauca cccgaugagg caaccagcca    420
gaacgccuga acgcaggcac auacuuccua uucuacaccc uaguaggcuc ccugcccua    480 cuccuccuag accuaaccug acuagaaaag cuauuaccua aaacaauuuc acagcaccaa    540
```
aucuccaccu ccaucaucac cucaacccaa aaaggcauaa uuaaacuuua cuuccucucu    600
uucuucuucc cacucauccu aacccuacuc cuaaucacau aa    642

<210> SEQ ID NO 35
<211> LENGTH: 129
<212> TYPE: RNA
<213> ORGANISM: Human

<400> SEQUENCE: 35
augccccaac uaaauacuac cguauggccc accauaauua ccccauacu ccuuacacua    60 uuccucauca cccaacuaaa aauauuaaac acaaacuacc accuaccucc cucaccauug    120
gcagccuag    129

<210> SEQ ID NO 36
<211> LENGTH: 261
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (261)..(261)
<223> OTHER INFORMATION: Xaa can be any naturally occurring amino acid

<400> SEQUENCE: 36

Met Ala His His Asn Tyr Pro His Thr Pro Tyr Thr Ile Pro His His
1               5                   10                  15

Pro Thr Lys Asn Ile Lys His Lys Leu Pro Pro Thr Ser Leu Thr Ile
            20                  25                  30

Gly Ser Leu Ala Leu Ala Gly Met Pro Phe Leu Thr Gly Phe Tyr Ser
        35                  40                  45

Lys Asp His Ile Ile Glu Thr Ala Asn Met Ser Tyr Thr Asn Ala Trp
    50                  55                  60

Ala Leu Ser Ile Thr Leu Ile Ala Thr Ser Leu Thr Ser Ala Tyr Ser
65                  70                  75                  80

Thr Arg Met Ile Leu Leu Thr Leu Thr Gly Gln Pro Arg Phe Pro Thr
                85                  90                  95

Leu Thr Asn Ile Asn Glu Asn Asn Pro Thr Leu Leu Asn Pro Ile Lys
            100                 105                 110

Arg Leu Ala Ala Gly Ser Leu Phe Ala Gly Phe Leu Ile Thr Asn Asn
        115                 120                 125

Ile Ser Pro Ala Ser Pro Phe Gln Thr Thr Ile Pro Leu Tyr Leu Lys
    130                 135                 140

Leu Thr Ala Leu Ala Val Thr Phe Leu Gly Leu Leu Thr Ala Leu Asp
145                 150                 155                 160

Leu Asn Tyr Leu Thr Asn Lys Leu Lys Met Lys Ser Pro Leu Cys Thr
                165                 170                 175

Phe Tyr Phe Ser Asn Met Leu Gly Phe Tyr Pro Ser Ile Thr His Arg
            180                 185                 190

Thr Ile Pro Tyr Leu Gly Leu Leu Thr Ser Gln Asn Leu Pro Leu Leu
        195                 200                 205

Leu Leu Asp Leu Thr Trp Leu Glu Lys Leu Leu Pro Lys Thr Ile Ser
    210                 215                 220

Gln His Gln Ile Ser Thr Ser Ile Ile Thr Ser Thr Gln Lys Gly Met
225                 230                 235                 240

Ile Lys Leu Tyr Phe Leu Ser Phe Phe Phe Pro Leu Ile Leu Thr Leu
                245                 250                 255

```
Leu Leu Ile Thr Xaa
            260

<210> SEQ ID NO 37
<211> LENGTH: 100
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (100)..(100)
<223> OTHER INFORMATION: Xaa can be any naturally occurring amino acid

<400> SEQUENCE: 37

Met Pro Leu Ile Tyr Met Asn Ile Met Leu Ala Phe Thr Ile Ser Leu
1               5                   10                  15

Leu Gly Met Leu Val Tyr Arg Ser His Leu Met Ser Ser Leu Leu Cys
            20                  25                  30

Leu Glu Gly Met Met Leu Ser Leu Phe Ile Met Ala Thr Leu Met Thr
        35                  40                  45

Leu Asn Thr His Ser Leu Leu Ala Asn Ile Val Pro Ile Ala Met Leu
    50                  55                  60

Val Phe Ala Ala Cys Glu Ala Ala Val Gly Leu Ala Leu Leu Val Ser
65                  70                  75                  80

Ile Ser Asn Thr Tyr Gly Leu Asp Tyr Val His Asn Leu Thr Leu Leu
                85                  90                  95

Leu Ile Thr Xaa
            100

<210> SEQ ID NO 38
<211> LENGTH: 261
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (261)..(261)
<223> OTHER INFORMATION: Xaa can be any naturally occurring amino acid

<400> SEQUENCE: 38

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Pro Asp Asn Tyr Thr Leu Ala Asn Pro Leu Asn Thr
    130                 135                 140
```

```
Pro Pro His Ile Lys Pro Glu Trp Tyr Phe Leu Phe Ala Tyr Thr Ile
145                 150                 155                 160

Leu Arg Ser Val Pro Asn Lys Leu Gly Gly Val Leu Ala Leu Leu Leu
            165                 170                 175

Ser Ile Leu Ile Leu Ala Met Ile Pro Ile Leu His Met Ser Lys Gln
        180                 185                 190

Gln Ser Met Met Phe Arg Pro Leu Ser Gln Ser Leu Tyr Trp Leu Leu
            195                 200                 205

Ala Ala Asp Leu Leu Ile Leu Thr Trp Ile Gly Gly Gln Pro Val Ser
210                 215                 220

Tyr Pro Phe Thr Ile Ile Gly Gln Val Ala Ser Val Leu Tyr Phe Thr
225                 230                 235                 240

Thr Ile Leu Ile Leu Met Pro Thr Ile Ser Leu Ile Glu Asn Lys Met
                245                 250                 255

Leu Lys Trp Ala Xaa
                260

<210> SEQ ID NO 39
<211> LENGTH: 189
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (189)..(189)
<223> OTHER INFORMATION: Xaa can be any naturally occurring amino acid

<400> SEQUENCE: 39

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Ala Ala Asp Leu Leu Ile Leu Thr
130                 135                 140

Trp Ile Gly Gly Gln Pro Val Ser Tyr Pro Phe Thr Ile Ile Gly Gln
145                 150                 155                 160

Val Ala Ser Val Leu Tyr Phe Thr Thr Ile Leu Ile Leu Met Pro Thr
                165                 170                 175

Ile Ser Leu Ile Glu Asn Lys Met Leu Lys Trp Ala Xaa
            180                 185

<210> SEQ ID NO 40
<211> LENGTH: 392
<212> TYPE: PRT
<213> ORGANISM: Artificial
<220> FEATURE:
```

<223> OTHER INFORMATION: putative protein sequence
<220> FEATURE:
<221> NAME/KEY: misc_feature
<222> LOCATION: (392)..(392)
<223> OTHER INFORMATION: Xaa can be any naturally occurring amino acid

<400> SEQUENCE: 40

```
Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Met Phe Leu His Glu Thr Gly Ser Asn Asn Pro Leu Gly Ile Thr Ser
    210                 215                 220

His Ser Asp Lys Ile Thr Phe His Pro Tyr Tyr Thr Ile Lys Asp Ala
225                 230                 235                 240

Leu Gly Leu Leu Leu Phe Leu Leu Ser Leu Met Thr Leu Thr Leu Phe
                245                 250                 255

Ser Pro Asp Leu Leu Gly Asp Pro Asp Asn Tyr Thr Leu Ala Asn Pro
            260                 265                 270

Leu Asn Thr Pro Pro His Ile Lys Pro Glu Trp Tyr Phe Leu Phe Ala
        275                 280                 285

Tyr Thr Ile Leu Arg Ser Val Pro Asn Lys Leu Gly Gly Val Leu Ala
    290                 295                 300

Leu Leu Leu Ser Ile Leu Ile Leu Ala Met Ile Pro Ile Leu His Met
305                 310                 315                 320

Ser Lys Gln Gln Ser Met Met Phe Arg Pro Leu Ser Gln Ser Leu Tyr
                325                 330                 335

Trp Leu Leu Ala Ala Asp Leu Leu Ile Leu Thr Trp Ile Gly Gly Gln
            340                 345                 350

Pro Val Ser Tyr Pro Phe Thr Ile Ile Gly Gln Val Ala Ser Val Leu
        355                 360                 365

Tyr Phe Thr Thr Ile Leu Ile Leu Met Pro Thr Ile Ser Leu Ile Glu
    370                 375                 380
```

```
Asn Lys Met Leu Lys Trp Ala Xaa
385                 390
```

<210> SEQ ID NO 41
<211> LENGTH: 432
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (432)..(432)
<223> OTHER INFORMATION: Xaa can be any naturally occurring amino acid
<400> SEQUENCE: 41

```
Met Asn Glu Asn Leu Phe Ala Ser Phe Ile Ala Pro Thr Ile Leu Gly
1               5                   10                  15

Leu Pro Ala Ala Val Leu Ile Ile Leu Phe Pro Pro Leu Leu Ile Pro
                20                  25                  30

Thr Ser Lys Tyr Leu Ile Asn Asn Arg Leu Ile Thr Thr Gln Gln Trp
            35                  40                  45

Leu Ile Lys Leu Thr Ser Lys Gln Met Met Thr Met His Asn Thr Lys
50                  55                  60

Gly Arg Thr Trp Ser Leu Met Leu Val Ser Leu Ile Ile Phe Ile Ala
65                  70                  75                  80

Thr Thr Asn Leu Leu Gly Leu Leu Pro His Ser Phe Thr Pro Thr Thr
                85                  90                  95

Gln Leu Ser Met Asn Leu Ala Met His Tyr Ser Pro Asp Ala Ser Thr
            100                 105                 110

Ala Phe Ser Ser Ile Ala His Ile Thr Arg Asp Val Asn Tyr Gly Trp
        115                 120                 125

Ile Ile Arg Tyr Leu His Ala Asn Gly Ala Ser Met Phe Phe Ile Cys
130                 135                 140

Leu Phe Leu His Ile Gly Arg Gly Leu Tyr Tyr Gly Ser Phe Leu Tyr
145                 150                 155                 160

Ser Glu Thr Trp Asn Ile Gly Ile Ile Leu Leu Leu Ala Thr Met Ala
                165                 170                 175

Thr Ala Phe Met Gly Tyr Val Leu Pro Trp Gly Gln Met Ser Phe Trp
            180                 185                 190

Gly Ala Thr Val Ile Thr Asn Leu Leu Ser Ala Ile Pro Tyr Ile Gly
        195                 200                 205

Thr Asp Leu Val Gln Trp Ile Trp Gly Gly Tyr Ser Val Asp Ser Pro
210                 215                 220

Thr Leu Thr Arg Phe Phe Thr Phe His Phe Ile Leu Pro Phe Ile Ile
225                 230                 235                 240

Ala Ala Leu Ala Thr Leu His Leu Leu Phe Leu His Glu Thr Gly Ser
                245                 250                 255

Asn Asn Pro Leu Gly Ile Thr Ser His Ser Asp Lys Ile Thr Phe His
            260                 265                 270

Pro Tyr Tyr Thr Ile Lys Asp Ala Leu Gly Leu Leu Leu Phe Leu Leu
        275                 280                 285

Ser Leu Met Thr Leu Thr Leu Phe Ser Pro Asp Leu Leu Gly Asp Pro
290                 295                 300

Asp Asn Tyr Thr Leu Ala Asn Pro Leu Asn Thr Pro Pro His Ile Lys
305                 310                 315                 320

Pro Glu Trp Tyr Phe Leu Phe Ala Tyr Thr Ile Leu Arg Ser Val Pro
                325                 330                 335
```

Asn Lys Leu Gly Gly Val Leu Ala Leu Leu Ser Ile Leu Ile Leu
            340                 345                 350

Ala Met Ile Pro Ile Leu His Met Ser Lys Gln Gln Ser Met Met Phe
            355                 360                 365

Arg Pro Leu Ser Gln Ser Leu Tyr Trp Leu Leu Ala Ala Asp Leu Leu
    370                 375                 380

Ile Leu Thr Trp Ile Gly Gly Gln Pro Val Ser Tyr Pro Phe Thr Ile
385                 390                 395                 400

Ile Gly Gln Val Ala Ser Val Leu Tyr Phe Thr Thr Ile Leu Ile Leu
            405                 410                 415

Met Pro Thr Ile Ser Leu Ile Glu Asn Lys Met Leu Lys Trp Ala Xaa
            420                 425                 430

<210> SEQ ID NO 42
<211> LENGTH: 410
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (410)..(410)
<223> OTHER INFORMATION: Xaa can be any naturally occurring amino acid

<400> SEQUENCE: 42

Met Pro Leu Ile Tyr Met Asn Ile Met Leu Ala Phe Thr Ile Ser Leu
1               5                   10                  15

Leu Gly Met Leu Val Tyr Arg Ser His Leu Met Ser Ser Leu Leu Cys
            20                  25                  30

Leu Glu Gly Met Met Leu Ser Leu Phe Ile Met Ala Thr Leu Met Thr
            35                  40                  45

Leu Asn Thr His Ser Leu Leu Ala Asn Ile Val Pro Ile Ala Met Leu
    50                  55                  60

Val Phe Gly Ala Cys Leu Ile Leu Gln Ile Thr Thr Gly Leu Phe Leu
65                  70                  75                  80

Ala Met His Tyr Ser Pro Asp Ala Ser Thr Ala Phe Ser Ser Ile Ala
            85                  90                  95

His Ile Thr Arg Asp Val Asn Tyr Gly Trp Ile Ile Arg Tyr Leu His
            100                 105                 110

Ala Asn Gly Ala Ser Met Phe Phe Ile Cys Leu Phe Leu His Ile Gly
            115                 120                 125

Arg Gly Leu Tyr Tyr Gly Ser Phe Leu Tyr Ser Glu Thr Trp Asn Ile
    130                 135                 140

Gly Ile Ile Leu Leu Leu Ala Thr Met Ala Thr Ala Phe Met Gly Tyr
145                 150                 155                 160

Val Leu Pro Trp Gly Gln Met Ser Phe Trp Gly Ala Thr Val Ile Thr
            165                 170                 175

Asn Leu Leu Ser Ala Ile Pro Tyr Ile Gly Thr Asp Leu Val Gln Trp
            180                 185                 190

Ile Trp Gly Gly Tyr Ser Val Asp Ser Pro Thr Leu Thr Arg Phe Phe
    195                 200                 205

Thr Phe His Phe Ile Leu Pro Phe Ile Ile Ala Ala Leu Ala Thr Leu
210                 215                 220

His Leu Leu Phe Leu His Glu Thr Gly Ser Asn Asn Pro Leu Gly Ile
225                 230                 235                 240

Thr Ser His Ser Asp Lys Ile Thr Phe His Pro Tyr Tyr Thr Ile Lys
            245                 250                 255

```
Asp Ala Leu Gly Leu Leu Phe Leu Ser Leu Met Thr Leu Thr
            260                 265                 270

Leu Phe Ser Pro Asp Leu Leu Gly Asp Pro Asp Asn Tyr Thr Leu Ala
        275                 280                 285

Asn Pro Leu Asn Thr Pro Pro His Ile Lys Pro Glu Trp Tyr Phe Leu
290                 295                 300

Phe Ala Tyr Thr Ile Leu Arg Ser Val Pro Asn Lys Leu Gly Gly Val
305                 310                 315                 320

Leu Ala Leu Leu Leu Ser Ile Leu Ile Leu Ala Met Ile Pro Ile Leu
                325                 330                 335

His Met Ser Lys Gln Gln Ser Met Met Phe Arg Pro Leu Ser Gln Ser
            340                 345                 350

Leu Tyr Trp Leu Leu Ala Ala Asp Leu Leu Ile Leu Thr Trp Ile Gly
        355                 360                 365

Gly Gln Pro Val Ser Tyr Pro Phe Thr Ile Ile Gly Gln Val Ala Ser
    370                 375                 380

Val Leu Tyr Phe Thr Thr Ile Leu Ile Leu Met Pro Thr Ile Ser Leu
385                 390                 395                 400

Ile Glu Asn Lys Met Leu Lys Trp Ala Xaa
                405                 410

<210> SEQ ID NO 43
<211> LENGTH: 174
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (174)..(174)
<223> OTHER INFORMATION: Xaa can be any naturally occurring amino acid

<400> SEQUENCE: 43

Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala Leu Ala Val Thr
    50                  55                  60

Phe Leu Gly Leu Leu Thr Ala Leu Asp Leu Asn Tyr Leu Thr Asn Lys
65                  70                  75                  80

Leu Lys Met Lys Ser Pro Leu Cys Thr Phe Tyr Phe Ser Asn Met Leu
                85                  90                  95

Gly Phe Tyr Pro Ser Ile Thr His Arg Thr Ile Pro Tyr Leu Gly Leu
            100                 105                 110

Leu Thr Ser Gln Asn Leu Pro Leu Leu Leu Asp Leu Thr Trp Leu
        115                 120                 125

Glu Lys Leu Leu Pro Lys Thr Ile Ser Gln His Gln Ile Ser Thr Ser
    130                 135                 140

Ile Ile Thr Ser Thr Gln Lys Gly Met Ile Lys Leu Tyr Phe Leu Ser
145                 150                 155                 160

Phe Phe Phe Pro Leu Ile Leu Thr Leu Leu Ile Thr Xaa
                165                 170

<210> SEQ ID NO 44
<211> LENGTH: 194
```

```
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (194)..(194)
<223> OTHER INFORMATION: Xaa can be any naturally occurring amino acid

<400> SEQUENCE: 44

Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Leu Leu Asp
    130                 135                 140

Leu Thr Trp Leu Glu Lys Leu Leu Pro Lys Thr Ile Ser Gln His Gln
145                 150                 155                 160

Ile Ser Thr Ser Ile Ile Thr Ser Thr Gln Lys Gly Met Ile Lys Leu
                165                 170                 175

Tyr Phe Leu Ser Phe Phe Pro Leu Ile Leu Thr Leu Leu Ile
            180                 185                 190

Thr Xaa

<210> SEQ ID NO 45
<211> LENGTH: 736
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (736)..(736)
<223> OTHER INFORMATION: Xaa can be any naturally occurring amino acid

<400> SEQUENCE: 45

Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95
```

```
Met Asn Asn Met Ser Phe Trp Leu Leu Pro Ser Leu Leu Leu Leu
            100                 105                 110

Leu Ala Ser Ala Met Val Glu Ala Gly Ala Gly Thr Gly Trp Thr Val
            115                 120                 125

Tyr Pro Pro Leu Ala Gly Asn Tyr Ser His Pro Gly Ala Ser Val Asp
130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Thr Gln Tyr Gln Thr Pro Leu Phe Val Trp Ser Val Leu Ile Thr Ala
            180                 185                 190

Val Leu Leu Leu Leu Ser Leu Pro Val Leu Ala Ala Gly Ile Thr Met
            195                 200                 205

Leu Leu Thr Asp Arg Asn Leu Asn Thr Thr Phe Phe Asp Pro Ala Gly
            210                 215                 220

Gly Gly Asp Pro Ile Leu Tyr Gln His Leu Phe Trp Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly
                260                 265                 270

Met Val Trp Ala Met Met Ser Ile Gly Phe Leu Gly Phe Ile Val Trp
            275                 280                 285

Ala His His Met Phe Thr Val Gly Met Asp Val Asp Thr Arg Ala Tyr
            290                 295                 300

Phe Thr Ser Ala Thr Met Ile Ile Ala Ile Pro Thr Gly Val Lys Val
305                 310                 315                 320

Phe Ser Trp Leu Ala Thr Leu His Gly Ser Asn Met Lys Trp Ser Ala
                325                 330                 335

Ala Val Leu Trp Ala Leu Gly Phe Ile Phe Leu Phe Thr Val Gly Gly
            340                 345                 350

Leu Thr Gly Ile Val Leu Ala Asn Ser Ser Leu Asp Ile Val Leu His
            355                 360                 365

Asp Thr Tyr Tyr Val Val Ala His Phe His Tyr Val Leu Ser Met Gly
            370                 375                 380

Ala Val Phe Ala Ile Met Gly Gly Phe Ile His Trp Phe Pro Leu Phe
385                 390                 395                 400

Ser Gly Tyr Thr Leu Asp Gln Thr Tyr Ala Lys Ile His Phe Thr Ile
                405                 410                 415

Met Phe Ile Gly Val Asn Leu Thr Phe Phe Pro Gln His Phe Leu Gly
            420                 425                 430

Leu Ser Gly Met Pro Arg Arg Tyr Ser Asp Tyr Pro Asp Ala Tyr Thr
            435                 440                 445

Thr Trp Asn Ile Leu Ser Ser Val Gly Ser Phe Ile Ser Leu Thr Ala
450                 455                 460

Val Met Leu Met Ile Phe Met Ile Trp Glu Ala Phe Ala Ser Lys Arg
465                 470                 475                 480

Lys Val Leu Met Val Glu Glu Pro Ser Met Asn Leu Glu Trp Leu Tyr
                485                 490                 495

Gly Cys Pro Pro Pro Tyr His Thr Phe Glu Glu Pro Val Tyr Met Lys
                500                 505                 510

Ala Gly Met Pro Phe Leu Thr Gly Phe Tyr Ser Lys Asp His Ile Ile
```

```
                515                 520                 525

Glu Thr Ala Asn Met Ser Tyr Thr Asn Ala Trp Ala Leu Ser Ile Thr
        530                 535                 540

Leu Ile Ala Thr Ser Leu Thr Ser Ala Tyr Ser Thr Arg Met Ile Leu
545                 550                 555                 560

Leu Thr Leu Thr Gly Gln Pro Arg Phe Pro Thr Leu Thr Asn Ile Asn
                565                 570                 575

Glu Asn Asn Pro Thr Leu Leu Asn Pro Ile Lys Arg Leu Ala Ala Gly
        580                 585                 590

Ser Leu Phe Ala Gly Phe Leu Ile Thr Asn Asn Ile Ser Pro Ala Ser
                595                 600                 605

Pro Phe Gln Thr Thr Ile Pro Leu Tyr Leu Lys Leu Thr Ala Leu Ala
        610                 615                 620

Val Thr Phe Leu Gly Leu Leu Thr Ala Leu Asp Leu Asn Tyr Leu Thr
625                 630                 635                 640

Asn Lys Leu Lys Met Lys Ser Pro Leu Cys Thr Phe Tyr Phe Ser Asn
                645                 650                 655

Met Leu Gly Phe Tyr Pro Ser Ile Thr His Arg Thr Ile Pro Tyr Leu
        660                 665                 670

Gly Leu Leu Thr Ser Gln Asn Leu Pro Leu Leu Leu Asp Leu Thr
                675                 680                 685

Trp Leu Glu Lys Leu Leu Pro Lys Thr Ile Ser Gln His Gln Ile Ser
        690                 695                 700

Thr Ser Ile Ile Thr Ser Thr Gln Lys Gly Met Ile Lys Leu Tyr Phe
705                 710                 715                 720

Leu Ser Phe Phe Phe Pro Leu Ile Leu Thr Leu Leu Ile Thr Xaa
                725                 730                 735

<210> SEQ ID NO 46
<211> LENGTH: 269
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (269)..(269)
<223> OTHER INFORMATION: Xaa can be any naturally occurring amino acid

<400> SEQUENCE: 46

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45

Lys Leu Thr Asn Thr Asn Ile Ser Asp Ala Gln Glu Met Glu Thr Ala
        50                  55                  60

Asn Met Ser Tyr Thr Asn Ala Trp Ala Leu Ser Ile Thr Leu Ile Ala
65                  70                  75                  80

Thr Ser Leu Thr Ser Ala Tyr Ser Thr Arg Met Ile Leu Leu Thr Leu
                85                  90                  95

Thr Gly Gln Pro Arg Phe Pro Thr Leu Thr Asn Ile Asn Glu Asn Asn
            100                 105                 110

Pro Thr Leu Leu Asn Pro Ile Lys Arg Leu Ala Ala Gly Ser Leu Phe
        115                 120                 125

Ala Gly Phe Leu Ile Thr Asn Asn Ile Ser Pro Ala Ser Pro Phe Gln
```

```
                    130                 135                 140
Thr Thr Ile Pro Leu Tyr Leu Lys Leu Thr Ala Leu Ala Val Thr Phe
145                 150                 155                 160

Leu Gly Leu Leu Thr Ala Leu Asp Leu Asn Tyr Leu Thr Asn Lys Leu
                165                 170                 175

Lys Met Lys Ser Pro Leu Cys Thr Phe Tyr Phe Ser Asn Met Leu Gly
                180                 185                 190

Phe Tyr Pro Ser Ile Thr His Arg Thr Ile Pro Tyr Leu Gly Leu Leu
                195                 200                 205

Thr Ser Gln Asn Leu Pro Leu Leu Leu Asp Leu Thr Trp Leu Glu
        210                 215                 220

Lys Leu Leu Pro Lys Thr Ile Ser Gln His Gln Ile Ser Thr Ser Ile
225                 230                 235                 240

Ile Thr Ser Thr Gln Lys Gly Met Ile Lys Leu Tyr Phe Leu Ser Phe
                245                 250                 255

Phe Phe Pro Leu Ile Leu Thr Leu Leu Leu Ile Thr Xaa
                260                 265

<210> SEQ ID NO 47
<211> LENGTH: 262
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (262)..(262)
<223> OTHER INFORMATION: Xaa can be any naturally occurring amino acid

<400> SEQUENCE: 47

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45

Lys Leu Thr Asn Thr Asn Ile Ser Asp Ala Gln Glu Met Glu Thr Val
        50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Ile Val Leu Asp Leu Thr Trp Leu Glu Lys Leu Leu Pro Lys Thr Ile
```

```
                    210                 215                 220
Ser Gln His Gln Ile Ser Thr Ser Ile Ile Thr Ser Thr Gln Lys Gly
225                 230                 235                 240

Met Ile Lys Leu Tyr Phe Leu Ser Phe Phe Phe Pro Leu Ile Leu Thr
                    245                 250                 255

Leu Leu Leu Ile Thr Xaa
                260

<210> SEQ ID NO 48
<211> LENGTH: 635
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (635)..(635)
<223> OTHER INFORMATION: Xaa can be any naturally occurring amino acid

<400> SEQUENCE: 48

Met Asn Glu Asn Leu Phe Ala Ser Phe Ile Ala Pro Thr Ile Leu Gly
1               5                   10                  15

Leu Pro Ala Ala Val Leu Ile Ile Leu Phe Pro Pro Leu Leu Ile Pro
                20                  25                  30

Thr Ser Lys Tyr Leu Ile Asn Asn Arg Leu Ile Thr Thr Gln Gln Trp
            35                  40                  45

Leu Ile Lys Leu Thr Ser Lys Gln Met Met Thr Met His Asn Thr Lys
50                  55                  60

Gly Arg Thr Trp Ser Leu Met Leu Val Ser Leu Ile Ile Phe Ile Ala
65                  70                  75                  80

Thr Thr Asn Leu Leu Gly Leu Leu Pro His Ser Phe Thr Pro Thr Thr
                85                  90                  95

Gln Leu Ser Met Asn Leu Ala Met Ala Ile Pro Leu Trp Ala Gly Thr
            100                 105                 110

Val Ile Met Gly Phe Arg Ser Lys Ile Lys Asn Ala Leu Ala His Phe
        115                 120                 125

Leu Pro Gln Gly Thr Pro Thr Pro Leu Ile Pro Met Leu Val Ile Ile
130                 135                 140

Glu Thr Ile Ser Leu Leu Ile Gln Pro Met Ala Leu Ala Val Arg Leu
145                 150                 155                 160

Thr Ala Asn Ile Thr Ala Gly His Leu Leu Met His Leu Ile Gly Ser
                165                 170                 175

Ala Thr Leu Ala Met Ser Thr Ile Asn Leu Pro Ser Thr Leu Ile Ile
            180                 185                 190

Phe Thr Ile Leu Ile Leu Leu Thr Ile Leu Glu Ile Ala Val Ala Leu
        195                 200                 205

Ile Gln Ala Tyr Val Phe Thr Leu Leu Val Ser Leu Tyr Leu His Ser
    210                 215                 220

Asn Ser Trp Asp Pro Gln Gln Met Ala Leu Leu Asn Ala Asn Pro Ser
225                 230                 235                 240

Leu Thr Pro Leu Leu Gly Leu Leu Ala Ala Gly Lys Ser Ala
                245                 250                 255

Gln Leu Gly Leu His Pro Trp Leu Pro Ser Ala Met Glu Gly Pro Thr
            260                 265                 270

Pro Val Ser Ala Leu Leu His Ser Ser Thr Met Val Val Ala Gly Ile
        275                 280                 285

Phe Leu Leu Ile Arg Phe His Pro Leu Ala Glu Asn Ser Pro Leu Ile
```

```
                290                 295                 300
Gln Thr Leu Thr Leu Cys Leu Gly Ala Ile Thr Thr Leu Phe Ala Ala
305                 310                 315                 320

Val Cys Ala Leu Thr Gln Asn Asp Ile Lys Lys Ile Val Ala Phe Ser
                325                 330                 335

Thr Ser Ser Gln Leu Gly Leu Met Met Val Thr Ile Gly Ile Asn Gln
                340                 345                 350

Pro His Leu Ala Phe Leu His Ile Cys Thr His Ala Phe Phe Lys Ala
                355                 360                 365

Met Leu Phe Met Cys Ser Gly Ser Ile Ile His Asn Leu Asn Asn Glu
370                 375                 380

Gln Asp Ile Arg Lys Met Gly Gly Leu Leu Lys Thr Met Pro Leu Thr
385                 390                 395                 400

Ser Thr Ser Leu Thr Ile Gly Ser Leu Ala Leu Ala Gly Met Pro Phe
                405                 410                 415

Leu Thr Gly Phe Tyr Ser Lys Asp His Ile Ile Glu Thr Ala Asn Met
                420                 425                 430

Ser Tyr Thr Asn Ala Trp Ala Leu Ser Ile Thr Leu Ile Ala Thr Ser
                435                 440                 445

Leu Thr Ser Ala Tyr Ser Thr Arg Met Ile Leu Leu Thr Leu Thr Gly
450                 455                 460

Gln Pro Arg Phe Pro Thr Leu Thr Asn Ile Asn Glu Asn Asn Pro Thr
465                 470                 475                 480

Leu Leu Asn Pro Ile Lys Arg Leu Ala Ala Gly Ser Leu Phe Ala Gly
                485                 490                 495

Phe Leu Ile Thr Asn Asn Ile Ser Pro Ala Ser Pro Phe Gln Thr Thr
                500                 505                 510

Ile Pro Leu Tyr Leu Lys Leu Thr Ala Leu Ala Val Thr Phe Leu Gly
                515                 520                 525

Leu Leu Thr Ala Leu Asp Leu Asn Tyr Leu Thr Asn Lys Leu Lys Met
530                 535                 540

Lys Ser Pro Leu Cys Thr Phe Tyr Phe Ser Asn Met Leu Gly Phe Tyr
545                 550                 555                 560

Pro Ser Ile Thr His Arg Thr Ile Pro Tyr Leu Gly Leu Leu Thr Ser
                565                 570                 575

Gln Asn Leu Pro Leu Leu Leu Asp Leu Thr Trp Leu Glu Lys Leu
                580                 585                 590

Leu Pro Lys Thr Ile Ser Gln His Gln Ile Ser Thr Ser Ile Ile Thr
                595                 600                 605

Ser Thr Gln Lys Gly Met Ile Lys Leu Tyr Phe Leu Ser Phe Phe Phe
610                 615                 620

Pro Leu Ile Leu Thr Leu Leu Ile Thr Xaa
625                 630                 635

<210> SEQ ID NO 49
<211> LENGTH: 515
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (515)..(515)
<223> OTHER INFORMATION: Xaa can be any naturally occurring amino acid

<400> SEQUENCE: 49

Met Thr His Gln Ser His Ala Tyr His Met Val Lys Pro Ser Pro Trp
```

```
           1               5                  10                 15
       Pro Leu Thr Gly Ala Leu Ser Ala Leu Leu Met Thr Ser Gly Leu Ala
                        20                  25                  30

Met Trp Phe His Phe His Ser Met Thr Leu Leu Met Leu Gly Leu Leu
                        35                  40                  45

Thr Asn Thr Leu Thr Met Tyr Gln Trp Trp Arg Asp Val Thr Arg Glu
                    50                  55                  60

Ser Thr Tyr Gln Gly His His Thr Pro Pro Val Gln Lys Gly Leu Arg
       65                  70                  75                  80

Tyr Gly Met Ile Leu Phe Ile Thr Ser Glu Val Phe Phe Ala Gly
                            85                  90                  95

Phe Phe Trp Ala Phe Tyr His Ser Ser Leu Ala Pro Thr Pro Gln Leu
                        100                 105                 110

Gly Gly His Trp Pro Pro Thr Gly Ile Thr Pro Leu Leu Gly Leu Leu
                        115                 120                 125

Leu Ala Ala Ala Gly Lys Ser Ala Gln Leu Gly Leu His Pro Trp Leu
                        130                 135                 140

Pro Ser Ala Met Glu Gly Pro Thr Pro Val Ser Ala Leu Leu His Ser
       145                 150                 155                 160

Ser Thr Met Val Val Ala Gly Ile Phe Leu Leu Ile Arg Phe His Pro
                        165                 170                 175

Leu Ala Glu Asn Ser Pro Leu Ile Gln Thr Leu Thr Leu Cys Leu Gly
                        180                 185                 190

Ala Ile Thr Thr Leu Phe Ala Ala Val Cys Ala Leu Thr Gln Asn Asp
                        195                 200                 205

Ile Lys Lys Ile Val Ala Phe Ser Thr Ser Ser Gln Leu Gly Leu Met
                        210                 215                 220

Met Val Thr Ile Gly Ile Asn Gln Pro His Leu Ala Phe Leu His Ile
       225                 230                 235                 240

Cys Thr His Ala Phe Phe Lys Ala Met Leu Phe Met Cys Ser Gly Ser
                        245                 250                 255

Ile Ile His Asn Leu Asn Asn Glu Gln Asp Ile Arg Lys Met Gly Gly
                        260                 265                 270

Leu Leu Lys Thr Met Pro Leu Thr Ser Thr Ser Leu Thr Ile Gly Ser
                        275                 280                 285

Leu Ala Leu Ala Gly Met Pro Phe Leu Thr Gly Phe Tyr Ser Lys Asp
                        290                 295                 300

His Ile Ile Glu Thr Ala Asn Met Ser Tyr Thr Asn Ala Trp Ala Leu
       305                 310                 315                 320

Ser Ile Thr Leu Ile Ala Thr Ser Leu Thr Ser Ala Tyr Ser Thr Arg
                        325                 330                 335

Met Ile Leu Leu Thr Leu Thr Gly Gln Pro Arg Phe Pro Thr Leu Thr
                        340                 345                 350

Asn Ile Asn Glu Asn Asn Pro Thr Leu Leu Asn Pro Ile Lys Arg Leu
                        355                 360                 365

Ala Ala Gly Ser Leu Phe Ala Gly Phe Leu Ile Thr Asn Asn Ile Ser
                        370                 375                 380

Pro Ala Ser Pro Phe Gln Thr Thr Ile Pro Leu Tyr Leu Lys Leu Thr
       385                 390                 395                 400

Ala Leu Ala Val Thr Phe Leu Gly Leu Leu Thr Ala Leu Asp Leu Asn
                        405                 410                 415

Tyr Leu Thr Asn Lys Leu Lys Met Lys Ser Pro Leu Cys Thr Phe Tyr
                        420                 425                 430
```

-continued

```
Phe Ser Asn Met Leu Gly Phe Tyr Pro Ser Ile Thr His Arg Thr Ile
        435                 440                 445

Pro Tyr Leu Gly Leu Leu Thr Ser Gln Asn Leu Pro Leu Leu Leu Leu
450                 455                 460

Asp Leu Thr Trp Leu Glu Lys Leu Leu Pro Lys Thr Ile Ser Gln His
465                 470                 475                 480

Gln Ile Ser Thr Ser Ile Ile Thr Ser Thr Gln Lys Gly Met Ile Lys
                485                 490                 495

Leu Tyr Phe Leu Ser Phe Phe Phe Pro Leu Ile Leu Thr Leu Leu Leu
            500                 505                 510

Ile Thr Xaa
        515

<210> SEQ ID NO 50
<211> LENGTH: 543
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (543)..(543)
<223> OTHER INFORMATION: Xaa can be any naturally occurring amino acid

<400> SEQUENCE: 50

Met Asn Phe Ala Leu Ile Leu Met Ile Asn Thr Leu Leu Ala Leu Leu
1               5                   10                  15

Leu Met Ile Ile Thr Phe Trp Leu Pro Gln Leu Asn Gly Tyr Met Glu
            20                  25                  30

Lys Ser Thr Pro Tyr Glu Cys Gly Phe Asp Pro Met Ser Pro Ala Arg
        35                  40                  45

Val Pro Phe Ser Met Lys Phe Phe Leu Val Ala Ile Thr Phe Leu Leu
50                  55                  60

Phe Asp Leu Glu Ile Ala Leu Leu Leu Pro Leu Pro Trp Ala Leu Gln
65                  70                  75                  80

Thr Thr Asn Leu Pro Leu Met Val Met Ser Ser Leu Leu Leu Ile Ile
            85                  90                  95

Ile Leu Ala Leu Ser Leu Ala Asn Thr Ala Ala Ile Gln Ala Ile Leu
            100                 105                 110

Tyr Asn Arg Ile Gly Asp Ile Gly Phe Ile Leu Ala Leu Ala Trp Phe
            115                 120                 125

Ile Leu His Ser Asn Ser Trp Asp Pro Gln Gln Met Ala Leu Leu Asn
        130                 135                 140

Ala Asn Pro Ser Leu Thr Pro Leu Leu Gly Leu Leu Leu Ala Ala Ala
145                 150                 155                 160

Gly Lys Ser Ala Gln Leu Gly Leu His Pro Trp Leu Pro Ser Ala Met
                165                 170                 175

Glu Gly Pro Thr Pro Val Ser Ala Leu Leu His Ser Ser Thr Met Val
            180                 185                 190

Val Ala Gly Ile Phe Leu Leu Ile Arg Phe His Pro Leu Ala Glu Asn
        195                 200                 205

Ser Pro Leu Ile Gln Thr Leu Thr Leu Cys Leu Gly Ala Ile Thr Thr
210                 215                 220

Leu Phe Ala Ala Val Cys Ala Leu Thr Gln Asn Asp Ile Lys Lys Ile
225                 230                 235                 240

Val Ala Phe Ser Thr Ser Ser Gln Leu Gly Leu Met Met Val Thr Ile
            245                 250                 255
```

-continued

Gly Ile Asn Gln Pro His Leu Ala Phe Leu His Ile Cys Thr His Ala
                260                 265                 270

Phe Phe Lys Ala Met Leu Phe Met Cys Ser Gly Ser Ile Ile His Asn
            275                 280                 285

Leu Asn Asn Glu Gln Asp Ile Arg Lys Met Gly Gly Leu Leu Lys Thr
        290                 295                 300

Met Pro Leu Thr Ser Thr Ser Leu Thr Ile Gly Ser Leu Ala Leu Ala
305                 310                 315                 320

Gly Met Pro Phe Leu Thr Gly Phe Tyr Ser Lys Asp His Ile Ile Glu
                325                 330                 335

Thr Ala Asn Met Ser Tyr Thr Asn Ala Trp Ala Leu Ser Ile Thr Leu
            340                 345                 350

Ile Ala Thr Ser Leu Thr Ser Ala Tyr Ser Thr Arg Met Ile Leu Leu
        355                 360                 365

Thr Leu Thr Gly Gln Pro Arg Phe Pro Thr Leu Thr Asn Ile Asn Glu
370                 375                 380

Asn Asn Pro Thr Leu Leu Asn Pro Ile Lys Arg Leu Ala Ala Gly Ser
385                 390                 395                 400

Leu Phe Ala Gly Phe Leu Ile Thr Asn Asn Ile Ser Pro Ala Ser Pro
                405                 410                 415

Phe Gln Thr Thr Ile Pro Leu Tyr Leu Lys Leu Thr Ala Leu Ala Val
            420                 425                 430

Thr Phe Leu Gly Leu Leu Thr Ala Leu Asp Leu Asn Tyr Leu Thr Asn
        435                 440                 445

Lys Leu Lys Met Lys Ser Pro Leu Cys Thr Phe Tyr Phe Ser Asn Met
450                 455                 460

Leu Gly Phe Tyr Pro Ser Ile Thr His Arg Thr Ile Pro Tyr Leu Gly
465                 470                 475                 480

Leu Leu Thr Ser Gln Asn Leu Pro Leu Leu Leu Asp Leu Thr Trp
                485                 490                 495

Leu Glu Lys Leu Leu Pro Lys Thr Ile Ser Gln His Gln Ile Ser Thr
                500                 505                 510

Ser Ile Ile Thr Ser Thr Gln Lys Gly Met Ile Lys Leu Tyr Phe Leu
            515                 520                 525

Ser Phe Phe Phe Pro Leu Ile Leu Thr Leu Leu Ile Thr Xaa
            530                 535                 540

<210> SEQ ID NO 51
<211> LENGTH: 214
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (214)..(214)
<223> OTHER INFORMATION: Xaa can be any naturally occurring amino acid

<400> SEQUENCE: 51

Met Leu Lys Leu Ile Val Pro Thr Ile Met Leu Leu Pro Leu Thr Trp
1               5                   10                  15

Leu Ser Lys Lys His Met Ile Trp Ile Asn Thr Thr His Ser Leu
            20                  25                  30

Ile Ile Ser Ile Ile Pro Leu Leu Phe Phe Asn Gln Ile Asn Asn Asn
        35                  40                  45

Leu Phe Ser Cys Ser Pro Thr Phe Ser Ser Asp Pro Leu Thr Thr Pro
50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
            85                  90                  95

Ser Met Leu Ile Ser Leu Gln Ile Ser Leu Ile Met Thr Phe Thr Ala
            100                 105                 110

Thr Glu Leu Ile Met Phe Tyr Ile Phe Phe Glu Thr Thr Leu Ile Pro
            115                 120                 125

Thr Leu Ala Ile Ile Thr Arg Trp Gly Asn Gln Pro Glu Arg Leu Asn
        130                 135                 140

Ala Gly Thr Tyr Phe Leu Phe Tyr Thr Leu Val Gly Ser Leu Pro Leu
145                 150                 155                 160

Leu Leu Leu Asp Leu Thr Trp Leu Glu Lys Leu Leu Pro Lys Thr Ile
            165                 170                 175

Ser Gln His Gln Ile Ser Thr Ser Ile Ile Thr Ser Thr Gln Lys Gly
            180                 185                 190

Met Ile Lys Leu Tyr Phe Leu Ser Phe Phe Pro Leu Ile Leu Thr
            195                 200                 205

Leu Leu Leu Ile Thr Xaa
        210

<210> SEQ ID NO 52
<211> LENGTH: 43
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (43)..(43)
<223> OTHER INFORMATION: Xaa can be any naturally occurring amino acid

<400> SEQUENCE: 52

Met Pro Gln Leu Asn Thr Thr Val Trp Pro Thr Met Ile Thr Pro Met
1               5                   10                  15

Leu Leu Thr Leu Phe Leu Ile Thr Gln Leu Lys Met Leu Asn Thr Asn
            20                  25                  30

Tyr His Leu Pro Pro Ser Pro Leu Ala Ala Xaa
            35                  40

<210> SEQ ID NO 53
<211> LENGTH: 951
<212> TYPE: RNA
<213> ORGANISM: Human

<400> SEQUENCE: 53
augaacgaaa aucuguucgc uucauucauu gcccccacaa uccuaggccu acccgccgca      60
guacugauca uucuauuucc cccucuauug auccccaccu ccaaauaucu caucaacaac     120
cgacuaauca ccacccaaca augacuaauc aaacuaaccu caaaacaaau gauaaccaua    180
cacaacacua aaggacgaac cugaucucuu auacuaguau ccuuaaucau uuuuauugcc    240
acaacuaacc uccucggacu ccugccucac ucauuuacac caaccaccca acuaucuaua    300
aaccuagcca uggccauccc cuuaugagcg ggcacaguga uuauaggcuu ucgcucuaag    360
auuaaaaaug cccuagccca cuucuuacca caaggcacac cuacaccccu auccccauua   420
cuaguuauua ucgaaaccau cagccuacuc auucaaccaa uagcccuggc cguacgccua    480
accgcuaaca uuacgcagg ccaccuacuc augcaccuaa uggaagcgc cacccuagca    540 auaucaacca uuaaccuucc cucuacacuu aucaucuuca caauucuaau ucuacugacu    600

| | | |
|---|---|---|
| auccuagaaa ucgcugucac uuuccuagga cuucuaacag cccuagaccu caacuaccua | 660 | |
| accaacaaac uuaaaauaaa aucccacua ugcacauuuu auuucuccaa cauacucgga | 720 | |
| uucuacccua gcaucacaca ccgcacaauc cccuaucuag gccuucuuac gagccaaaac | 780 | |
| cugccccuac uccuccuaga ccuaaccuga cuagaaaagc uauuaccuaa aacaauuuca | 840 | |
| cagcaccaaa ucuccaccuc caucaucacc ucaacccaaa aaggcauaau uaaacuuuac | 900 | |
| uuccucucuu ucuucuuccc acucauccua acccuacucc uaaucacaua a | 951 | |

<210> SEQ ID NO 54
<211> LENGTH: 951
<212> TYPE: DNA
<213> ORGANISM: Artificial
<220> FEATURE:
<223> OTHER INFORMATION: cDNA

<400> SEQUENCE: 54

| | | |
|---|---|---|
| atgaacgaaa atctgttcgc ttcattcatt gcccccacaa tcctaggcct acccgccgca | 60 | |
| gtactgatca ttctatttcc ccctctattg atccccacct ccaaatatct catcaacaac | 120 | |
| cgactaatca ccacccaaca atgactaatc aaactaacct caaacaaat gataaccata | 180 | |
| cacaacacta aaggacgaac ctgatctctt atactagtat ccttaatcat ttttattgcc | 240 | |
| acaactaacc tcctcggact cctgcctcac tcatttacac caaccaccca actatctata | 300 | |
| aacctagcca tggccatccc cttatgagcg ggcacagtga ttataggctt cgctctaag | 360 | |
| attaaaaatg ccctagccca cttcttacca caaggcacac ctacacccct tatccccata | 420 | |
| ctagttatta tcgaaaccat cagcctactc attcaaccaa tagccctggc cgtacgccta | 480 | |
| accgctaaca ttactgcagg ccacctactc atgcacctaa ttggaagcgc caccctagca | 540 | |
| atatcaacca ttaaccttcc ctctacactt atcatcttca caattctaat tctactgact | 600 | |
| atcctagaaa tcgctgtcac tttcctagga cttctaacag ccctagacct caactaccta | 660 | |
| accaacaaac ttaaaataaa atccccacta tgcacatttt atttctccaa catactcgga | 720 | |
| ttctacccta gcatcacaca ccgcacaatc ccctatctag gccttcttac gagccaaaac | 780 | |
| ctgccctac tcctcctaga cctaacctga ctagaaaagc tattacctaa aacaatttca | 840 | |
| cagcaccaaa tctccacctc catcatcacc tcaacccaaa aaggcataat taaactttac | 900 | |
| ttcctctctt tcttcttccc actcatccta accctactcc taatcacata a | 951 | |

<210> SEQ ID NO 55
<211> LENGTH: 317
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (317)..(317)
<223> OTHER INFORMATION: Xaa can be any naturally occurring amino acid

<400> SEQUENCE: 55

Met Asn Glu Asn Leu Phe Ala Ser Phe Ile Ala Pro Thr Ile Leu Gly
1               5                   10                  15

Leu Pro Ala Ala Val Leu Ile Ile Leu Phe Pro Pro Leu Leu Ile Pro
                20                  25                  30

Thr Ser Lys Tyr Leu Ile Asn Asn Arg Leu Ile Thr Thr Gln Gln Trp
            35                  40                  45

Leu Ile Lys Leu Thr Ser Lys Gln Met Met Thr Met His Asn Thr Lys
        50                  55                  60

```
Gly Arg Thr Trp Ser Leu Met Leu Val Ser Leu Ile Ile Phe Ile Ala
 65                  70                  75                  80

Thr Thr Asn Leu Leu Gly Leu Leu Pro His Ser Phe Thr Pro Thr Thr
                 85                  90                  95

Gln Leu Ser Met Asn Leu Ala Met Ala Ile Pro Leu Trp Ala Gly Thr
            100                 105                 110

Val Ile Met Gly Phe Arg Ser Lys Ile Lys Asn Ala Leu Ala His Phe
        115                 120                 125

Leu Pro Gln Gly Thr Pro Thr Pro Leu Ile Pro Met Leu Val Ile Ile
    130                 135                 140

Glu Thr Ile Ser Leu Leu Ile Gln Pro Met Ala Leu Ala Val Arg Leu
145                 150                 155                 160

Thr Ala Asn Ile Thr Ala Gly His Leu Leu Met His Leu Ile Gly Ser
                165                 170                 175

Ala Thr Leu Ala Met Ser Thr Ile Asn Leu Pro Ser Thr Leu Ile Ile
            180                 185                 190

Phe Thr Ile Leu Ile Leu Leu Thr Ile Leu Glu Ile Ala Val Thr Phe
        195                 200                 205

Leu Gly Leu Leu Thr Ala Leu Asp Leu Asn Tyr Leu Thr Asn Lys Leu
    210                 215                 220

Lys Met Lys Ser Pro Leu Cys Thr Phe Tyr Phe Ser Asn Met Leu Gly
225                 230                 235                 240

Phe Tyr Pro Ser Ile Thr His Arg Thr Ile Pro Tyr Leu Gly Leu Leu
                245                 250                 255

Thr Ser Gln Asn Leu Pro Leu Leu Leu Asp Leu Thr Trp Leu Glu
            260                 265                 270

Lys Leu Leu Pro Lys Thr Ile Ser Gln His Gln Ile Ser Thr Ser Ile
    275                 280                 285

Ile Thr Ser Thr Gln Lys Gly Met Ile Lys Leu Tyr Phe Leu Ser Phe
290                 295                 300

Phe Phe Pro Leu Ile Leu Thr Leu Leu Leu Ile Thr Xaa
305                 310                 315
```

<210> SEQ ID NO 56
<211> LENGTH: 747
<212> TYPE: RNA
<213> ORGANISM: Human
<220> FEATURE:
<221> NAME/KEY: misc_feature
<223> OTHER INFORMATION: Fusion transcript P0026 (MT-CO2 (7586-8038) +
      MT-ND3 (10110-10404))

<400> SEQUENCE: 56

```
auggcacaug cagcgcaagu aggucuacaa gacgcuacuu ccccuaucau agaagagcuu    60
aucaccuuuc augaucacgc ccucauaauc auuuuccuua ucugcuuccu aguccuguau   120
gcccuuuucc uaacacucac aacaaaacua acuaauacua cauucucaga cgcucaggaa   180
auagaaaccg ucugaacuau ccugcccgcc aucauccuag uccucaucgc ccucccaucc   240
cuacgcaucc uuuacauaac agacgaagsu aacgaucccu cccuuaccau caaaucaauu   300
ggccaccaau gguacugaac cuacgaguac accgacuacg cggacuauau cuucaacucc   360
uacauacuuc ccccauuauu ccuagaacca ggcgaccugc gacuccuuga cguugacaau   420
cgaguaguac ucccgauuga agcccccauu cguauaauua uuacauuuug acuaccacaa   480
cucaacggcu acaugaaaaa auccacccu uacgagugcg gcuucgaccc uauauccccc   540 gcccgcguec cuuucuccau aaaauucuuc uuaguagcua uuaccuucuu auuauuugau   600
```

```
cuagaaauug cccuccuuuu accccuacca ugagcccuac aaacaacuaa ccugccacua    660
auaguuaugu caucccucuu auuaaucauc auccagcccu aagucuggc cuaugaguga     720 cuacaaaaag gauuagacug aaccgaa                                       747
```

<210> SEQ ID NO 57
<211> LENGTH: 747
<212> TYPE: DNA
<213> ORGANISM: Human
<220> FEATURE:
<221> NAME/KEY: misc_feature
<223> OTHER INFORMATION: Mutant DNA for fusion transcript P0026

<400> SEQUENCE: 57

```
atggcacatg cagcgcaagt aggtctacaa gacgctactt cccctatcat agaagagctt    60
atcacctttc atgatcacgc cctcataatc attttcctta tctgcttcct agtcctgtat   120
gcccttttcc taaacactca acaaaaacta actaatacta acatctcaga cgctcaggaa   180
atagaaaccg tctgaactat cctgcccgcc atcatcctag tcctcatcgc cctcccatcc   240
ctacgcatcc tttacataac agacgaggtc aacgatccct cccttaccat caaatcaatt   300
ggccaccaat ggtactgaac ctacgagtac accgactacg gcggactaat cttcaactcc   360
tacatacttc cccattatt cctagaacca ggcgacctgc gactccttga cgttgacaat   420
cgagtagtac tcccgattga agcccccatt cgtataatta ttacattttg actaccacaa   480
ctcaacggct acatagaaaa atccaccct tacgagtgcg gcttcgaccc tatatccccc   540
gcccgcgtcc ctttctccat aaaattcttc ttagtagcta ttaccttctt attatttgat   600
ctagaaattg ccctccttt accctacca tgagccctac aaacaactaa cctgccacta   660
atagttatgt catccctctt attaatcatc atcctagccc taagtctggc ctatgagtga   720
ctacaaaaag gattagactg aaccgaa                                       747
```

<210> SEQ ID NO 58
<211> LENGTH: 249
<212> TYPE: PRT
<213> ORGANISM: Human
<220> FEATURE:
<221> NAME/KEY: misc_feature
<223> OTHER INFORMATION: Fusion protein corresponding to P0026

<400> SEQUENCE: 58

```
Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
```

```
                130               135               140
Pro Ile Glu Ala Pro Ile Arg Met Ile Ile Thr Phe Trp Leu Pro Gln
145                 150                 155                 160

Leu Asn Gly Tyr Met Glu Lys Ser Thr Pro Tyr Glu Cys Gly Phe Asp
                165                 170                 175

Pro Met Ser Pro Ala Arg Val Pro Phe Ser Met Lys Phe Phe Leu Val
                180                 185                 190

Ala Ile Thr Phe Leu Leu Phe Asp Leu Glu Ile Ala Leu Leu Leu Pro
                195                 200                 205

Leu Pro Trp Ala Leu Gln Thr Thr Asn Leu Pro Leu Met Val Met Ser
210                 215                 220

Ser Leu Leu Leu Ile Ile Ile Leu Ala Leu Ser Leu Ala Tyr Glu Trp
225                 230                 235                 240

Leu Gln Lys Gly Leu Asp Trp Thr Glu
                245

<210> SEQ ID NO 59
<211> LENGTH: 1544
<212> TYPE: RNA
<213> ORGANISM: Human
<220> FEATURE:
<221> NAME/KEY: misc_feature
<223> OTHER INFORMATION: Fusion transcript P0062 (MT-ND1 (3307-4246) +
      MT-ATP6 (8603-9207))

<400> SEQUENCE: 59
auacccaugg ccaaccuccu acuccucauu guacccauuc uaaucgcaau ggcauuccua      60
augcuuaccg aacgaaaaau ucuaggcuau auacaacuac gcaaaggccc caacguugua    120
ggccccuacg gcuacuaca cccuucgcu gacgccauaa aacucuucac caaagagccc      180
cuaaaacccg ccacaucuac caucacccuc uacaucaccg ccccgaccuu agcucucacc    240
aucgcucuuc uacuaugaac cccccucccc auacccaacc cccuggucaa ccucaaccua    300
ggccuccuau uuauucuagc caccucuagc cuagccguuu acucaauccu cugaucaggg    360
ugagcaucaa acucaaacua cgcccugauc ggcgcacugc gagcaguagc ccaacaauc     420
ucaugaag ucacccuagc caucauucua cuaucaacau acuaauaag uggcuccuuu       480
aaccucucca cccuuaucac aacacaagaa caccucugau acuccugcc aucaugaccc     540
uuggccauaa uaugauuuau cuccacacua gcagagacca accgaacccc cuucgaccuu    600
gccgaagggg aguccgaacu agucucaggc uucaacaucg aauacgccgc aggcccuuc     660
gcccuauucu ucauagccga auacacaaac auuauuauaa uaaacacccu caccacuaca    720
aucuuccuag gaacaacaua ugacgcacuc uccccugaac ucuacacaac auauuugc     780
accaagaccc uacuucuaac cucccuguuc uuaugaauuc gaacagcaua ccccgauuc     840
cgcuacgacc aacucauaca ccuccuauga aaaaacuucc uaccacucac ccuagcauua    900
cuuauaugau augucuccau acccauuaca aucuccagca uuccccucu auugauccc     960
accuccaaau aucuaucaa caaccgacua aucaccaccc aacaaugacu aaucaaacua   1020
accucaaaac aaaugauaac cauacacaac acuaaaggac gaaccugauc ucuuauacua   1080
guaccuuaa ucauuuuau ugccacaacu aaccuccucg gacuccugcc ucacucauuu    1140
acaccaacca cccaacuauc uauaaaccua gccauggcca uccccuuaug agcgggcaca   1200
gugauuauag gcuuucgcuc uaagauuaaa aaugcccuag ccacuucuu accacaaggc   1260
acaccucacac cccuuauccc cauacuaguu auuacgaaa ccaucagccu acucauucaa   1320
ccaauagccc uggccguacg ccuaaccgcu aacauuacug caggccaccu acucaugcac   1380
```

| | |
|---|---:|
| cuaauuggaa gcgccacccu agcaauauca accauuaacc uucccucuac acuuaucauc | 1440 |
| uucacaauuc uaauucuacu gacuauccua gaaaucgcug ucgccuuaau ccaagccuac | 1500 |
| guuuucacac uucuaguaag ccucuaccug cacgacaaca caua | 1544 |

```
<210> SEQ ID NO 60
<211> LENGTH: 1544
<212> TYPE: DNA
<213> ORGANISM: Human
<220> FEATURE:
<221> NAME/KEY: misc_feature
<223> OTHER INFORMATION: Mutant DNA for fusion transcript P0062

<400> SEQUENCE: 60
```

| | |
|---|---:|
| atacccatgg ccaacctcct actcctcatt gtacccattc taatcgcaat ggcattccta | 60 |
| atgcttaccg aacgaaaaat tctaggctat atacaactac gcaaaggccc caacgttgta | 120 |
| ggccccuacg ggctactaca acccttcgct gacgccataa aactcttcac caaagagccc | 180 |
| ctaaaacccg ccacatctac catcaccctc tacatcaccg ccccgacctt agctctcacc | 240 |
| atcgctcttc tactatgaac cccccuccc atacccaacc cctggtcaa cctcaaccta | 300 |
| ggcctcctat ttattctagc cacctctagc ctagccgttt actcaatcct ctgatcaggg | 360 |
| tgagcatcaa actcaaacta cgccctgatc ggcgcactgc gagcagtagc ccaaacaatc | 420 |
| tcatatgaag tcaccctagc catcattcta ctatcaacat tactaataag tggctccttt | 480 |
| aacctctcca cccttatcac aacacaagaa cacctctgat tactcctgcc atcatgaccc | 540 |
| ttggccataa tatgatttat ctccacacta gcagagacca accgaacccc cttcgacctt | 600 |
| gccgaagggg agtccgaact agtctcaggc ttcaacatcg aatacgccgc aggcccctttc | 660 |
| gccctattct tcatagccga atacacaaac attattataa taaacaccct caccactaca | 720 |
| atcttcctag gaacaacata tgacgcactc tcccctgaac tctacacaac atattttgtc | 780 |
| accaagaccc tacttctaac ctcccttgtttc ttatgaattc gaacagcata ccccgattc | 840 |
| cgctacgacc aactcataca cctcctgatg aaaaactttcc taccactcac cctagcatta | 900 |
| cttatatgat atgtctccat acccattaca atctccagca ttccccctct attgatcccc | 960 |
| acctccaaat atctcatcaa caaccgacta atcaccaccc aacaatgact aatcaaacta | 1020 |
| acctcaaaac aaatgataac catacacaac actaaaggac gaacctgatc tcttatacta | 1080 |
| gtatccttaa tcatttttat tgccacaact aacctcctcg gactcctgcc tcactcattt | 1140 |
| acaccaacca cccaactatc tataaaaccta gccatggcca tccccttatg agcgggcaca | 1200 |
| gtgattatag gctttcgctc taagattaaa aatgccctag cccacttctt accacaaggc | 1260 |
| acacctacac cccttatccc catactagtt attatcgaaa ccatcagcct actcattcaa | 1320 |
| ccaatagccc tggccgtacg cctaaccgct aacattactg caggccacct actcatgcac | 1380 |
| ctaattggaa gcgccacccct agcaatatca accattaacc ttccctctac acttatcatc | 1440 |
| ttcacaattc taattctact gactatccta gaaatcgctg tcgccttaat ccaagcctac | 1500 |
| gttttcacac ttctagtaag cctctacctg cacgacaaca cata | 1544 |

```
<210> SEQ ID NO 61
<211> LENGTH: 515
<212> TYPE: PRT
<213> ORGANISM: Human
<220> FEATURE:
<221> NAME/KEY: misc_feature
<223> OTHER INFORMATION: Fusion protein corresponding to P0062
<220> FEATURE:
<221> NAME/KEY: misc_feature
```

<222> LOCATION: (515)..(515)
<223> OTHER INFORMATION: Xaa can be any naturally occurring amino acid

<400> SEQUENCE: 61

```
Met Pro Met Ala Asn Leu Leu Leu Ile Val Pro Ile Leu Ile Ala
1               5                   10                  15

Met Ala Phe Leu Met Leu Thr Glu Arg Lys Ile Leu Gly Tyr Met Gln
            20                  25                  30

Leu Arg Lys Gly Pro Asn Val Val Gly Pro Tyr Gly Leu Leu Gln Pro
            35                  40                  45

Phe Ala Asp Ala Met Lys Leu Phe Thr Lys Glu Pro Leu Lys Pro Ala
    50                  55                  60

Thr Ser Thr Ile Thr Leu Tyr Ile Thr Ala Pro Thr Leu Ala Leu Thr
65              70                  75                  80

Ile Ala Leu Leu Leu Trp Thr Pro Leu Pro Met Pro Asn Pro Leu Val
                85                  90                  95

Asn Leu Asn Leu Gly Leu Leu Phe Ile Leu Ala Thr Ser Ser Leu Ala
                100                 105                 110

Val Tyr Ser Ile Leu Trp Ser Gly Trp Ala Ser Asn Ser Asn Tyr Ala
            115                 120                 125

Leu Ile Gly Ala Leu Arg Ala Val Ala Gln Thr Ile Ser Tyr Glu Val
            130                 135                 140

Thr Leu Ala Ile Ile Leu Leu Ser Thr Leu Leu Met Ser Gly Ser Phe
145                 150                 155                 160

Asn Leu Ser Thr Leu Ile Thr Thr Gln Glu His Leu Trp Leu Leu Leu
                165                 170                 175

Pro Ser Trp Pro Leu Ala Met Met Trp Phe Ile Ser Thr Leu Ala Glu
            180                 185                 190

Thr Asn Arg Thr Pro Phe Asp Leu Ala Glu Gly Glu Ser Glu Leu Val
            195                 200                 205

Ser Gly Phe Asn Ile Glu Tyr Ala Ala Gly Pro Phe Ala Leu Phe Phe
210                 215                 220

Met Ala Glu Tyr Thr Asn Ile Ile Met Met Asn Thr Leu Thr Thr Thr
225                 230                 235                 240

Ile Phe Leu Gly Thr Thr Tyr Asp Ala Leu Ser Pro Glu Leu Tyr Thr
                245                 250                 255

Thr Tyr Phe Val Thr Lys Thr Leu Leu Leu Thr Ser Leu Phe Leu Trp
                260                 265                 270

Ile Arg Thr Ala Tyr Pro Arg Phe Arg Tyr Asp Gln Leu Met His Leu
            275                 280                 285

Leu Trp Lys Asn Phe Leu Pro Leu Thr Leu Ala Leu Leu Met Trp Tyr
            290                 295                 300

Val Ser Met Pro Ile Thr Ile Ser Ser Ile Pro Pro Leu Leu Ile Pro
305                 310                 315                 320

Thr Ser Lys Tyr Leu Ile Asn Asn Arg Leu Ile Thr Thr Gln Gln Trp
                325                 330                 335

Leu Ile Lys Leu Thr Ser Lys Gln Met Met Thr Met His Asn Thr Lys
            340                 345                 350

Gly Arg Thr Trp Ser Leu Met Leu Val Ser Leu Ile Ile Phe Ile Ala
            355                 360                 365

Thr Thr Asn Leu Leu Gly Leu Leu Pro His Ser Phe Thr Pro Thr Thr
            370                 375                 380

Gln Leu Ser Met Asn Leu Ala Met Ala Ile Pro Leu Trp Ala Gly Thr
385                 390                 395                 400
```

-continued

```
Val Ile Met Gly Phe Arg Ser Lys Ile Lys Asn Ala Leu Ala His Phe
            405                 410                 415

Leu Pro Gln Gly Thr Pro Thr Pro Leu Ile Pro Met Leu Val Ile Ile
            420                 425                 430

Glu Thr Ile Ser Leu Leu Ile Gln Pro Met Ala Leu Ala Val Arg Leu
            435                 440                 445

Thr Ala Asn Ile Thr Ala Gly His Leu Leu Met His Leu Ile Gly Ser
            450                 455                 460

Ala Thr Leu Ala Met Ser Thr Ile Asn Leu Pro Ser Thr Leu Ile Ile
465                 470                 475                 480

Phe Thr Ile Leu Ile Leu Leu Thr Ile Leu Glu Ile Ala Val Ala Leu
            485                 490                 495

Ile Gln Ala Tyr Val Phe Thr Leu Leu Val Ser Leu Tyr Leu His Asp
            500                 505                 510

Asn Thr Xaa
        515

<210> SEQ ID NO 62
<211> LENGTH: 999
<212> TYPE: RNA
<213> ORGANISM: Human
<220> FEATURE:
<221> NAME/KEY: misc_feature
<223> OTHER INFORMATION: Fusion transcript  P0064 (MT-ND1 (3307-3752) +
      MT-ND2 (4958-5511))

<400> SEQUENCE: 62 aucccaugg  ccaaccuccu  acuccucauu  guacccauuc  uaaucgcaau  ggcauuccua      60
augcuuaccg  aacgaaaaau  ucuaggcuau  auacaacuac  gcaaaggccc  caacguugua    120
ggccccuacg  ggcuacuaca  acccuucgcu  gacgccauaa  aacucuucac  caaagagccc   180
cuaaaacccg  ccacaucuac  caucacccuc  uacaucaccg  ccccgaccuu  agcucucacc   240
aucgcucuuc  uacuaugaac  cccccucccc  uacccaaccc  cccuggucaa  ccucaaccua   300
ggccuccuau  uuauucuagc  caccucuagc  cuagccguuu  acucaauccu  cugaucaggg   360
ugagcaucaa  acucaaacua  cgccugauc  ggcgcacugc  gagcaguagc  ccaaacaauc    420
ucauaugaag  ucacccuagc  caucauagca  ggcaguugag  guggauuaaa  ccaaacccag   480
cuacgcaaaa  ucuuagcaua  ucccucaauu  acccacauag  gaugaauaau  agcaguucca   540
ccguacaacc  cuaacauaac  cauucuuaau  uuaacuauuu  auauuauccu  aacuacuacc   600 gcauccuac  uacucaacuu  aaacccagc  accacgaccc  uacuacuauc  ucgcaccuga    660
aacaagcuaa  caugacuaac  acccuuaauu  ccauccaccc  uccucucccu  aggaggccug   720
cccccgcuaa  ccggcuuuuu  gcccaaaugg  ccauuaucg  aagaauucac  aaaaaacaau    780
agccucauca  uccccaccau  cauagccacc  aucccucc  uuaaccucua  cuucuaccua     840
cgccuaaucu  acuccaccuc  aaucacacua  cuccccauau  cuaacaacgu  aaaaauaaaa   900
ugacaguuug  aacauacaaa  acccacccca  uuccucccca  cacucaucgc  ccuuaccacg   960
cuacuccuac  cuaucuccc  uuuuauacua  auaaucuua                             999

<210> SEQ ID NO 63
<211> LENGTH: 999
<212> TYPE: DNA
<213> ORGANISM: Human
<220> FEATURE:
<221> NAME/KEY: misc_feature
<223> OTHER INFORMATION: Mutant DNA for fusion transcript P0064

<400> SEQUENCE: 63
```

```
atacccatgg ccaacctcct actcctcatt gtacccattc taatcgcaat ggcattccta      60
atgcttaccg aacgaaaaat tctaggctat atacaactac gcaaaggccc caacgttgta     120
ggcccctacg ggctactaca acccttcgct gacgccataa aactcttcac caaagagccc     180
ctaaaacccg ccacatctac catcaccctc tacatcaccg ccccgacctt agctctcacc     240
atcgctcttc tactatgaac ccccctcccc atacccaacc cctggtcaa cctcaaccta     300 ggcctcctat ttattctagc cacctctagc ctagccgttt actcaatcct ctgatcaggg     360
tgagcatcaa actcaaacta cgccctgatc ggcgcactgc gagcagtagc ccaaacaatc     420
tcatatgaag tcaccctagc catcatagca ggcagttgag gtggattaaa ccaaacccag     480
ctacgcaaaa tcttagcata ctcctcaatt acccacatag gatgaataat agcagttcta     540
ccgtacaacc ctaacataac cattcttaat ttaactattt atattatcct aactactacc     600
gcattcctac tactcaactt aaactccagc accacgaccc tactactatc tcgcacctga     660
aacaagctaa catgactaac ccccttaatt ccatccaccc tcctctcccct aggaggcctg     720 cccccgctaa ccggcttttt gcccaaatgg gccattatcg aagaattcac aaaaaacaat     780
agcctcatca tcccaccat catagccacc atcaccctcc ttaacctcta cttctaccta     840
cgcctaatct actccaccctc aatcacacta ctccccatat ctaacaacgt aaaaataaaa     900
tgacagtttg aacatacaaa acccaccccca ttcctcccca cactcatcgc ccttaccacg     960
ctactcctac ctatctcccc ttttatacta ataatctta                            999
```

<210> SEQ ID NO 64
<211> LENGTH: 333
<212> TYPE: PRT
<213> ORGANISM: Human
<220> FEATURE:
<221> NAME/KEY: misc_feature
<223> OTHER INFORMATION: Fusion protein corresponding to P0064

<400> SEQUENCE: 64

```
Met Pro Met Ala Asn Leu Leu Leu Ile Val Pro Ile Leu Ile Ala
1               5                   10                  15

Met Ala Phe Leu Met Leu Thr Glu Arg Lys Ile Leu Gly Tyr Met Gln
                20                  25                  30

Leu Arg Lys Gly Pro Asn Val Val Gly Pro Tyr Gly Leu Leu Gln Pro
            35                  40                  45

Phe Ala Asp Ala Met Lys Leu Phe Thr Lys Glu Pro Leu Lys Pro Ala
        50                  55                  60

Thr Ser Thr Ile Thr Leu Tyr Ile Thr Ala Pro Thr Leu Ala Leu Thr
65                  70                  75                  80

Ile Ala Leu Leu Leu Trp Thr Pro Leu Pro Met Pro Asn Pro Leu Val
                85                  90                  95

Asn Leu Asn Leu Gly Leu Leu Phe Ile Leu Ala Thr Ser Ser Leu Ala
            100                 105                 110

Val Tyr Ser Ile Leu Trp Ser Gly Trp Ala Ser Asn Ser Asn Tyr Ala
        115                 120                 125

Leu Ile Gly Ala Leu Arg Ala Val Ala Gln Thr Ile Ser Tyr Glu Val
    130                 135                 140

Thr Leu Ala Ile Met Ala Gly Ser Trp Gly Gly Leu Asn Gln Thr Gln
145                 150                 155                 160

Leu Arg Lys Ile Leu Ala Tyr Ser Ser Ile Thr His Met Gly Trp Met
                165                 170                 175

Met Ala Val Leu Pro Tyr Asn Pro Asn Met Thr Ile Leu Asn Leu Thr
```

```
              180                 185                 190
Ile Tyr Ile Ile Leu Thr Thr Thr Ala Phe Leu Leu Leu Asn Leu Asn
            195                 200                 205

Ser Ser Thr Thr Thr Leu Leu Leu Ser Arg Thr Trp Asn Lys Leu Thr
210                 215                 220

Trp Leu Thr Pro Leu Ile Pro Ser Thr Leu Leu Ser Leu Gly Gly Leu
225                 230                 235                 240

Pro Pro Leu Thr Gly Phe Leu Pro Lys Trp Ala Ile Ile Glu Glu Phe
                245                 250                 255

Thr Lys Asn Asn Ser Leu Ile Ile Pro Thr Ile Met Ala Thr Ile Thr
                260                 265                 270

Leu Leu Asn Leu Tyr Phe Tyr Leu Arg Leu Ile Tyr Ser Thr Ser Ile
                275                 280                 285

Thr Leu Leu Pro Met Ser Asn Asn Val Lys Met Lys Trp Gln Phe Glu
            290                 295                 300

His Thr Lys Pro Thr Pro Phe Leu Pro Thr Leu Ile Ala Leu Thr Thr
305                 310                 315                 320

Leu Leu Leu Pro Ile Ser Pro Phe Met Leu Met Ile Leu
                325                 330

<210> SEQ ID NO 65
<211> LENGTH: 1481
<212> TYPE: RNA
<213> ORGANISM: Human
<220> FEATURE:
<221> NAME/KEY: misc_feature
<223> OTHER INFORMATION: Fusion transcript P0176 (MT-ND1 (3307-3872) +
      MT-CO1 (6530-7445))

<400> SEQUENCE: 65
auacccaugg ccaaccuccu acuccucauu guacccauuc uaaucgcaau ggcauuccua      60
augcuuaccg aacgaaaaau ucuaggcuau auacaacuac gcaaaggccc caacguugua    120
ggccccuacg ggcuacuaca acccuucgcu gacgccauaa aacucuucac caaagagccc    180
cuaaaacccg ccacaucuac caucacccuc uacaucaccg ccccgaccuu agcucucacc    240
aucgcucuuc uacuaugaac cccccucccc auacccaacc cccuggucaa ccucaaccua    300
ggccuccuau uuauucuagc caccucuagc cuagccguuu acucaauccu cugaucaggg    360
ugagcaucaa acucaaacua cgcccugauc ggcgcacugc gagcaguagc ccaaacaauc    420
ucauaugaag ucacccuagc caucauucua cuaucaacau uacuaauaag uggcuccuuu    480
aaccucucca cccuuaucac aacacaagaa caccucugau uacuccugcc aucaugaccc    540
uuggccauaa uaugauuuau cuccacacua acagaccgca accucaacac caccuucuuc    600
gaccccgccg gaggaggaga ccccauucua uaccaacacc uauucugauu uucggucac     660 ccugaaguuu auauucuuau ccuaccaggc uucggaauaa ucucccauau uguaacuuac    720
uacuccggaa aaaagaacc auuuggauac auagguaugg ucuagcuau gauaucaauu     780 ggcuuccuag gguuuaucgu gugagcacac cauauauuua caguaggaau agacguagac    840
acacgagcau auuucaccuc cgcuaccaua aucaucgcua uccccaccgg cgucaaagua    900
uuuagcugac ucgccacacu ccacggaagc aauaugaaau gaucugcugc agugcucuga    960
gcccuaggau ucaucuuucu uuucaccgua gguggccuga cuggcauugu auuagcaaac   1020
ucaucacuag acaucguacu acacgacacg uacuacguug uagcccacuu ccacuauguc   1080
cuaucaauag gagcuguauu ugccaucaua ggaggcuuca ucacugauu cccccuauuc    1140 ucaggcuaca cccuagacca aaccuacgcc aaaauccauu ucacuaucau auucaucggc   1200
```

```
guaaaucuaa cuuucuuccc acaacacuuu cucggccuau ccggaaugcc ccgacguuac    1260
ucggacuacc ccgaugcaua caccacauga aacauccuau caucuguagg cucauucauu    1320
ucucuaacag caguaauauu aauaauuuuc augauuugag aagccuucgc uucgaagcga    1380
aaaguccuaa uaguagaaga acccuccaua aaccuggagu gacuauaugg augccccca     1440 cccuaccaca cauucgaaga acccguauac auaaaaucua g                       1481
```

<210> SEQ ID NO 66
<211> LENGTH: 1481
<212> TYPE: DNA
<213> ORGANISM: Human
<220> FEATURE:
<221> NAME/KEY: misc_feature
<223> OTHER INFORMATION: Mutant DNA for fusion transcript P0176

<400> SEQUENCE: 66

```
atacccatgg ccaacctcct actcctcatt gtacccattc taatcgcaat ggcattccta    60
atgcttaccg aacgaaaaat tctaggctat atacaactac gcaaaggccc caacgttgta   120
ggcccctacg ggctactaca acccttcgct gacgccataa aactcttcac caaagagccc   180
ctaaaacccg ccacatctac catcaccctc tacatcaccg ccccgacctt agctctcacc   240
atcgctcttc tactatgaac ccccctcccc atacccaacc cctggtcaa  cctcaaccta   300 ggcctcctat ttattctagc cacctctagc ctagccgttt actcaatcct ctgatcaggg   360
tgagcatcaa actcaaacta cgccctgatc ggcgcactgc gagcagtagc ccaaacaatc   420
tcatatgaag tcaccctagc catcattcta ctatcaacat tactaataag tggctccttt   480
aacctctcca cccttatcac aacacaagaa cacctctgat tactcctgcc atcatgaccc   540
ttggccataa tatgatttat ctccacacta acagaccgca acctcaacac caccttcttc   600
gaccccgccg gaggaggaga ccccattcta taccaacacc tattctgatt tttcggtcac   660
cctgaagttt atattcttat cctaccaggc ttcggaataa tctcccatat tgtaacttac   720
tactccggaa aaaagaacc atttggatac ataggtatgg tctgagctat gatatcaatt   780
ggcttcctag ggtttatcgt gtgagcacac catatattta cagtaggaat agacgtagac   840
acacgagcat atttcacctc cgctaccata atcatcgcta tccccaccgg cgtcaaagta   900
tttagctgac tcgccacact ccacggaagc aatatgaaat gatctgctgc agtgctctga   960
gccctaggat tcatctttct tttcaccgta ggtggcctga ctggcattgt attagcaaac  1020
tcatcactag acatcgtact acacgacacg tactacgttg tagcccactt ccactatgtc  1080
ctatcaatag gagctgtatt tgccatcata ggaggcttca ttcactgatt tcccctattc  1140
tcaggctaca ccctagacca aacctacgcc aaaatccatt tcactatcat attcatcggc  1200
gtaaatctaa ctttcttccc acaacacttt ctcggcctat ccggaatgcc ccgacgttac  1260
tcggactacc ccgatgcata caccacatga aacatcctat catctgtagg ctcattcatt  1320
tctctaacag cagtaatatt aataattttc atgatttgag aagccttcgc ttcgaagcga  1380
aaagtcctaa tagtagaaga accctccata aacctggagt gactatatgg atgcccccca  1440
ccctaccaca cattcgaaga acccgtatac ataaaatcta g                       1481
```

<210> SEQ ID NO 67
<211> LENGTH: 494
<212> TYPE: PRT
<213> ORGANISM: Human
<220> FEATURE:
<221> NAME/KEY: misc_feature
<223> OTHER INFORMATION: Fusion protein corresponding to P0176

<220> FEATURE:
<221> NAME/KEY: misc_feature
<222> LOCATION: (494)..(494)
<223> OTHER INFORMATION: Xaa can be any naturally occurring amino acid

<400> SEQUENCE: 67

| | | | | | | | | | | | | | | | |
|---|---|---|---|---|---|---|---|---|---|---|---|---|---|---|---|
| Met | Pro | Met | Ala | Asn | Leu | Leu | Leu | Ile | Val | Pro | Ile | Leu | Ile | Ala |
| 1 | | | | 5 | | | | | 10 | | | | | 15 |
| Met | Ala | Phe | Leu | Met | Leu | Thr | Glu | Arg | Lys | Ile | Leu | Gly | Tyr | Met | Gln |
| | | | 20 | | | | | 25 | | | | | 30 | | |
| Leu | Arg | Lys | Gly | Pro | Asn | Val | Val | Gly | Pro | Tyr | Gly | Leu | Leu | Gln | Pro |
| | | | 35 | | | | 40 | | | | | 45 | | | |
| Phe | Ala | Asp | Ala | Met | Lys | Leu | Phe | Thr | Lys | Glu | Pro | Leu | Lys | Pro | Ala |
| | 50 | | | | | 55 | | | | | 60 | | | | |
| Thr | Ser | Thr | Ile | Thr | Leu | Tyr | Ile | Thr | Ala | Pro | Thr | Leu | Ala | Leu | Thr |
| 65 | | | | | 70 | | | | | 75 | | | | | 80 |
| Ile | Ala | Leu | Leu | Leu | Trp | Thr | Pro | Leu | Pro | Met | Pro | Asn | Pro | Leu | Val |
| | | | | 85 | | | | | 90 | | | | | 95 | |
| Asn | Leu | Asn | Leu | Gly | Leu | Leu | Phe | Ile | Leu | Ala | Thr | Ser | Ser | Leu | Ala |
| | | | 100 | | | | | 105 | | | | | 110 | | |
| Val | Tyr | Ser | Ile | Leu | Trp | Ser | Gly | Trp | Ala | Ser | Asn | Ser | Asn | Tyr | Ala |
| | | 115 | | | | | 120 | | | | | 125 | | | |
| Leu | Ile | Gly | Ala | Leu | Arg | Ala | Val | Ala | Gln | Thr | Ile | Ser | Tyr | Glu | Val |
| | 130 | | | | | 135 | | | | | 140 | | | | |
| Thr | Leu | Ala | Ile | Ile | Leu | Leu | Ser | Thr | Leu | Leu | Met | Ser | Gly | Ser | Phe |
| 145 | | | | | 150 | | | | | 155 | | | | | 160 |
| Asn | Leu | Ser | Thr | Leu | Ile | Thr | Thr | Gln | Glu | His | Leu | Trp | Leu | Leu | Leu |
| | | | | 165 | | | | | 170 | | | | | 175 | |
| Pro | Ser | Trp | Pro | Leu | Ala | Met | Met | Trp | Phe | Ile | Ser | Thr | Leu | Thr | Asp |
| | | | 180 | | | | | 185 | | | | | 190 | | |
| Arg | Asn | Leu | Asn | Thr | Thr | Phe | Phe | Asp | Pro | Ala | Gly | Gly | Gly | Asp | Pro |
| | | | 195 | | | | | 200 | | | | | 205 | | |
| Ile | Leu | Tyr | Gln | His | Leu | Phe | Trp | Phe | Phe | Gly | His | Pro | Glu | Val | Tyr |
| | 210 | | | | | 215 | | | | | 220 | | | | |
| Ile | Leu | Ile | Leu | Pro | Gly | Phe | Gly | Met | Ile | Ser | His | Ile | Val | Thr | Tyr |
| 225 | | | | | 230 | | | | | 235 | | | | | 240 |
| Tyr | Ser | Gly | Lys | Lys | Glu | Pro | Phe | Gly | Tyr | Met | Gly | Met | Val | Trp | Ala |
| | | | | 245 | | | | | 250 | | | | | 255 | |
| Met | Met | Ser | Ile | Gly | Phe | Leu | Gly | Phe | Ile | Val | Trp | Ala | His | His | Met |
| | | | 260 | | | | | 265 | | | | | 270 | | |
| Phe | Thr | Val | Gly | Met | Asp | Val | Asp | Thr | Arg | Ala | Tyr | Phe | Thr | Ser | Ala |
| | | 275 | | | | | 280 | | | | | 285 | | | |
| Thr | Met | Ile | Ile | Ala | Ile | Pro | Thr | Gly | Val | Lys | Val | Phe | Ser | Trp | Leu |
| | | 290 | | | | | 295 | | | | | 300 | | | |
| Ala | Thr | Leu | His | Gly | Ser | Asn | Met | Lys | Trp | Ser | Ala | Ala | Val | Leu | Trp |
| 305 | | | | | 310 | | | | | 315 | | | | | 320 |
| Ala | Leu | Gly | Phe | Ile | Phe | Leu | Phe | Thr | Val | Gly | Gly | Leu | Thr | Gly | Ile |
| | | | | 325 | | | | | 330 | | | | | 335 | |
| Val | Leu | Ala | Asn | Ser | Ser | Leu | Asp | Ile | Val | Leu | His | Asp | Thr | Tyr | Tyr |
| | | | 340 | | | | | 345 | | | | | 350 | | |
| Val | Val | Ala | His | Phe | His | Tyr | Val | Leu | Ser | Met | Gly | Ala | Val | Phe | Ala |
| | | | 355 | | | | | 360 | | | | | 365 | | |
| Ile | Met | Gly | Gly | Phe | Ile | His | Trp | Phe | Pro | Leu | Phe | Ser | Gly | Tyr | Thr |
| | 370 | | | | | 375 | | | | | 380 | | | | |
| Leu | Asp | Gln | Thr | Tyr | Ala | Lys | Ile | His | Phe | Thr | Ile | Met | Phe | Ile | Gly |

-continued

```
385                 390                 395                 400

Val Asn Leu Thr Phe Phe Pro Gln His Phe Leu Gly Leu Ser Gly Met
                405                 410                 415

Pro Arg Arg Tyr Ser Asp Tyr Pro Asp Ala Tyr Thr Thr Trp Asn Ile
                420                 425                 430

Leu Ser Ser Val Gly Ser Phe Ile Ser Leu Thr Ala Val Met Leu Met
            435                 440                 445

Ile Phe Met Ile Trp Glu Ala Phe Ala Ser Lys Arg Lys Val Leu Met
        450                 455                 460

Val Glu Glu Pro Ser Met Asn Leu Glu Trp Leu Tyr Gly Cys Pro Pro
465                 470                 475                 480

Pro Tyr His Thr Phe Glu Glu Pro Val Tyr Met Lys Ser Xaa
                485                 490
```